(12) United States Patent
Kumta

(10) Patent No.: US 11,732,334 B2
(45) Date of Patent: Aug. 22, 2023

(54) PROPERTIES AND PARAMETERS OF NOVEL BIODEGRADABLE METALLIC ALLOYS

(71) Applicant: UNIVERSITY OF PITTSBURGH-OF THE COMMONWEALTH SYSTEM OF HIGHER EDUCATION, Pittsburgh, PA (US)

(72) Inventor: Prashant N. Kumta, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 16/500,928

(22) PCT Filed: Apr. 12, 2018

(86) PCT No.: PCT/US2018/027346
§ 371 (c)(1),
(2) Date: Oct. 4, 2019

(87) PCT Pub. No.: WO2018/191527
PCT Pub. Date: Oct. 18, 2018

(65) Prior Publication Data
US 2020/0399742 A1 Dec. 24, 2020

Related U.S. Application Data

(60) Provisional application No. 62/484,564, filed on Apr. 12, 2017, provisional application No. 62/484,560, filed on Apr. 12, 2017.

(51) Int. Cl.
*C22C 23/06* (2006.01)

(52) U.S. Cl.
CPC .................................. *C22C 23/06* (2013.01)

(58) Field of Classification Search
CPC ....................................................... C22C 23/06
See application file for complete search history.

(56) References Cited

U.S. PATENT DOCUMENTS

| | | | | |
|---|---|---|---|---|
| 2008/0031765 A1* | 2/2008 | Gerold | ................. | A61L 31/148 420/404 |
| 2011/0192500 A1* | 8/2011 | Uggowitzer | .......... | A61L 31/022 148/406 |
| 2014/0248288 A1* | 9/2014 | Kumta | ................... | A61L 27/58 424/172.1 |

FOREIGN PATENT DOCUMENTS

| JP | 2011-524465 A | 9/2011 |
|---|---|---|
| WO | 2017035072 A1 | 3/2017 |

OTHER PUBLICATIONS

Moosbrugger et al. ("Corrosion Resistance of Magnesium Alloys". ASM handbook. Eds. Stephen D. Cramer, and Bernard S. Covino Jr. vol. 13. Materials Park, Ohio: ASM international, 2003.) (Year: 2003).*

(Continued)

*Primary Examiner* — Anthony J Zimmer
*Assistant Examiner* — Ricardo D Morales
(74) *Attorney, Agent, or Firm* — Carol A. Marmo; Eckert Seamans Cherin & Mellott, LLC

(57) ABSTRACT

The invention relates to biodegradable, metal alloys, methods for their preparation and applications for their use. The alloys include magnesium and other components, such as, yttrium, calcium, zirconium, and zinc. These elements are alloyed together in specific combinations and amounts in order to achieve an alloy having desired properties and characteristics. In certain embodiments, strontium or cerium may be included as an additive. The resulting alloys are (Continued)

particularly suitable for forming various medical devices for implantation into the body of a patient.

6 Claims, 72 Drawing Sheets

(56) References Cited

OTHER PUBLICATIONS

Watanabe et al. ("Fine-grain processing by equal channel angular extrusion of rapidly quenched bulk Mg—Y—Zn alloy." Journal of materials research 20.1 (2005): 93-101.) (Year: 2005).*

Chou et al., In vitro and in vivo corrosion, cell response, and biocompatibility of high strength Mg—Ca—Zr, Mg—Y—Ca—Zr, and Mg—Y—Zn—Ca—Zr alloys for orthopaedic implant applications, eCM Meeting Abstracts, Collection 7, 8th Biometal, 2016. Retrieved from the Internet: <URL: file:///C:/Users/lk02/Downloads/collection7.pdf>, p. 13.

Hong et al., In Vitro Degradation and Cytotoxicity Response of Mg-4% Zn-0.5% Zr (ZK40) Alloy as a Potential Biodegradable Material, Acta Biomaterialia (Nov. 1, 2013), 9(10):8534-8547.

Extended European Search Report Issued in EP Patent Application No. 18783808.1 Dated Nov. 20, 2020.

\* cited by examiner

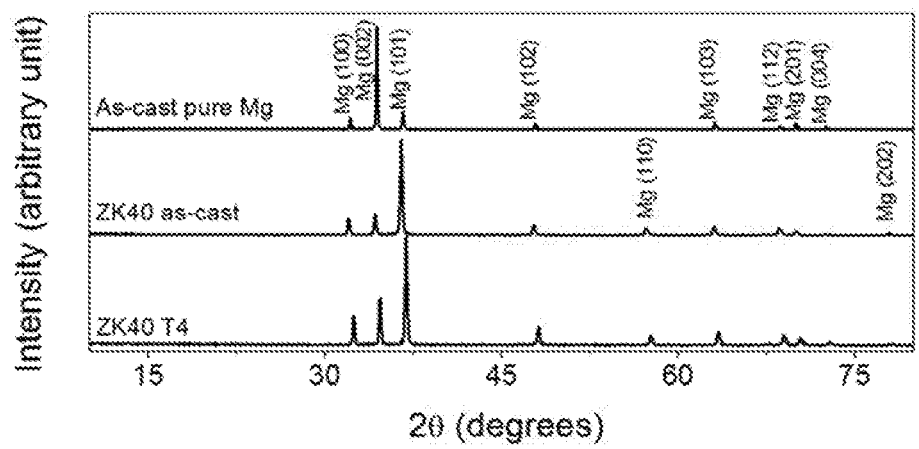
FIGURE 1.1
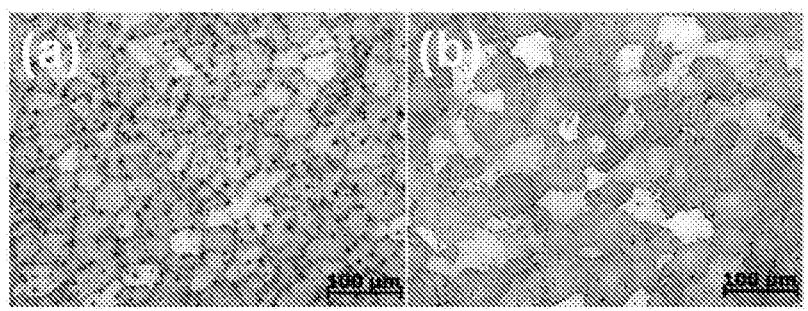
FIGURE 1.2

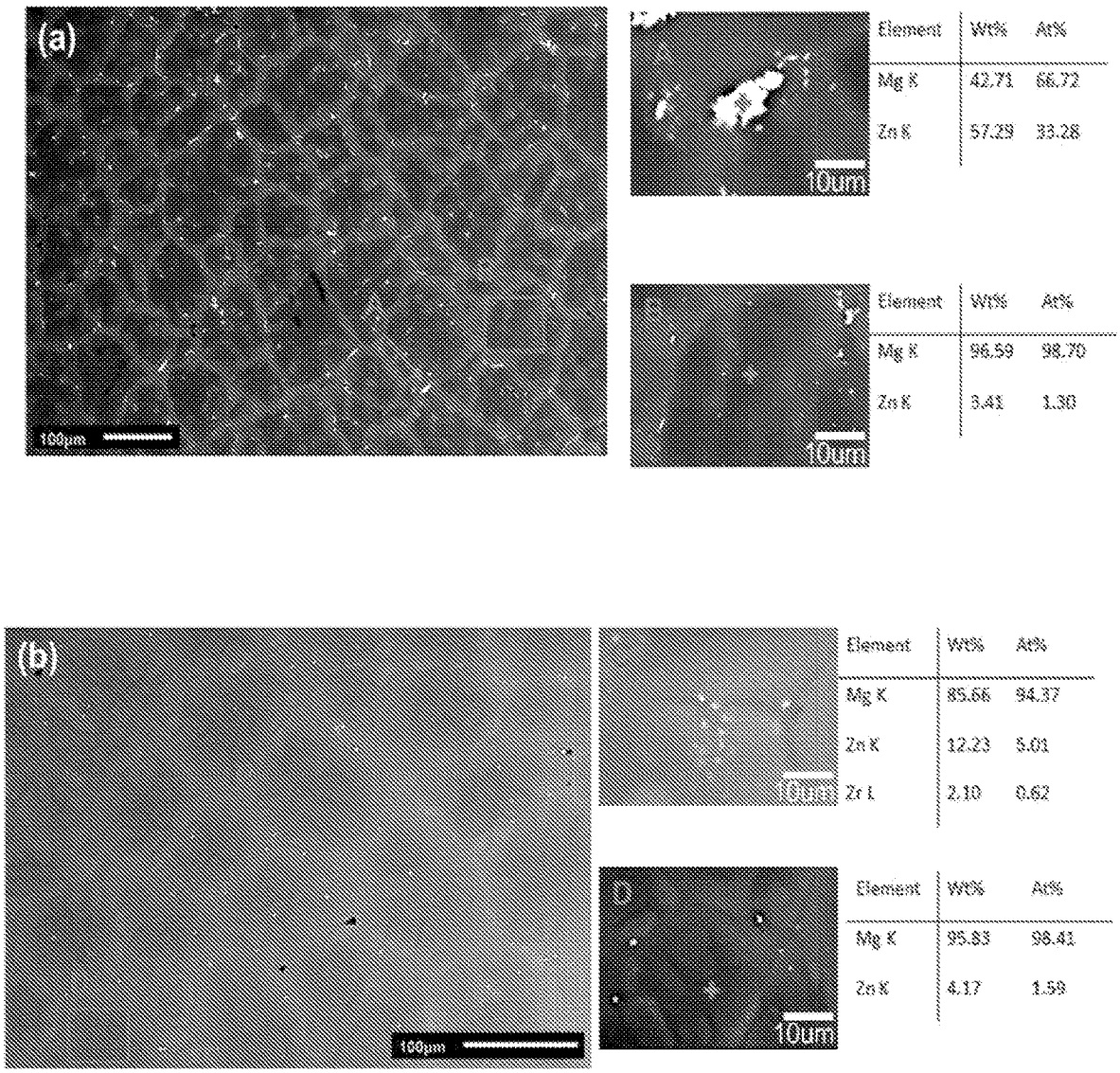
FIGURE 1.3

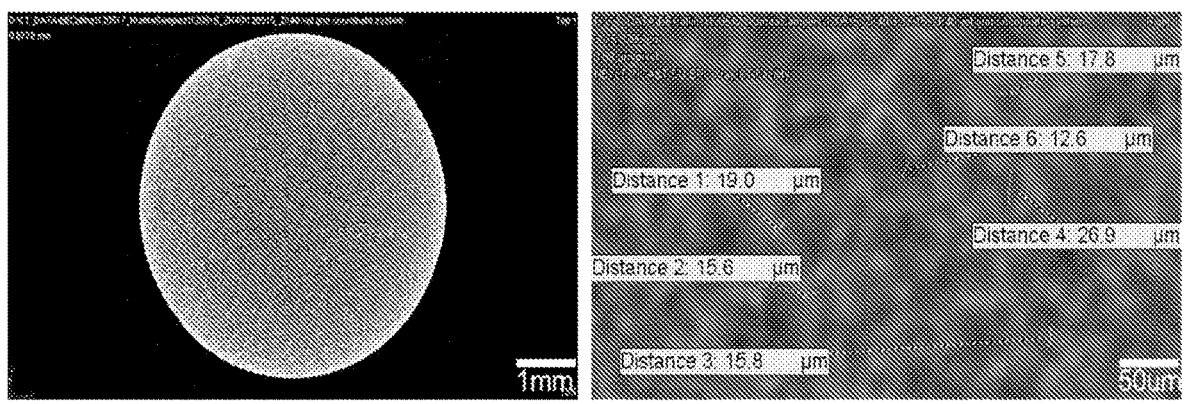
FIGURE 1.4

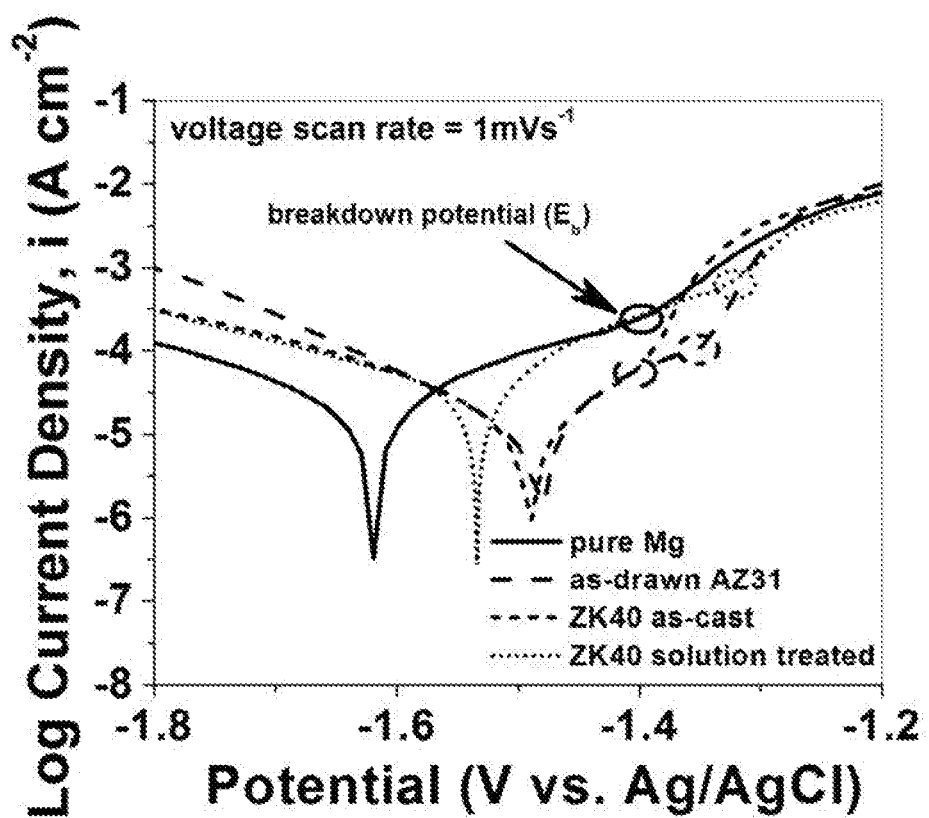
FIGURE 1.5

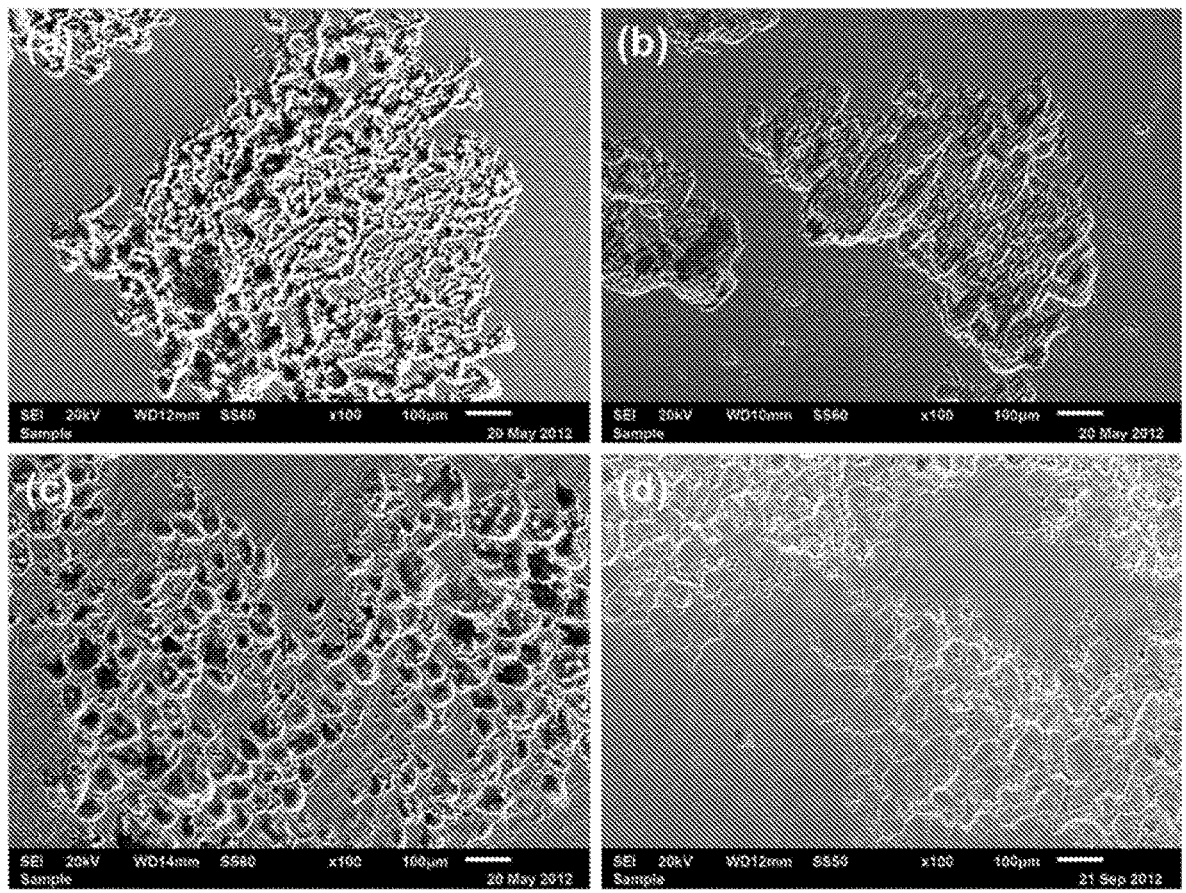
FIGURE 1.6
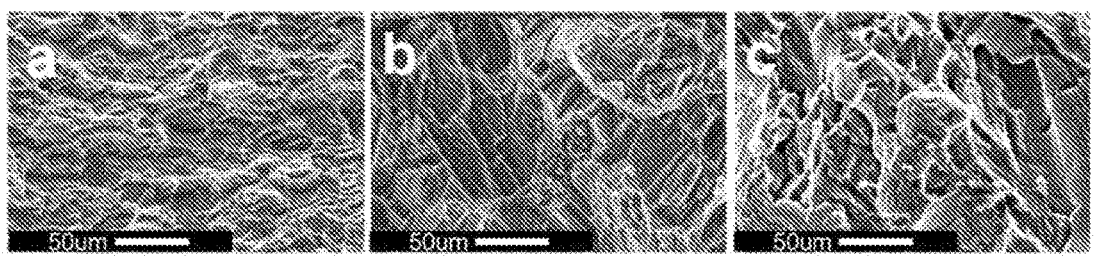
FIGURE 2.1

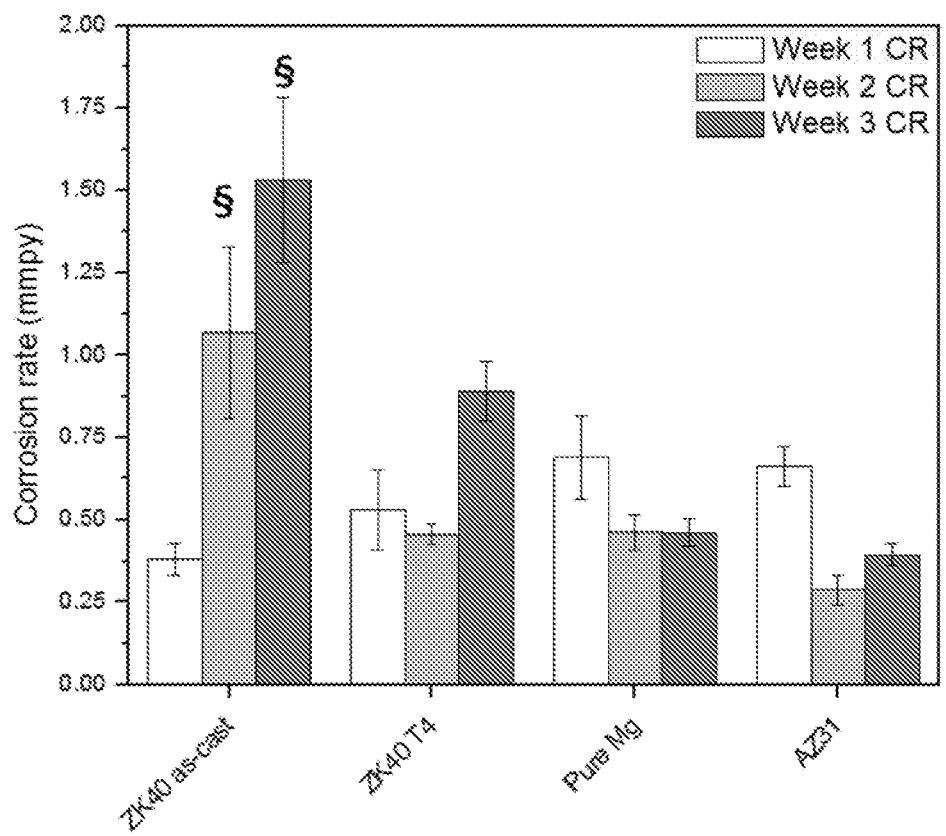
FIGURE 2.2

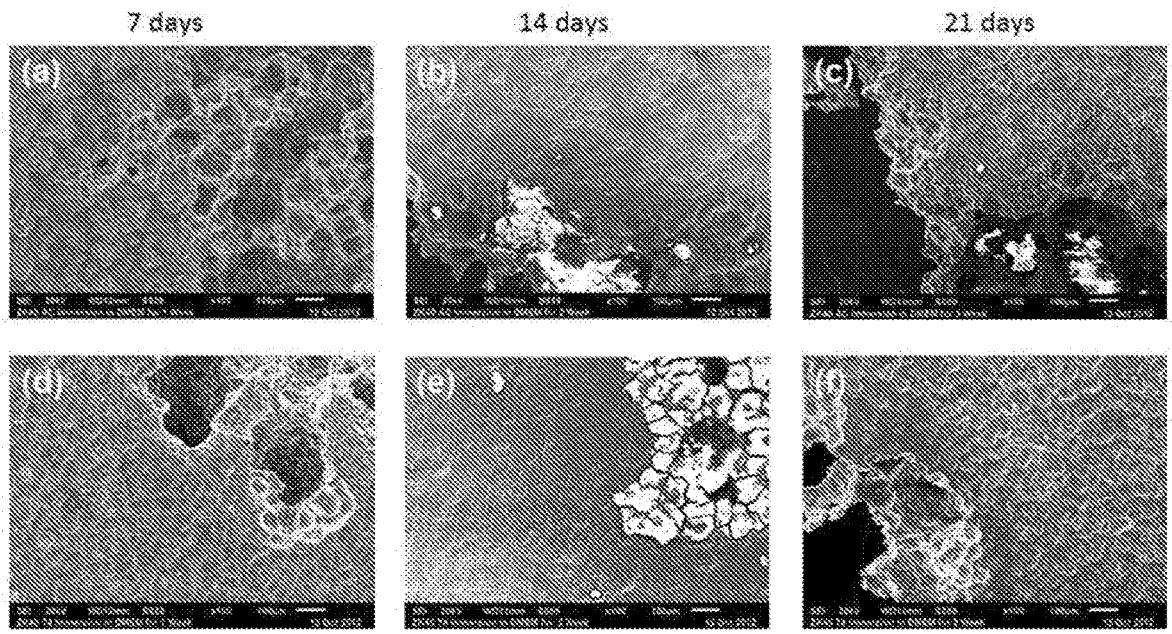
FIGURE 2.3
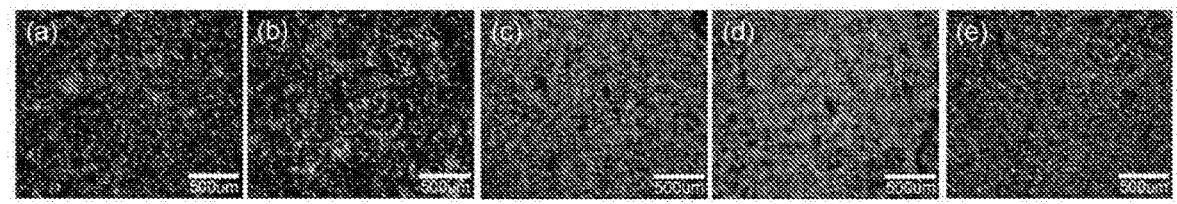
FIGURE 2.4
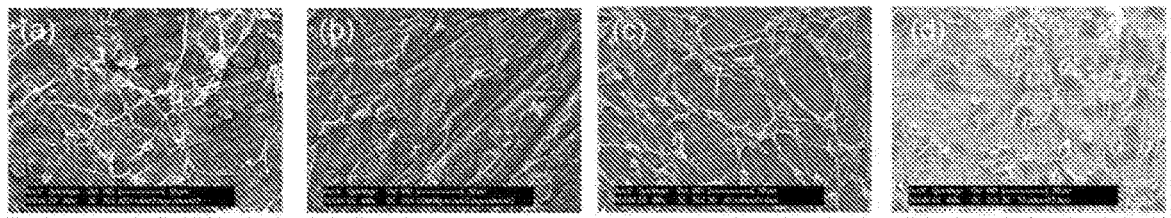
FIGURE 2.5

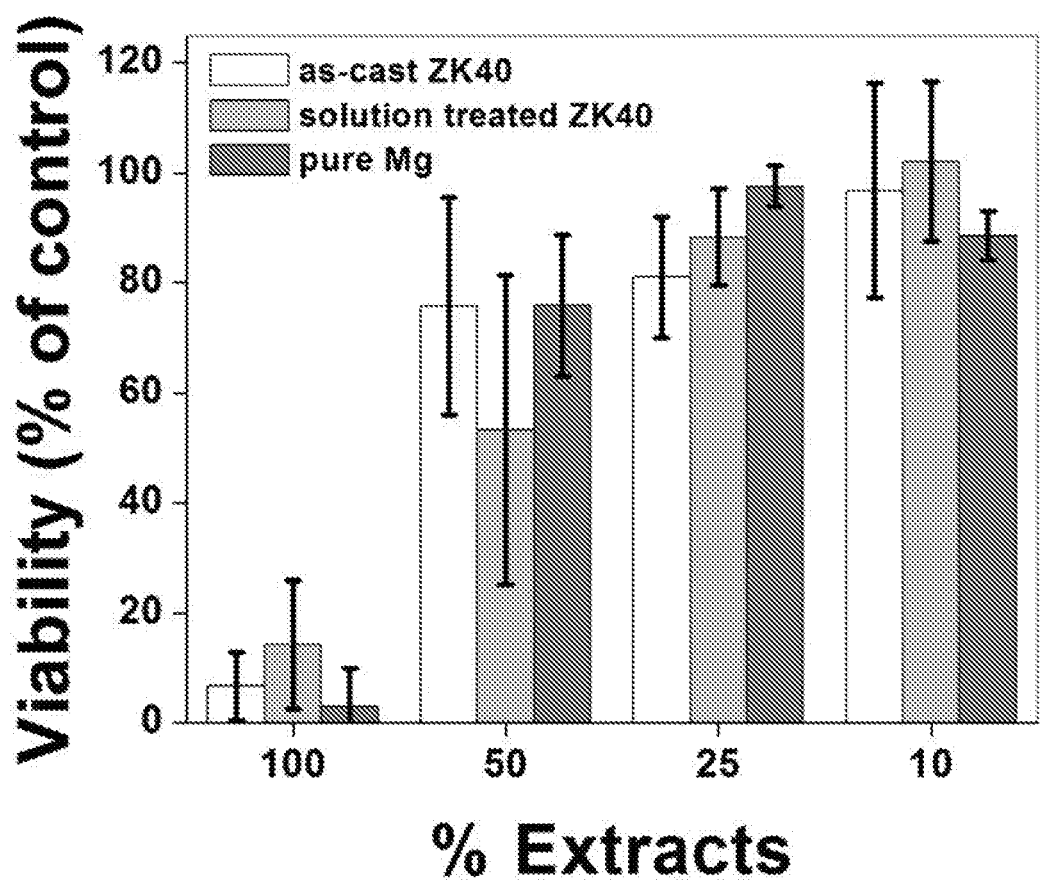
FIGURE 2.6

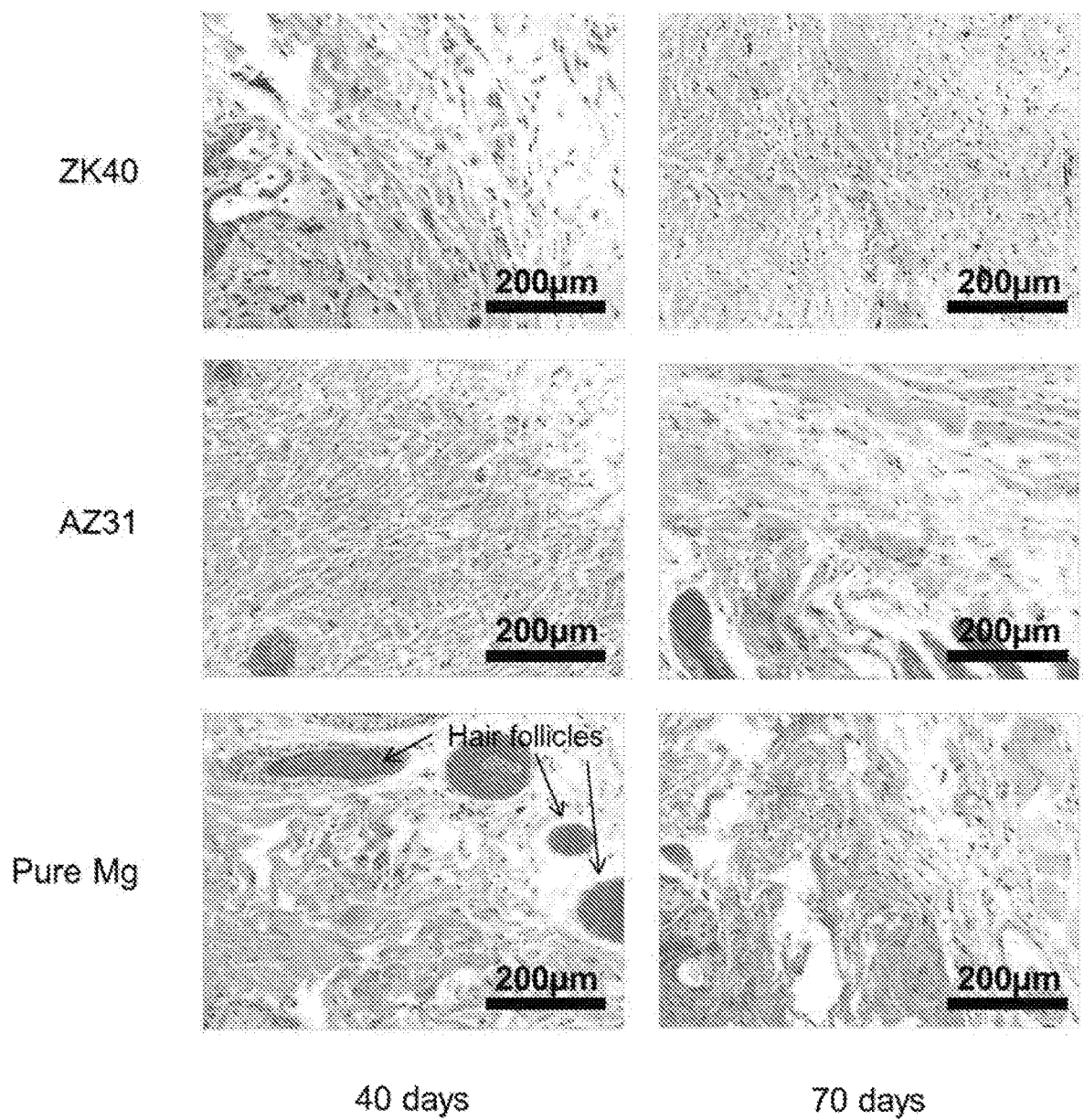
FIGURE 2.7

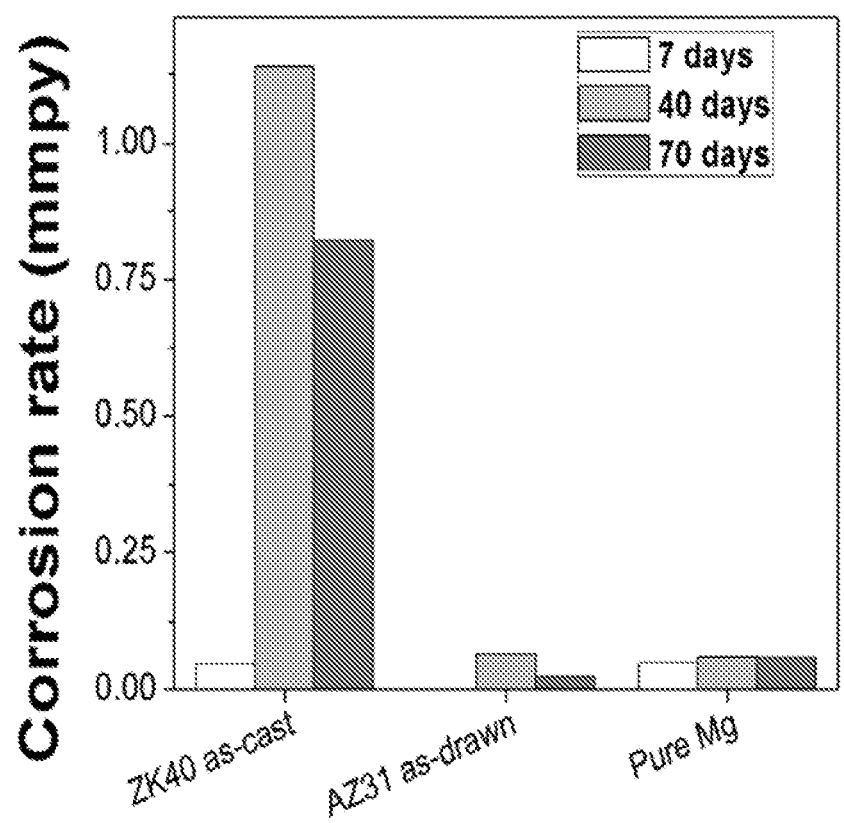
FIGURE 2.8

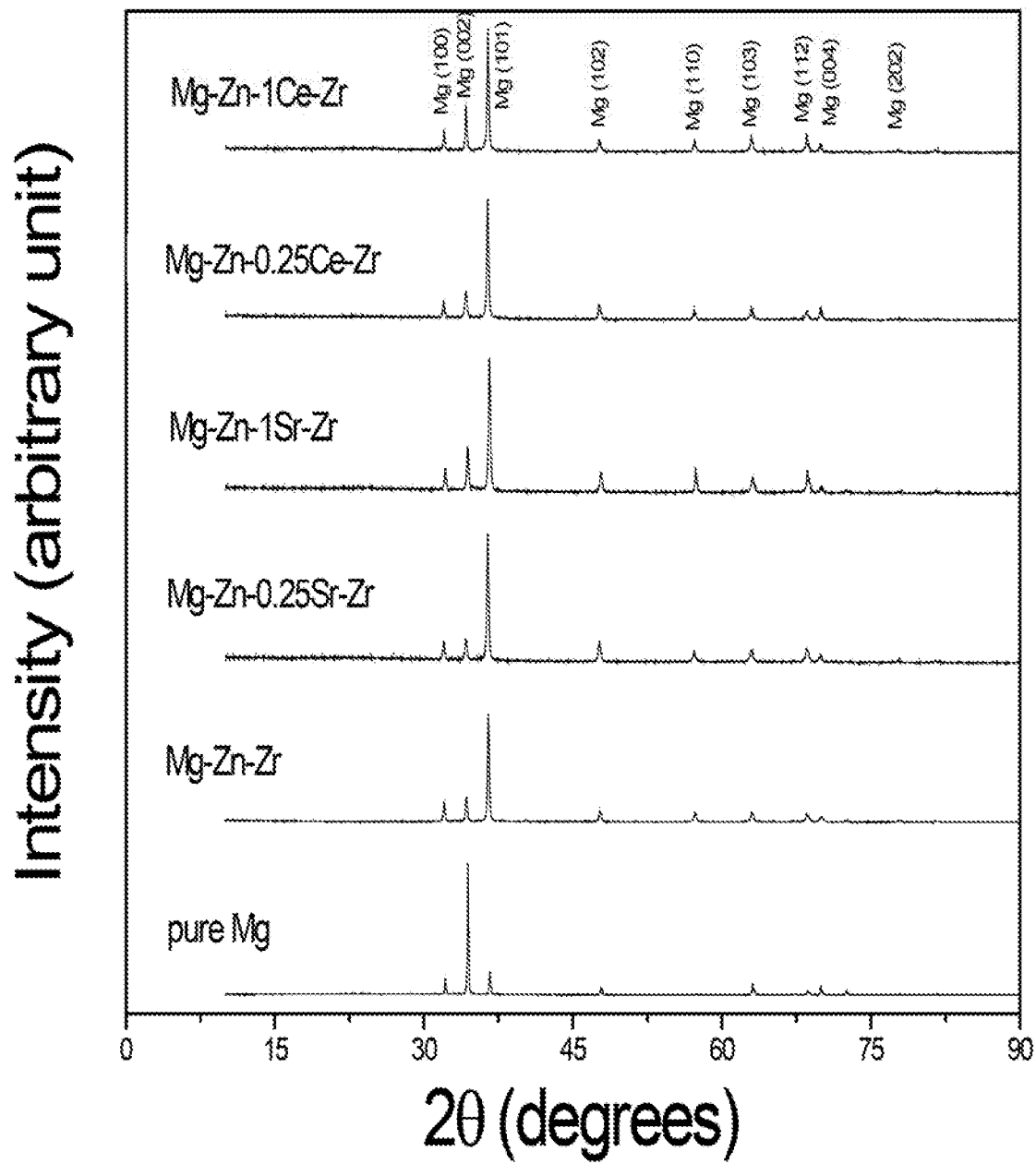
FIGURE 3.1

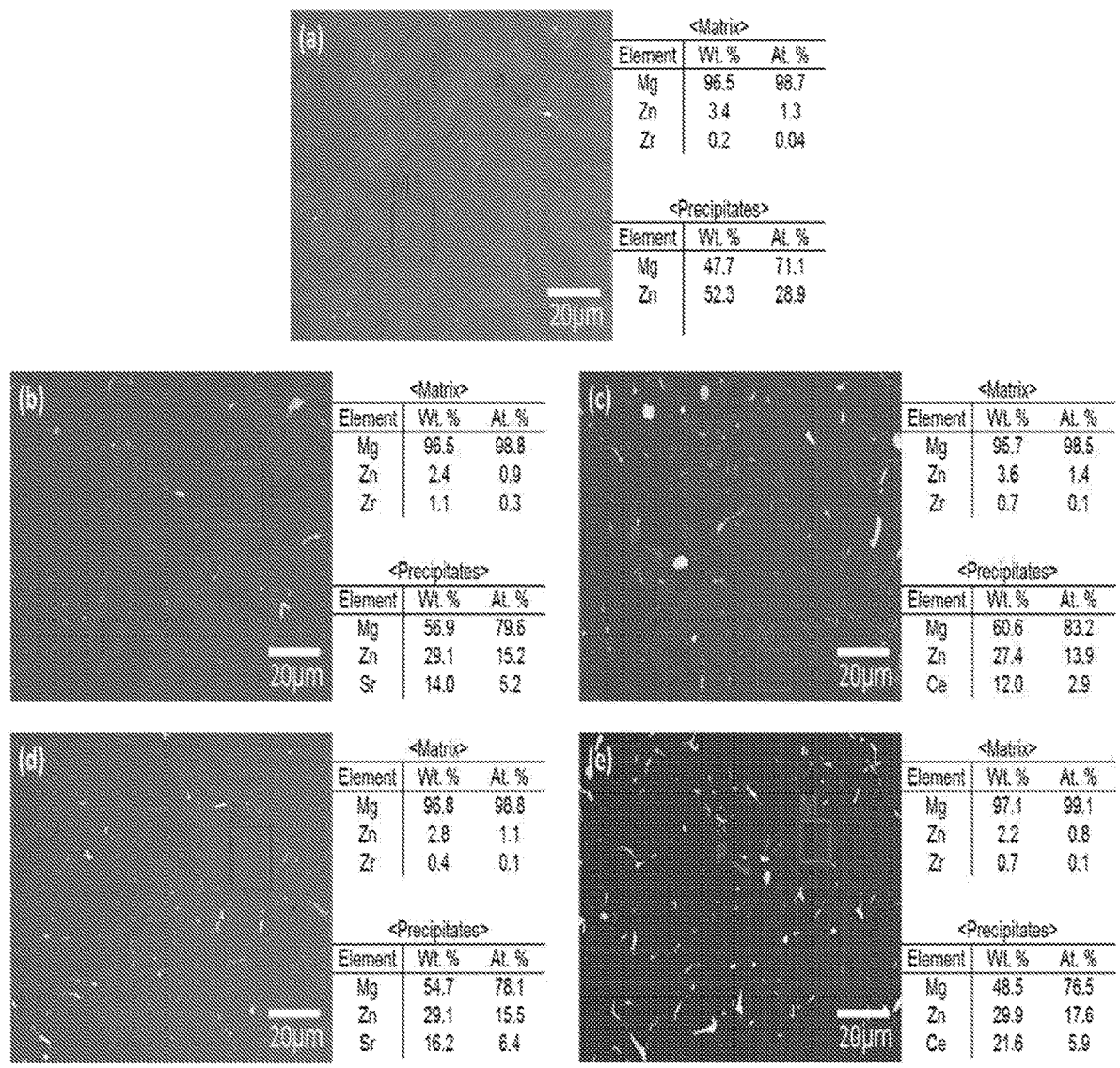
FIGURE 3.2

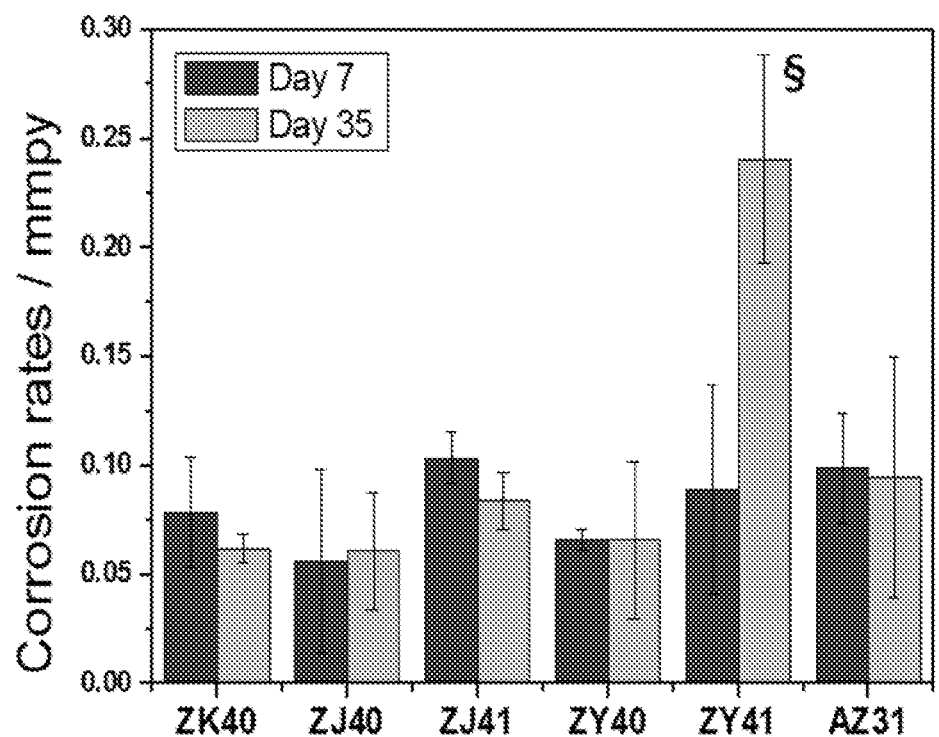
FIGURE 3.3

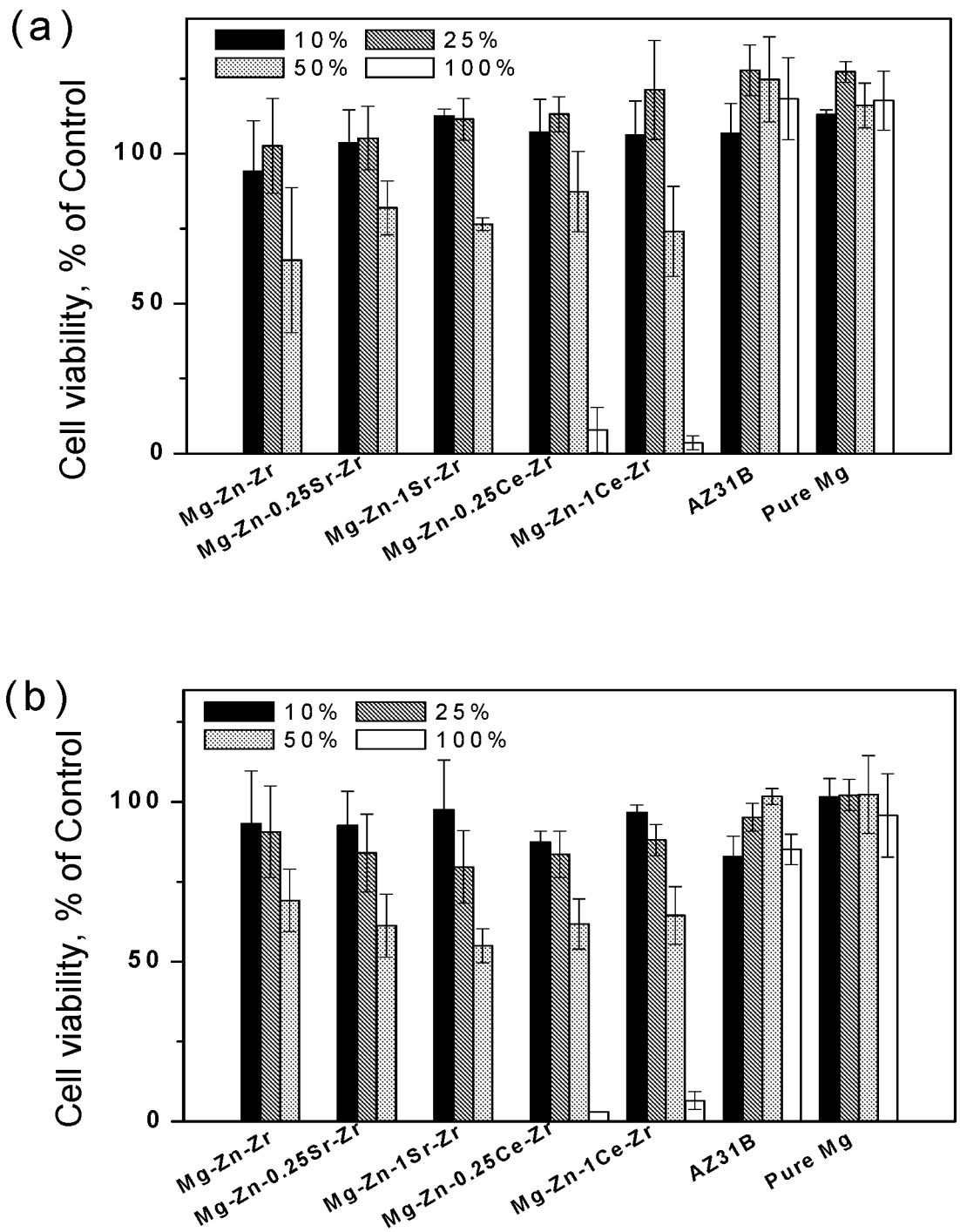
FIGURE 3.4

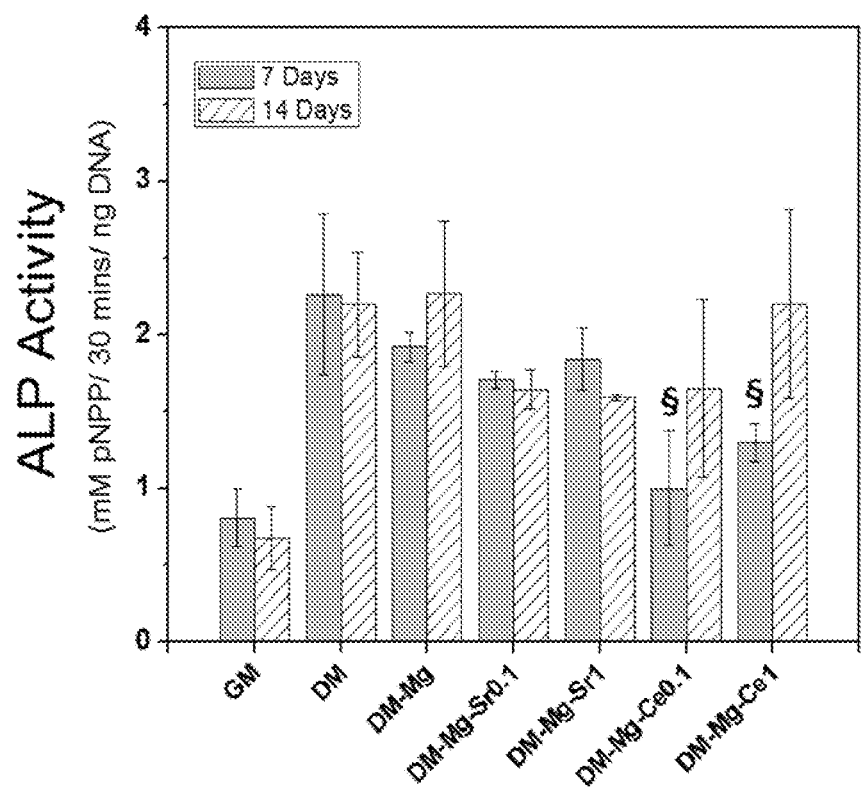
FIGURE 3.5

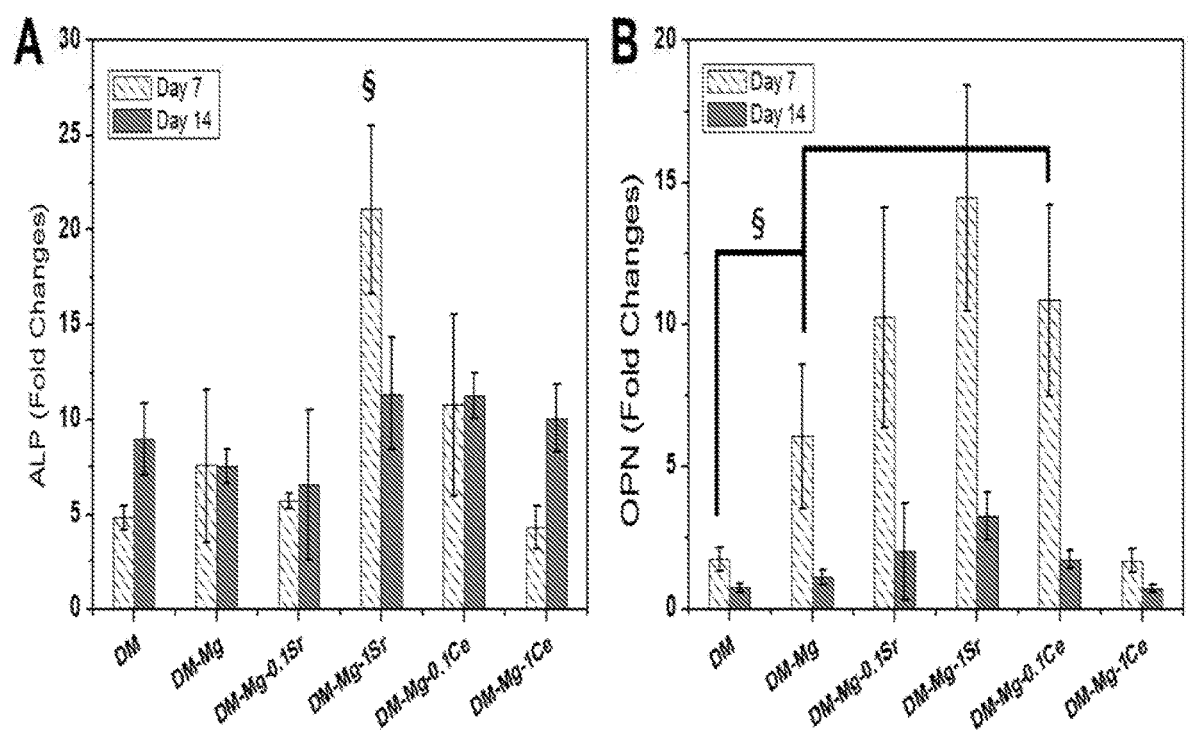
FIGURE 3.6

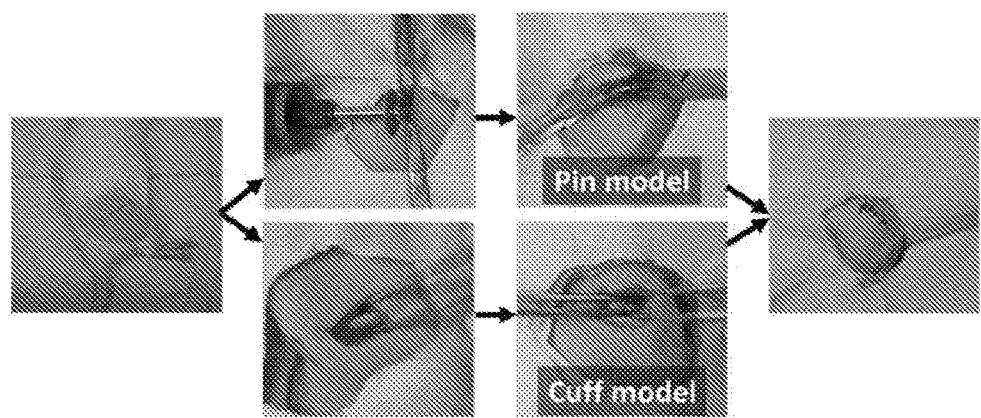
FIGURE 4.1
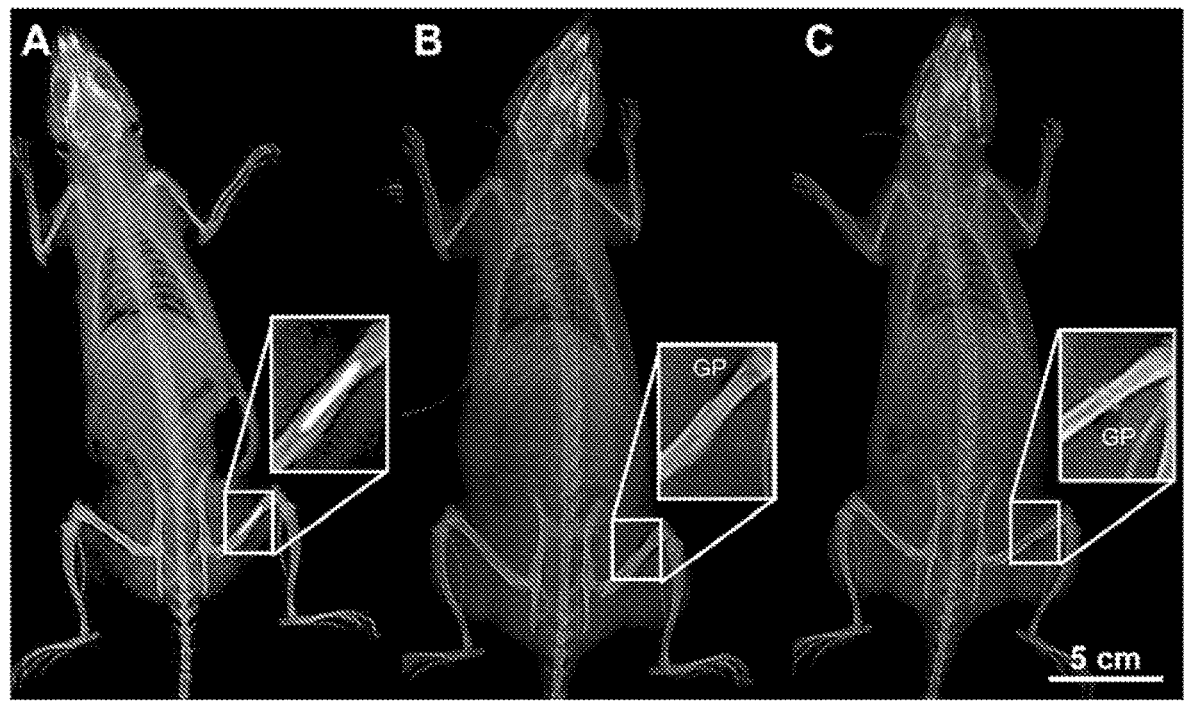
FIGURE 4.2

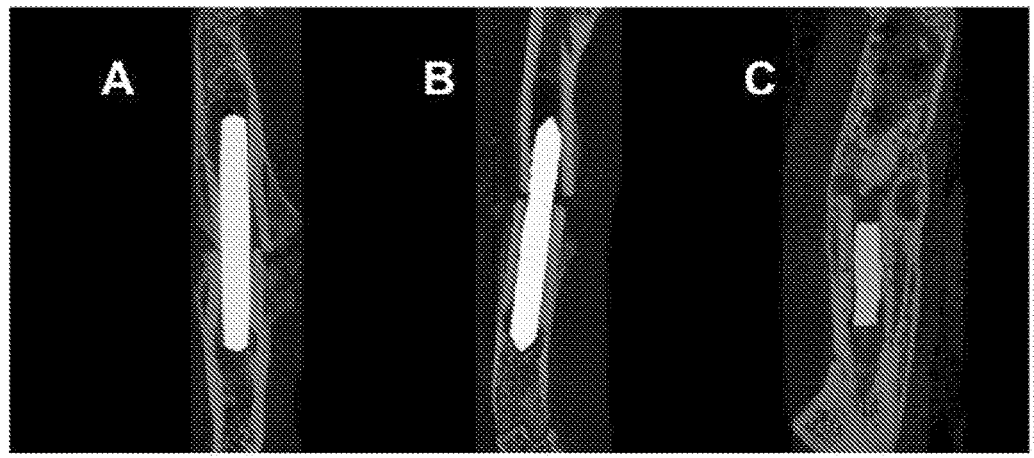
FIGURE 4.3
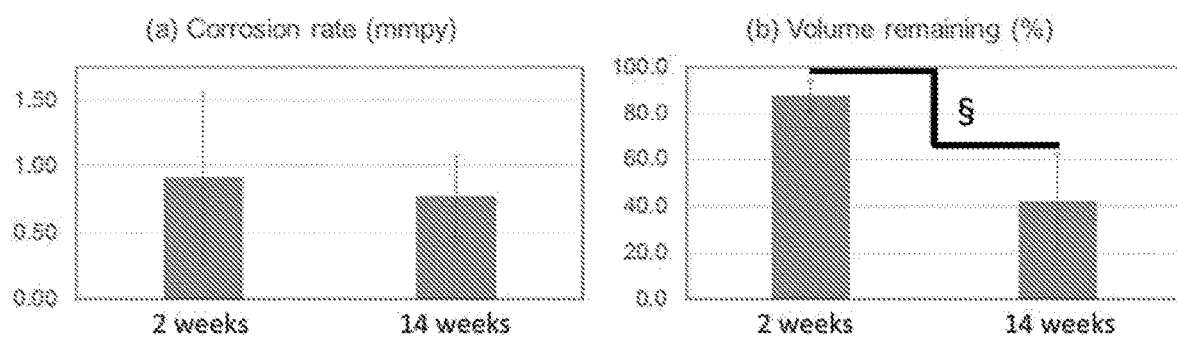
FIGURE 4.4

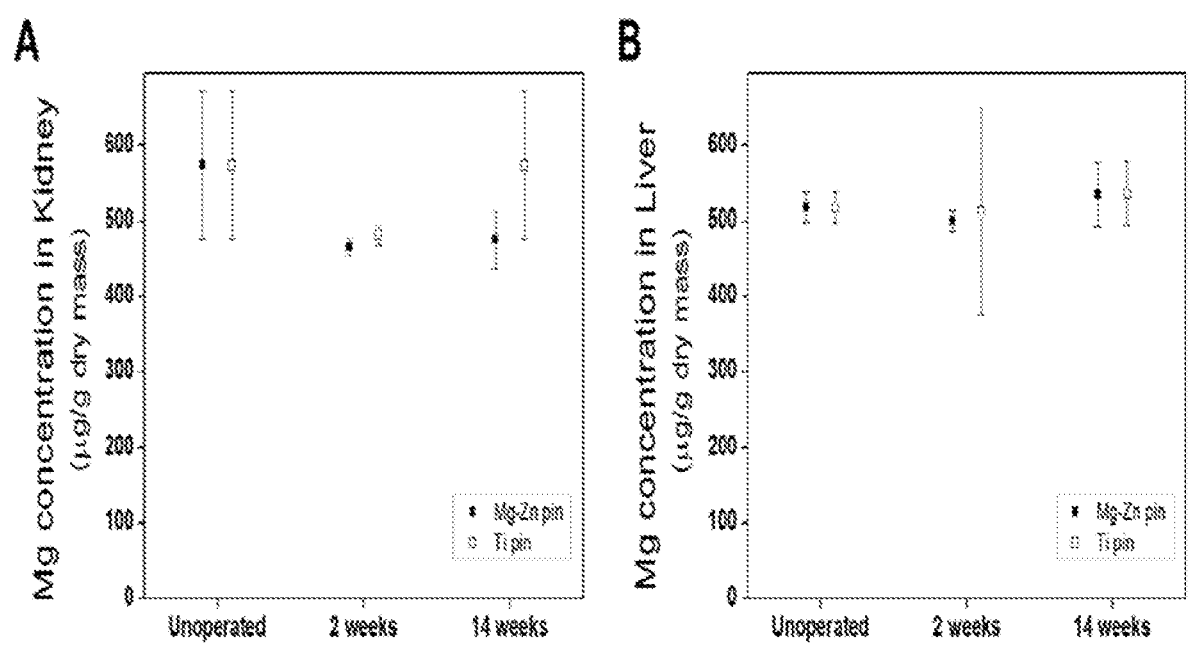
FIGURE 4.5

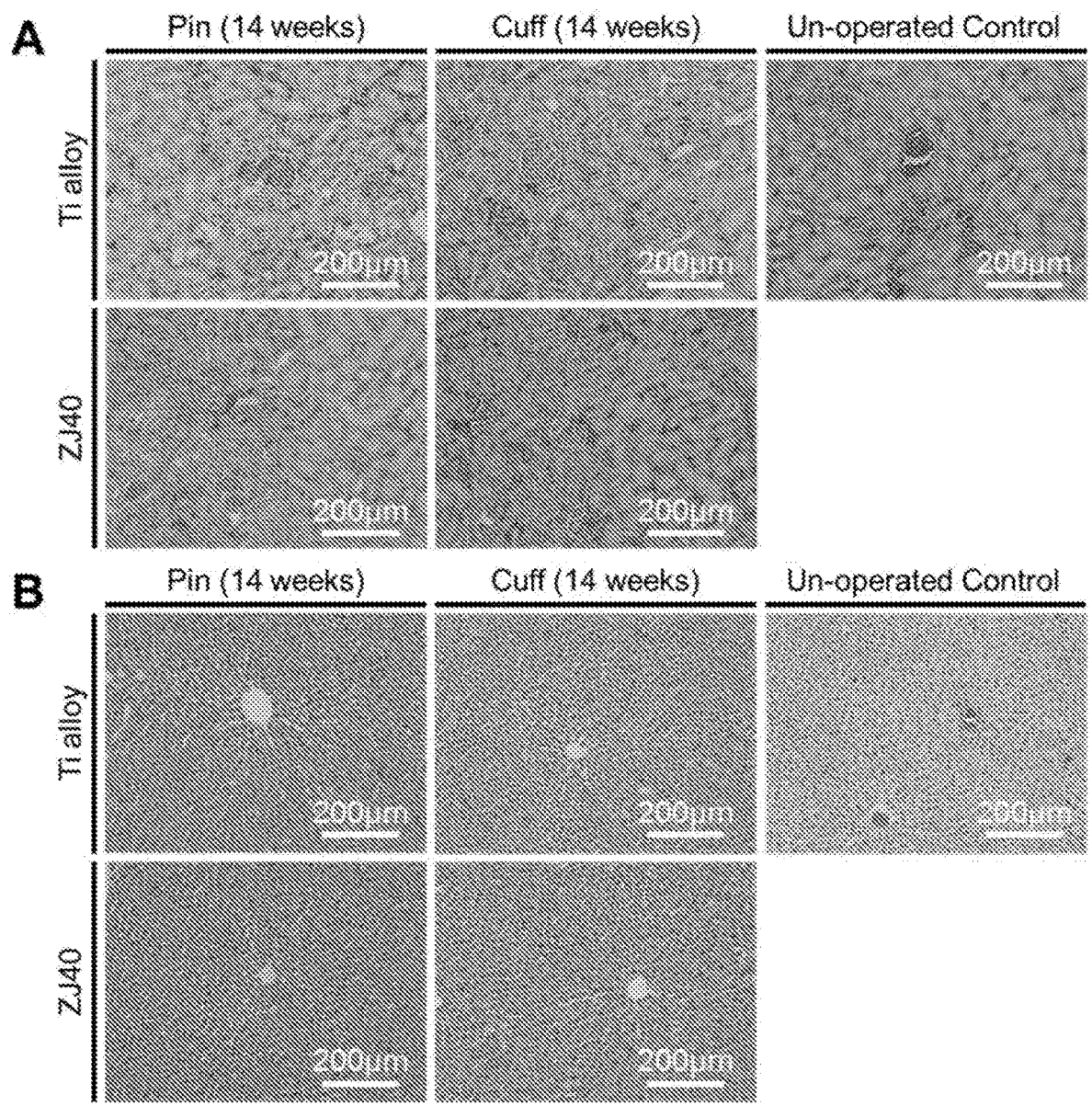
FIGURE 4.6

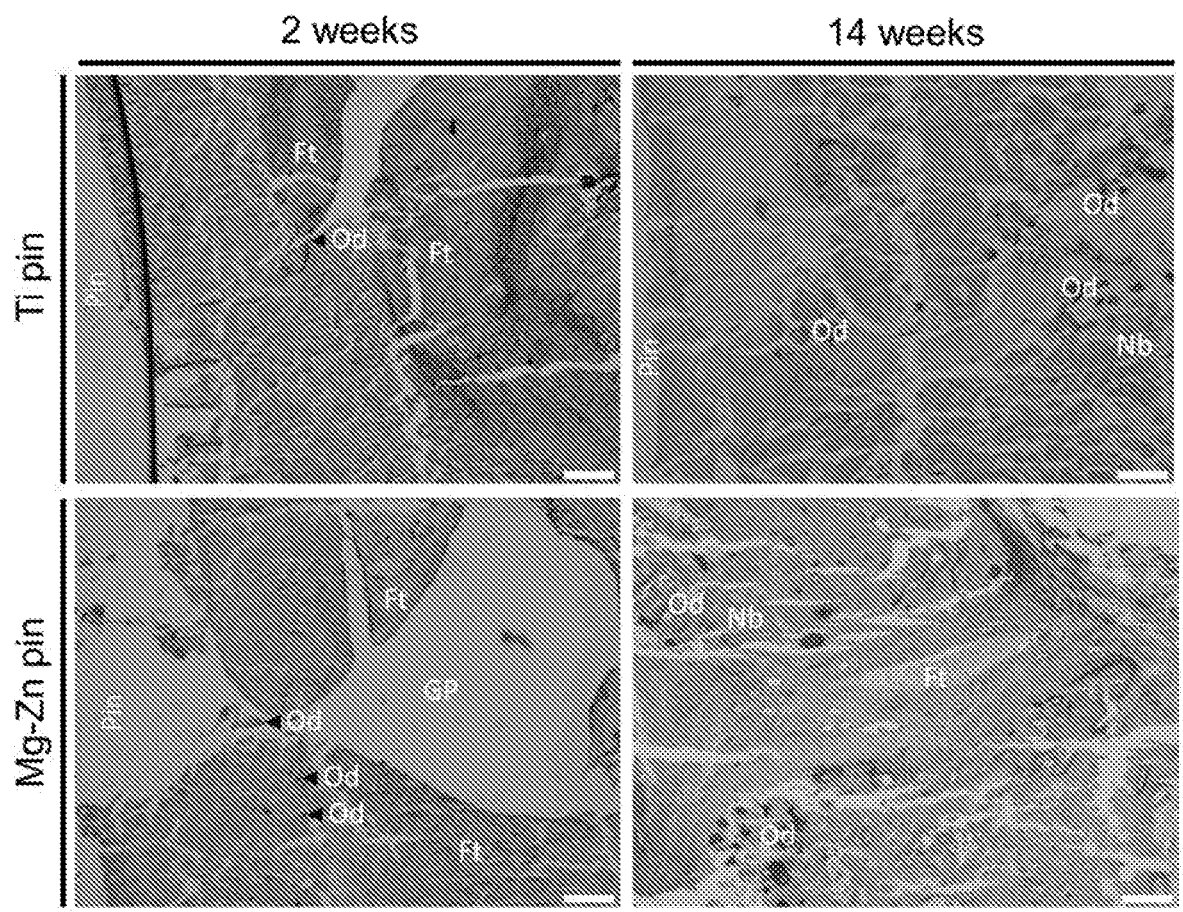
FIGURE 4.7

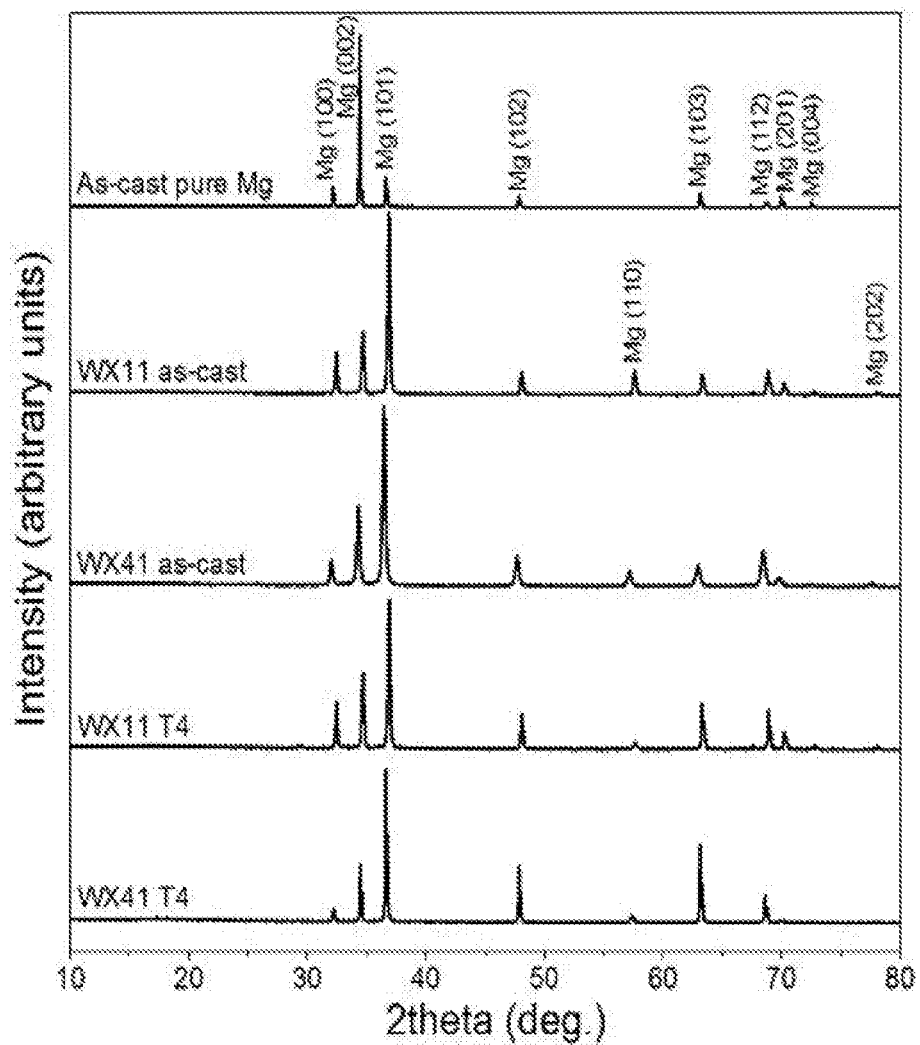
FIGURE 5.1

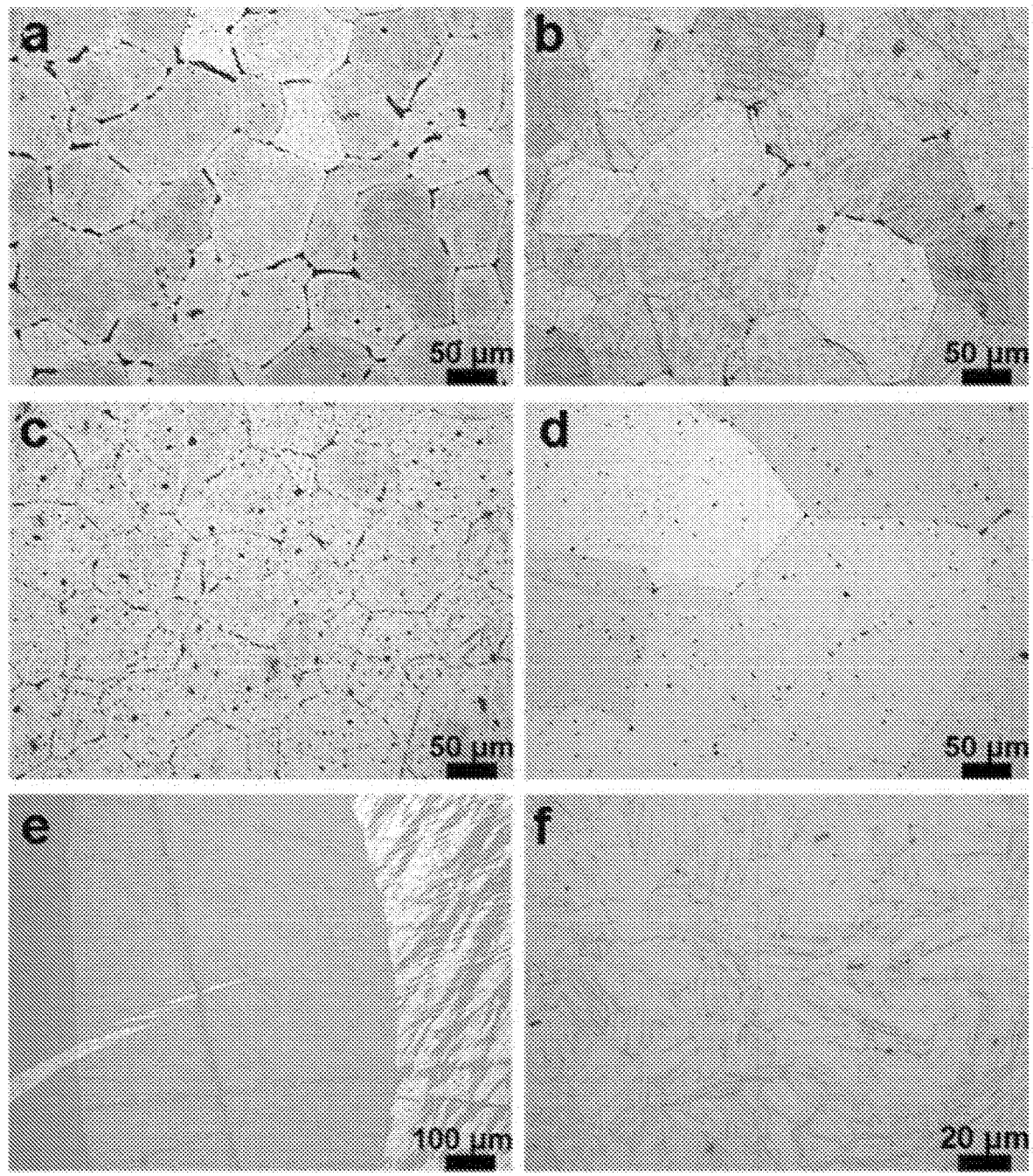
FIGURE 5.2

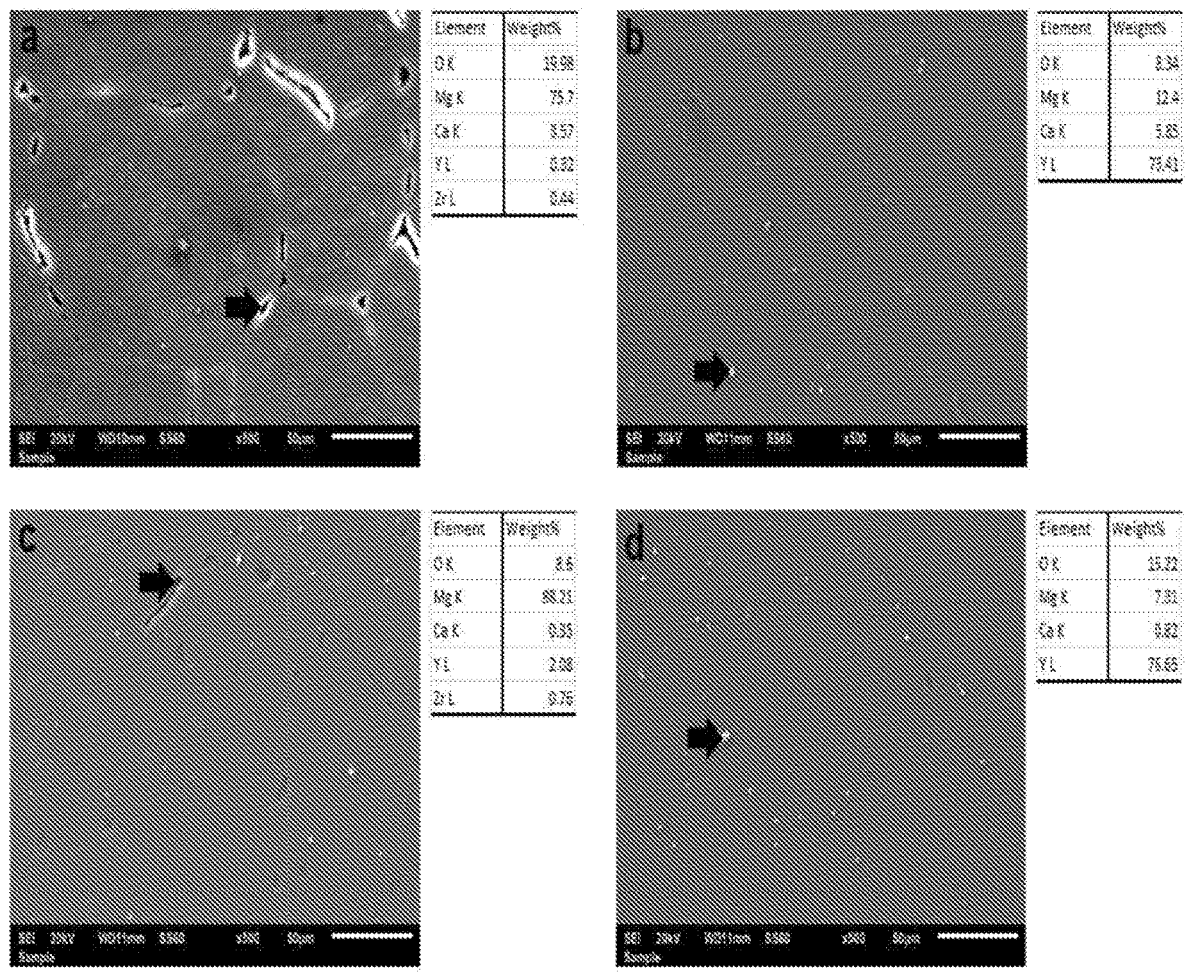
FIGURE 5.3

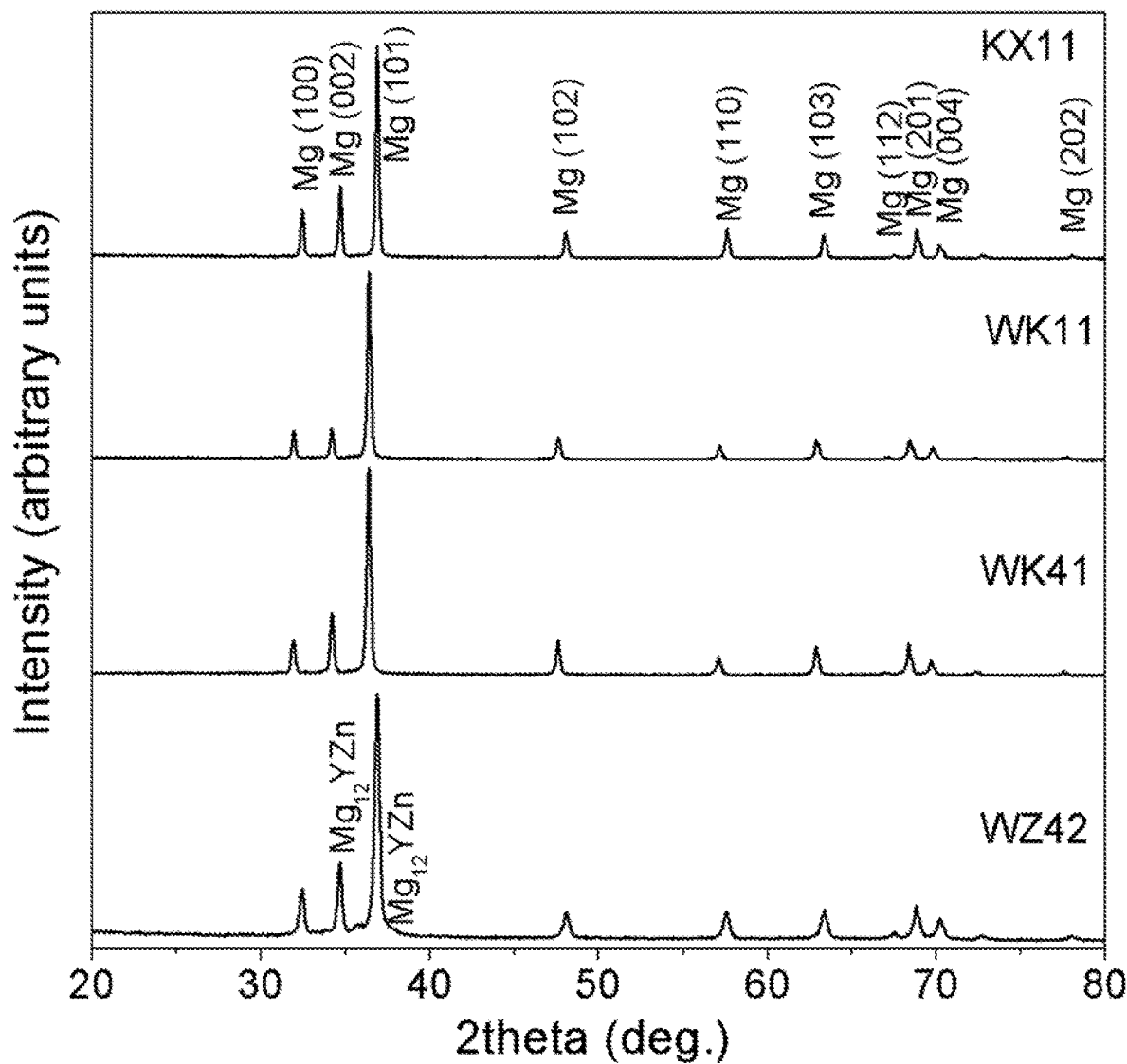
FIGURE 5.4

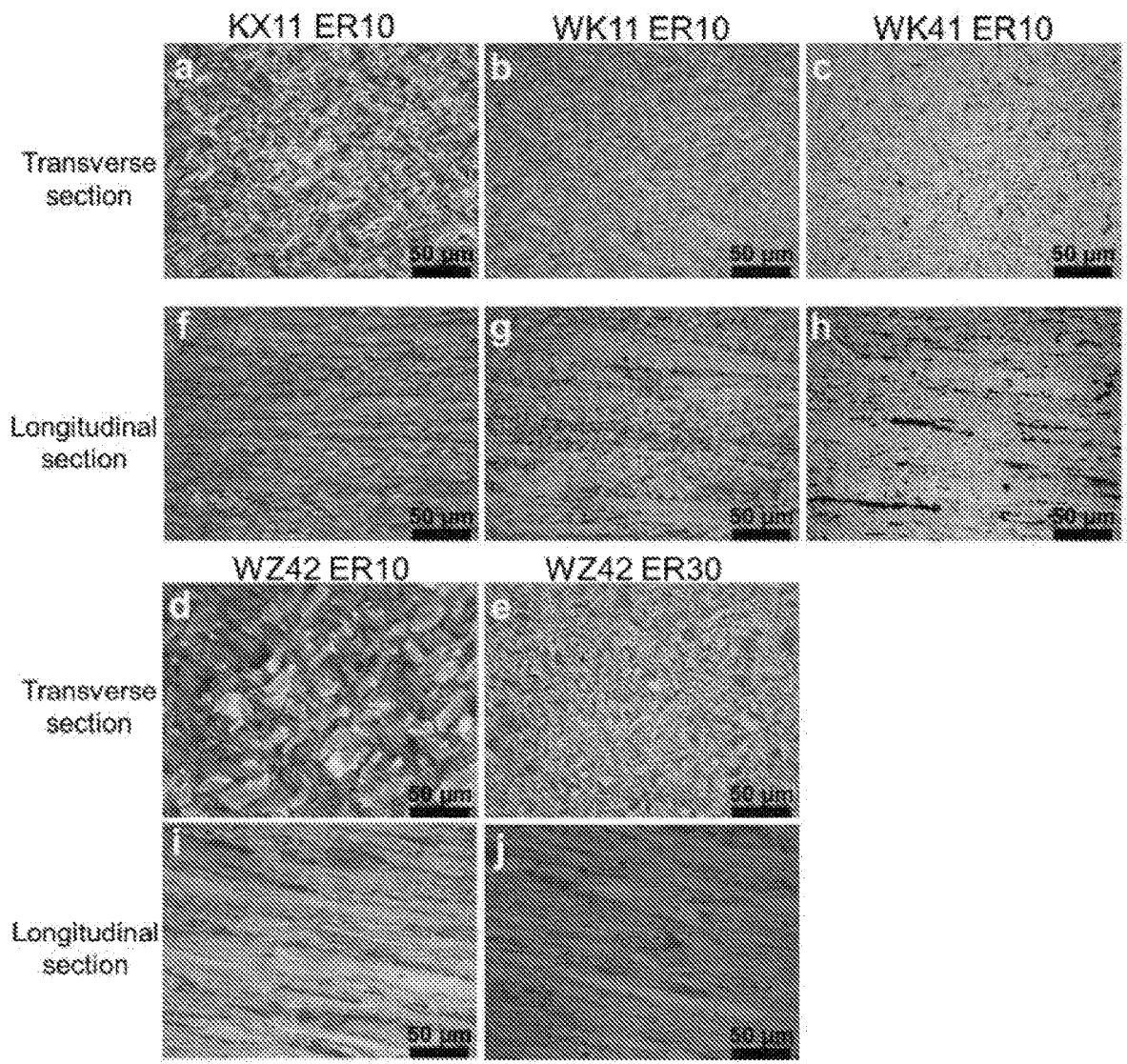
FIGURE 5.5

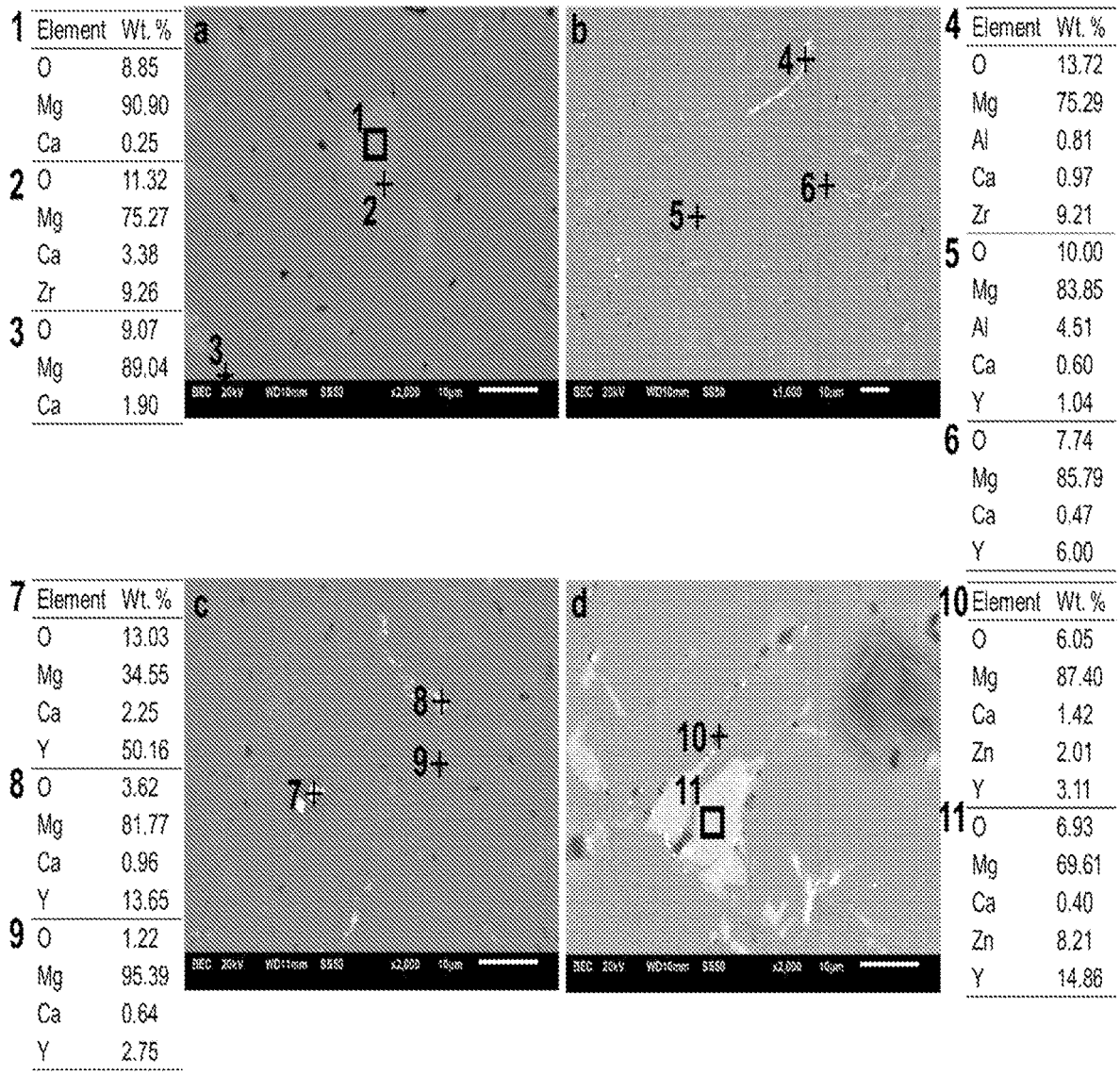
FIGURE 5.6

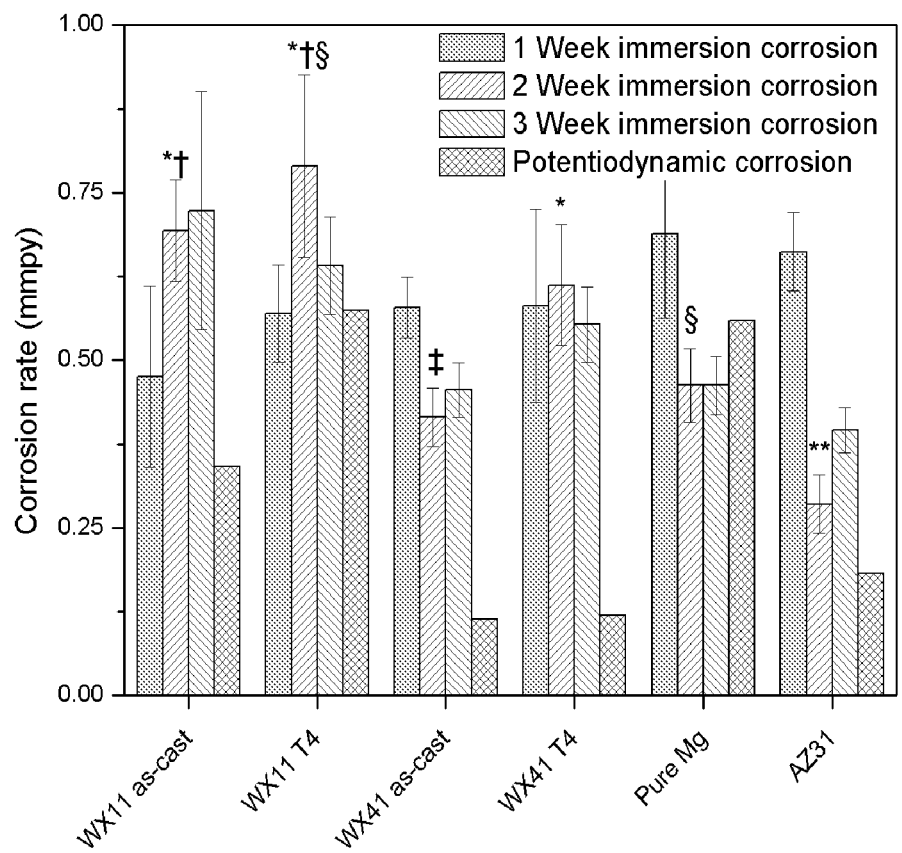
FIGURE 6.1

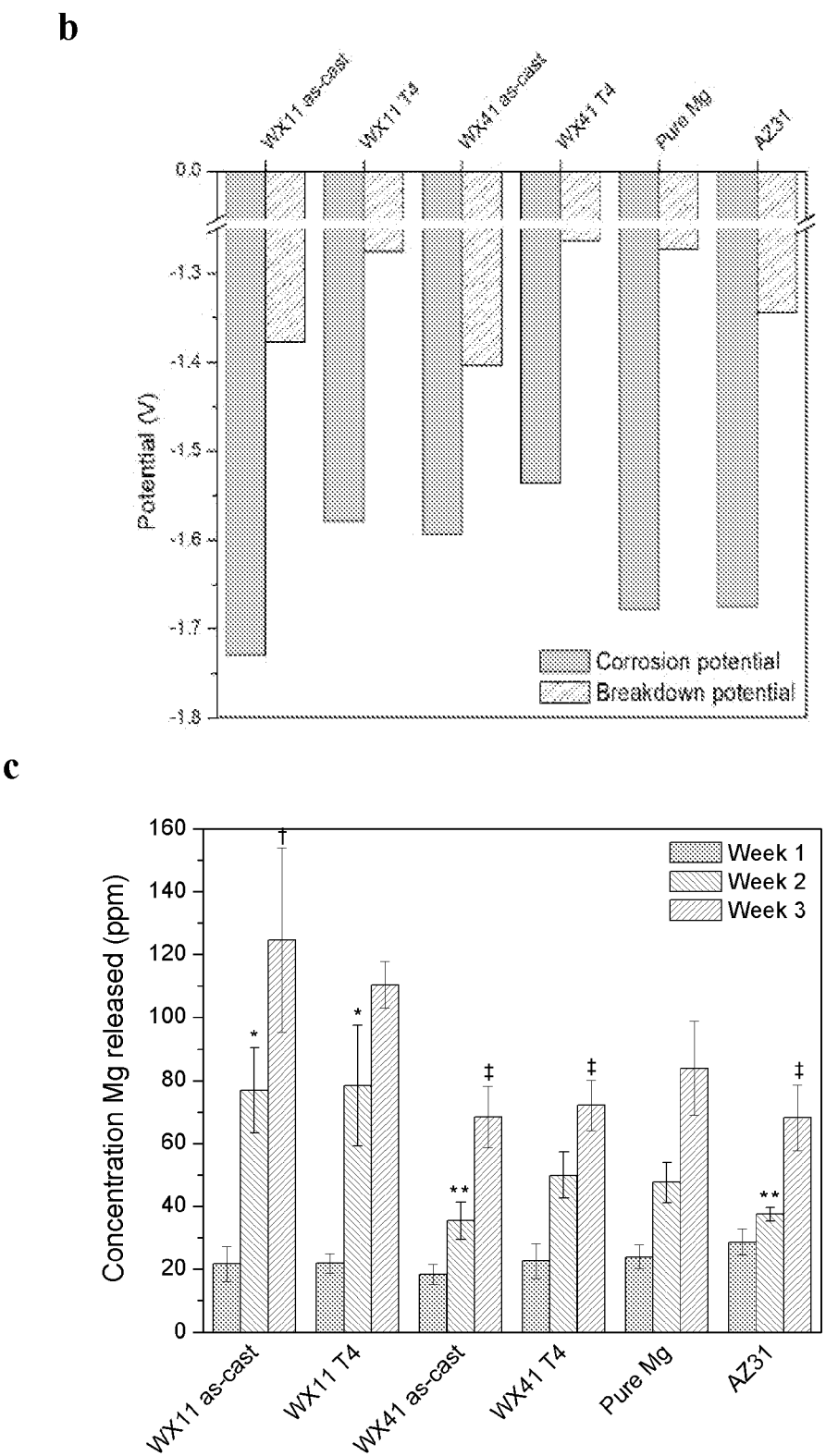
FIGURE 6.1

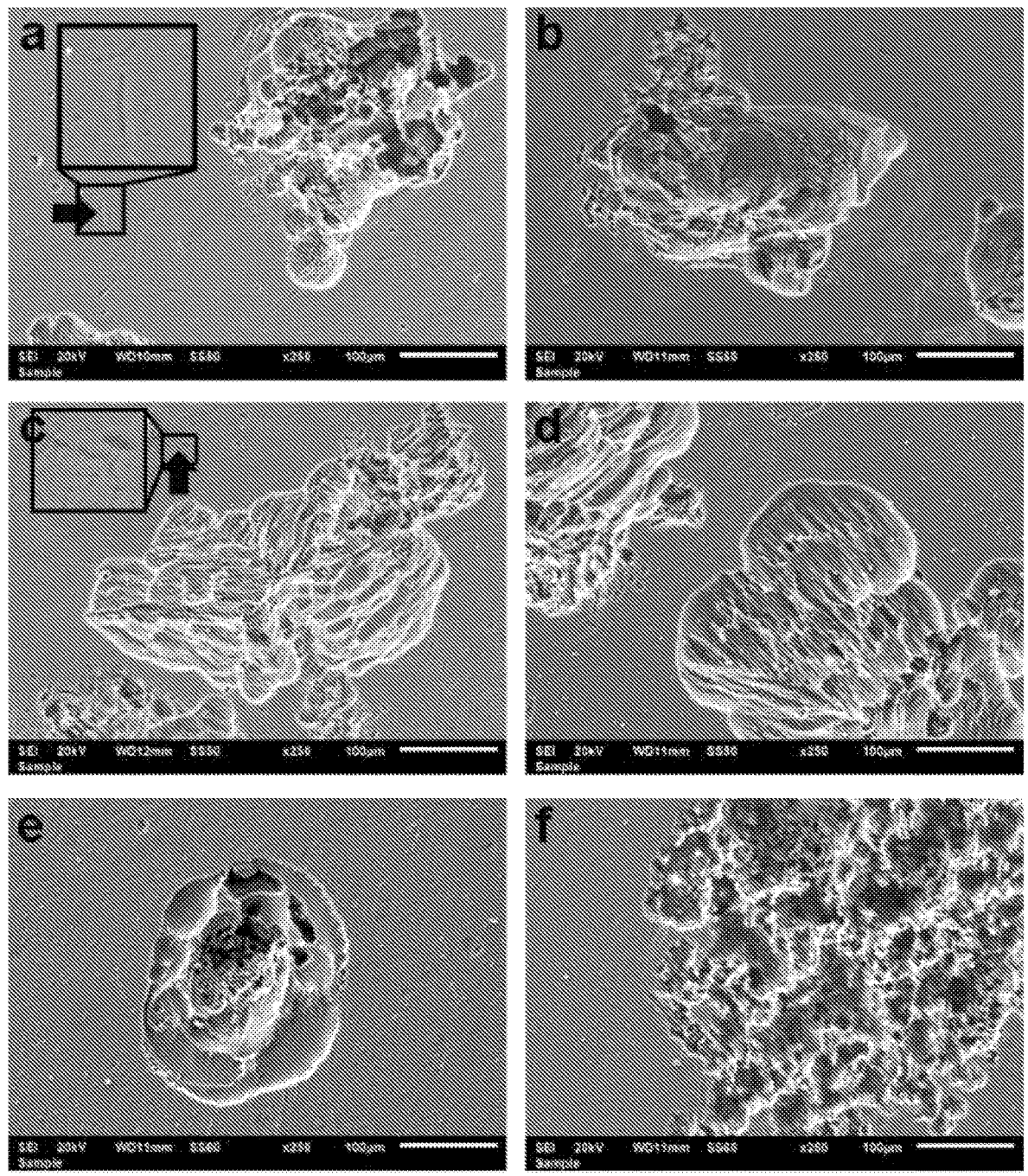
FIGURE 6.2

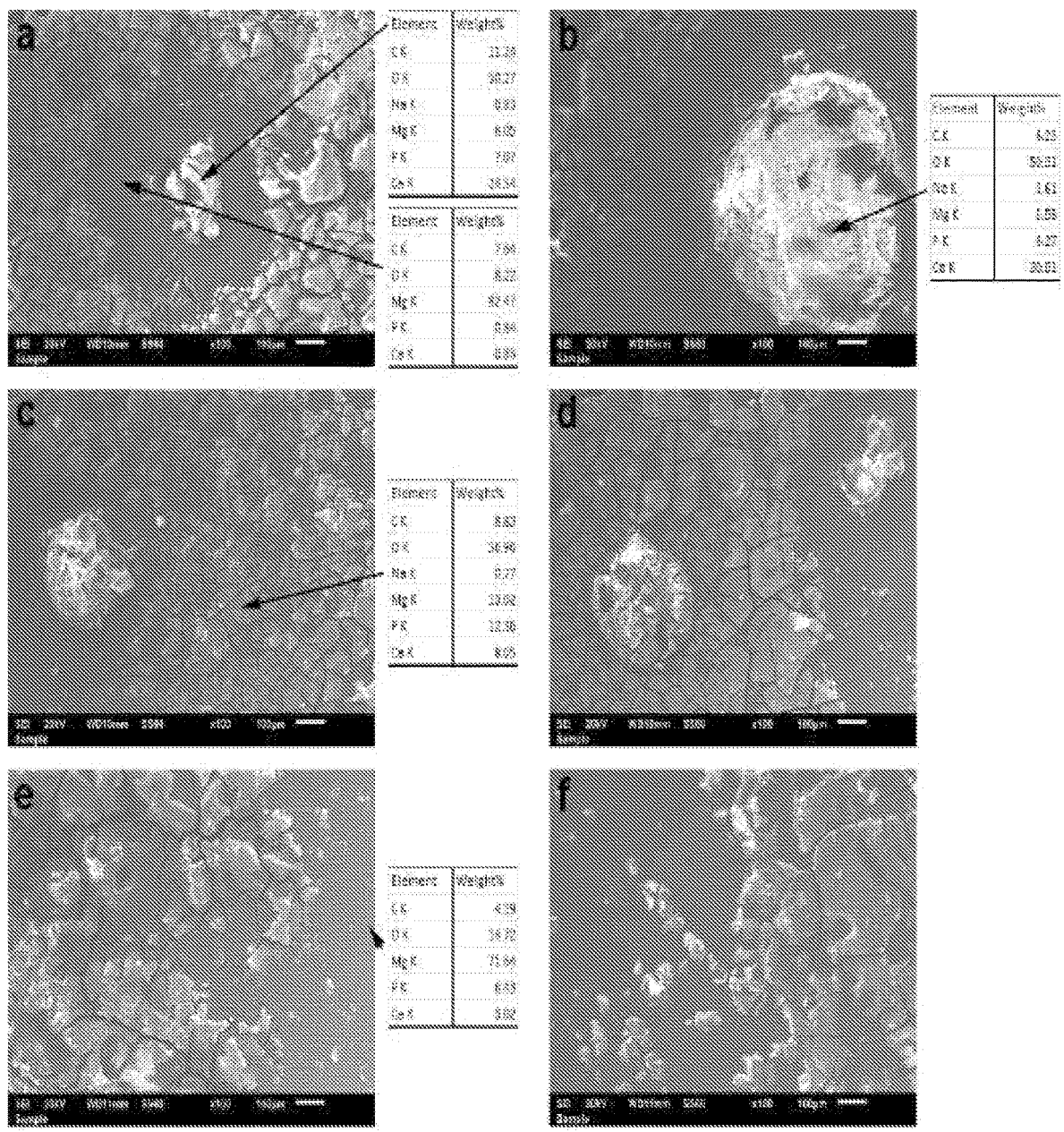
FIGURE 6.3

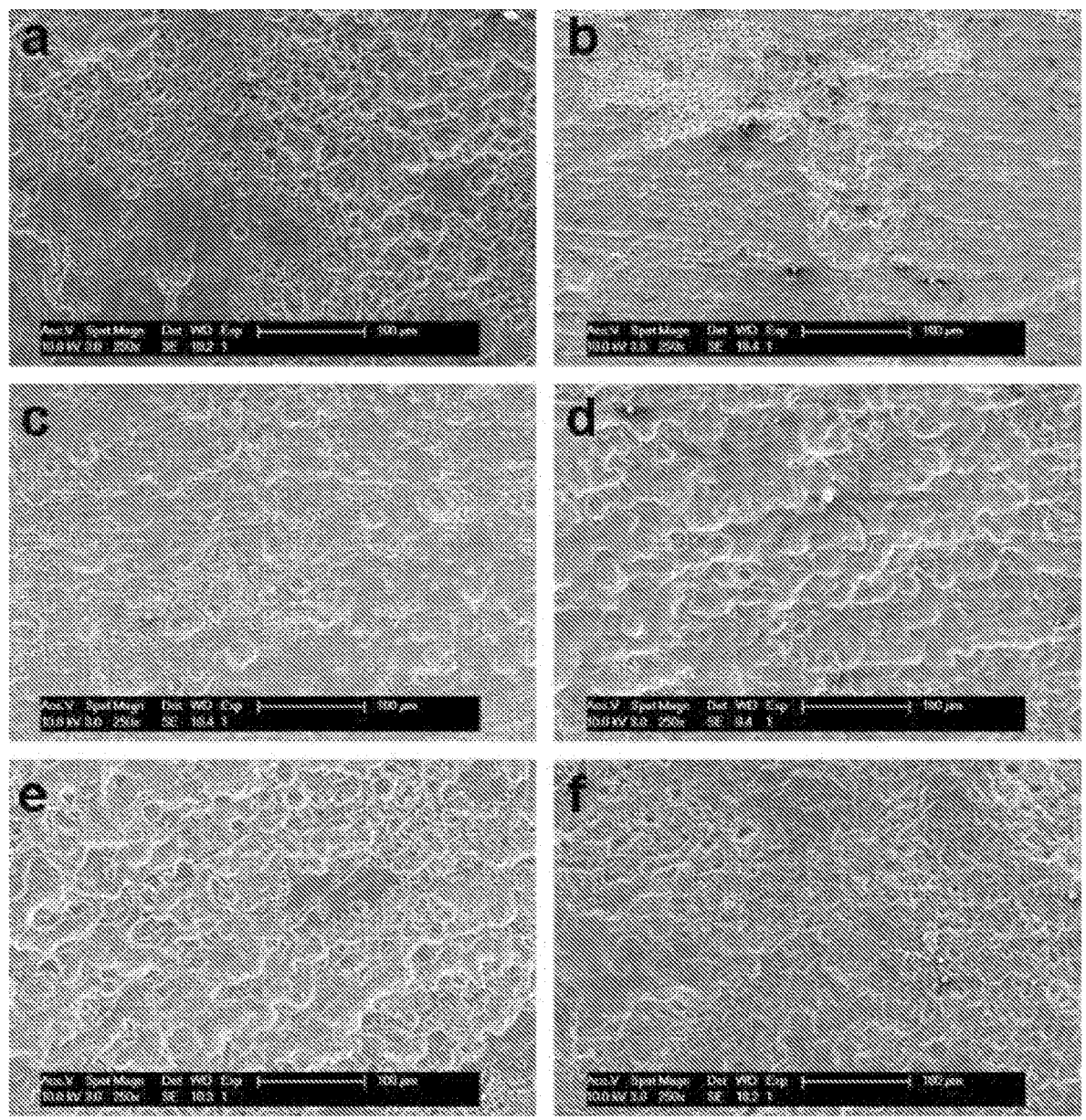
FIGURE 6.4

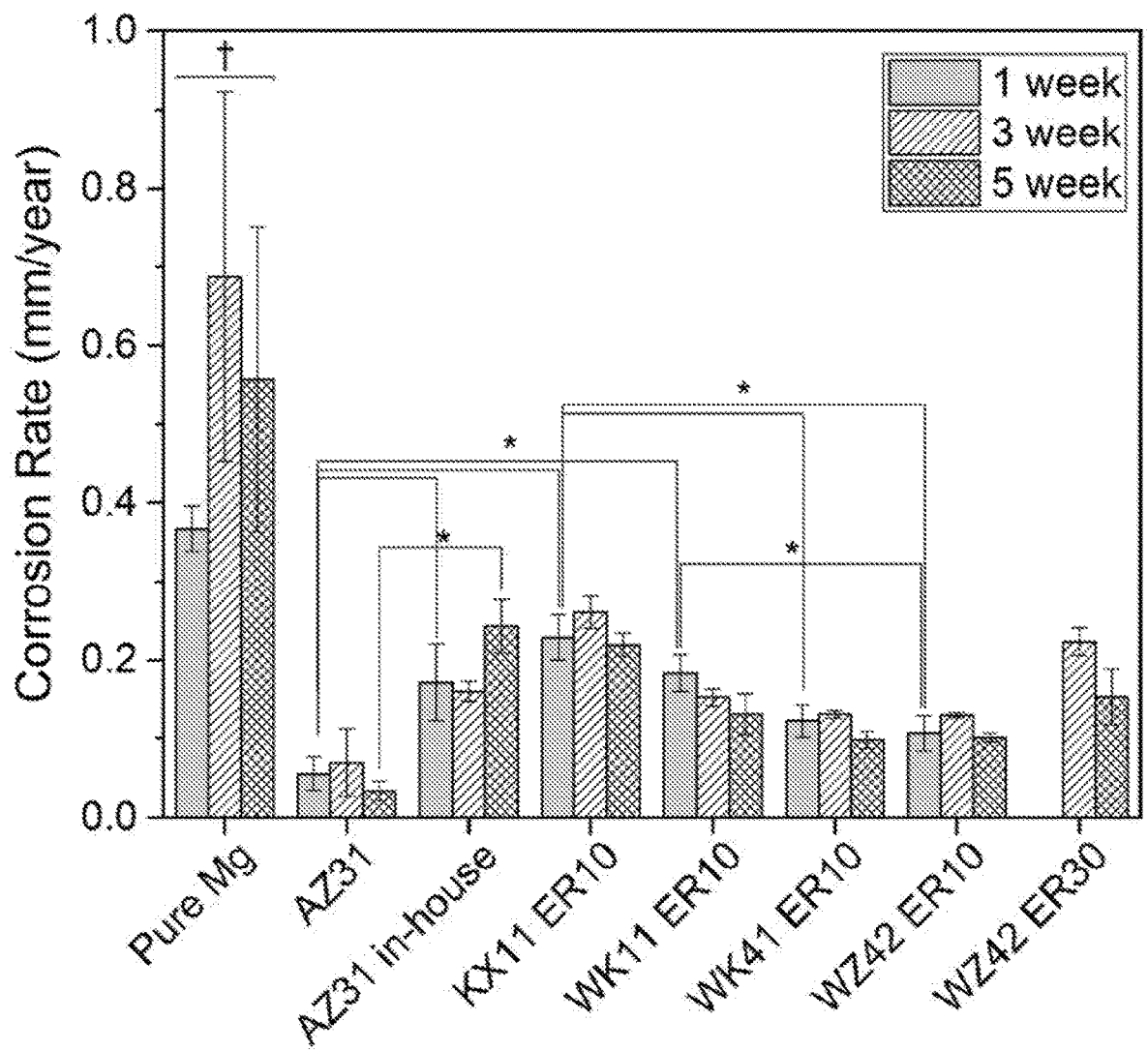
FIGURE 6.5

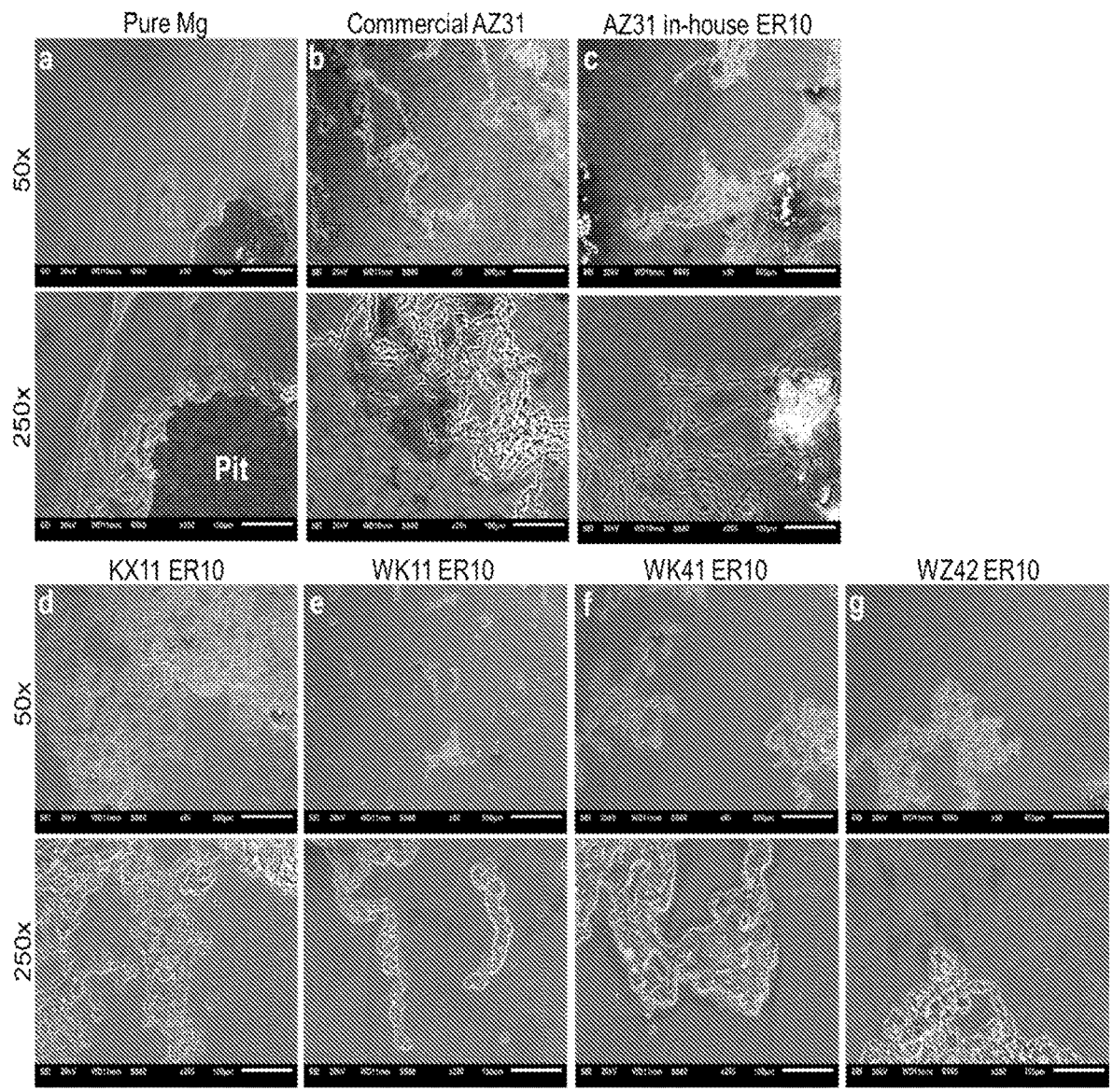
FIGURE 6.6

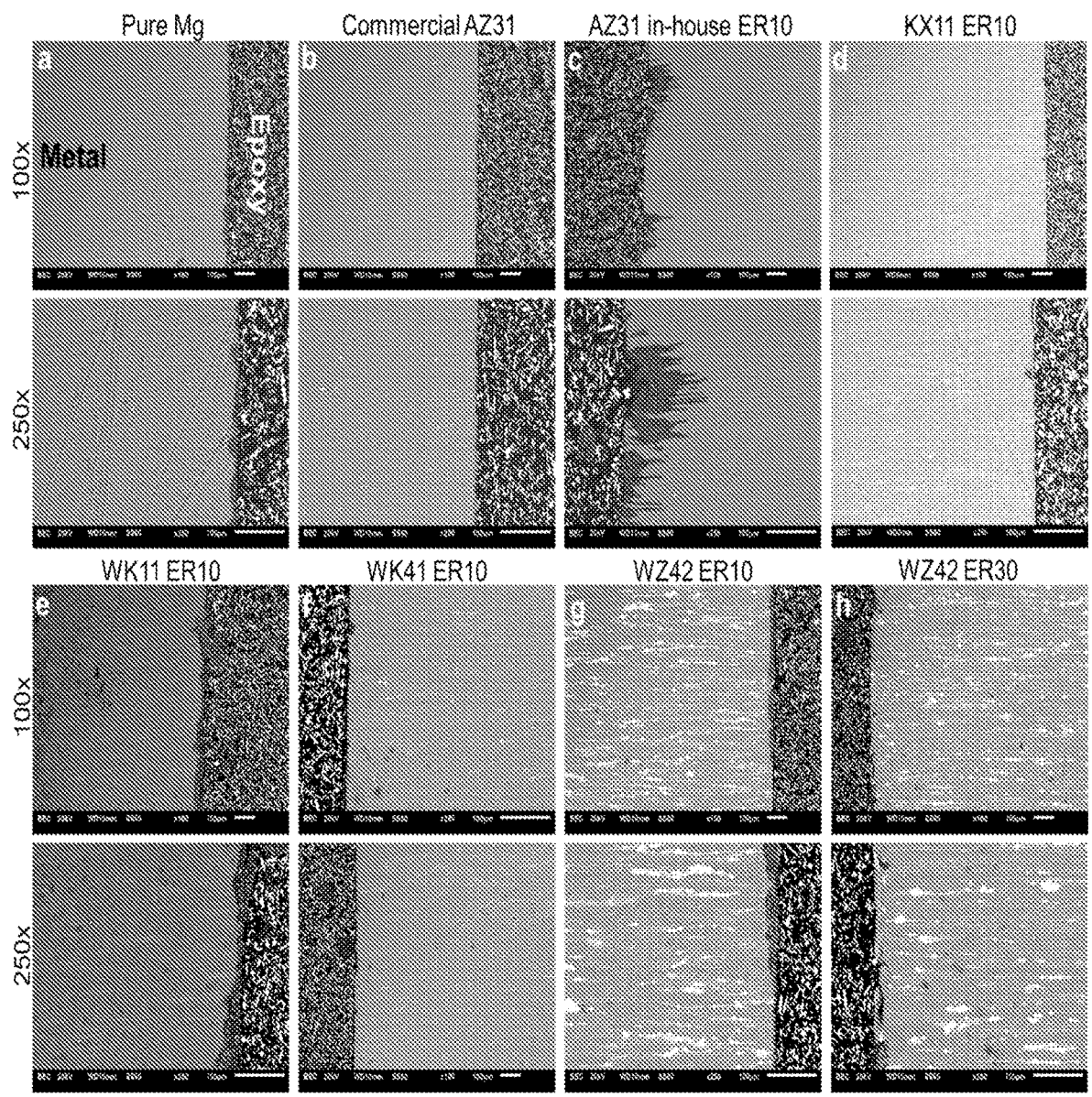
FIGURE 6.7

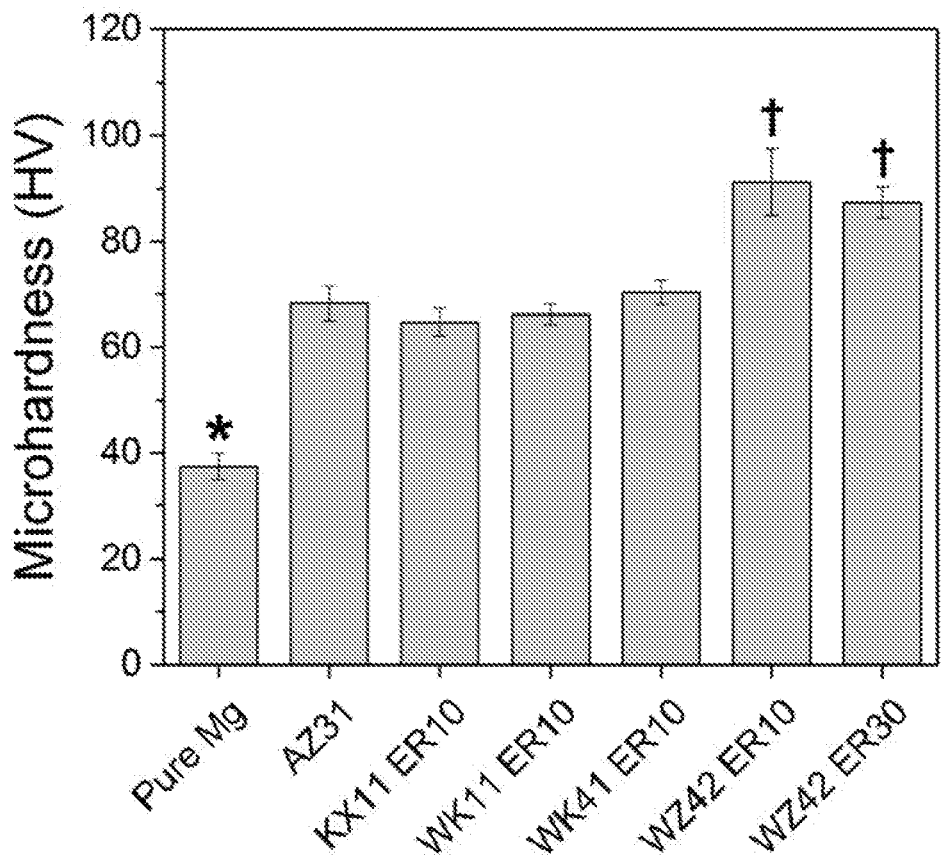
FIGURE 6.8

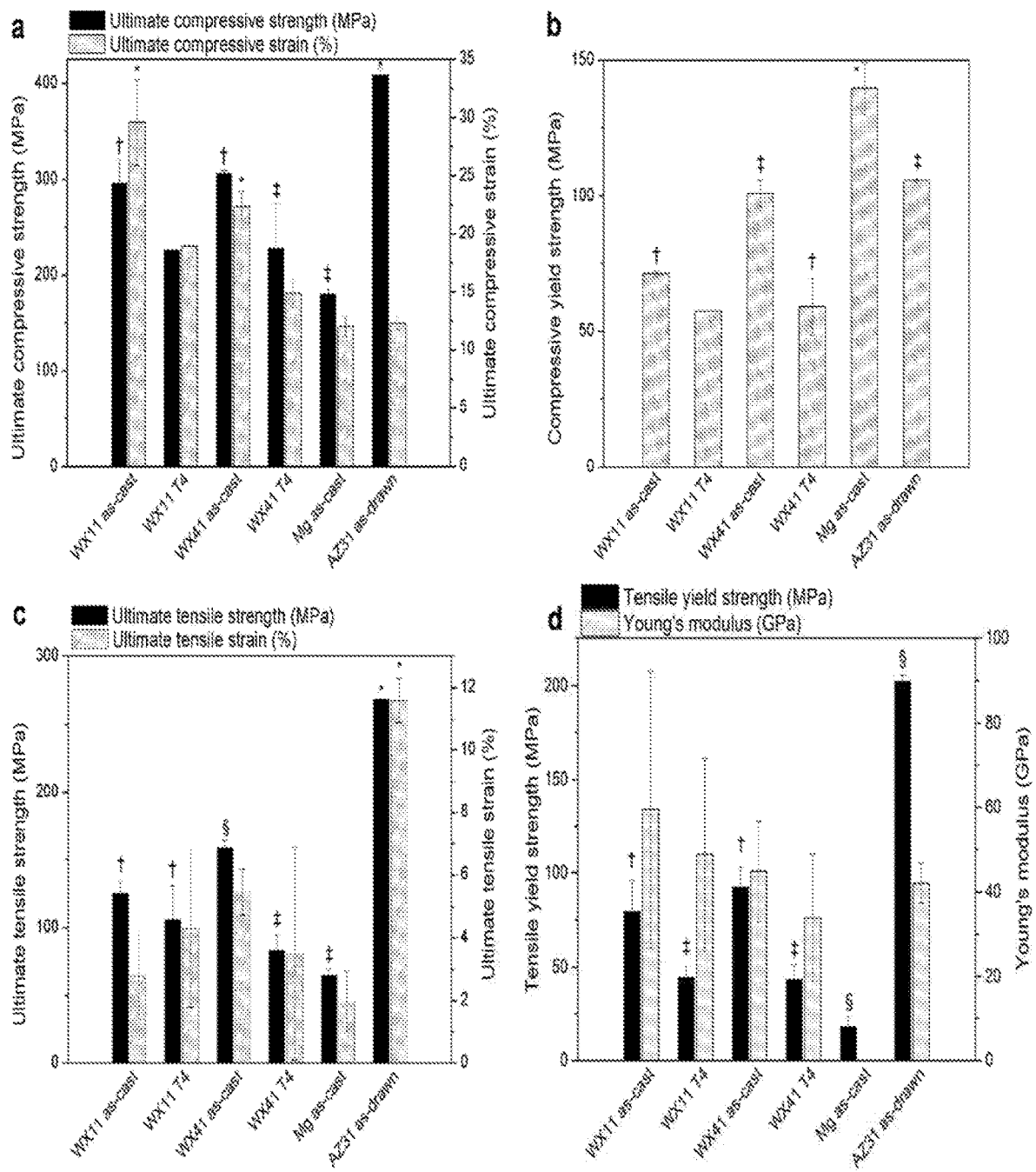
FIGURE 6.9

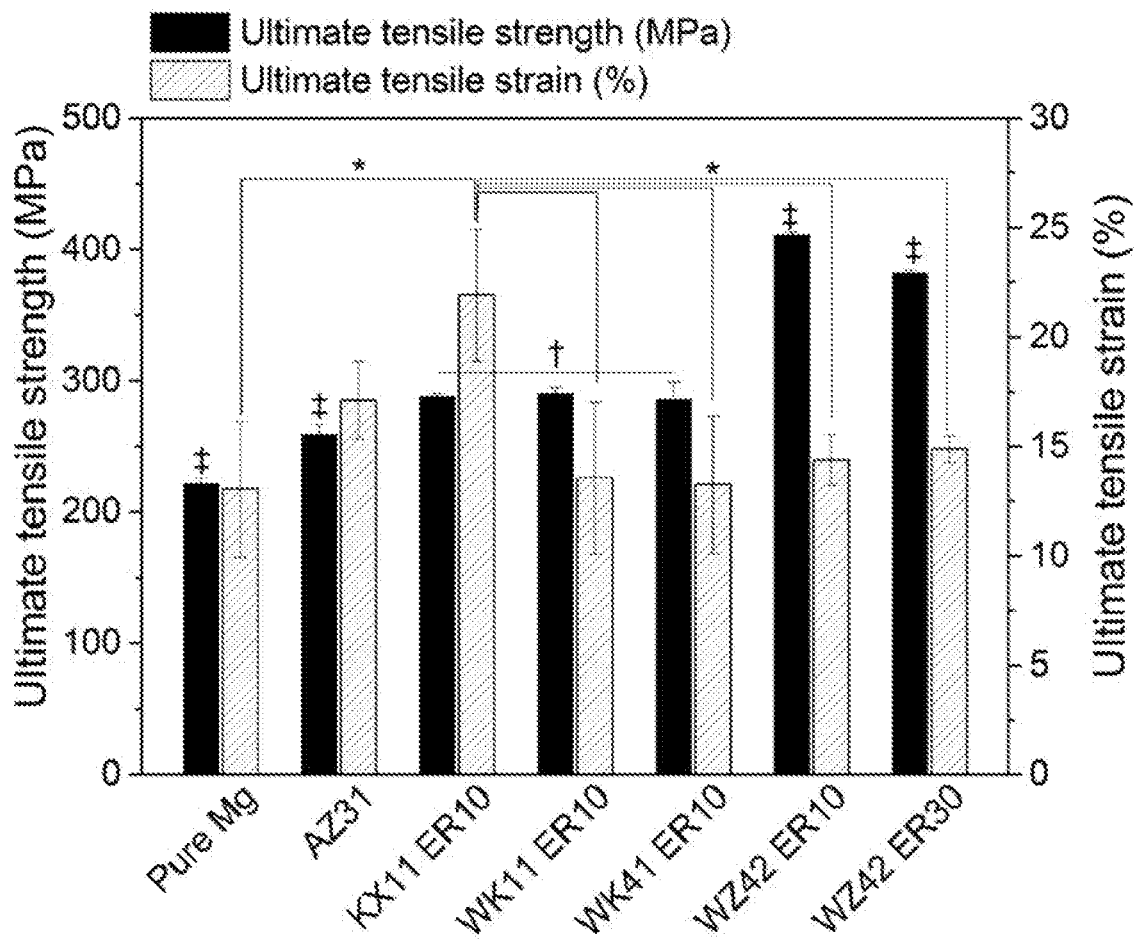
FIGURE 6.10

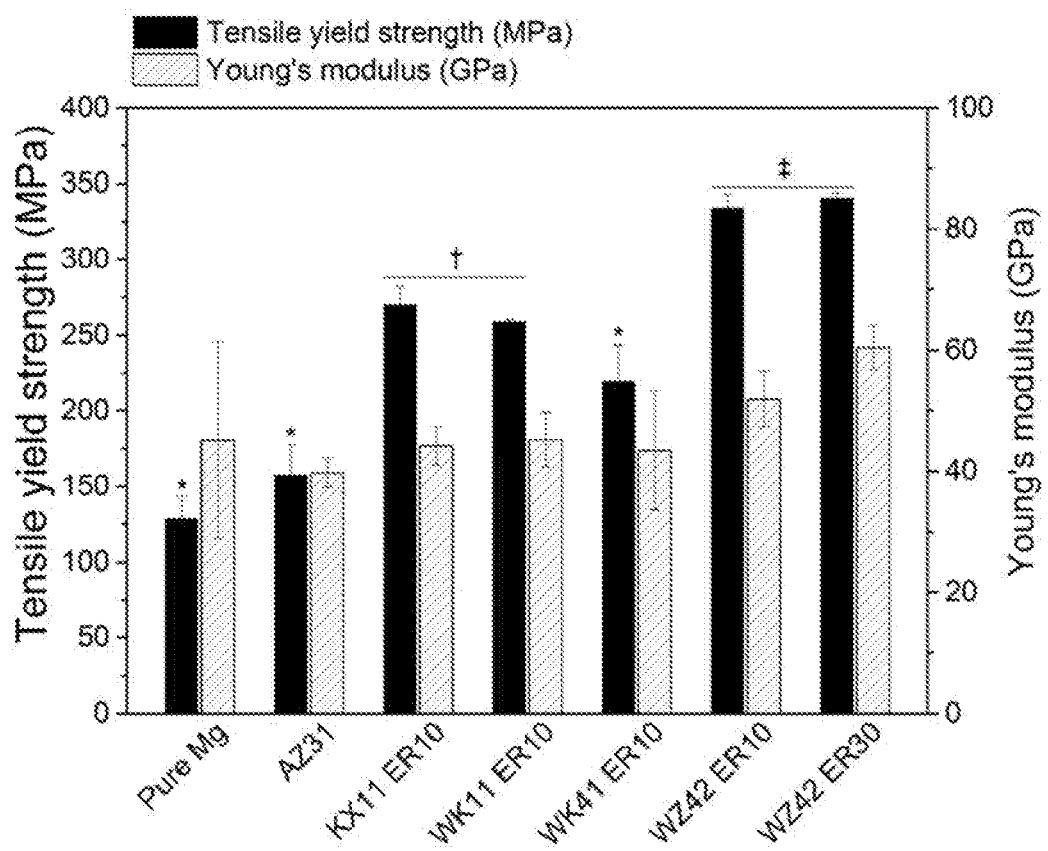
FIGURE 6.11

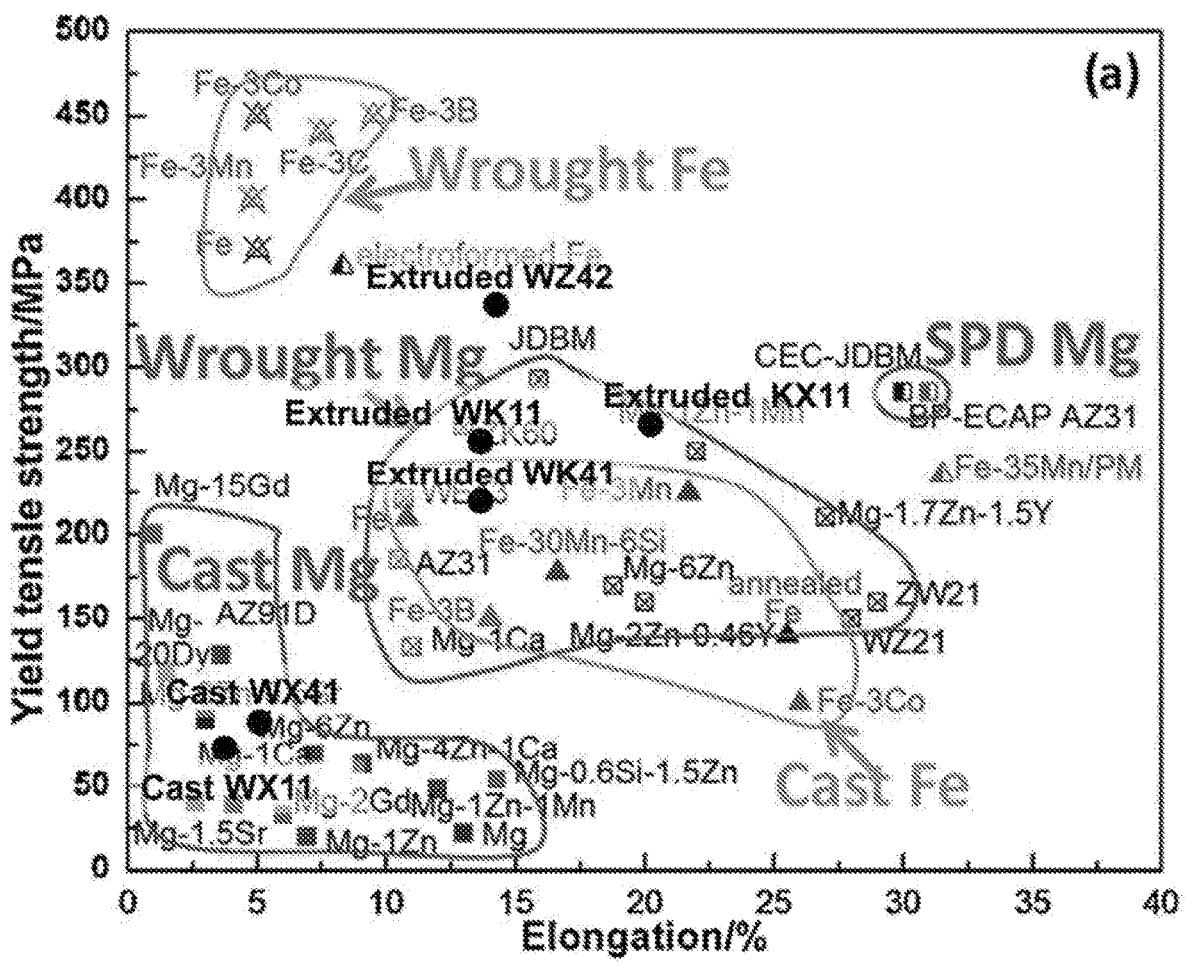
FIGURE 6.12

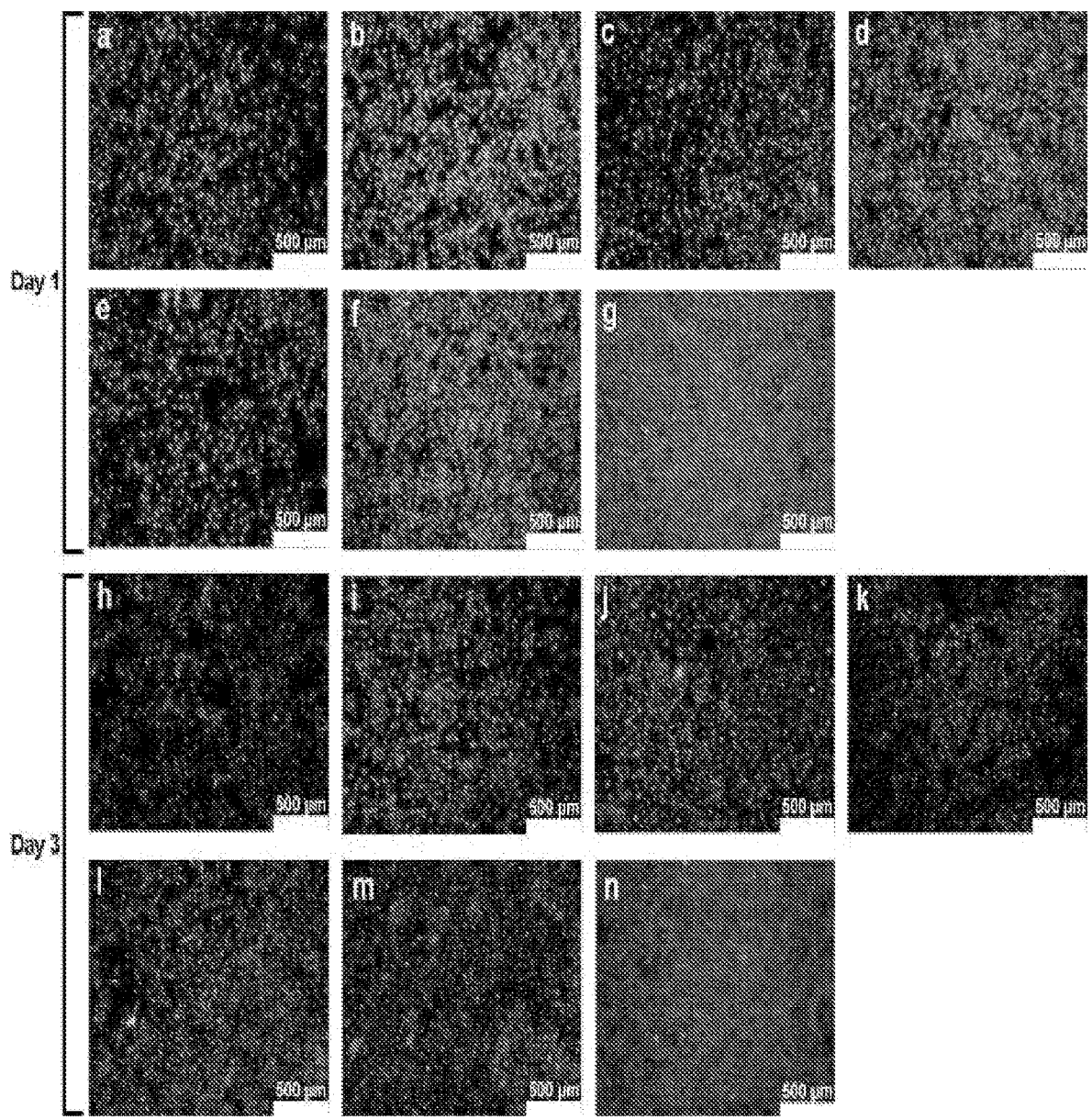
FIGURE 7.1

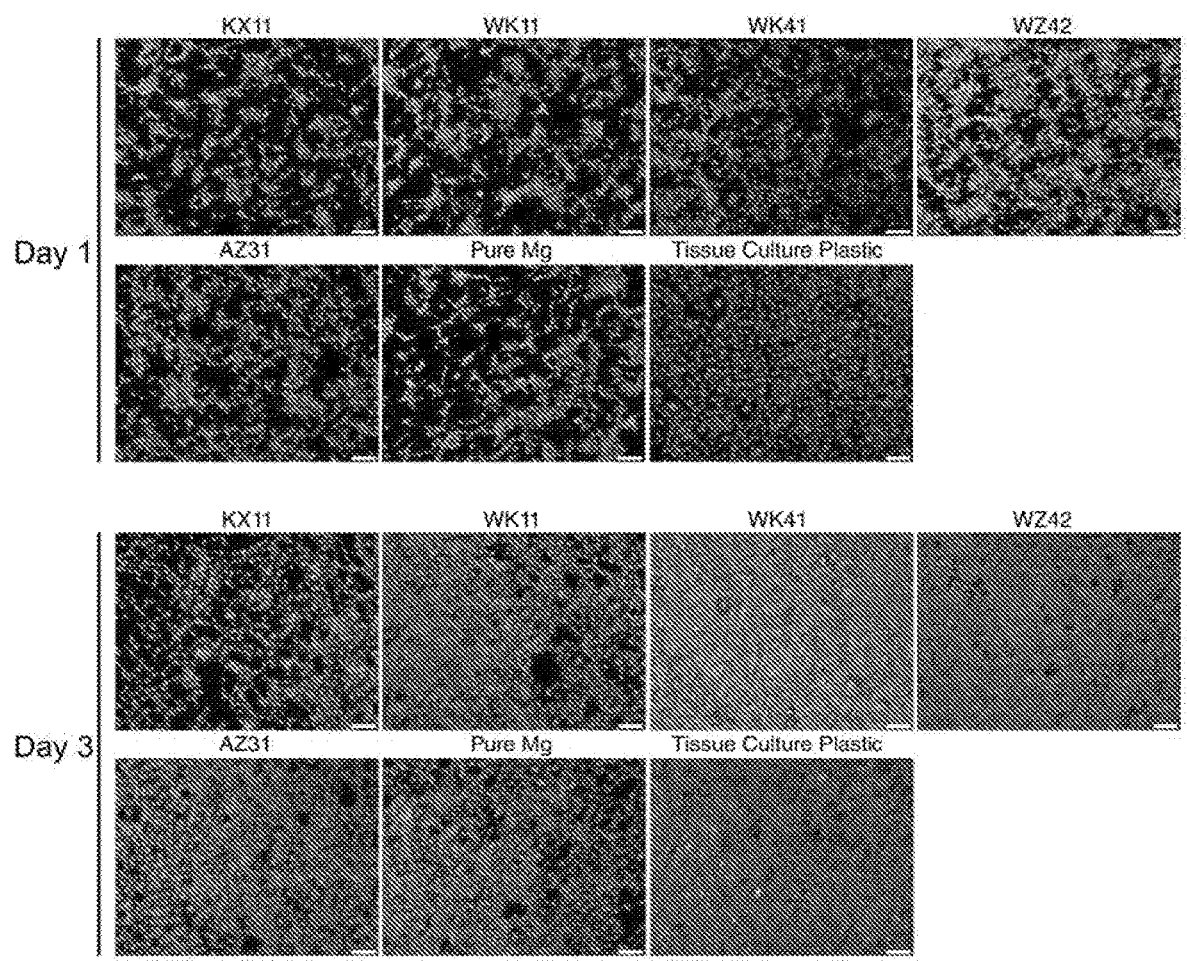
FIGURE 7.2

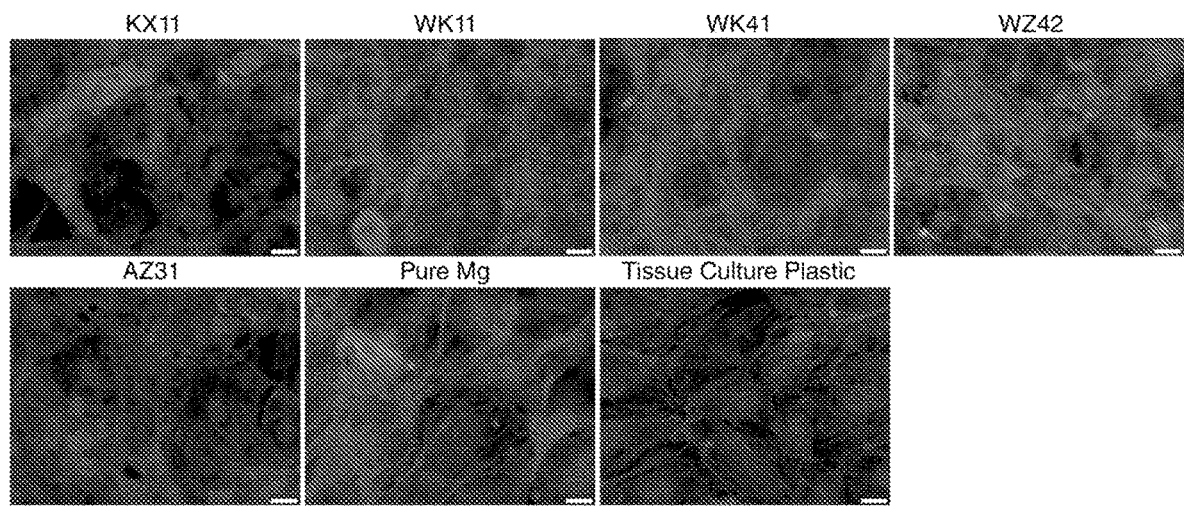
FIGURE 7.3

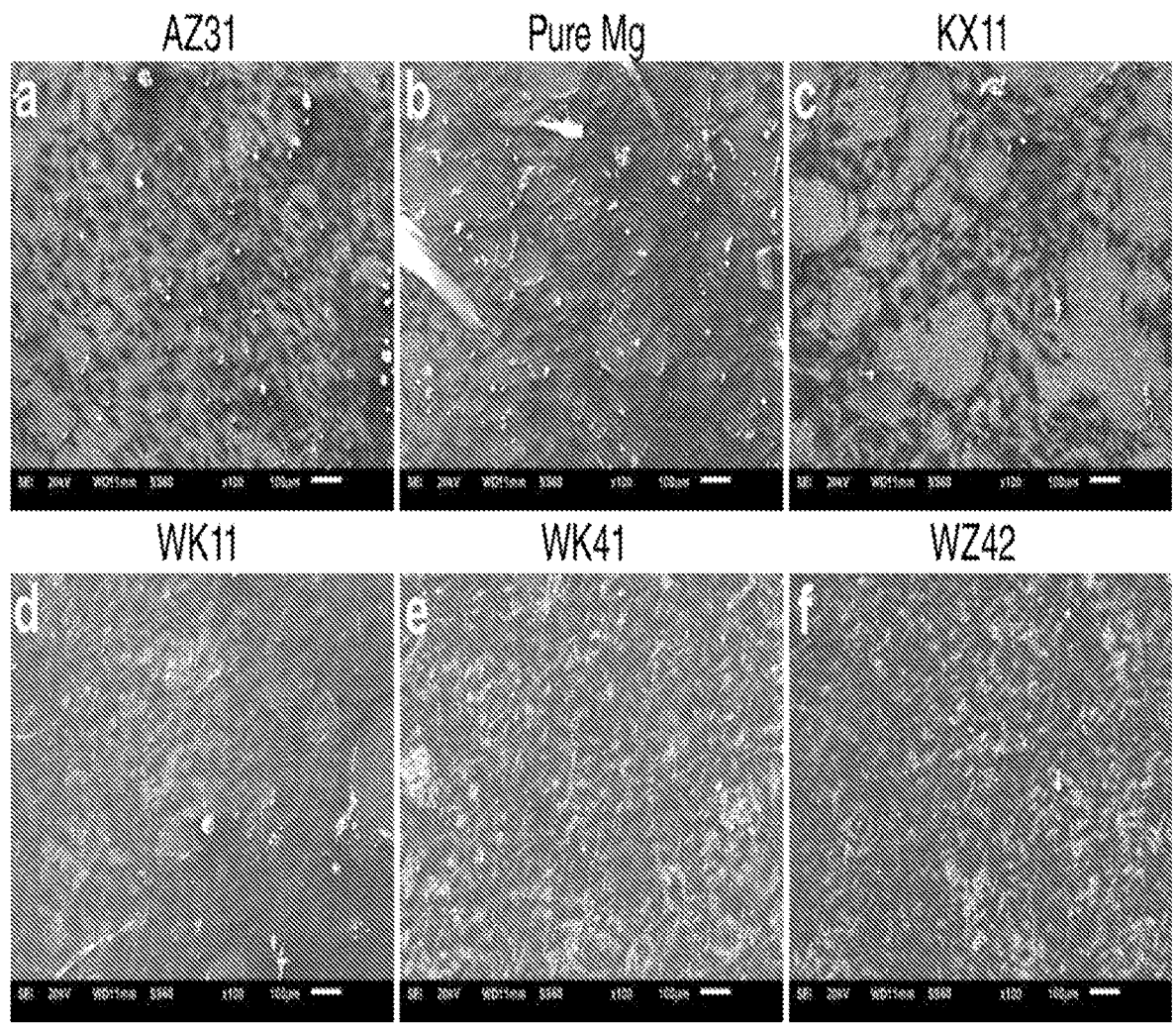
FIGURE 7.4

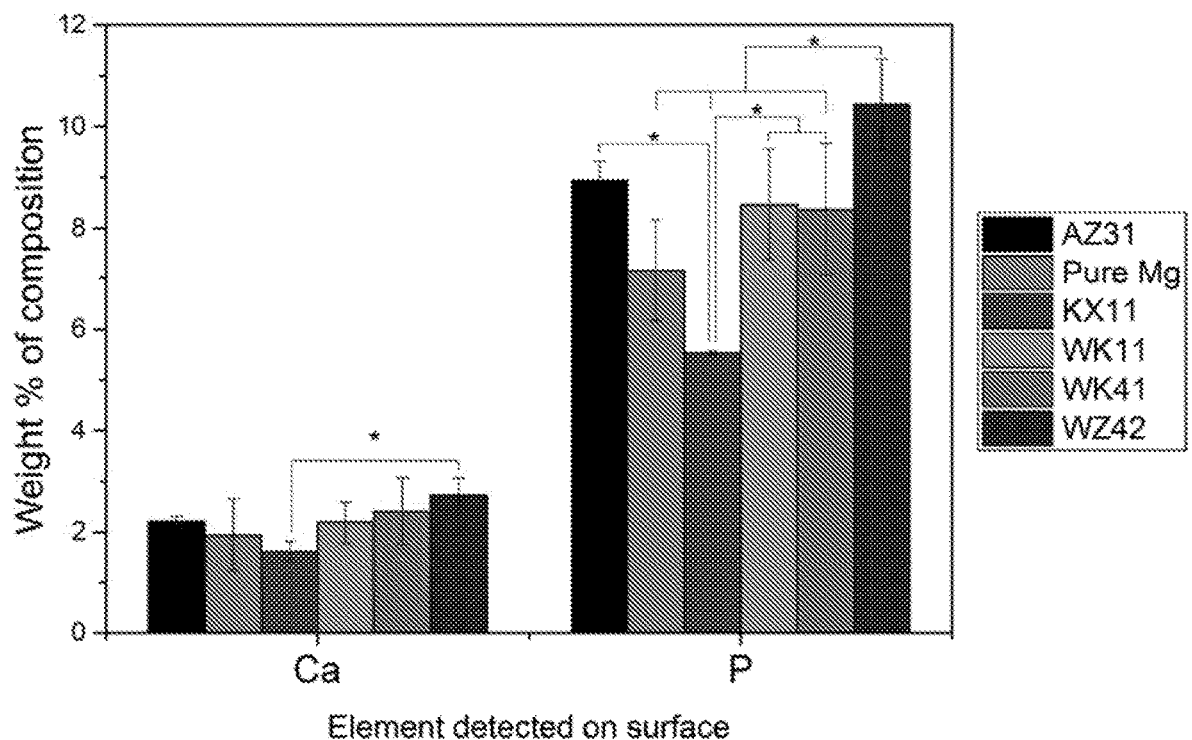
FIGURE 7.5

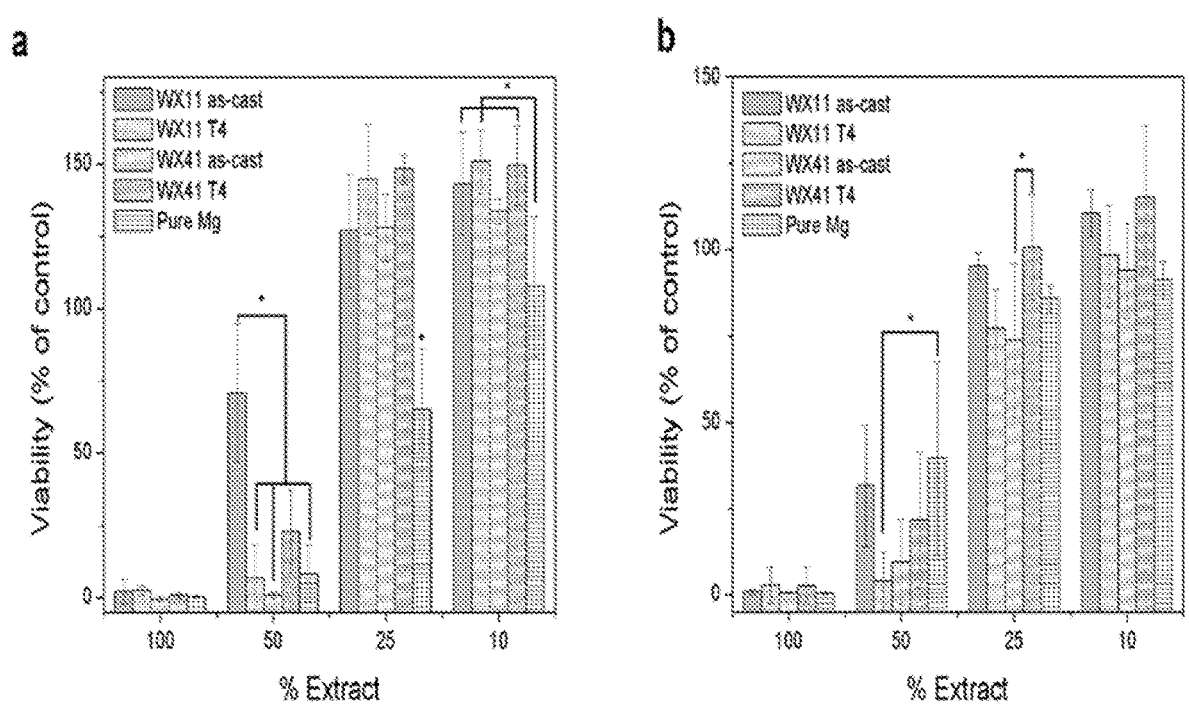
FIGURE 7.6

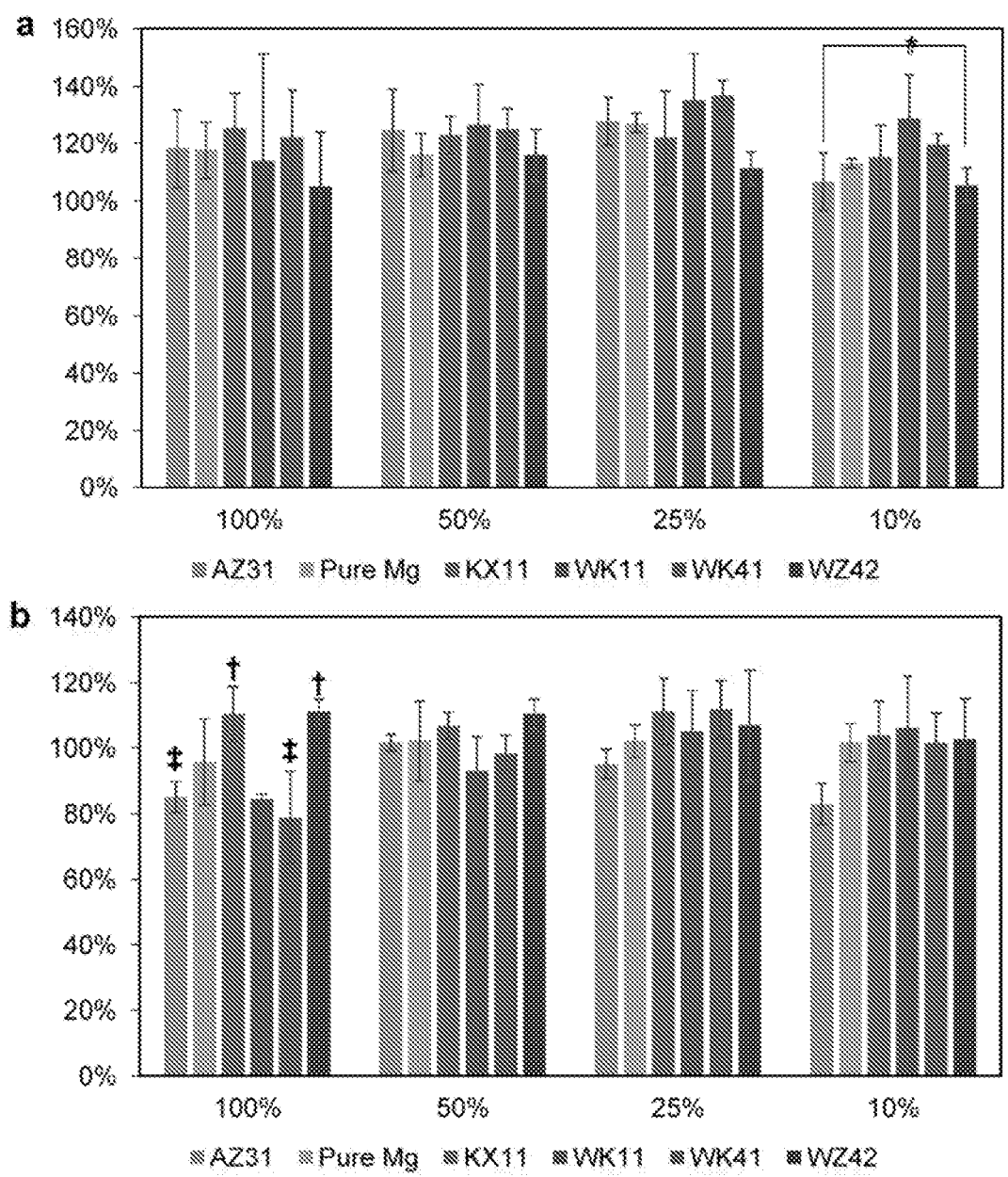
FIGURE 7.7

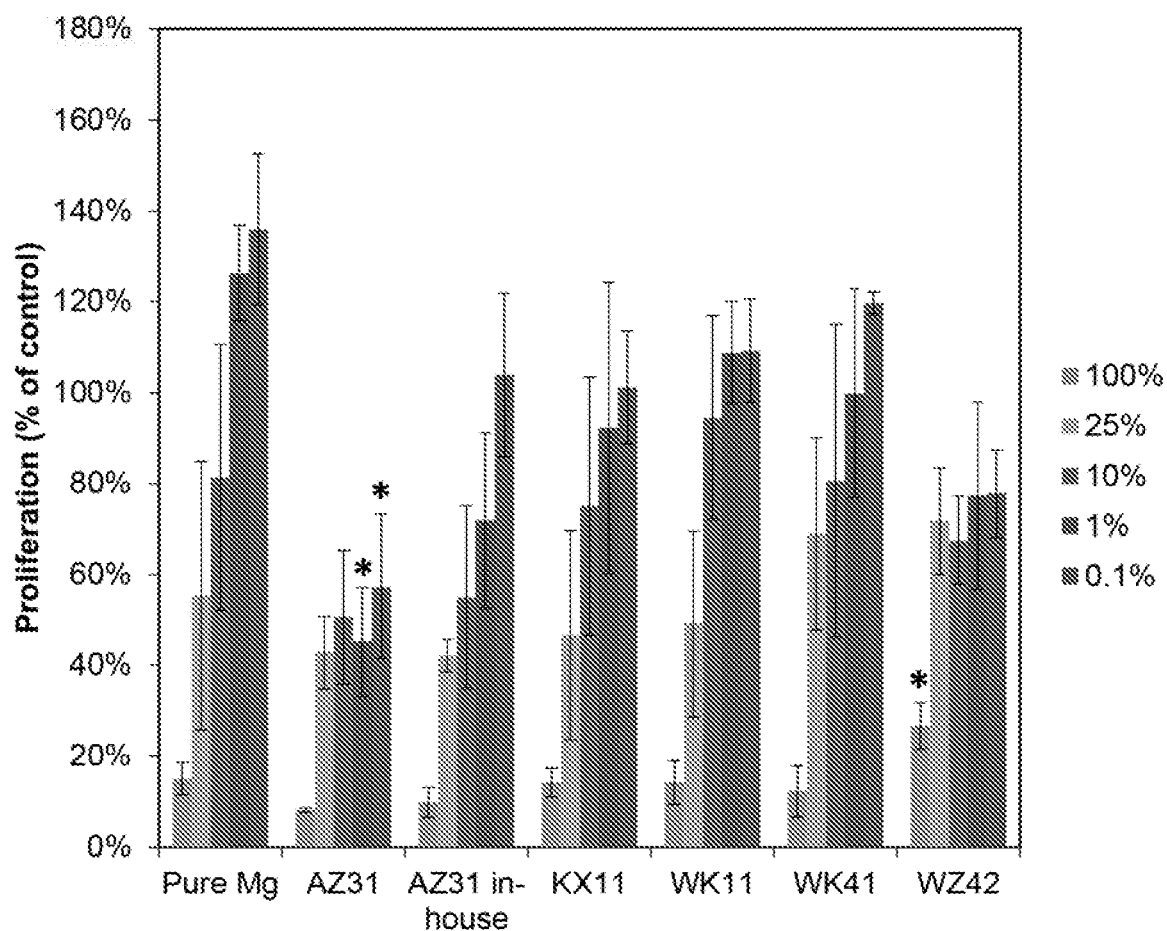
FIGURE 7.8

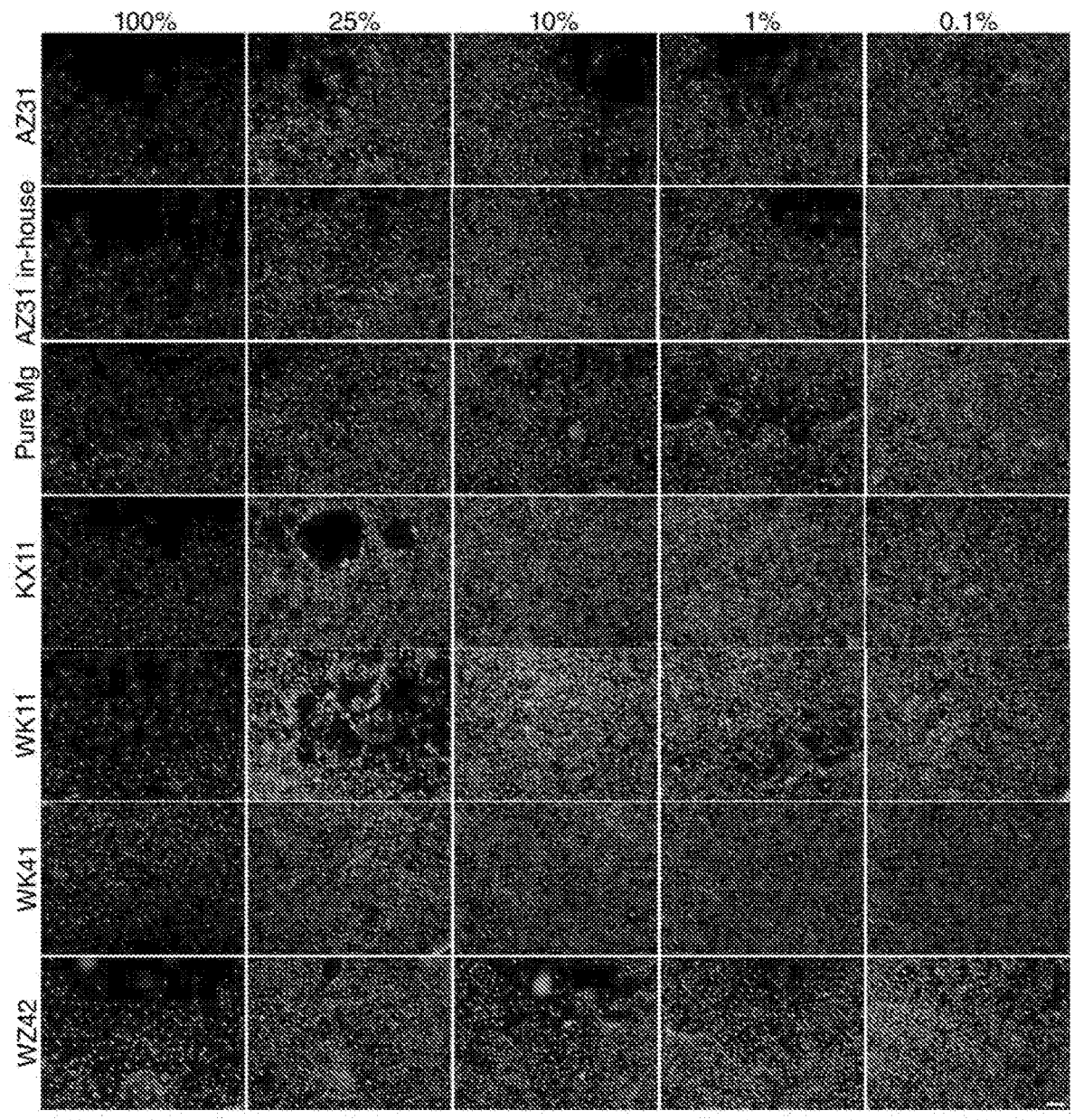
FIGURE 7.9

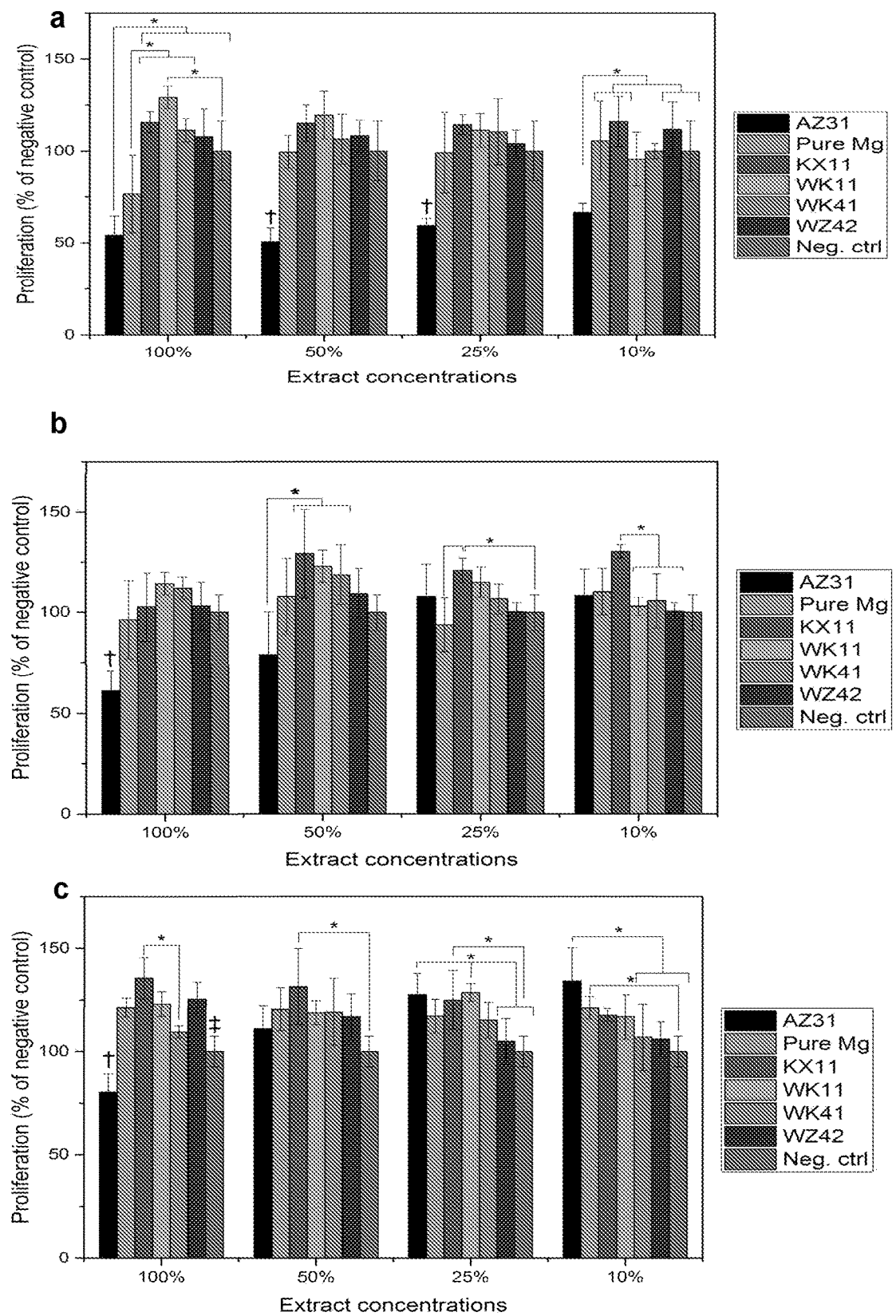
FIGURE 7.10

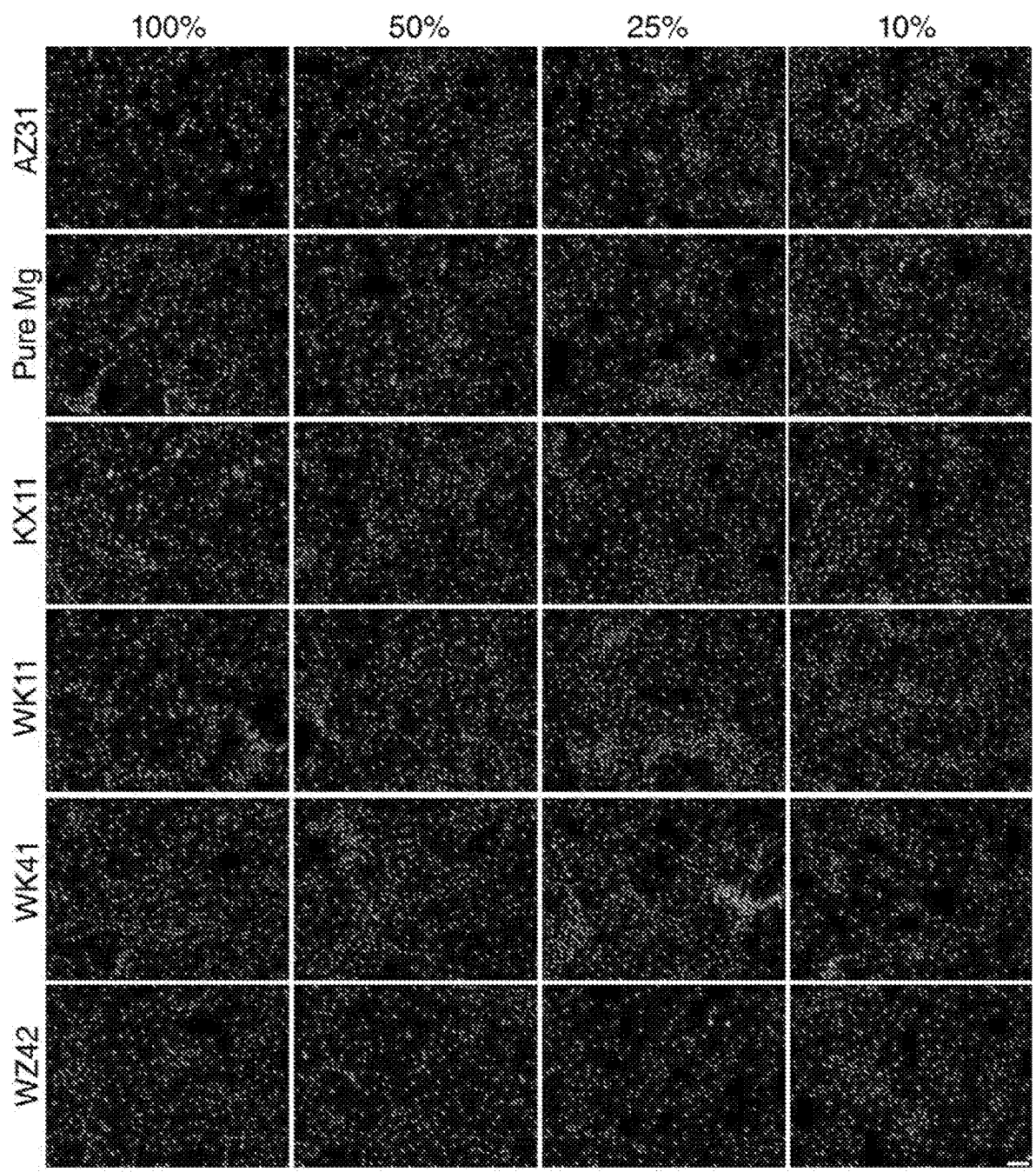
FIGURE 7.11

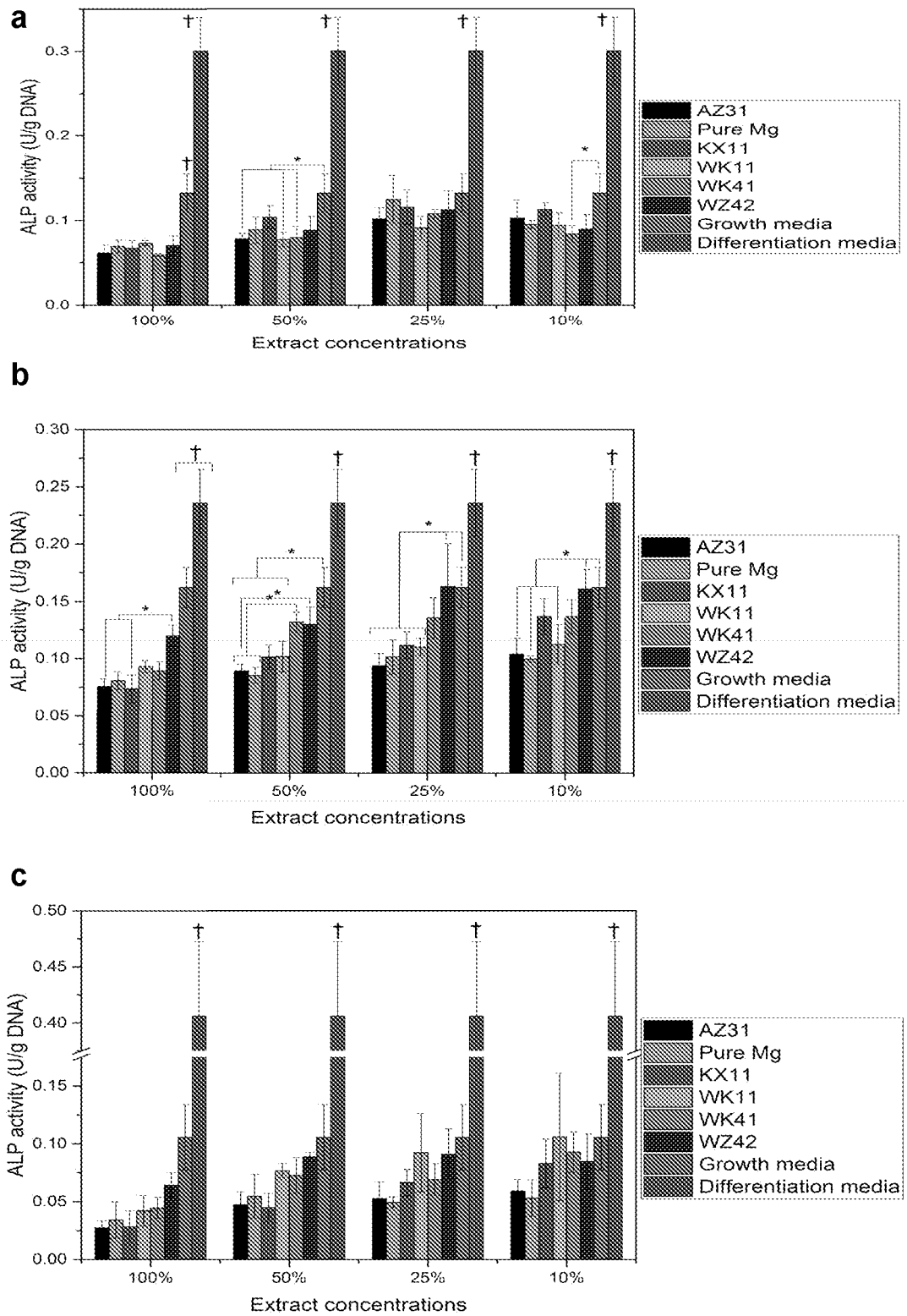
FIGURE 7.12

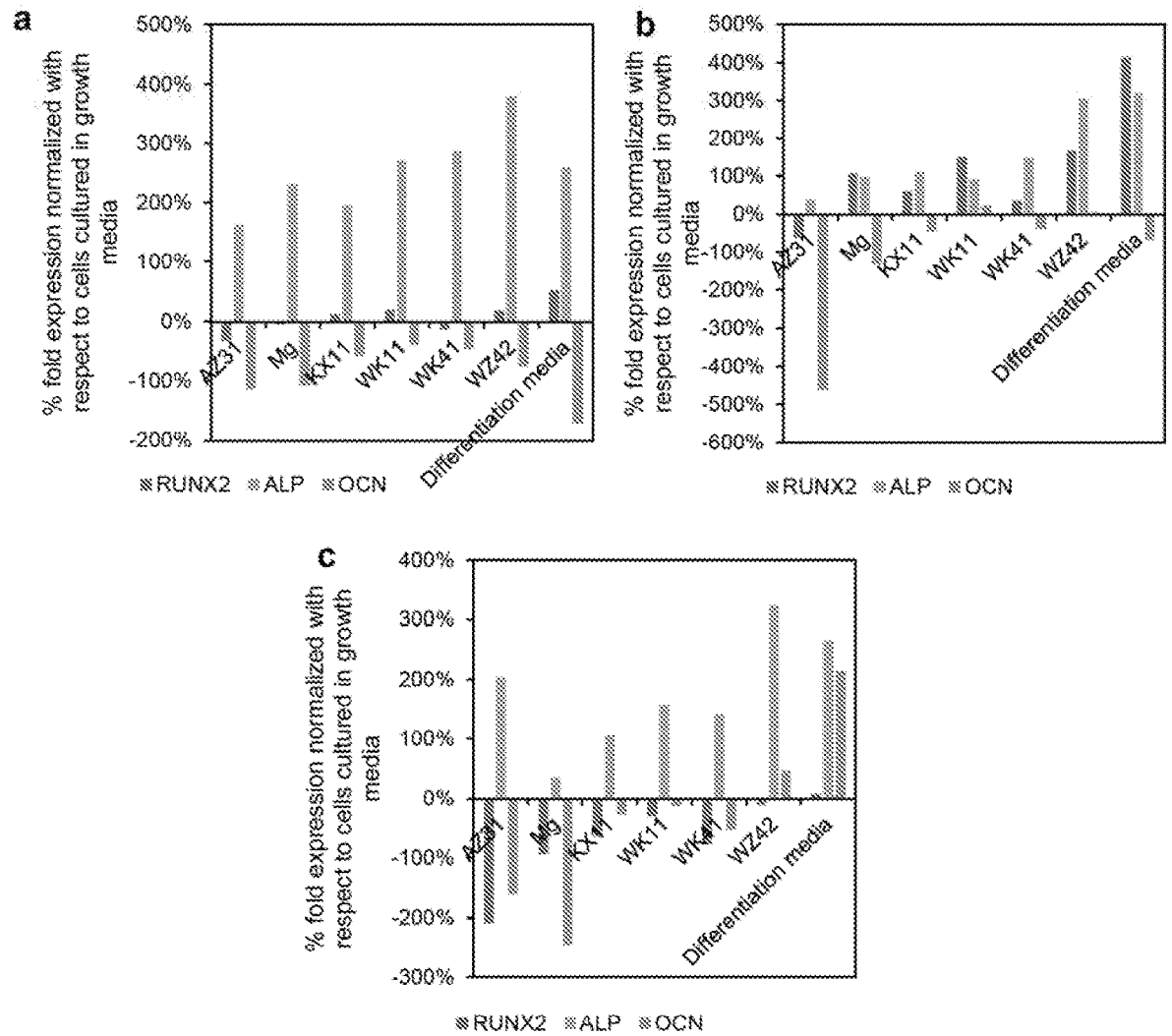
FIGURE 7.13

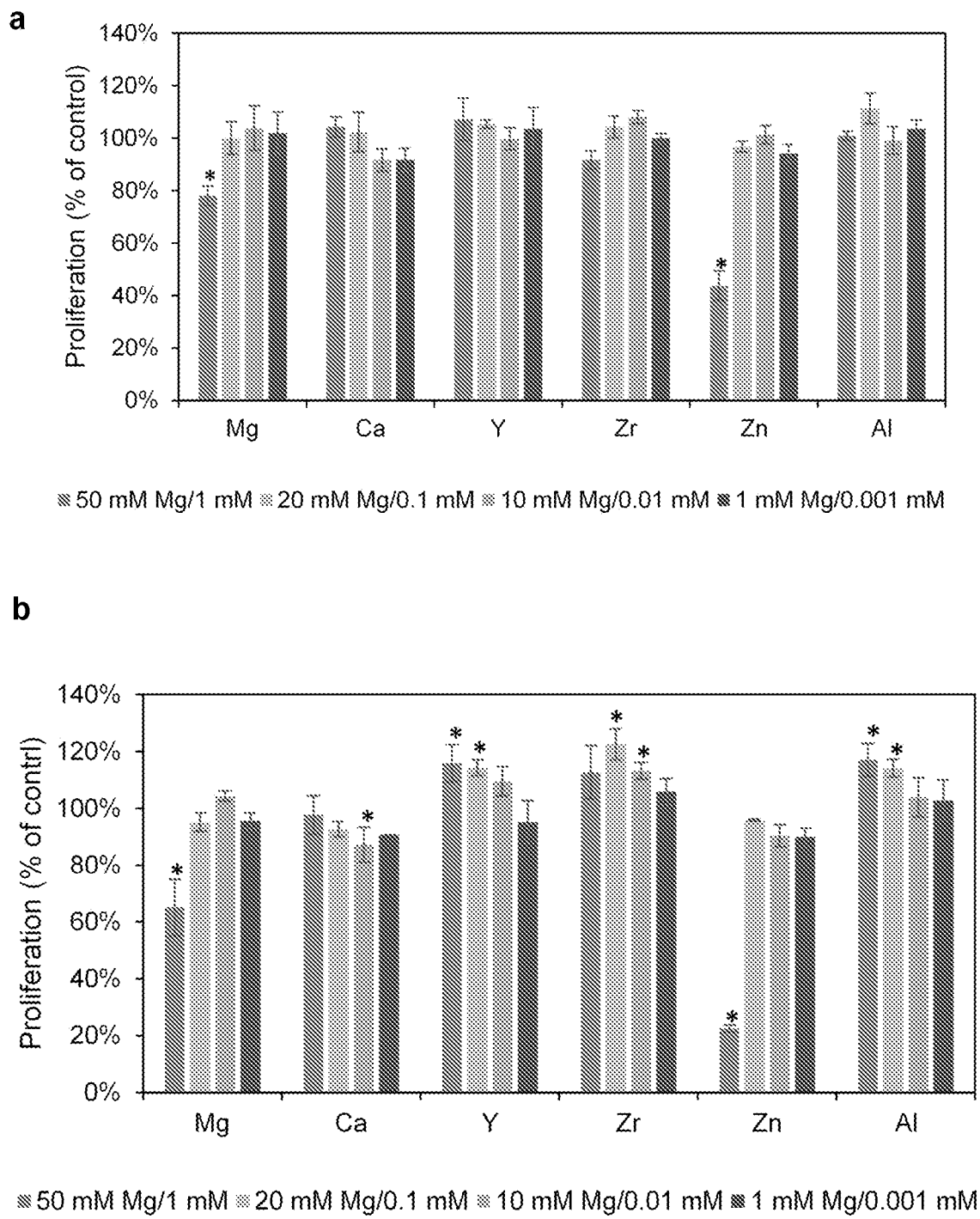
FIGURE 7.14

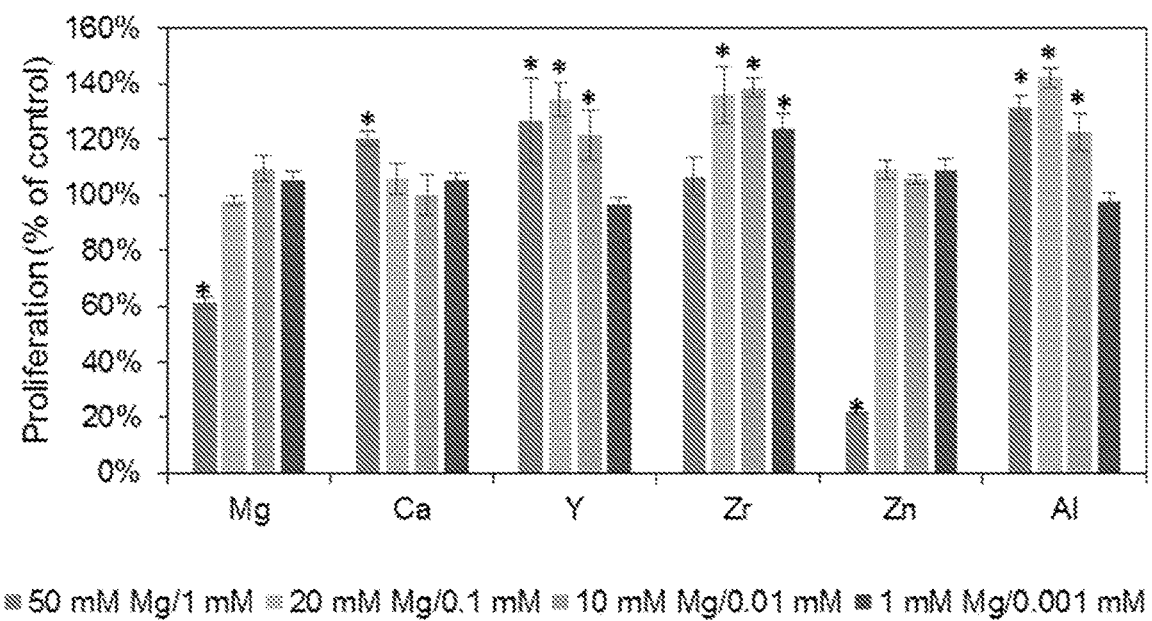
FIGURE 7.14

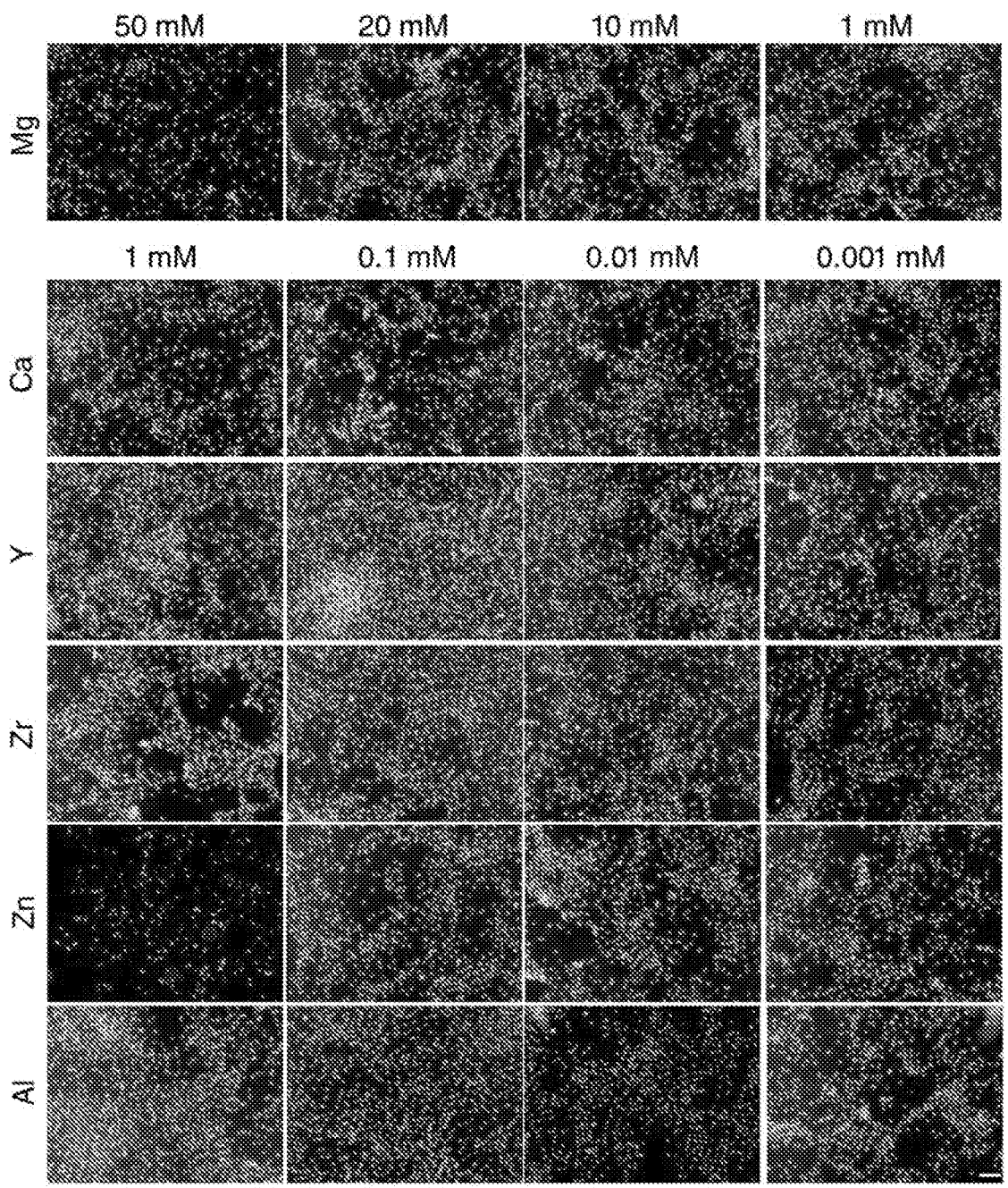
FIGURE 7.15

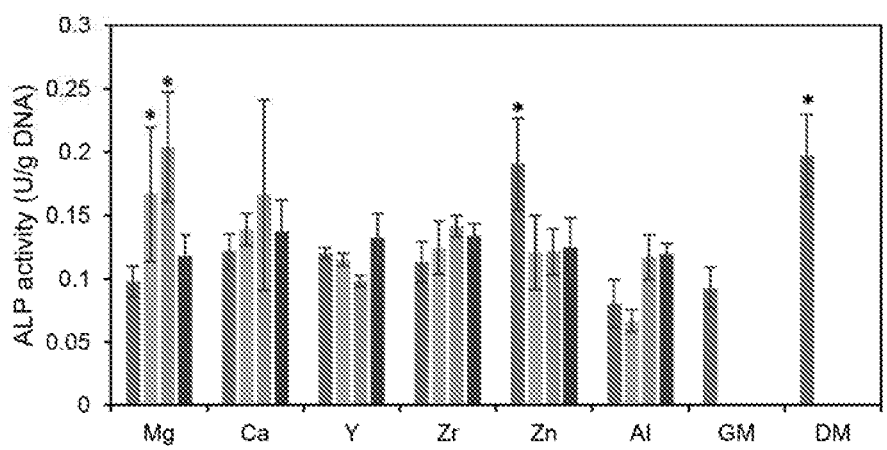
FIGURE 7.16

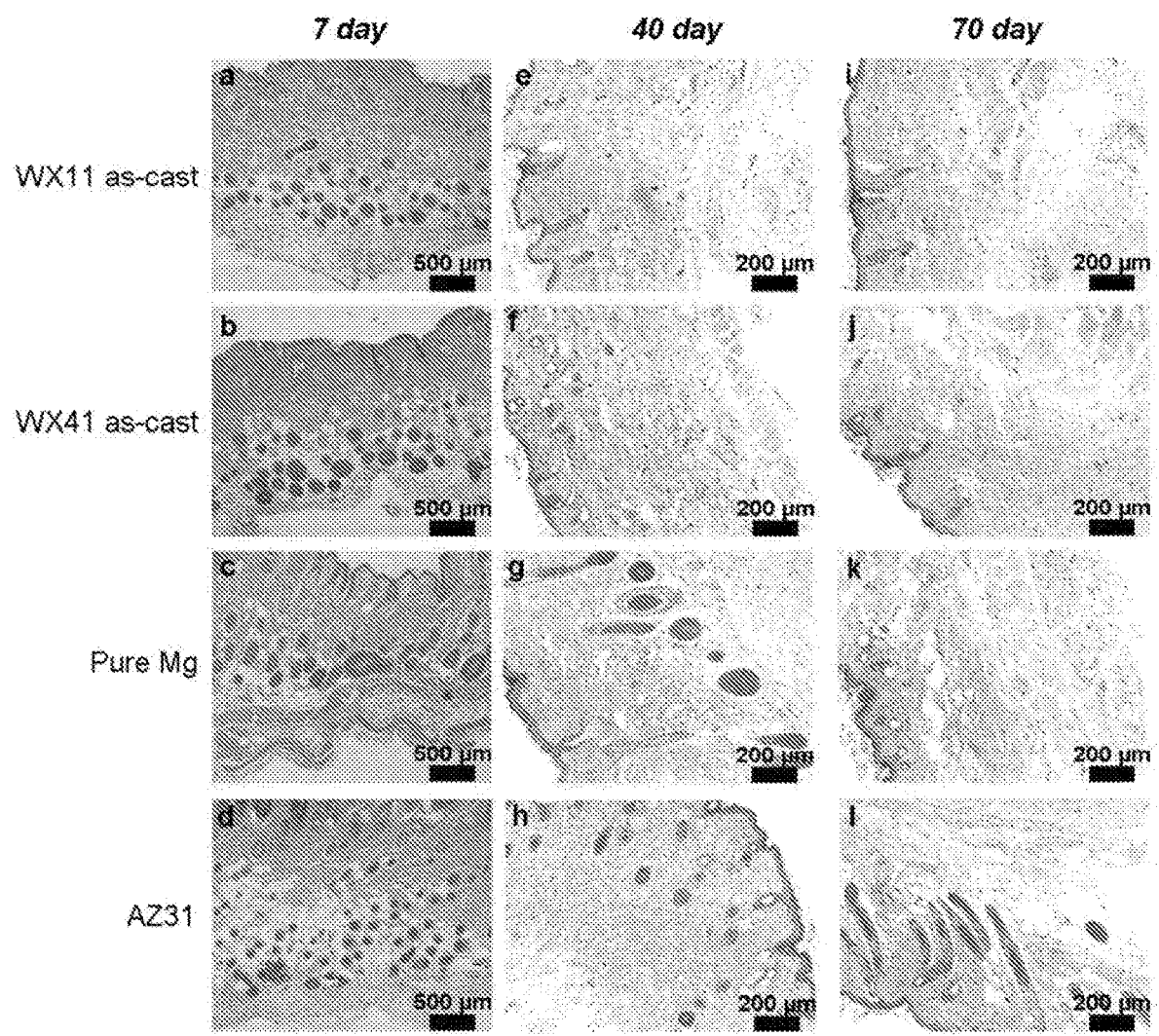
FIGURE 7.17

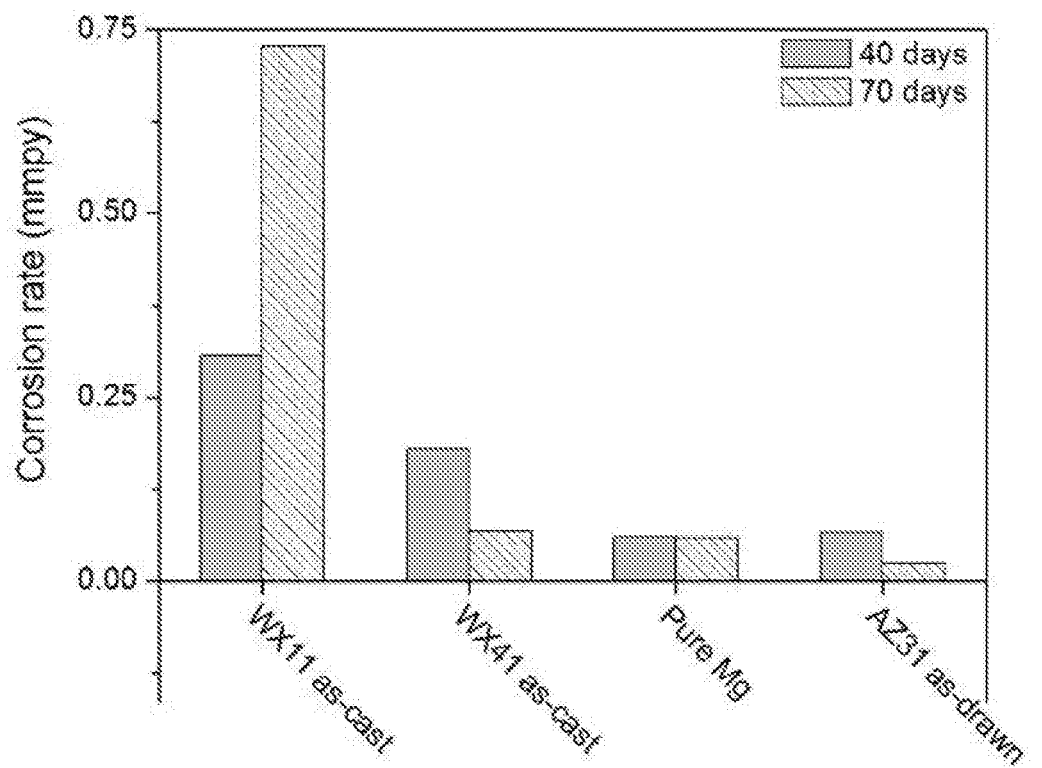
FIGURE 7.18

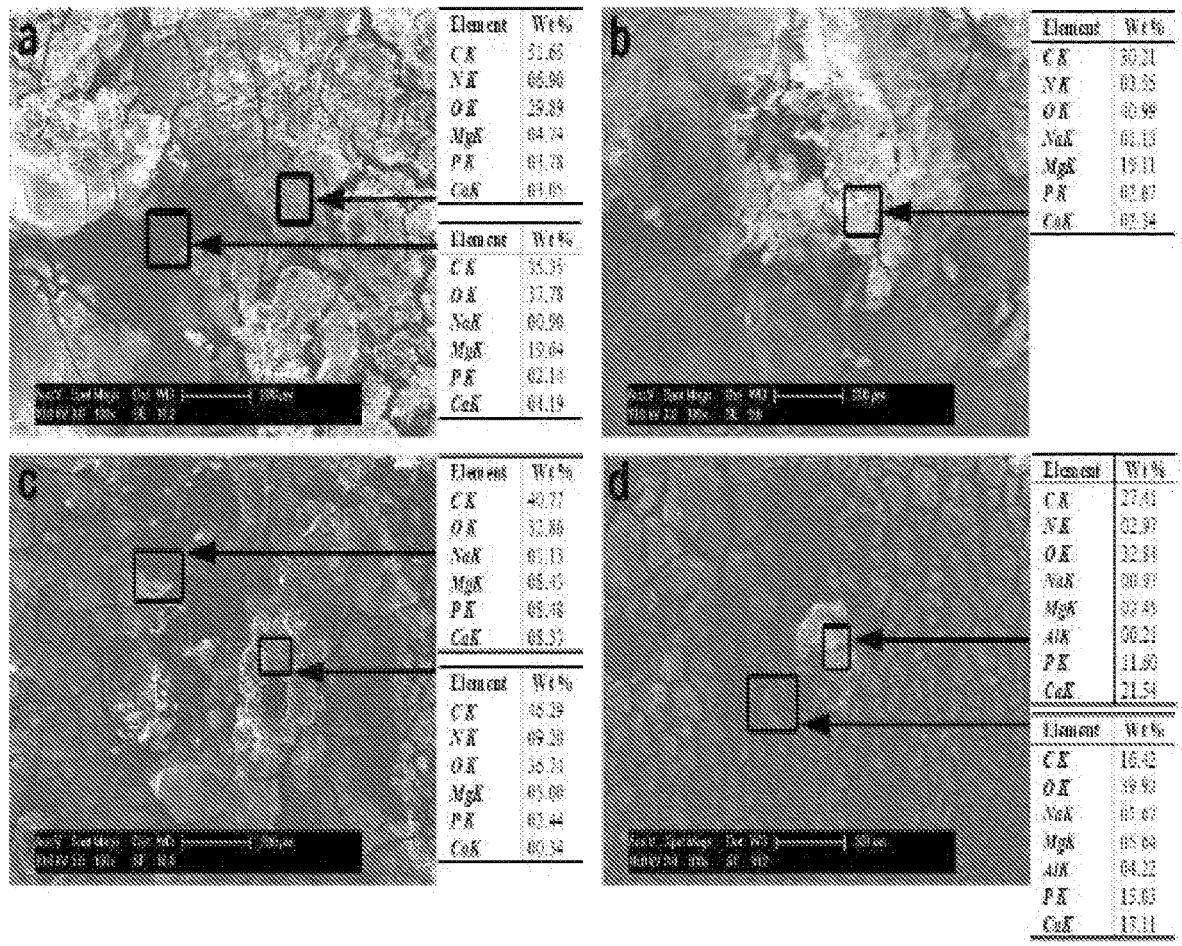
FIGURE 7.19

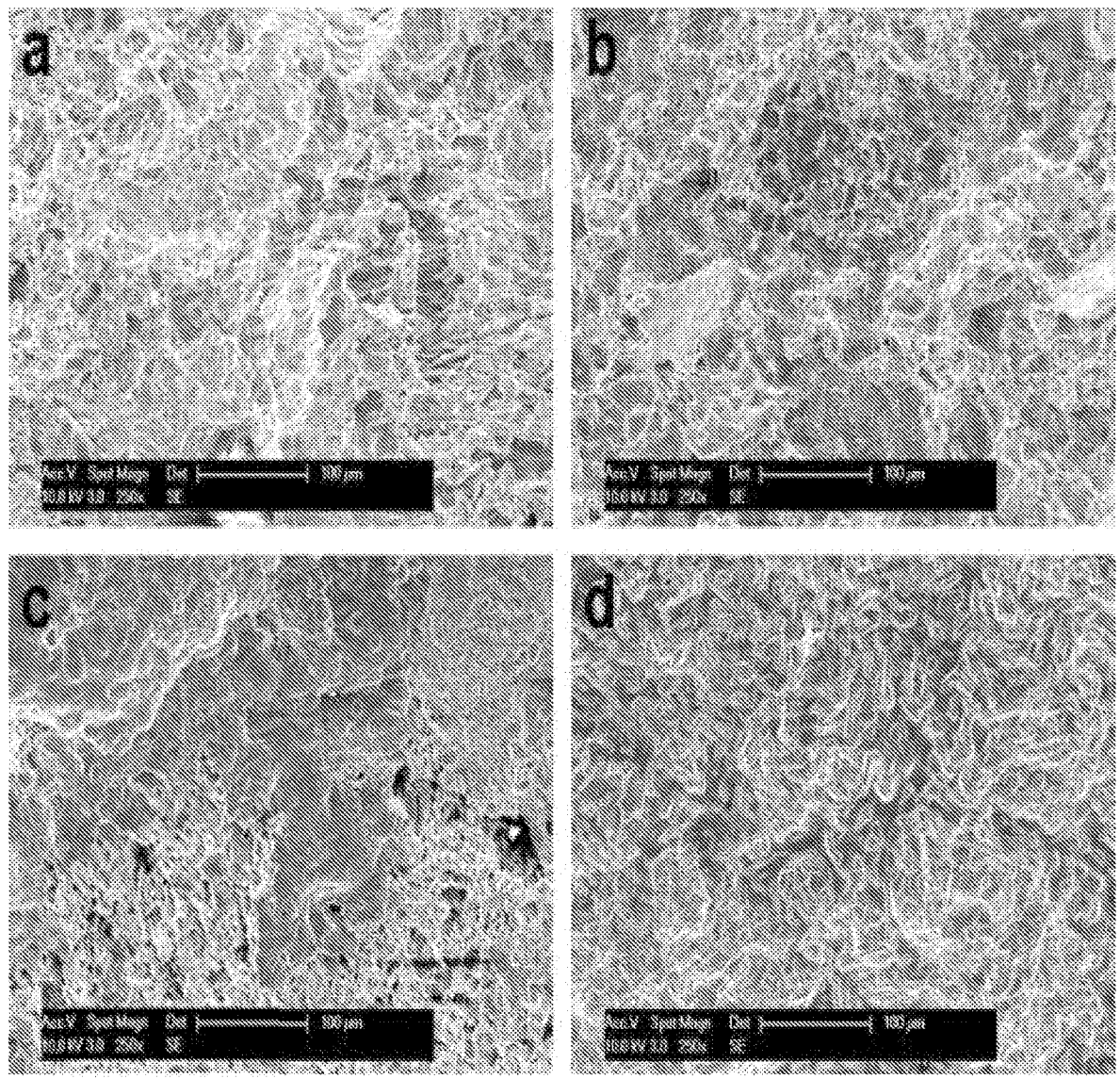
FIGURE 7.20

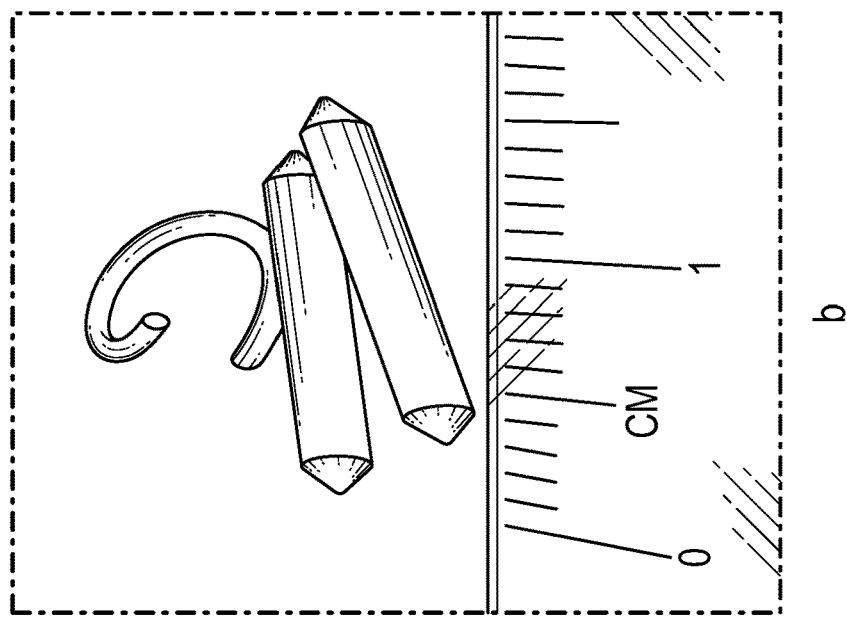
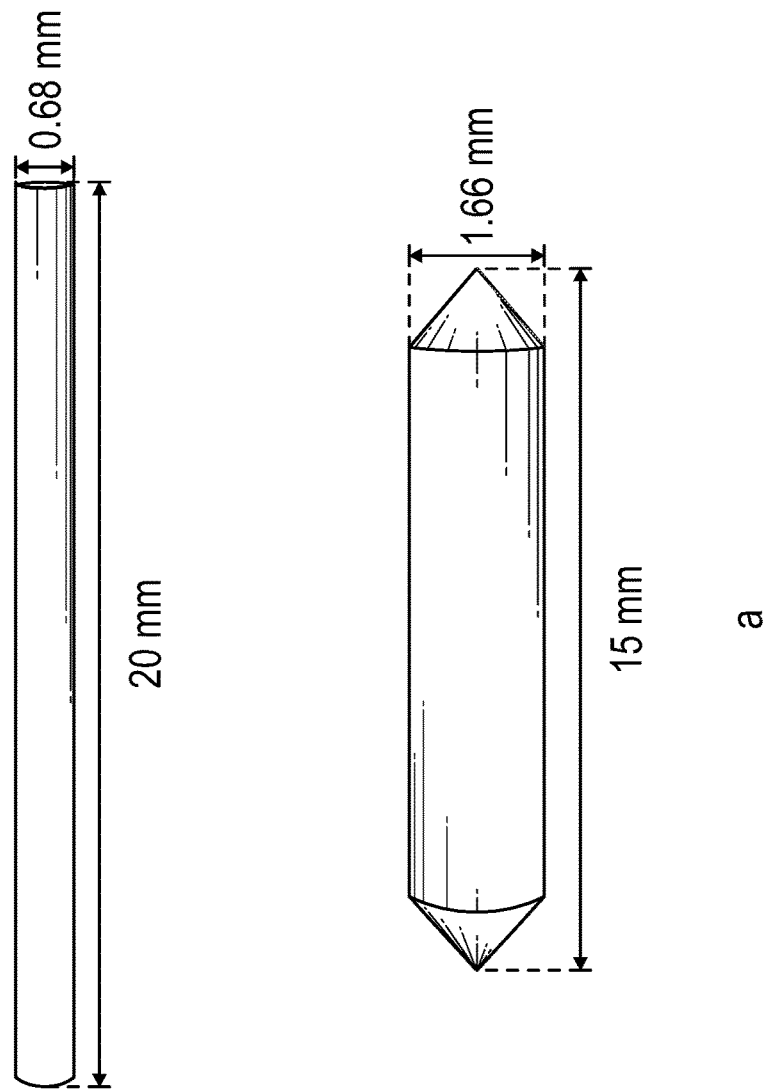
FIGURE 8.1

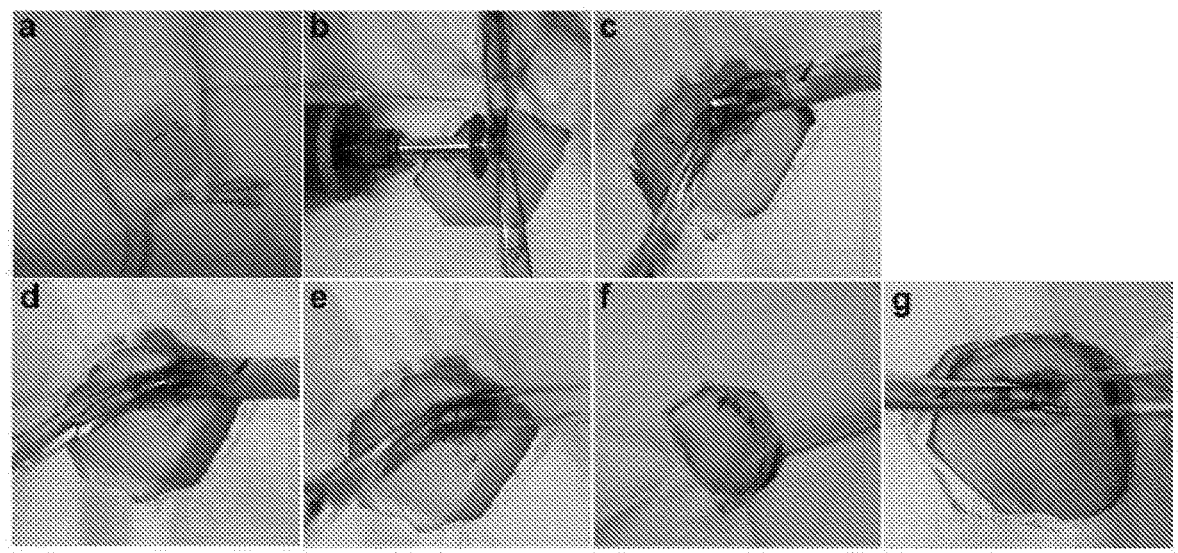
FIGURE 8.2

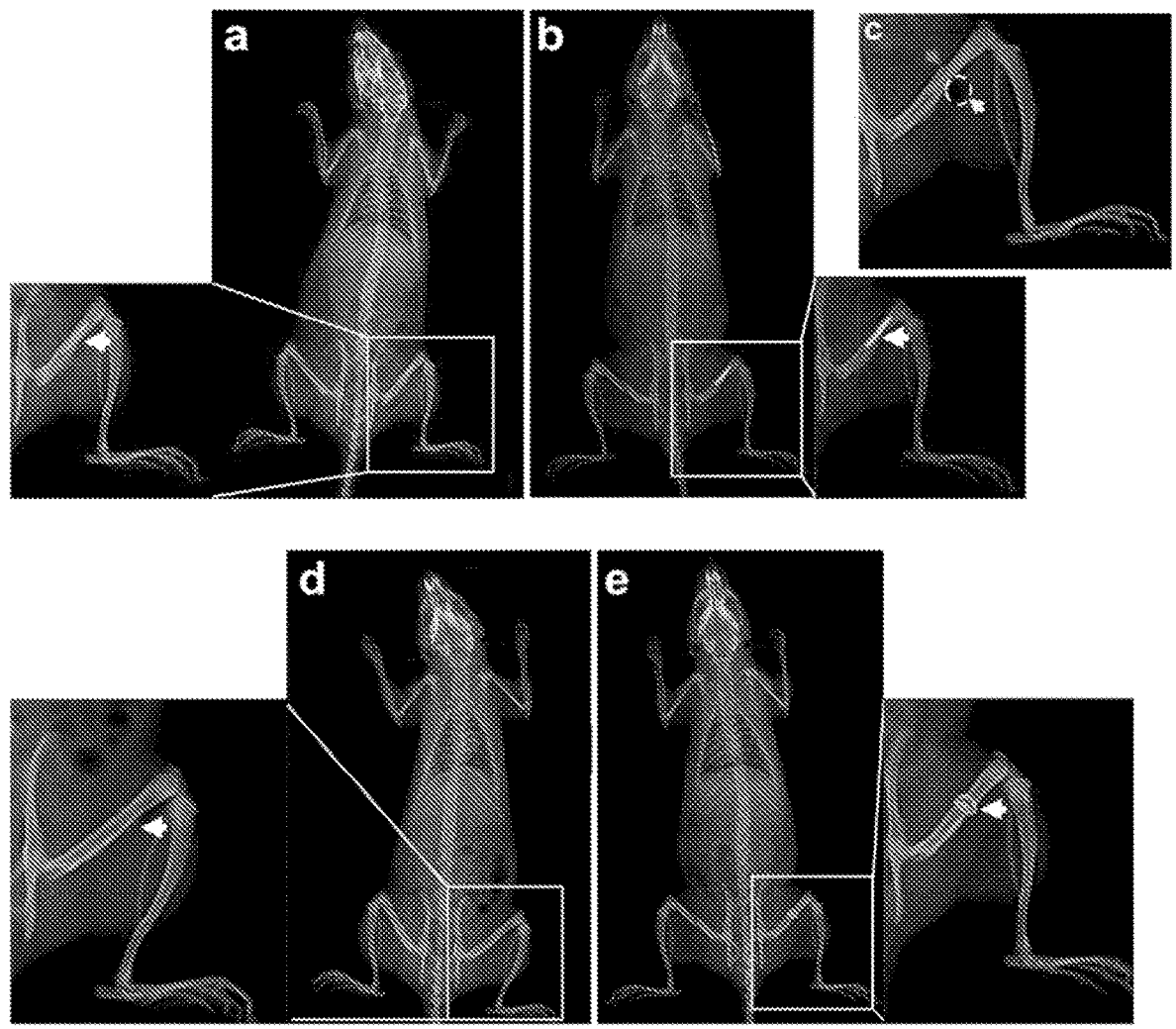
FIGURE 8.3

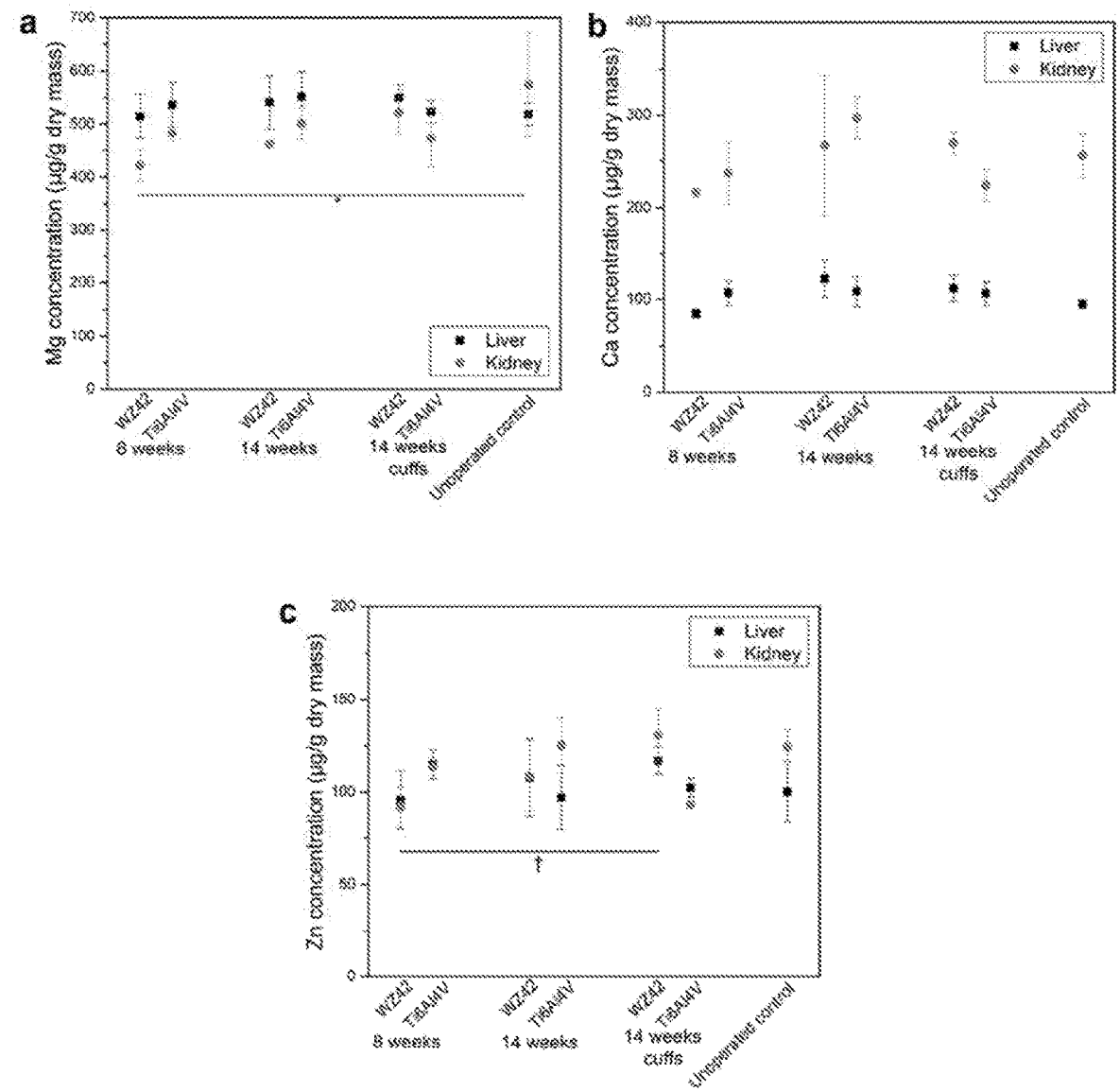
FIGURE 8.4

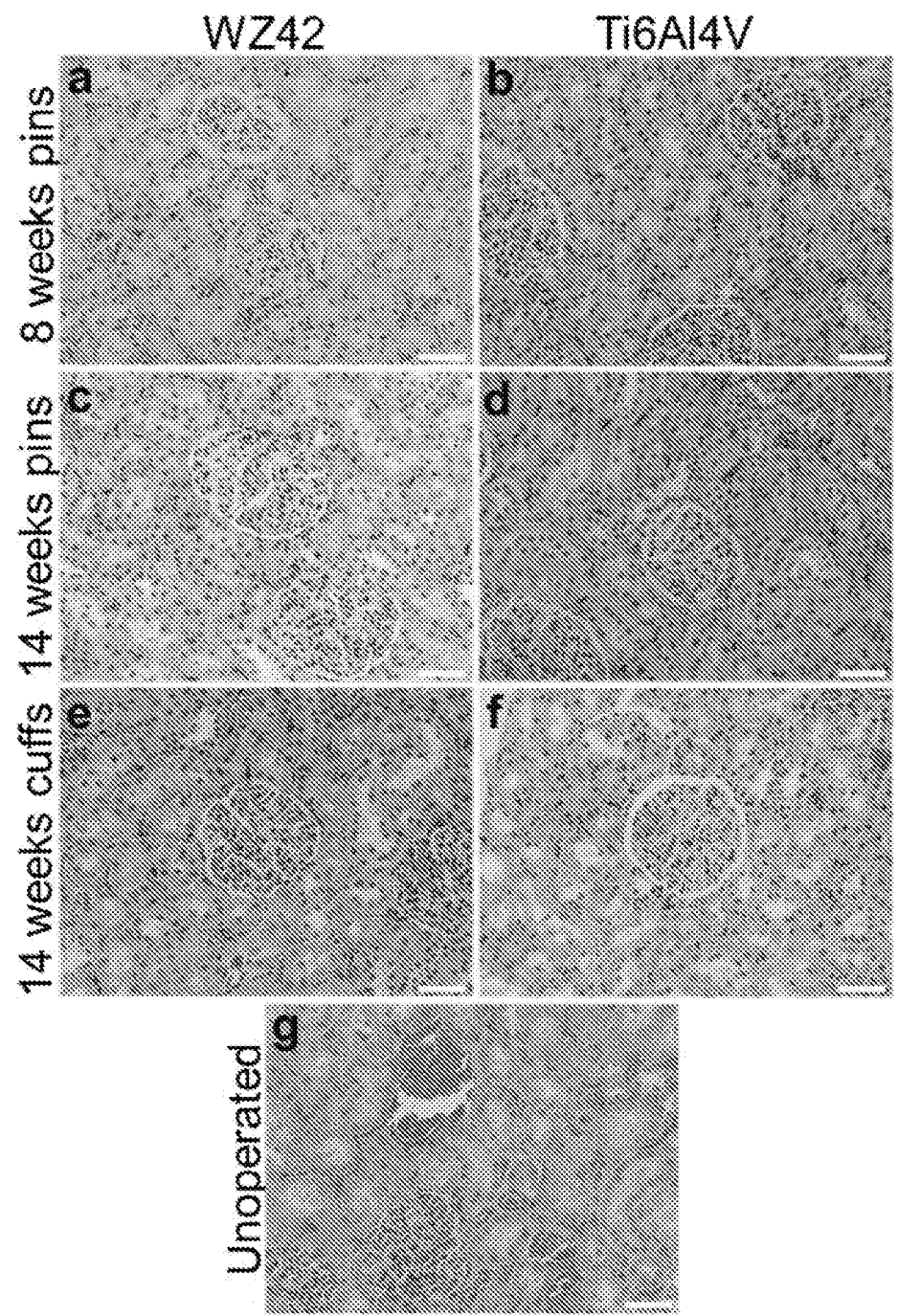
FIGURE 8.5

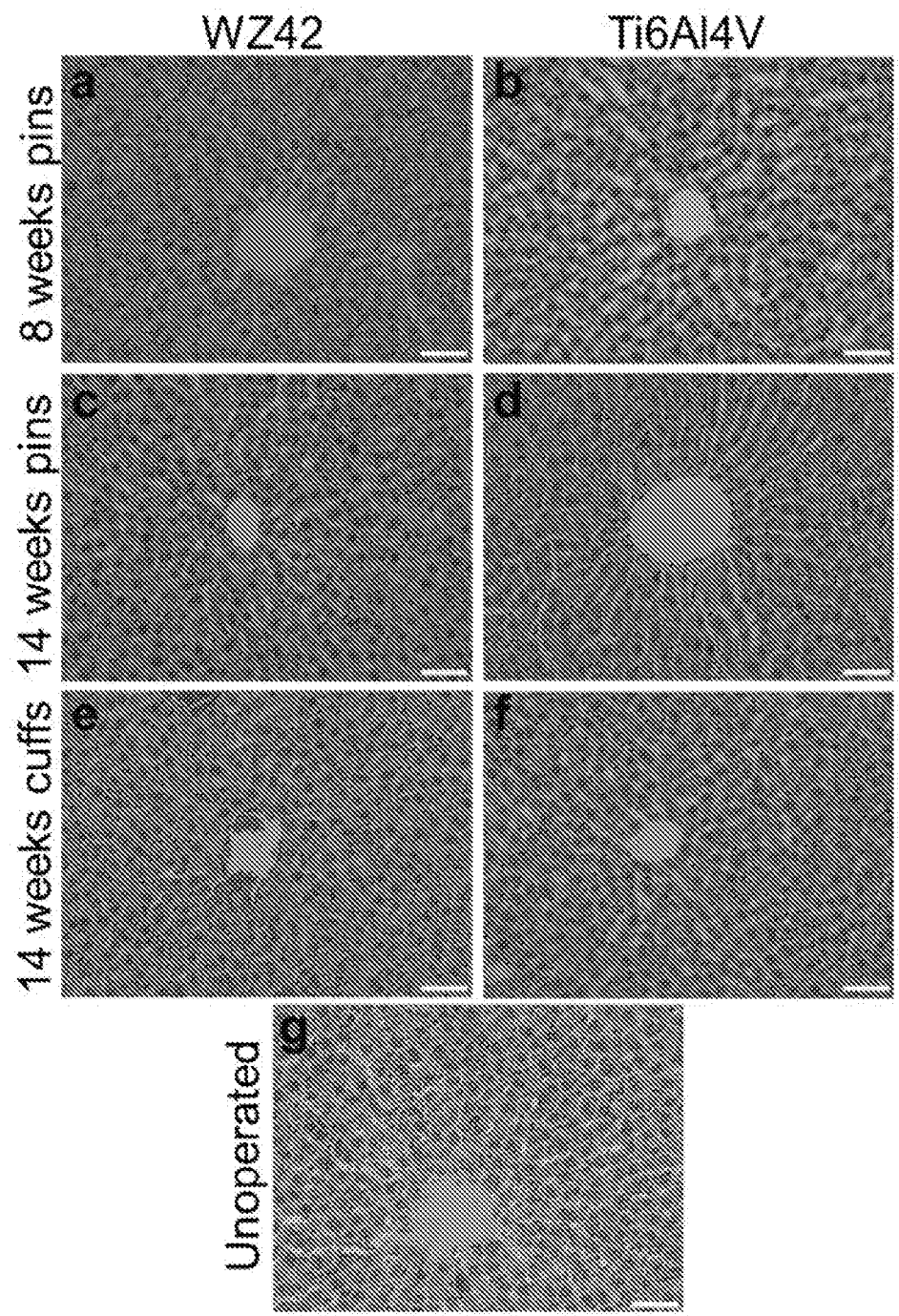
FIGURE 8.6

FIGURE 8.7

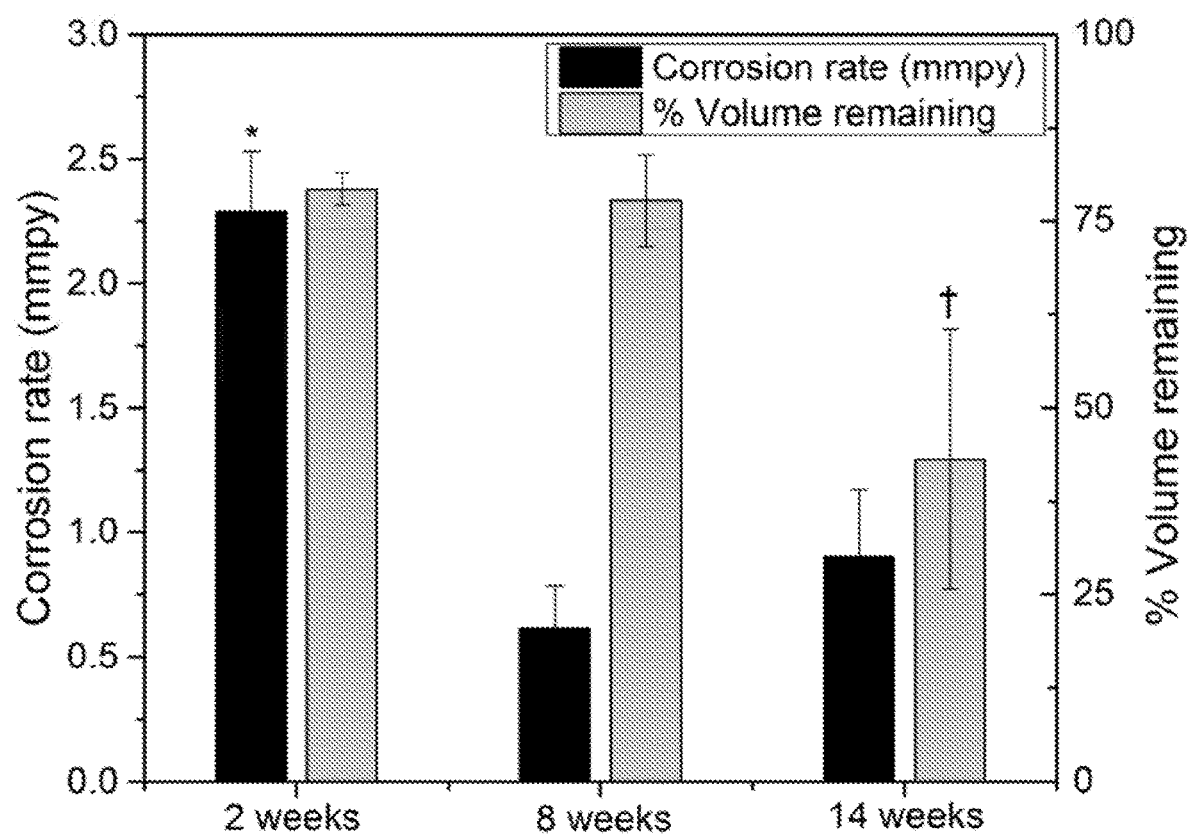
FIGURE 8.8

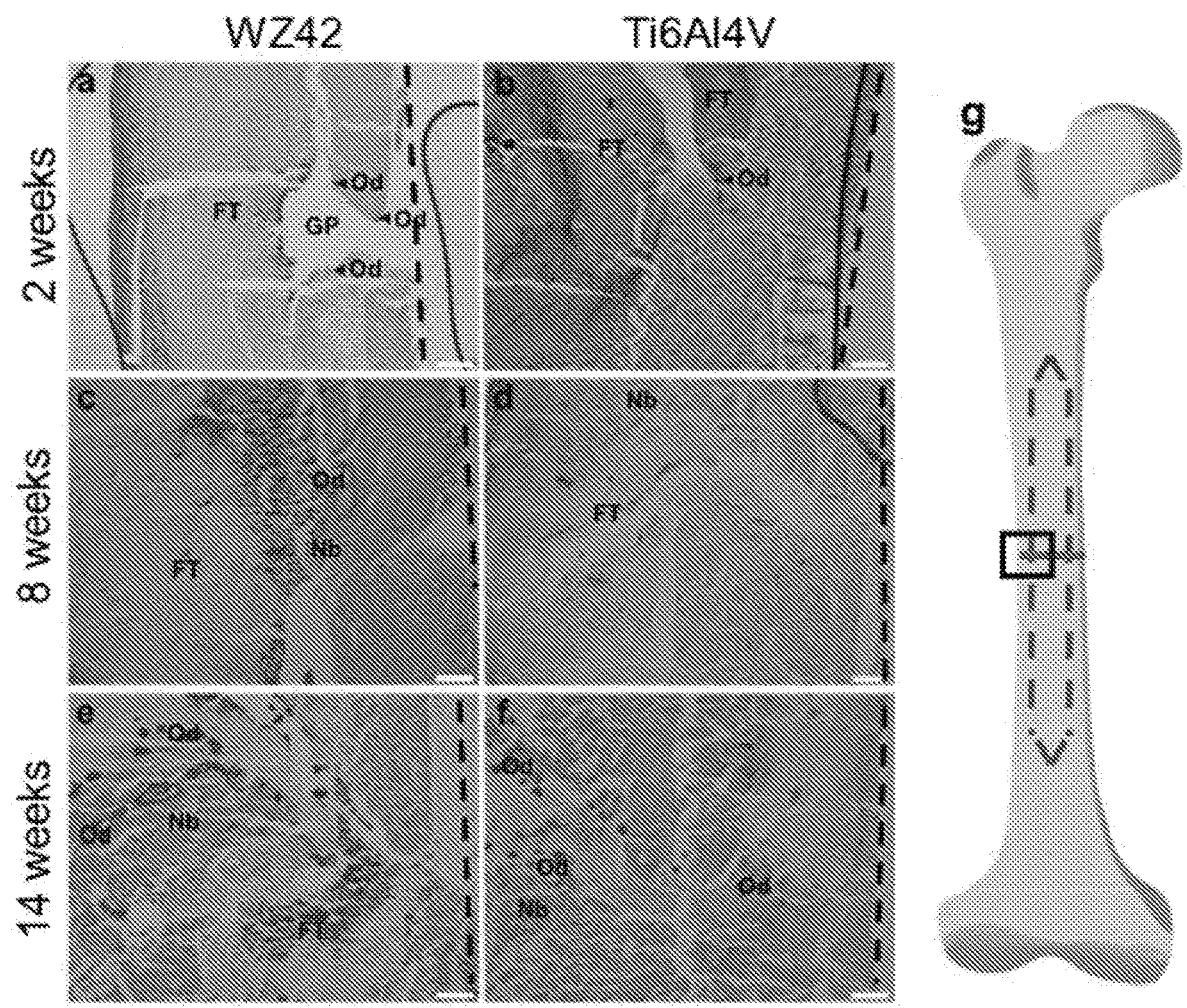
FIGURE 8.9

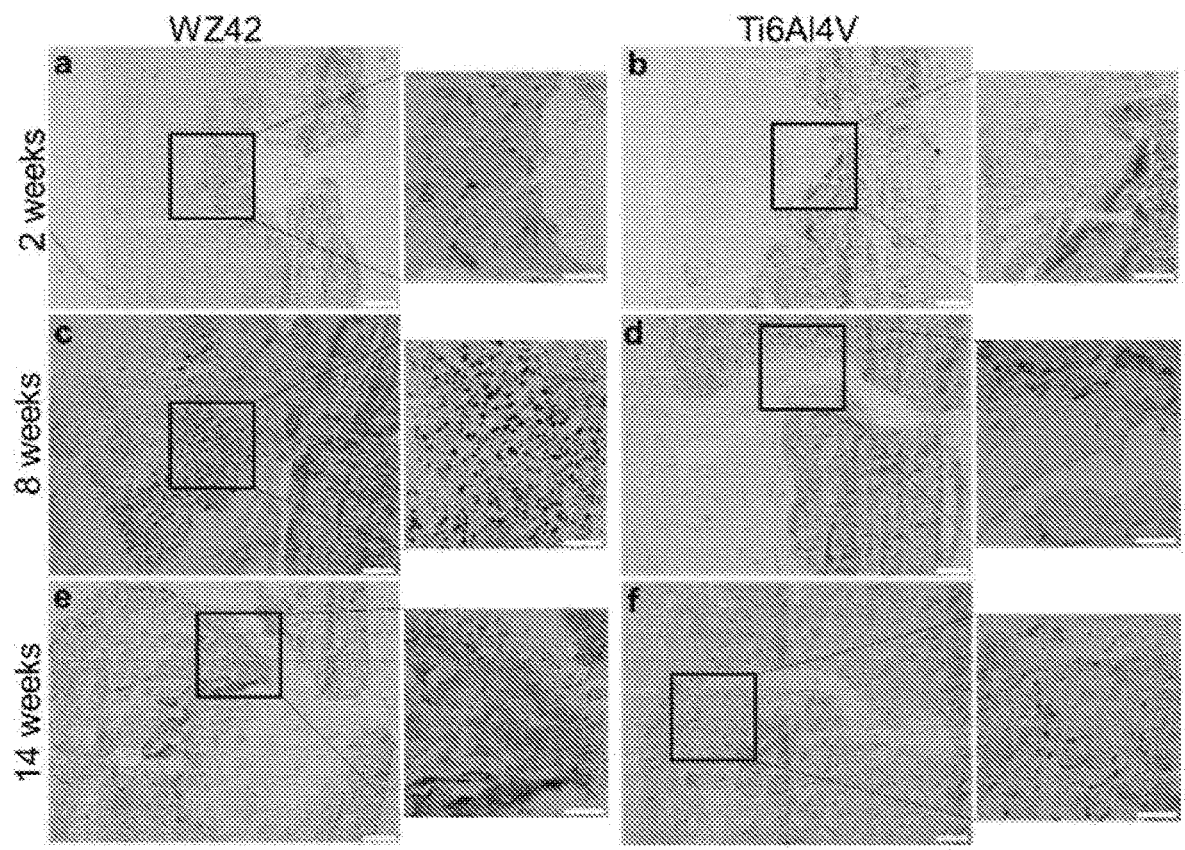
FIGURE 8.10

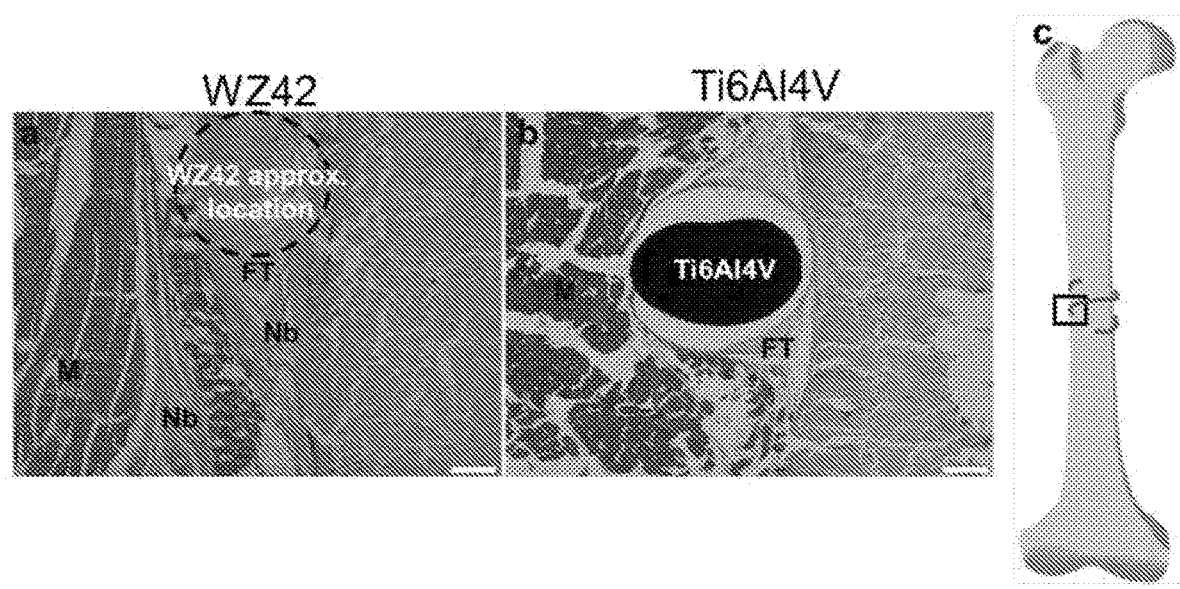
FIGURE 8.11

PROPERTIES AND PARAMETERS OF NOVEL BIODEGRADABLE METALLIC ALLOYS

CROSS-REFERENCE TO RELATED APPLICATIONS

This application is a U.S. National Stage Application under 35 U.S.C. § 371 of PCT International Application No. PCT/US2018/027346, entitled "PROPERTIES AND PARAMETERS OF NOVEL BIODEGRADABLE METALLIC ALLOYS," filed on Apr. 12, 2018, which claims priority under 35 U.S.C. § 119(e) to U.S. Provisional Patent Application Ser. Nos. 62/484,560, filed Apr. 12, 2017, entitled "PROPERTIES AND PARAMETERS OF NOVEL BIODEGRADABLE METALLIC ALLOYS", and 62/484,564, filed Apr. 12, 2017, entitled "UNIQUE CHARACTERISTICS AND PROPERTIES OF NOVEL BIODEGRADABLE METALLIC ALLOYS", which are herein incorporated by reference.

GOVERNMENT SUPPORT

This invention was made with government support under #EEC-0812348 awarded by the National Science Foundation (NSF). The government has certain rights in the invention.

FIELD OF THE INVENTION

The invention relates to metal alloys and articles therefrom, and methods for their preparation. The invention is particularly suitable for use in fabricating biodegradable materials and medical devices for implantation into a body of a patient, such as for example, orthopedic, craniofacial, bronchotracheal, Eustachian tubes and stents, ureteral stents, and cardiovascular implant devices.

BACKGROUND OF THE INVENTION

Metallic implant devices, such as plates, screws, nails and pins are commonly used in the practice of orthopedic, craniofacial and cardiovascular implant surgery. Furthermore, metallic stents are also implanted into a body of a patient to support lumens, for example, coronary arteries. Most of these metallic implant devices which are currently used are constructed of stainless steel, cobalt-chromium (Co—Cr) or titanium alloys. Advantageously, these materials of construction exhibit good biomechanical properties. However, disadvantageously, implant devices constructed of these materials do not degrade over a period of time. Thus, surgery may be required when there is no longer a medical need for the implant device and when, for various reasons, it may be desired to remove the implant device from a body of a patient. For example, in certain instances, such as pediatric applications, there may be a concern that if an implant device is not removed, it may eventually be rejected by the body and cause complications for the patient. Thus, it would be advantageous for: (i) the implant device to be constructed of a material that is capable of degrading over a period of time, (ii) for the implant device to dissolve in a physiological environment such that it would not remain in the body when there is no longer a medical need for it, and (iii) surgery not to be required to remove the implant device from the body of the patient.

Currently, biomaterials used for orthopedic, craniofacial and cardiovascular applications are primarily chosen based on their ability to withstand cyclic load-bearing. Metallic biomaterials in particular have appropriate properties such as high strength, ductility, fracture toughness, hardness, corrosion resistance, formability, and biocompatibility to make them attractive for most load bearing applications. The most prevalent metals for load-bearing applications are stainless steels, Ti, and Co—Cr based alloys, though their stiffness, rigidity, and strength far exceed those of natural bone. Their elastic modulus differs significantly from bone, causing stress-shielding effects that may lead to reduced loading of bone with this decrease in stimulation resulting in insufficient new bone growth and remodeling, decreasing implant stability. Current metallic biomaterials also suffer from the risk of releasing toxic metallic ions and particles through corrosion or wear causing implant site immune response. They may also lead to hypersensitivity, growth restriction (most significantly for pediatric implants), implant migration, and imaging interference. Due to these complications, it is estimated that 10% of patients will require a second operation for the removal of permanent metallic plates and screws, and other bone related fixation devices involving inert metals exposing patients to additional risks, and increasing surgical time and resources.

Based on at least these issues, there is a desire to design and develop a new class of load-bearing biomaterials with the goal of providing adequate support while the bone is healing that harmlessly degrades over time.

To avoid complications associated with permanent fixation implants, degradable biomaterials have recently been developed. These typically involve polymeric systems. However, resorbable polymer fixation plates and screws are relatively weaker and less rigid compared to metals, and have demonstrated local inflammatory reactions. Furthermore, they do not exhibit any osteogenic characteristics. For example, biodegradable materials which are currently used in the construction of implant devices include polymers, such as polyhydroxy acids, polylactic acid (PLA), polyglycolic acid (PGA), and the like. These materials, however, have been found to exhibit relatively poor strength and ductility, and have a tendency to react with human tissue which can limit bone growth.

Magnesium alloys have recently emerged as a new class of biodegradable materials for orthopedic applications with more comparable properties to natural bone. Magnesium is known to be a non-toxic metal element that degrades in a physiological environment and therefore, may be considered a suitable element for use in constructing biodegradable implant devices. Magnesium is attractive as a biomaterial for several reasons. It is very lightweight, with a density similar to cortical bone, and much less than stainless steel, titanium alloys, and Co—Cr alloys. The elastic modulus of magnesium is much closer to natural bone compared to other commonly used metallic implants, thus reducing the risk of stress shielding and consequent fracture of bone associated with retrieval of the implanted fixation systems. Magnesium is also essential to human metabolism, is a cofactor for many enzymes, and stabilizes the structures of DNA and RNA. Most importantly, magnesium degrades to produce a soluble, non-toxic corrosion hydroxide product which is harmlessly excreted through urine. Unfortunately, accelerated corrosion of magnesium alloys may lead to accumulation of hydrogen gas pockets around the implant as well as insufficient mechanical performance and implant stability throughout the degradation and tissue healing process. The degradation of magnesium in a physiological environment yields magnesium hydroxide and hydrogen gas. This process is known in the art as magnesium corrosion. The hydrogen gas produced in the body of the patient as a result of magnesium corrosion can produce complications because the ability of the human body to absorb or release hydrogen gas is limited.

The various biodegradable metallic alloys known in the art may exhibit low biocompatibility and/or high corrosion rates, which render these materials unsuitable for use in medical applications, such as implant devices. Further, compositions of matter for use as implant devices should not include toxic elements, such as zinc and aluminum, or at least include these elements only in non-toxic amounts. Moreover, the composition should exhibit a corrosion rate that is suitable for implantation in a physiological environment, i.e., a body of a patient.

In the field of biomedical applications, there is a desire to develop biodegradable metal alloy-containing implant materials having good compressive strength with improved corrosion resistance and biocompatibility. Further, it is desirable to control the corrosion resistance and the hydrogen evolution therefrom, which is associated with the presence of magnesium in a physiological environment.

SUMMARY OF THE INVENTION

In one aspect, the invention provides a biodegradable, metal alloy including about 4.0 weight percent of yttrium, from about 0.5-0.6 weight percent of calcium, from about 0.6-1.0 weight percent of zirconium, about 2.0 weight percent of zinc, and a balance of magnesium including impurities, based on the total weight of the composition. In certain embodiments, the metal alloy includes about 4.0 weight percent of yttrium, about 0.6 weight percent of calcium, about 1.0 weight percent of zirconium, about 2.0 weight percent of zinc, and a balance of magnesium including impurities, based on the total weight of the composition. In other embodiments, the metal alloy includes about 4.0 weight percent of yttrium, from about 0.5-0.6 weight percent of calcium, about 0.6 weight percent of zirconium, about 2.0 weight percent of zinc, and a balance of magnesium including impurities, based on the total weight of the composition.

In another aspect, the invention provides a biodegradable, metal alloy including from about 4.0-4.5 weight percent of zinc, from about 0.3-0.5 weight percent of zirconium, and a balance of magnesium including impurities, based on the total weight of the composition. In certain embodiments, the metal alloy includes about 4.0 weight percent of zinc, about 0.5 weight percent of zirconium, and a balance of magnesium including impurities, based on the total weight of the composition. In other embodiments, the metal alloy includes about 4.4 weight percent of zinc, from about 0.3-0.4 weight percent of zirconium, and a balance of magnesium including impurities, based on the total weight of the composition. The metal alloy may further include strontium or cerium, each of which constitutes from about 0.25-1.0 weight percent of the metal alloy. In certain embodiments, the stontium or cerium constitutes about 0.25 weight percent or about 1.0 weight percent of the metal alloy. The impurities can include one or more of iron, nickel and copper, and may be present in the metal alloy in a total amount of less than 20 ppm. The metal alloy may be a solid solution single phase. The Mg—Zn—Zr alloy system may include a primary phase including Mg(ZnZr). The Mg—Zn—Zr alloy system may include a secondary intermetallic phase including $Mg_7Zn_3$ precipitate, which may be minimized or precluded in the metal alloy.

In another aspect, the invention provides a method of preparing a biodegradable, metal alloy including melting about 4.0 weight percent of yttrium, from about 0.5-0.6 weight percent of calcium, from about 0.5-0.6 weight percent of zirconium, about 2.0 weight percent of zinc, and a balance of magnesium including impurities, based on the total weight of the composition, to obtain a melted mixture and casting the melt mixture to obtain said biodegradable, metal alloy.

In another aspect, the invention provides a method of preparing a biodegradable, metal alloy including melting about 4.0 weight percent of zinc, about 0.5 weight percent of zirconium, and a balance of magnesium including impurities, based on the total weight of the composition, to obtain a melted mixture and casting the melt mixture to obtain said biodegradable, metal alloy. In certain embodiments, this method further includes melting strontium or cerium, each of which constitutes from 0.25-1.0 weight percent of the metal alloy.

In yet another aspect, the invention includes a biodegradable, metal alloy-containing article including about 4.0 weight percent of yttrium, from about 0.5-0.6 weight percent of calcium, from about 0.5-0.6 weight percent of zirconium, about 2.0 weight percent of zinc, and a balance of magnesium including impurities, based on the total weight of the composition.

In yet another aspect, the invention includes a biodegradable, metal alloy-containing article including about 4.0 weight percent of zinc, about 0.5 weight percent of zirconium, and a balance of magnesium including impurities, based on the total weight of the composition. In certain embodiments, this metal alloy further includes strontium or cerium, each of which constitutes from 0.25-1.0 weight percent of the metal alloy.

In certain embodiments, the article is a medical device. The medical device can be implantable in a body of a patient. In another embodiment, the medical device can be an orthopedic device. In yet another embodiment, the medical device can be a craniofacial device. In still another embodiment, the medical device can be a cardiovascular device as well as a device for pulmonary and bronchotracheal device applications, including Eustachian tubes and tents, and ureteral stents.

BRIEF DESCRIPTION OF THE DRAWINGS

A further understanding of the invention can be gained from the following description of the preferred embodiments when read in conjunction with the accompanying drawings in which:

FIG. 1.1 shows XRD patterns of metal alloys, in accordance with certain embodiments of the invention;

FIG. 1.2 shows optical micrographs of metal alloys, in accordance with certain embodiments of the invention;

FIG. 1.3 is a SEM micrograph of as-cast Mg alloy, in accordance with certain embodiments of the invention;

FIG. 1.4 is shows the nanoCT scan image of as-cast Mg—Zn—Zr alloys, in accordance with certain embodiments of the invention;

FIG. 1.5 shows the formation of a passivation layer for metal alloys, in accordance with certain embodiments of the invention;

FIG. 1.6 shows corrosion morphology for metal alloys, in accordance with certain embodiments of the invention;

FIG. 2.1 shows fractographs of the cross-sectional surfaces after tensile testing of Mg alloys, in accordance with certain embodiments of the invention;

FIG. 2.2 is a bar graph showing corrosion rate of Mg and Mg alloys for 1, 2 and 3 weeks, in accordance with certain embodiments of the invention;

FIG. 2.3 shows the surface morphology of the corroded surfaces of as-cast and solution treated Mg alloys, in accordance with certain embodiments of the invention;

FIG. 2.4 shows osteoblastic cultured MC3T3 cells;

FIG. 2.5 shows the morphology of fixed MC3T3 cells;

FIG. 2.6 is a bar graph showing the viability of Mg, and as-cast and solution treated Mg alloys, in accordance with certain embodiments of the invention;

FIG. 2.7 is a histological image of local sites of implants of Mg alloys, in accordance with certain embodiments of the invention;

FIG. 2.8 is a bar graph showing the corrosion rate of Mg, and as-cast and solution treated Mg alloys, in accordance with certain embodiments of the invention;

FIG. 3.1 shows XRD patterns of metal alloys, in accordance with certain embodiments of the invention;

FIG. 3.2 shows BSE microscopy images of Mg alloys, in accordance with certain embodiments of the invention;

FIG. 3.3 is a bar graph showing the corrosion rate of Mg alloys for 7 and 35 days, in accordance with certain embodiments of the invention;

FIG. 3.4 are bar graphs showing cell viability for Mg and Mg alloys, in accordance with certain embodiments of the invention;

FIG. 3.5 is a bar graph showing ALP activity for 7 days and 14 days, in accordance with certain embodiments of the invention;

FIG. 3.6 are bar graphs showing ALP and OPN gene expression for samples, in accordance with certain embodiments of the invention;

FIG. 4.1 are photographs showing implantation of sample devices, in accordance with certain embodiments of the invention;

FIG. 4.2 are x-ray images showing implanted Mg alloy, in accordance with certain embodiments of the invention;

FIG. 4.3 are micro-CT images of implanted Mg alloy, in accordance with certain embodiments of the invention;

FIG. 4.4 are bar graphs showing corrosion rate and volume remaining after 2 weeks and 14 weeks, in accordance with certain embodiments of the invention;

FIG. 4.5 are plots showing Mg concentratin in the kidney and liver after 2 weeks and 14 weeks, in accordance with certain embodiments of the invention;

FIG. 4.6 shows hematoxylin and eosin staining of liver and kidney tissue sections to illustrate tissue morphology due to implantation, in accordance with certain embodiments of the invention;

FIG. 4.7 shows staining of rat femoral sections to illustrate a typical fracture healing, in accordance with certain embodiments of the invention;

FIG. 5.1 shows XRD patterns of as-cast pure Mg;

FIG. 5.2a-f are optical micrographs of alloys after polishing and etching, in accordance with certain embodiments of the invention;

FIG. 5.3a-d are SEM images of alloys after polishing and etching, in accordance with certain embodiments of the invention;

FIG. 5.4 shows XRD patterns of extruded alloys, in accordance with certain embodiments of the invention;

FIG. 5.5a-j are optical micrographs showing the microstructure of Mg alloys extruded with extrusion ratio 10, in accordance with certain embodiments of the invention;

FIG. 5.6a-d are SEM images and EDX analysis at indicated locations of Mg alloys after polishing and etching, in accordance with certain embodiments of the invention;

FIG. 6.1 shows corrosion properties of Mg—Y—Ca—Zr alloys, as-cast 99.99% pure Mg and AS31 in DMEM with 10% FBS, in accordance with certain embodiments of the invention;

FIG. 6.2 are SEM images that show surface morphologies of metal alloys, in accordance with certain embodiments of the invention:

FIG. 6.3 are SEM images that show surface morphologies of metal alloys, in accordance with certain embodiments of the invention;

FIG. 6.4 are SEM images that show surface morphologies of metal alloys, in accordance with certain embodiments of the invention;

FIG. 6.5 shows average corrosion rates of extruded metal alloys, in accordance with certain embodiments of the invention;

FIG. 6.6 are SEM images that show surface morphologies of extruded metal alloys, in accordance with certain embodiments of the invention;

FIG. 6.7 are SEM images that show cross-sectional morphologies of extruded metal alloys, in accordance with certain embodiments of the invention;

FIG. 6.8 shows Vickers microhardness of extruded Mg alloys, in accordance with certain embodiments of the invention;

FIG. 6.9 shows mechanical properties of metal alloys, in accordance with certain embodiments of the invention;

FIG. 6.10 shows average ultimate tensile strength and strain of extruded Mg alloys, in accordance with certain embodiments of the invention;

FIG. 6.11 shows average tensile yield strength and Young's modulus of extruded Mg alloys, in accordance with certain embodiments of the invention;

FIG. 6.12 shows yield tensile strength and elongation of cast and wrought Mg alloys, in accordance with certain embodiments of the invention;

FIG. 7.1 shows fluorescent images of cells attached on a metal alloy, in accordance with certain embodiments of the invention;

FIG. 7.2 shows cells on the surface of polished and extruded Mg alloy surfaces, in accordance with certain embodiments of the invention;

FIG. 7.3 shows phalloidin staining of MC3T3 cells on the surface of polished and extruded Mg alloy surfaces, in accordance with certain embodiments of the invention;

FIG. 7.4 shows SEM images of MC3T3 cells attached to the surface of extruded metal alloys, in accordance with certain embodiments of the invention;

FIG. 7.5 shows average weight percent of Ca and P on the surface of extruded Mg alloy samples, in accordance with certain embodiments of the invention;

FIG. 7.6 shows the viability of cultured MC3T3 cells, in accordance with certain embodiments of the invention;

FIG. 7.7 shows the viability of cultured MC3T3 cells, in accordance with certain embodiments of the invention;

FIG. 7.8 shows the proliferation of cultured MC3T3 cells, in accordance with certain embodiments of the invention;

FIG. 7.9 shows fluorescense images of MC3T3 cells esposed to extruded alloy extracts, in accordance with certain embodiments of the invention;

FIGS. 7.10a, b and c are bar graphs showing extract concentrations for 1 day, 3 days and 5 days, respectively, in accordance with certain embodiments of the invention;

FIG. 7.11 shows fluorescence images of hMSCs, in accordance with certain embodiments of the invention;

FIGS. 7.12a, b and c are bar graphs showing extract concentrations for 3 days, 7 days and 14 days, respectively, in accordance with certain embodiments of the invention;

FIGS. 7.13a, b and c are bar graphs showing gene expression data of hMSCs cultured for 7 days, 14 days and 21 days, respectively, in accordance with certain embodiments of the invention;

FIGS. 7.14a, b and c are bar graphs showing proliferation data of hMSCs cultured for 1 day, 3 days and 5 days, respectively, in accordance with certain embodiments of the invention;

FIG. 7.15 shows fluorescence images of hMSCs, in accordance with certain embodiments of the invention;

FIG. 7.16 is a bar graph showing SLP activity for hMSCs, in accordance with certain embodiments of the invention;

FIG. 7.17a-l show histology images of skin above implants after 7 days (a-d), 40 days (e-h), and 70 days (i-l), in accordance with certain embodiments of the invention;

FIG. 7.18 is a bar graph showing corrosion rate at 40 days and 70 days, in accordance with certain embodiments of the invention;

FIG. 7.19a-d are SEM images showing surface morphologies after 70 days implantation, in accordance with certain embodiments of the invention;

FIG. 7.20a-d are SEM images showing surface morphologies after 70 days implantation, in accordance with certain embodiments of the invention;

FIGS. 7.21a and b is a schematic and photograph, respectively, of pins and wire, in accordance with certain embodiments of the invention;

FIG. 8.1 a-b show sample devices in accordance with certain embodiments.

FIG. 8.2a-g are photographs showing implantation of sample devices, in accordance with certain embodiments of the invention;

FIG. 8.3a-e are x-ray images showing implanted magnesium alloy, in accordance with certain embodiments of the invention;

FIG. 8.4a-c are plots showing Mg, Ca and Zn concentration, respectively, of implants, in accordance with certain embodiments of the invention;

FIG. 8.5a-g are photomicrographs of H&E stained kidneys after 8 weeks (a,b) and 16 weeks (c,d), in accordance with certain embodiments of the invention;

FIG. 8.6a-g are photomicrographs of H&E stained kidneys after 8 weeks (a,b) and 16 weeks (c,d), in accordance with certain embodiments of the invention;

FIG. 8.7a-d are micro-CT scans of degrading alloy implants at 2 weeks, 8 weeks and 14 weeks, respectively, in accordance with certain embodiments of the invention;

FIG. 8.8 is a bar graph showing corrosion rate of implants at 2 weeks, 8 weeks and 14 weeks, respectively, in accordance with certain embodiments of the invention;

FIG. 8.9a-f are photomicrographs of stained sections of soft and hard tissue at a defect site fixed by pins of metal alloys, in accordance with certain embodiments of the invention;

FIG. 8.10a-f are photomicrographs of localization of ALP of tissue at a defect site fixed by pins of metal alloys, in accordance with certain embodiments of the invention; and FIG. 8.11 a-c are photomicrographs of stained sections of soft and hard tissue at a defect site fixed by pins of metal alloys, in accordance with certain embodiments of the invention.

DETAILED DESCRIPTION OF THE PREFERRED EMBODIMENTS

The invention relates to novel, biodegradable metal alloys. Further, the invention relates to articles, such as medical devices for implantation into a body of a patient, which are constructed or fabricated from the biodegradable metal alloys of the invention. Moreover, the invention relates to methods of preparing these biodegradable, metal alloy-containing compositions and articles for use in medical applications, such as but not limited to, orthopedic, craniofacial, bronchotracheal, Eustachian, ureteral and cardiovascular surgery.

In addition to the biodegradability of the metal alloys of the invention include at least one of the following characteristics: biocompatibility, corrosion resistance, cell attachment, viability and mechanical strength, which make them suitable for use as implant devices in a body of a patient.

In certain embodiments, the biodegradable, metal alloys of the invention are based on the presence of magnesium. The amount of magnesium and additional elements are selected such that the resulting alloys exhibit the desired characteristics identified herein. For example, alloy elements and their amounts are selected such that the alloys exhibit corrosion resistance in the presence of water and simulated body fluids which allow the compositions to be suitable for in vitro use, for example, in a physiological environment, such as a body of a patient.

In other embodiments, the biodegradable, metal alloys of the invention are prepared using selected elements in specified amounts such that the alloys exhibit corrosion resistance with minimal or no evolution of hydrogen gas. The evolution of hydrogen, such as, hydrogen bubbles can result in complications within a body of a patient.

This invention includes controlling the corrosion rate and improving mechanical properties of magnesium alloys through the introduction of alloying elements and processing conditions. Magnesium corrosion and mechanical properties are strongly affected by alloying elements in the solid solution.

The alloy elements are selected to provide a solid solution, single phase alloy. For example, wherein the alloy includes magnesium, zinc and zirconium, a desired primary phase of Mg(ZnZr) is formed in the Mg—Zn—Zr system, and a secondary phase (intermetallic phase) of $Mg_7Zn_3$ precipitate may be formed from the Mg—Zn—Zr system, which is preferably minimized or precluded. It has been found that preparation of magnesium alloys can result in the formation of an intermetallic phase along grain boundaries. The metal alloys of the invention can have an average grain size less than about 100 μm. In certain embodiments, the average grain size is from about 50-100 μm. Further, it is preferable to minimize the presence of impurities. Impurities can include one or more of iron, nickel and copper. In certain embodiments, the total impurities constitute less than 20 ppm of the alloy.

The biodegradable, metal alloys of the invention include the following components: yttrium, calcium, zirconium, zinc and magnesium. In certain embodiments, strontium and/or cerium may be added. The biodegradable, metal alloys of the invention also include the following components: zinc and magnesium, and optionally strontium and/or cerium; and zirconium, zinc and magnesium, and optionally strontium and/or cerium. The amount of each of these components in the compositions can vary. In general, the amounts of each of these components are selected in order that the resulting compositions are within acceptable non-toxic limits such that the compositions are sufficiently biocompatible for implantation into a body of a patient, and are degradable over a period of time so that the implantation device does not remain in the body of the patient for prolonged periods of time, e.g., not beyond the period of time when there is a medical need for the implantation device. An implantation device fabricated in accordance with the invention will degrade and preferably completely dissolve within an acceptable time frame. For example, an implant device fabricated in accordance with the invention can serve as filler or support material during a bone healing process and following completion of this process, the implant device will degrade within an acceptable time period and therefore, will not remain in the body for a prolonged period of time. The acceptable non-toxic limits and the acceptable time frame for degradation can vary and can depend on particular physical and physiological characteristics of the patient, the particular in vivo site of the implantation device, and the particular medical use of the implantation device.

In certain embodiments, the metal alloys of the invention include about 4.0 weight percent of yttrium, from about 0.5-0.6 weight percent of calcium, from about 0.6-1.0 weight percent of zirconium, about 2.0 weight percent of zinc, and a balance of magnesium including impurities, based on the total weight of the composition. In other embodiments, the metal alloys include about 4.0 weight percent of yttrium, about 0.6 weight percent of calcium, about 1.0 weight percent of zirconium, about 2.0 weight percent of zinc, and a balance of magnesium including impurities, based on the total weight of the composition. In other embodiments, the metal alloys include about 4.0 weight percent of yttrium, from about 0.5-0.6 weight percent of calcium, about 0.6 weight percent of zirconium, about 2.0 weight percent of zinc, and a balance of magnesium including impurities, based on the total weight of the composition.

In certain embodiments, the metal alloys of the invention include from about 4.0-4.5 weight percent of zinc, from about 0.3-0.5 weight percent of zirconium, and a balance of magnesium including impurities, based on the total weight of the composition. In certain embodiments, the metal alloys include about 4.0 weight percent of zinc, about 0.5 weight percent of zirconium, and a balance of magnesium including impurities, based on the total weight of the composition. In other embodiments, the metal alloys include about 4.4 weight percent of zinc, from about 0.3-0.4 weight percent of zirconium, and a balance of magnesium including impurities, based on the total weight of the composition. The metal alloys may further include strontium or cerium, each of which constitutes from about 0.25-1.0 weight percent of the metal alloy. In certain embodiments, the stontium or cerium constitutes about 0.25 weight percent or about 1.0 weight percent of the metal alloy.

As aforementioned, the impurities can include one or more of iron, nickel and copper, and may be present in the metal alloy in a total amount of less than 20 ppm. The metal alloy may be a solid solution single phase. An intermetallic phase may be minimized or precluded.

Without intending to be bound by any particular theory, it is believed that the presence of yttrium contributes to the improved mechanical strength and corrosion resistance of the biodegradable, metal alloy-containing compositions. Calcium is used in a low quantity to prevent oxidation during the casting of the alloy. Zirconium is known to act as a grain refiner and is used to improve mechanical properties of the compositions.

As described previously herein, the use of magnesium-containing compositions in a physiological environment results in the evolution or production of hydrogen gas. The degradation of magnesium involves a process (i.e., a corrosion process) in which hydrogen is released. In the invention, the amount of magnesium and the other alloying element are specified such that the corrosion rate corresponds to a rate of hydrogen formation which is acceptable such that large amounts of hydrogen bubbles do not form and accumulate within a body of a patient.

In certain embodiments, the amounts of yttrium, calcium, zirconium, zinc and magnesium are specified and adjusted such as to control at least one of the following, namely, corrosion resistance, biodegradation, biocompatibility, toxicity, cell attachment, mechanical strength and flexibility. In other embodiments, the amounts of zinc, zirconium and magnesium are specified and adjusted such as to control at least one of the following, namely, corrosion resistance, biodegradation, biocompatibility, toxicity, cell attachment, mechanical strength and flexibility.

Further, in certain embodiments, other compounds may be added to impart additional characteristics and properties to the resulting biodegradable, metal alloy-containing compositions. As aforementioned, strontium or cerium may be added. In addition, one or more of aluminum, manganese and silver may be added in an amount that is effective to provide anti-microbial properties. In certain embodiments, aluminum is present in an amount of from about 1.0 to 9.0 weight percent based on total weight of the composition. In other embodiments, the aluminum is present in an amount of about 2.0 weight percent based on total weight of the composition. In certain embodiments, manganese is present in an amount of from about 0.1 to about 1.0 weight percent based on total weight of the composition. In other embodiments, the manganese is present in an amount of about 0.2 weight percent based on total weight of the composition. In certain embodiments, silver is present in an amount of from about 0.25 to about 1.0 weight percent based on total weight of the composition. In other embodiments, the silver is present in an amount of about 0.25 weight percent based on total weight of the composition.

Non-limiting examples of medical devices in which the compositions and articles of the invention can be used include, but are not limited to plates, wires, tubes, stents, membranes, meshes, staples, screws, pins, tacks, rods, suture anchors, tubular mesh, coils, x-ray markers, catheters, endoprostheses, pipes, shields, bolts, clips or plugs, dental implants or devices, graft devices, bone-fracture healing devices, bone replacement devices, joint replacement devices, tissue regeneration devices, cardiovascular stents, bronchotracheal stents, ureteral stents, Eustachian tubes and membranes, intercranial aneurism device, tracheal stents, nerve guides, surgical implants and wires. In a preferred embodiment, the medical devices include fixation bone plates and screws, temporamandibular joints, cardiovascular stents, and nerve guides.

The medical devices described herein can have at least one active substance attached thereto. The active substance can be either attached to the surface or encapsulated within. As used herein, the term "active substance" describes a molecule, compound, complex, adduct and/or composite that exhibits one or more beneficial activities such as therapeutic activity, diagnostic activity, biocompatibility, corrosion, and the like. Active substances that exhibit a therapeutic activity can include bioactive agents, pharmaceutically active agents, drugs and the like. Non-limiting examples of bioactive agents that can be incorporated in the compositions, articles and devices of the invention include, but are not limited to, bone growth promoting agents such as growth factors, drugs, proteins, antibiotics, antibodies, ligands, aptamers, DNA, RNA, peptides, enzymes, vitamins, cells and the like, and combinations thereof.

The biodegradable, metal alloy-containing compositions of the invention can be prepared using various methods and processes. In general, melting and casting methods and processes are employed. It is known in the art of metallurgy that casting is a production technique in which a metal or a mixture of metals is heated until molten and then, poured into a mold, allowed to cool, and thereby solidify. In certain embodiments, the melted or molten metal or mixture of metals is poured into the mild steel/copper mold at room temperature to 500° C. In certain embodiments, following melting and/or casting, the metal alloy is subjected to a subsequent heat treatment at a temperature from about 250° C. to 350° C. In certain embodiments, the temperature of the heat treatment is about 300° C.

Casting of the compositions of the invention can be affected by using any casting procedure known in the art, such as, but not limited to, sand casting, gravity casting, permanent mold casting, direct chill casting, centrifugal casting, low/high pressure die casting, squeeze casting, continuous casting, vacuum casting, plaster casting, lost foam casting, investment casting, and lost wax casting including injection molding. It is believed that the particular process used for casting can affect the properties and characteristics of the cast composition. Further, it is believed that the temperature at which the melting procedure is performed can also affect the composition. Thus, the temperature may be carefully selected so as to maintain the desired composition of the alloy.

In certain embodiments of the invention, yttrium, calcium, zirconium, zinc and magnesium elements (in specified amounts as described herein) are melted by heating at an elevated temperature, preferably under a protective atmosphere, and then poured into a mold, in the presence or absence of a ceramic filter, allowed to cool and solidify. In another embodiment of the invention, zinc, zirconium and magnesium elements (in specified amounts as described herein) are melted by heating at an elevated temperature, preferably under a protective atmosphere, and then poured into a mold, in the presence or absence of a ceramic filter, allowed to cool and solidify.

In certain embodiments, prior to solidification, the molten mixture is tested to determine the amount of the various components therein and therefore, to provide an opportunity to adjust the amounts as desired prior to solidification.

In other embodiments, the melting and/or casting steps are/is performed under a protective atmosphere to preclude, minimize or reduce oxidation/decomposition of the components in the composition. In particular, it is desirable to preclude, minimize or reduce the oxidation/decomposition of magnesium in the composition. The protective atmosphere can include compounds selected from those known in the art, such as but not limited to, argon, sulfur hexafluoride, carbon dioxide, dry air and mixtures thereof.

In yet other embodiments, subsequent to the casting process, the magnesium-containing cast is subjected to homogenization. Without intending to be bound by any particular theory, it is believed that a homogenization treatment can cause the spreading of, or more even or uniform distribution of, impurities, secondary phase(s), and intermetallic phases, if present therein.

In further embodiments, the resulting cast can be subjected to various forming and finishing processes known in the art. Non-limiting examples of such processes include, but are not limited to, extrusion, forging, rolling, equal channel angular extrusion, stamping, deep-drawing, wire-drawing, polishing (by mechanical and/or chemical means), surface treating (to form a superficial layer on the surface), injection molding, and combinations thereof. In certain embodiments, wherein extrusion is performed, the extrusion ratio is from about 10 to 700, or from about 10 to 100, or about 30. Further, the extrusion temperature may be from about 350° C. to 450° C.

The resulting cast can be formed, finished, machined and manipulated to produce articles and devices for use in medical applications, such as medical devices for implantation into a body of a patient. Furthermore, these medical devices can be used in orthopedic, craniofacial and cardiovascular applications.

Detailed exemplary procedures for performing the melting and casting processes are depicted in the following examples.

The biodegradable, metal alloy-containing compositions of the invention can be used to produce various articles, such as medical devices suitable for implantation into a body of a patient. In preferred embodiments, the medical implant devices include orthopedic, bronchotracheal, Eustachian tubes and stents, ureteral stents, craniofacial and cardiovascular devices.

Additional objects, advantages and novel features of the invention may become apparent to one of ordinary skill in the art based on the following examples, which are provided for illustrative purposes and are not intended to be limiting.

EXAMPLES

Example 1

Mg—Zn—Zr alloys may be suitable for corrosion resistant lightweight structural applications to replace certain steel and aluminum materials. Its corrosion resistance and favorable mechanical properties are essential characteristics for biodegradable metal application. Optimal processing conditions are needed to obtain a high quality Mg alloy with low impurities and desired microstructure. Low impurities and microstructure directly correlate with corrosion and mechanical properties. Impurities such as ion (Fe), nickel (Ni), and copper (Cu) serve as a nucleation site for initiating corrosion and causing pitting corrosion which leads to heterogeneous degradation of the biodegradable Mg alloys. Micro structure also contributes to the mechanical properties of Mg alloys. Processing conditions such as melting temperature, settling time, heat treatment techniques, and impurity level of pure ingots essentially control the quality of Mg alloys in terms of impurities and microstructure. Therefore, processing conditions can impact, e.g., control, the impurity levels and the microstructure to calibrate the integrity of Mg alloy assessment in terms of achieving acceptable corrosion resistance, mechanical properties, combined with cytocompatibility as well as biocompatibility.

Experimental Design

Conventional Melting and Casting

High-purity pure Mg (US Magnesium, 99.97%), Zn (Alfa aesar, 99.99%), and Zirmax (Mg-33Zr master alloy, Mg Elektron, Commercial grade) were used for producing Mg-4 wt. % Zn-0.5 wt. % Zr (ZK40) alloy to minimize the impurity level in the final alloy ingot. Pure Mg, Zn, and Zirmax were weighed and melted in a stainless steel crucible using an electrical resistant furnace at 700° C. under protective atmosphere. The molten metal was stirred using a stainless steel rod, allowed to set for 30 minutes, and cast in a mild steel mold preheated at 500° C. Following melting and casting of the alloys, 1 cm from the top, bottom, and side of the cast ingots were correspondingly removed, and the remaining piece of ingots were used to minimize the probability of retention of voids and impurities resulting from the melting and casting processes.

Post Processing

Solution treatment was mainly investigated to solubilize the solutes into α-Mg matrix in the microstructure of ZK40 alloy. Based on the Mg—Zn binary phase diagram, a eutectic composition of $Mg_7Zn_3$ at 325° C. transforms into α-Mg and MgZn intermetallic during solidification. The $Mg_7Zn_3$ composition is known to undergo eutectic transformation below 325° C. forming α-Mg(Zn, Zr) solid solution and MgZn intermetallic which can exist as the second phase precipitates nucleating along the grain boundaries. These second phase precipitates are undesired from the corrosion point of view contributing to galvanic corrosion albeit serving to improve the mechanical strength. The accelerated corrosion however outweighs the advantages of mechanical strengths and hence is undesired. Since the T4 treatment comprises heat treatment conducted above 325° C., this can lead to unwanted second phase precipitation which is undesirable as mentioned above and grain growth which is also not desirable since large grains can contribute to lower mechanical strengths. Thus, the ZK40 alloy was correspondingly heat-treated at 300° C. for 1 hour followed by quenching in silicon oil to suppress the precipitation of these undesired secondary phases.

Phase and Microstructure Characterization

X-ray diffraction (XRD) was performed to determine the phase(s) formation using Philips X'Pert Pro system employing the CuKα ($\lambda=1.54056$ Å) radiation operated at 45 kV and 40 mA at 2θ range of 10-80°. Alloy specimens were mounted in epoxy resin and polished using 9, 3, 1 μm diamond slurry, and 0.5 μm colloidal silica slurry to obtain mirror finish surface. Polished surface were imaged using back-scattered scanning electron microscopy (SEM) to observe the microstructure and precipitates. Energy-dispersive spectrometry (EDS) probe was used along with SEM to analyze the elemental content of precipitates and grain matrices. Finally, polished surface were etched and observed using optical microscopy to obtain the optical microstructure images.

Impurity Characterization

Impurities in ZK40 alloys were analyzed using inductively coupled plasma-optical emission spectroscopy (ICP-OES, iCAP duo 6500 Thermo Fisher, Waltham, Mass.) to confirm the real chemical composition of the as-cast ingots. Melting process can alter the final composition of the cast ingots due to evaporation and oxidation. Also, the presence of Fe, Ni, and Cu as mentioned earlier, can elevate the corrosion rates of Mg alloys. Therefore, ICP-OES measurement of ZK40 was performed utilizing Mg, Zn, Zr, Fe, Ni, and Cu as standards. The content of precipitation along the grain boundary observed in back-scattered SEM microstructure analysis was assessed using EDS probe attached to SEM to check if unwanted impurities exist.

Statistical Considerations

Grain sizes of ZK40 alloy after different heat treatment conditions will be analyzed using the t-test. The content of impurity levels from ICP analysis was saved for ANOVA analysis with corrosion rates as a dependent variable among the different batches, if batch to batch corrosion rates are observed to be very different. These statistical analyses were performed using Statistical Packages for Social Studies (SPSS) 17.0 (IBM). The results were correspondingly judged for significance at $p<0.05$.

Anticipated Results

Single phase form of Mg, α-Mg with restricted precipitation of the second phase is anticipated in the microstructure of the as-cast ingot. Correspondingly, low impurity levels (less than 20 ppm) for Fe, Ni, and Cu are also anticipated. Grain growth is also restricted to be in the size range lower than 100 μm to preserve the mechanical strength. Melting temperature, protective gas, heat treatment temperature and duration were thus investigated to optimize the impurity level and achieve the desired microstructure. Processing conditions were also correlated with corrosion resistance, mechanical properties, and biocompatibility, and further optimized during the development of the biodegradable Mg—Zn based alloy.

Mg Alloy Melting and Casting

Pure elemental ingots of Mg (US magnesium Inc. 99.97%), Zn shots (Alfa-Aesar 99.99%), were melted in a mild steel crucible inside an electrical resistance furnace (Wenesco Inc.). A typical melt size was 200 g. The melt was covered with (0.5% $SF_6$+balance Ar) protective gas atmosphere to prevent burning and loss of magnesium. Once the desired melting temperature (700° C.) was reached, equivalent amount of zirconium was added using Zirmax® (Mg-33.3 wt % Zr) master alloy (Magnesium Elektron Ltd.). The liquid melt after zirconium addition was stirred for 10 s after 1 min and 5 min intervals to dissolve and disperse the zirconium particles uniformly into the melt. Further, the melt was held for 30 min at 700° C. and then poured into a preheated mild steel mold (Ø44.5 mm×82.5 mm) at 500° C.

Heat Treatment

The as-cast ingots obtained were solution treated (T4) at 300° C. for 1 h inside a tubular furnace covered with magnesium powder as a getter under protective atmosphere of Ar and $SF_6$ and then quenched into water.

X-Ray Diffraction

The alloys were characterized for phase(s) formation using x-ray diffraction. Accordingly, x-ray diffraction (XRD) was performed using a Philips XPERT PRO system employing $CuK_\alpha$ ($\lambda=1.54056$ Å) radiation operated at 45 kV and 40 mA in the 2θ range of 10-80°.

Microstructure Analysis

The microstructure of as-cast and solution treated (T4) ZK40 alloys were observed using optical microscopy (Axiovert 40 MAT, Carl Zeiss, Jena, Germany). Square specimens were mounted in epoxy (EpoxiCure, Buehler), and mechanically polished using 9, 3, and 1 μm diamond slurry followed by 0.5 μm colloidal silica to obtain a mirror-like finish using semi-automatic polishing system (Tegramin-20, Struers, Ballerup, Denmark). Specimens following polishing were chemically etched in a solution of 5 mL acetic acid, 6 g picric acid, 10 mL water, and 100 mL ethanol and washed immediately using isopropanol to clearly reveal the grain boundaries. Grain size was calculated according to ASTM E112 linear intercept method, and the ASTM grain number G was converted to average grain size. The alloys were further characterized to observe the presence of voids/impurities/oxide scales using computerized nano-tomography. Correspondingly, nano computed tomographic (nanoCT) images were captured using the Phoenix Nanotom-m 180 kV/15 W X-ray nanoCT® system equipped with a tungsten filament. Disk samples of 1.5 mm dia×3 mm height was sectioned from the as-cast Mg-4% Zn-0.5% Zr alloy and nanoCT images were captured with a minimum voxel resolution ~300 nm to delineate the finer details of the microstructures.

Elemental Analysis

The alloy nominal compositions, determined by inductively coupled plasma optical emission spectroscopy (ICP-OES, iCAP duo 6500 Thermo Fisher, Waltham, Mass.), are listed in Table 1.1.

TABLE 1.1

Chemical composition of Mg-4wt % Zn-0.5wt % Zr (ZK40) alloy.

| Alloy | Chemical compositions (wt. %) | | | | | | | |
|---|---|---|---|---|---|---|---|---|
| | Zn | Zr | Cu | Fe | Mn | Ni | Si | Mg |
| Mg-4Zn-0.5Zr | 4.28+/−0.11 | 0.36+/−.008 | 0.014 | 0.002 | 0.003 | 0.018 | 0.007 | Balance |

Potentiodynamic Polarization (PDP) Measurement

Potentiodynamic polarization (PDP) test was carried out with an electrochemical workstation (CHI 604 Å, CH Instruments, Inc., Austin, Tex.) at a scanning rate of 1 mV/s and potential window of ~500 mV above and below the open circuit potential (OP). Square samples (surface area ~1 cm$^2$) were connected to a copper wire using silver epoxy, mounted in epoxy resin. The mounted samples were mechanically polished using 320, 600, and 1200 grits SiC papers, sonicated in isopropyl alcohol, and dried in air. A three electrode cell setup was employed for the electrochemical corrosion test with platinum being the counter electrode, Ag/AgCl as the reference electrode, and the epoxy mounted sample as the working electrode. The test was performed in Dulbecco's Modified Eagle Medium (DMEM, with 4.5 g/l glucose, L-glutamine, and sodium pyruvate, Cellgro, Manassas, Va.) supplemented with 10% fetal bovine serum (FBS), 100 U/ml penicillin, and 100 µg/ml streptomycin at pH 7.2±0.2 and temperature held at 37.4° C. Before each measurement, the sample was immersed in DMEM for 15 min at open circuit potential to provide voltage stability. The cathodic and anodic branches of the generated Tafel plots were extrapolated linearly to calculate the corrosion potential, $E_{corr}$, and corrosion current density, $i_{corr}$. Average and standard deviations of these 3 sample measurements are reported and one-way ANOVA was used to determine any significant mean differences with a p-value less than 0.05. Corroded samples following the test measurements were subsequently cleaned by immersion in 200 g/L of chromic acid and 10 g/L of $AgNO_3$ solution for 10 min at ambient temperature to remove the corrosion products and the corrosion surface was then characterized using scanning electron microscopy (SEM).

Results and Discussion

Phase Analysis

FIG. 1.1 shows the X-ray diffraction (XRD) patterns of the pure Mg, Mg-4% Zn-0.5% Zr (ZK40) as-cast and solution treated samples. All of the peaks were indexed to single phase α-Mg matrix with the hexagonal close packed (hcp) crystal structure in case of pure Mg. Interestingly, in the case of Mg-4% Zn-0.5% Zr, both for the as-cast and solution treated samples, only α-Mg peaks were found. The XRD patterns thus clearly show that the α-Mg(Zn, Zr) solid solution single phase was formed during solidification which should be observed in the final microstructure. However, the highest diffraction peak intensity observed corresponded to the pyramidal plane which suggests that the orientation of the α-Mg(Zn, Zr) solid solution single phase was altered during melting and solidification in comparison to pure α-Mg matrix suggesting the influence of either the alloying elements or the segregated elements within the crucible containing the melt acting as nucleating sites causing preferential aligning of the solidifying elements in the preferred plane.

FIG. 1.2 correspondingly illustrates the optical micrographs of the as-cast and solution treated Mg-4% Zn-0.5% Zr alloys. It can be seen that the microstructures of both, the as-cast and solution treated alloys contain primary α-Mg matrix and minor secondary phase(s) precipitated along the grain boundaries. The average grain size for the as-cast and solution treated alloys were 50±10 m and 87±10 µm, respectively. The grains were uniform and equiaxed throughout the microstructures, likely suggesting the excellent grain refinement ability of Zr inoculants added during solidification of the liquid melt. It is well-known that Zr is an excellent grain refiner for magnesium and in the presence of solute (here zinc), the effective barrier for nucleation is likely much reduced leading to a large number of critical sized zirconium nuclei serving as active sites for nucleation, hence effectively refining the structure. Zinc which is present as a solute also tends to segregate in the diffusion layer ahead of the solid/liquid interface of the growing grains during constitutional undercooling which helps to restrict α-Mg grains to grow further. The grain refinement efficacy of a solute can be determined by the growth restriction factors (GRF). It has been determined that Zr and Zn have GRF values of 38.29 and 5.31 respectively, which thus together, impart a powerful grain refinement effect in the resultant alloy validating the observed microstructure. The slight increase in the average grain size of the T4-treated sample was likely due to coalescence of smaller grains along the triple junction grain boundary regions and eventually formation of supersaturated α-Mg(Zn, Zr) solid solution after the precipitates dissolve into the matrix. The SEM of the as-cast and solution treated alloys were also captured using back-scattered electron (BSE) mode to reveal clearly the compositional contrast due to the large difference in the atomic number of Mg with Zn and Zr FIG. 1.3(a) shows the BSE mode SEM micrograph of as-cast ZK40 alloy. It can be observed that Zn/Zr rich second phase is continuously distributed along the grain boundary regions. Energy dispersive spectra (EDS) analysis of the Zn and Zr rich second phase shown in FIG. 1.3(a) identified the elemental composition of the precipitates to be $Mg_7Zn_3$. According to the magnesium-zinc phase diagram there exist a eutectic composition of $Mg_7Zn_3$ ~325° C. which eventually transform in to α-Mg and MgZn intermetallic during solidification. It is believed that $Mg_7Zn_3$ undergoes eutectic transformation and formed σ-Mg(Zn, Zr) solid solution and MgZn intermetallic which is the second phase observed along the grain boundaries. Similarly, in the case of solution treated alloys the MgZn intermetallic was observed along the grain boundaries (see FIG. 1.3b). However, the reduction in the volume percent of second phase was evident due to rapid dissolution of MgZn intermetallic in to α-Mg grain during solution treatment.

FIG. 1.4(a) shows the nanoCT scan image of the as-cast Mg—Zn—Zr alloys. It clearly reveals the absence of any casting defects/inclusion suggesting the excellent castability of the Mg—Zn—Zr alloy composition and the cleanliness of the melting and casting approach adopted in this study. The high resolution nanoCT scan shown in FIG. 1.4(b) illustrates the average distance between grain interiors to the grain boundaries. Table 1.1 also illustrates the ICP data of the alloy composition which further validates that the impurity levels of the liquid melt was very low (combined impurity levels including Fe, Ni, Mn, Cu, and Si was ~440 ppm) ensuring the better biocompatibility and degradation properties of this alloy in the physiological environment.

TABLE 1.2

Chemical composition of DMEM + FBS (mM/L) + P/S (mg/L) used for the present biocorrosion study.

| Name | DMEM(L) + FBS |
|---|---|
| $CaCl_2$ | 200.00 |
| NaCl | 6400.00 |
| KCl | 400.00 |
| $NaHCO_3$ | 3700.00 |
| $NaH_2PO_4$ | 125.00 |
| $MgSO_4$ | 97.70 |
| $Fe(NO_3)_2$ | 0.10 |
| Glucose | 4500.00 |
| Amino acid | 1605.36 |
| Fetal bovine serum | 10% |
| Penicillin/streptomycin | 1% |

The potentiodynamic polarization (PDP) behavior of the ZK40 in both, the as-cast and solution treated conditions along with pure Mg and as-drawn AZ31 alloys have been studied extensively under DMEM+10% FBS+1% P/S physiological condition. The composition of the DMEM+10% FBS+1% P/S is listed in Table 1.2. The potentiodynamic polarization curves (Tafel plot) of the various samples and pure Mg, recorded at a scan rate of ~1 mV/s are plotted in FIG. 1.5. In general, the cathodic branch of the tafel plot shows the hydrogen evolution through a reduction process whereas the anodic branch represents the magnesium dissolution by oxidation.

The cathodic plateaus of pure Mg suggest that the corrosion potential, $E_{corr}$ for hydrogen evolution occurs at $-1.62$ V versus Ag/AgCl reference electrode. The calculated corrosion current density, $i_{corr}$ (tabulated in Table 1.3) for pure Mg is ~29.26 $\mu Acm^{-2}$ equivalent to corrosion rate ~ 0.7 mm/year if it is assumed that the general corrosion occurred on the surface. On the other hand, the as-cast ZK40 and as expected, the as-drawn AZ31 samples showed improved corrosion potential and $E_{corr}$ values displaced toward the more noble direction compared to pure Mg. It is already known that zinc contributes to elevation of the corrosion potential and thus improve the corrosion rate. Corrosion potentials for as-cast ZK40 and AZ31 alloys were determined to be $-1.49$ V and $-1.48$ V, respectively. The calculated corrosion rate, $i_{corr}$ (determined by Tafel extrapolation) values for the as-cast ZK40 and AZ31 was ~ 0.90 mm/year and 0.43 mm/year, respectively. Although the corrosion potential of solution treated ZK40 alloy is $-1.55$ V, which shifted slightly towards the cathodic direction, there was an improvement in the corrosion rate over the as-cast sample. The corrosion rate, $i_{corr}$ of the solution treated ZK40 sample is 0.87 mm/year. Improvement in the corrosion current density (~39.32 $gAcm^{-2}$) and corrosion rate of solution treated ZK40 alloy compared to the as-cast state is primarily due to reduction in the second phase ($Mg_7Zn_3$) intermetallic which was observed to be discontinuously precipitated along the grain boundaries in the as-cast sample as discussed earlier. Solution treatment of the as-cast sample at 300° C. for 1 h reduces the volume fraction of the second phase [$Mg_7Zn_3 \rightarrow \sigma$-Mg(Zn,Zr)+MgZn] occurring as a consequence of the eutectic transformation causing an increase in the amount of $\sigma$-Mg(Zn, Zr) primary phase resulting hence in the sudden drop in the corrosion potential.

FIG. 1.5 also illustrates the formation of a passivation layer in the anodic branch of the polarization plot. The breakdown potential, $E_b$ of pure Mg, AZ31, as-cast and solution treated ZK40 samples were correspondingly $-1.41$, $-1.35$, $-1.41$, and $-1.33$ V, respectively. It can be seen that the $E_b$ for AZ31 and solution treated ZK40 samples were both higher and thus better than pure Mg which suggests that pure Mg was more prone to localized corrosion by disruption of the protective oxide layers. On the other hand, both AZ31 and solution treated ZK40 exhibit resistance to localized corrosion by the well-known passivation phenomena. Interestingly, the as-cast ZK40 alloys exhibited a low breakdown potential ($-1.41$ V). In general, the anodic branch of polarization curve is characterized by a sudden drop in the anodic current representing a change in the slope, known as the breakdown Potential ($E_b$). During anodic polarization, a passive film formed on the surface provides a protective barrier that keeps the corrosion current at a low value so that the extent of corrosion damage is minimized. An effective protective layer is obviously characterized by one that provides a strong resistance to breakdown of the passivation layer. As the potential is increased, corrosion via surface breakdown will begin at a certain voltage value termed as the breakdown potential ($E_b$), the lowest potential at which corrosion occurs. Since corrosion relates to an increase in the oxidation rate, the $E_b$ is determined by the corresponding increase in measured anodic current. An increase in $E_b$ is associated with higher resistance to corrosion. Breakdown potentials cause the disruption of the passive film and thus expose bare sites of the surface to an aggressive physiological environment wherein the tendency for attack is very high contributing to the accelerated corrosion of the alloy.

TABLE 1.3

Corrosion rates (mm/year) determined by potentiodynamic polarization and immersiontechniques of pure Mg, as-drawn AZ31, as-cast and solution treated ZK40 alloys (n = 3, *p < 0.05 with all other groups).

| Materials | Corrosion potential, $E_{corr}$ (V) | Corrosion current density, $i_{corr}$ ($\mu A\ cm^{-2}$) | Breakdown Potential $E_b$ (V) | Corrosion rate CR (mm/year) |
|---|---|---|---|---|
| Pure Mg | $-1.62$ | $29.26 \pm 3.18$ | $-.141$ | $0.70 \pm 0.07$* |
| As-drawn AZ31 | $-1.48$ | $19.20 \pm 2.08$ | $-1.35$ | $0.43 \pm 0.05$* |
| As-cast ZK40 | $-1.49$ | $39.69 \pm 1.08$ | $-1.41$ | $0.90 \pm 0.02$ |
| T4 treated ZK40 | $-1.55$ | $39.32 \pm 2.01$ | $-1.33$ | $0.87 \pm 0.04$ |

FIG. 1.6 shows the corrosion morphology evolved during potentiodynamic polarization test of the samples, after the corrosion products were correspondingly cleaned by $CrO_3$ and $AgNO_3$ treatment. Previous scientific studies have shown that in a multi-phase alloy, the corrosion rate is primarily controlled by the following factors: a) purity, b) the composition of matrix, c) composition of second phase (s) and its distribution in the microstructure. Since, in the case of pure Mg, there is no second phase present, the corrosion mechanism was primarily governed by the total impurity present and the presence of weak grain boundary regions. FIG. 1.6(a) shows that, mainly irregular localized corrosion pits was evident which was laterally spread over the whole surface. The presences of small, discrete pits in the microstructure suggest that the presence of impurities do play a role for localized corrosion in case of pure magnesium. On the contrary, in the case of AZ31 sample, $Mg_{17}Al_{12}$ ($\beta$-phase) is the predominant second phase present along the grain boundaries. The presence of second phase will accelerates the corrosion of adjacent α-Mg matrix. FIG. 1.6(*b*) shows the corroded surface of AZ31 where pitting was the predominant corrosion mechanism evident by the presence of small interconnected pits throughout the corroded surface. FIG. 1.6(*c*) shows the corroded surface of ZK40 sample in the as-cast condition wherein the presence of irregular pits on the surface clearly suggests that pitting was indeed the dominant corrosion mechanism. Microstructural investigation of ZK40 as-cast sample outlined in section 3.3.1 shows that secondary phase (s) of $Mg_7Zn_3$ and MgZn are present along the grain boundaries likely causing the accelerated corrosion of the α-Mg matrix. However, in the case of solution treated ZK40 sample, the percentage of second phase(s) decreases with solution treatment having a direct consequence on the corrosion rate and morphology as clearly, no surface pits are observed on the corroded surface as shown in FIG. 1.6(*d*).

Conclusions

Microstructural analysis of the as-cast and solution treated Mg-4 wt % Zn-0.5 wt % Zr or ZK40 alloys by optical and SEM suggest the formation of uniform equiaxed grains throughout the microstructures with average grain size of 50±10 μm and 87±10 μm, respectively. SEM performed in the back-scattered mode and execution of the EDS analysis of the as-cast ZK40 alloy clearly shows the presence of $Mg_7Zn_3$ intermetallic phase along the grain boundaries which undergoes eutectic transformation during solution treatment at 300° C. for 1 h resulting in the formation □-Mg(Zn, Zr) primary phase and MgZn secondary phase contributing to improved corrosion resistance.

Example 2

Identification of the Potential of Mg—Zn Based Alloys as a Biodegradable System Using In Vitro Characterization Methods Rationale:

Corrosion resistance, mechanical properties, and cytocompatibility are three primary criteria required to be assessed comprehensively to prove the safety and function of biodegradable Mg alloy for orthopedic application. In vitro assessment of biodegradable Mg alloys is designed to focus on mimicking the physiological environment and replicating the trend of in vivo degradation of the different Mg alloys. Pure Mg and various commercial Mg alloys such as AZ31 and WE43 have been reported to exhibit suitable corrosion resistance, mechanical properties, and biocompatibility in the initial stages of in vivo and in vitro experiments. Thus, pure Mg and AZ31 are good negative controls for assessing the in vitro characteristics of ZK40 alloy and the result can determine the need for in vivo studies to understand the ZK40 alloy. Understanding in vitro corrosion resistance, mechanical properties, and cell cytotoxicity of ZK40 provide useful direction in developing Mg—Zn based alloys for orthopedic applications.

Experimental Design

Corrosion Measurement

Corrosion measurement of biodegradable Mg alloys can be achieved using different methods such as mass loss immersion, hydrogen evolution, electrochemical impedance spectroscopy (EIS), and potentiodynamic polarization (PDP). In this study, mass loss immersion and potentiodynamic polarization (PDP) were performed to assess the corrosion characteristics at different time points. Mass loss immersion has also exhibited similar trend of Mg alloy degradation compared to what is observed in in vivo subcutaneous implantation models. The specimens were immersed in cell culture media using a fishing line at 37.4° C. in a humidified atmosphere with 5% $CO_2$. Media volume to surface area ratio was maintained at 20 ml/cm² according to the ASTMG31-72 standard. Samples were removed after 1, 2 and 3 weeks of immersion, rinsed with distilled water and dried at room temperature. Further, the corrosion product layer of samples were cleaned with a solution mixture of chromic acid and $AgNO_3$. The difference in weight after immersion will be recorded, and the degradation rates (in units of mm/year) were obtained according to ASTMG31-72.

Potentiostatic Dynamic Polarization (PDP)

PDP was performed to measure the electrochemical stability of bare metal surface of Mg alloys. A three electrode cell setup was employed for the electrochemical corrosion test using platinum as the counter electrode, Ag/AgCl as the reference electrode, and the epoxy mounted sample as the working electrode. The tests were performed in the same culture media at pH 7.2±0.2, held at 37.4° C. Before each measurement, the sample was immersed in the media for 15 min at open circuit potential (OCP) to provide voltage stability. The cathodic and anodic branches of the generated Tafel plots were extrapolated linearly to calculate corrosion potential, $E_{corr}$, and corrosion current density, $i_{corr}$.

Mechanical Testing

Tension and compression tests were performed in accordance with ASTM standard practice for tensile testing ASTM-E8-04 and compressive testing ASTM-E9-09 at room temperature. For the tension tests, standard dog bone specimens of 12.7 mm in gauge length and 3×3 mm in gauge cross-section were machined and pulled to failure employing a cross-head speed of 1.3 mm/min. Specimens for compression test corresponded to dimensions of 10 mm diameter and 20 mm in length. The specimens were accordingly machined from the long axis of the ingots and loaded to failure at rate of 2 mm/min. Tensile and compressive stress-strain curves were utilized to determine the yield strength (YS), ultimate tensile strength (UTS), Young's modulus (E) during tension, total elongations (%), compressive yield strengths, and total compression (%) of each alloy specimens.

Cell Cytotoxicity

The mouse osteoblast-like cell line MC3T3 were cultured in Dulbecco's modified eagle medium (α-MEM) with 10% fetal bovine serum (FBS) and 1% p/s at 37.4° C. in a humidified atmosphere of 5% $CO_2$. Cells were seeded onto specimen surfaces and cultured for 72 h. The live/dead assay were performed subsequently with commercially available kit and fluorescence microscopy was used to determine the viability/cytotoxicity of cells. After fluorescence imaging, cells on the specimens were fixed by 2.5% glutaraldehyde and dehydrated by ethanol. Fixed cells were imaged by scanning electron microscopy after palladium sputtering. MTT(3-(4,5-Dimethylthiazol-2-yl)-2,5-diphenyltetrazolium bromide) assay was used to assess the cytotoxicity of degradation product after 72 h immersion of specimens in culture medium. Extract media in dilution of 1×, 2×, 4× and 10× were added to the 24 h cultured MC3T3 cell and MTT assay will be performed after 72 h.

Statistical Considerations

One-way ANOVA with graphical and summary statistics was used to assess the degradation rates, mechanical properties, and cell cytotoxicity results. MTT cell cytotoxicity test were normalized by the negative control (cell culture plastic) to compare the cytotoxicity levels between the different alloy groups. Cell count of live/dead assay images were accordingly examined using the ImageJ software to add more justification to the analyses.

Anticipated Results

In comparison to pure Mg and as-drawn AZ31, ZK40 alloy is expected to exhibit comparable characteristics to pure Mg and AZ31 with respect to degradation rates. Pure Mg and AZ31 are reported to have good corrosion resistance and as-cast and heat-treated ZK40 alloys are anticipated to perform similarly. In terms of mechanical properties, ZK40 alloys are expected to perform better than pure Mg. However, ZK 40 alloys are not expected to match the mechanical properties of commercial as-drawn AZ31 since the drawing technique will have a significantly higher level of grain refinement. Cell cytotoxicity result of ZK40 alloy on the other hand, is anticipated to perform better than AZ31 and as good as pure Mg following both MTT and live/dead assays.

Materials and Methods

Tensile and Compression Test

Tension tests were performed for both, the as-cast and T4 treated ZK40 alloys as well as AZ31, and pure Mg in accordance with ASTM standard practice for tensile testing ASTM-E8-04 at room temperature using an MTSI 1 frame with 50 kN load cells and LX500 laser extensometer (MITS Systems Corporation, Eden Prairie, Minn., USA) by Ortho-Kinetic® Testing Technologies. Standard dog bone specimens of 12.7 mm in gauge length and 3×3 mm in gauge cross-section were machined and used for the tension tests. Samples were accordingly pulled to failure at the cross-head speed of 1.3 mm/min. Tensile stress-strain curves were utilized to determine the yield strength (YS), ultimate tensile strength (UTS), Young's modulus (E) during tension, and total elongations (%) of each alloy specimens. Averages of 3 sample measurements were reported.

Immersion Corrosion Measurement

Immersion corrosion measurements were performed in conformation with ASTM G31-72. Pure Mg, ZK40 as-cast and ZK40 T4-treated specimens were prepared in dimension of 10×10×1 mm and polished up to 1200 grit using SiC paper. Surface area and the weight of each specimen was carefully recorded before the immersion test. The specimens were thoroughly cleaned in acetone using a sonicated bath followed by UV sterilization for 30 min for each side. After sterilization, the specimens were immersed in DMEM+10% FBS+100 U/ml penicillin, and 100 µg/ml streptomycin using a fishing line at 37.4° C. in a humidified atmosphere with 5% $CO_2$. DMEM+10% FBS media volume to surface area ratio was 20 ml/cm$^2$ according to the ASTMG31-72 standard. Specimens were removed after 1, 2 and 3 weeks of immersion, rinsed with distilled water and dried at room temperature. Further, the specimens were cleaned with 200 g/L of chromic acid and 10 g/L of $AgNO_3$ solution for 10 min to remove the corrosion products. The difference in weight before and after immersion was recorded and the degradation rates (in units of mm/year) were obtained according to ASTMG31-72. The corrosion rate is thus given by:

Corrosion rate=$(K \times W)/(A \times T \times D)$  Eq. (1)

where the time conversion coefficient K=$8.76 \times 10^4$, W is the weight difference before and after immersion (g), A is the sample area exposed to solution (cm$^2$), T is the exposure time (h) and D is the density of the material (g cm$^{-3}$). The pH value of the solution was also recorded during the immersion tests. Averages and standard deviations of 3 sample measurements were reported and one-way ANOVA was used to determine any significant mean differences with a p-value less than 0.05 for each time point.

Indirect MTT Cell Viability Assay

Pure Mg, ZK40 as-cast, and ZK40 T4-treated specimens were sectioned to exhibit dimensions of 10×10×1 mm, polished up to 1200 grit SiC paper, sonicated in isopropanol, and sterilized under ultraviolet radiation for 30 min before extract preparation. The specimens were incubated with modified Eagle's medium alpha (α-MEM) supplemented with 10% fetal bovine serum (FBS), 100 U/ml penicillin, and 100 µg/ml streptomycin at 37° C. in a humidified atmosphere with 5% $CO_2$ for 72 h. The specimen weight to extraction medium ratio was maintained at 0.2 g/mL in accordance with EN ISO standard 10993:12. This extraction ratio was designated as 100% extract, with less concentrated extracts prepared by diluting the 100% extract into 50%, 25%, and 10% extract solutions, respectively. Extracts were then sterile filtered using 0.2 m syringe filter before being added to cells.

Further, the murine osteoblastic cell line (MC3T3-E1, American Type Culture Collection, Rockville, Md.) was used in in vitro cell cytotoxicity experiments, cultured in modified Eagle's medium alpha (αMEM), 10% fetal bovine serum (FBS), 100 U/ml penicillin and 100 µg/ml streptomycin at 37.4° C. in a humidified atmosphere with 5% $CO_2$. The cells were seeded in a 96-well plate at cell density of 6000 cells/well and incubated for 24 h to attach before adding the extraction medium. The controls used as culture medium without extract as the negative control and 10% DMSO culture medium as the positive control Cell culture media with pre-cultured cell was replaced with the 200 µl extract media at 1×, 2×, 4×, and 10× extract dilution and incubated for 72 h under cell culture condition. The cytotoxicity of the extracts was tested using the MTT assay. Media and extracts were replaced with fresh cell culture medium to prevent interference of the magnesium ions in the extract from interacting with the tetrazolium salt. The MTT assay was performed according to the Vybrant MTT Cell Proliferation Kit (Invitrogen Corporation, Karlsruhe, Germany) by first adding 10 µl of 12 mM 3-(4,5-Dimethylthiazol-2-yl)-2,5-diphenyltetrazolium bromide (MTT) dissolved in phosphate buffer solution (PBS, pH=7.4) to each well. MTT salt was dissolved in PBS at the ratio of 5 mg/mL and diluted in phenol red free media in a 1:11 ratio to replace the magnesium ion containing media from interfering with the blue formazan measurement. The mixture of MTT solution and phenol red free media replaced the extract media after 72 h culture and was incubated for another 4 h under cell culture condition. Formazan crystals were solubilized using sodium dodecyl sulfide dissolved in 0.01 M hydrochloric acid at the ratio of 1 mg/10 mL (SDS-HCl). 100 ul of SDS-HCl was added to each well and incubated for 12 h under cell culture condition. The well plate was then analyzed by a ELISA microplate reader at a wavelength of 570 nm with a reference wavelength of 635 nm. Averages and standard deviations of 3 sample measurements were reported and one-way ANOVA was used to determine any significant mean differences with a p-value less than 0.05 for each dilution factors of the extract media.

Live/Dead Cell Viability Assay

The murine osteoblast-like cell line MC3T3 was cultured in Dulbecco's modified eagle medium (α-MEM) with 10% fetal bovine serum (FBS), 100 U/ml penicillin, and 100 µg/ml streptomycin at 37.4° C. in a humidified atmosphere of 5% $CO_2$. Cells were seeded onto specimen surfaces at cell density of $4 \times 10^4$ cells/mL and each well contained 2 mL of media to completely cover the specimen. After 72 h of incubation, the live/dead assay was performed using commercially available LIVE/DEAD viability/cytotoxicity kit (Invitrogen Inc. Karlsruhe, Germany) to stain the live and dead cells to glow in green (ethidium homodimer-1) and red (calcein-AM) respectively, under fluorescence microscopy at the excitation wavelength of 495 nm. After fluorescence imaging, cells on the specimens were fixed by 2.5% glutaraldehyde for 15 min and dehydrated by immersing the specimens in 70, 80, 90, 95, and 100% diluted ethanol for 15 min per dilution factor subsequently. Specimens with fixed cells were air dried and captured by SEM.

In Vivo Murine Subcutaneous Study

In vivo murine subcutaneous study was conducted to explore any acute host response of pure Mg, as-drawn AZ31, and as-cast ZK40 samples. Mice implantation was performed at University of Cincinnati with an approval of its Animal Care and Use Committee (IACUC) in collaboration with Dr. Zhonghyun Dong. For this study, discs of 5 mm diameter and 1.4 mm thickness were sectioned from as-cast ZK40, pure Mg, and AZ31 alloy specimens. The disc samples were than sonicated in acetone, air-dried, and further sterilized by UV radiation. Healthy nude mice were housed under controlled conditions and maintained with a standard diet and water. Mice were anesthetized by isoflurane and a small skin incision was made for implantation of the disc in the subcutaneous regions. Surgical staples were used to close the incisions. After 40 and 70 days, the animals were sacrificed using a $CO_2$ gas chamber and disc samples were removed followed by the cervical dislocation. The disc implants with surrounding tissue were recovered, carefully separated from the tissue, cleaned, air-dried, and weighed. The surrounding subcutaneous tissue was harvested and fixed using 10% formalin in PBS, paraffin-embedded, and sectioned (4 μm/section) for hematoxylin-eosin (H&E) staining.

Results and Discussion

Mechanical Properties of Mg—Zn—Zr Alloy

Table 2.1 summarizes the mechanical properties of both, the as-cast and solution treated Mg-4% Zn-0.5% Zr (ZK40) alloys as well as pure Mg, and commercial as-drawn AZ31 studied for the present work along with a direct comparison made with natural bone. Compared to pure Mg, the addition of zinc and a small amount of zirconium has a dramatic effect on the values of tensile strength. Yield strength and ultimate tensile strength (UTS) for the as-cast Mg-4% Zn-0.5% Zr was 96 MPa, and 176 MPa respectively. However, there was a little drop in the yield strength and UTS values of solution treated Mg-4% Zn-0.5% Zr alloy compared to as-cast alloys likely due to increase in the average grain size which invariably reduces the yield strength as is well-known in the physical metallurgy literature. As-drawn AZ31 showed the highest yield strength of 55 MPa and UTS of 202 MPa among all the alloys studied here. Elastic Modulus of the pure magnesium was low ~5 GPa, however, Mg-4% Zn-0.5% Zr alloys demonstrated excellent modulus (~64 GPa) suggesting that the alloy possesses high strength under tensile testing. Similarly, the as-drawn AZ31 also display a high stiffness value. It should be noted that all the alloys studied here possess a high modulus values compared to natural bone except pure magnesium. The total elongation to failure (%) for pure magnesium and as-drawn AZ31 samples were 7 and 12%, respectively.

TABLE 2.1

Mechanical properties of the as-drawn AZ31, pure Mg, ZK40, and ZK60 alloys (n = 3, *buckling noticed during the measurement due to the mismatch between sample size and load cell).

| Alloy | Density (g/cm³) | Modulus (GPa) | Yield Strength (MPa) | Ultimate Tensile Strength (MPa) | Compressive Yield Strength (MPa) | Elongation (%) | References |
|---|---|---|---|---|---|---|---|
| Cortical bone | 1.8-2.0 | 5-23 | 104.9-114.3 | 35-283 | 164-240 | 1.07-2.1 | (111) |
| Cancellous bone | 1.0-1.4 | 10-1570 (MPa) | — | 1.5-38 | — | — | (111) |
| As-drawn AZ31 | 1.78 | 55 | 202 | 268 | 105 | 12 | Present study |
| PureMg | 1.74 | 5* | 19 | 66 | 140 | 7 | Present study |
| As-cast ZK40 | 1.80 | 64 | 96 | 176 | 125 | 4 | Present study |
| ZK40 solution treated | 1.80 | 68 | 92 | 134 | 92 | 3 | Present study |
| As-cast ZK60 | — | — | 150 | 210 | 120 | 6 | (85) |
| ZK60 extruded | — | — | 290 | 335 | 250 | 16 | (85) |

In contrast, total elongation to failure under tension of Mg-4%Zn-0.5&Zr alloys in the as-cast and solution treated conditions was observed to be 4 and 3%, respectively. The low value of elongation to failure for both the as-cast and solution treated Mg-4% Zn-0.5% Zr alloy is likely due to the presence of second phase ($Mg_7Zn_3$) which increases the hardness and strength of the alloy while undermining the total elongation to failure. Similar observation was reported in the literature wherein it was observed that addition of more than 5 wt % zinc has a negative effect on the mechanical properties of the alloy due to the presence of number of MgZn intermetallic phase(s) which precipitate along the grain boundary during solidification. Commercial as-drawn AZ31 alloy displayed a higher yield and tensile strengths compared to all the alloys studied here. Increase in yield value and tensile strength with the addition of 4% zinc and 0.5% zirconium to the pure magnesium mainly originates from the strong grain refinement efficacy of zirconium on the alloy microstructure which is based on Hall-Petch relationship. According to the Mg—Zn establish phase diagram, the maximum solubility of zinc is 1.6 wt % in magnesium at room temperature. Thus, zinc mainly dissolve in primary α-Mg and imparts solid solution strengthening improving the castability of the alloy. It is also important to note that the presence of $Mg_7Zn_3$ intermetallic along the grain boundary regions in Mg-4%Zn-0.5% Zr alloys hinders the dislocation movements during plastic deformation causing an increase in the strength of the alloys at the expense of desired plasticity. However, the discontinuous precipitates formed along the grain boundaries may sometimes act as stress concentrators leading to brittle fracture of the alloy under tensile loading.

FIG. 2.1 provides the fractographs of the cross-sectional surfaces after tensile testing. The fracture surface of the as-drawn AZ31 alloy specimen (see FIG. 2.1a) shows a ductile mode fracture with the presence of dimples throughout the fracture surface. On the other hand, the as-cast ZK40 tensile specimen in FIG. 2.1b illustrates a mixed fracture mode including inter-granular cracks and cleavage patterns. The presence of cleavage and quasi cleavage patterns are common for Mg-4% Zn alloy which have been verified by others. The presence of intermetallic phase along the grain boundaries leads to crack propagation under tensile loading which may result brittle failure. However, solution treated ZK40 alloys exhibited both brittle-ductile fracture mode together supported by the presence of cleavage planes and dimples. The number of dimples observed on the fracture surface (FIG. 2.1c) was minimal and possibly appeared when the second phase was dissolved back in to the α-Mg matrix during solution treatment, causing grain softening leading to possible ductile mode failure.

Immersion Corrosion Properties of Mg—Zn—Zr Alloy

The average weight loss of pure Mg, as-drawn AZ31, as-cast and solution treated ZK40 alloys are displayed in FIG. 2.2. The average corrosion rate for pure Mg and AZ31 was determined to be 0.69±0.13 and 0.66±0.05 mm/year, respectively, after 7 days of static immersion in DMEM+ 10% FBS. The corrosion rate was decreased further during 14 days and 21 days immersion test which is in agreement with the reported values in literature. The decrease in the average weight loss rate was likely due to the formation of a passivation layer on the surface which retarded further corrosion. However, in the case of as-cast and solution treated ZK40 samples opposite trends were observed. The corrosion rates were increased in the order of 7, 14, and 21 days static immersion in DMEM+10% FBS. The average weight loss of the as-cast and T4 treated ZK40 alloys after 7 days of immersion were 0.39±0.05 and 0.53±0.12 mm/year, respectively. The corrosion rate was dramatically increased to 1.07±0.26 and 1.53±0.25 mm/year for the as-cast ZK40 sample during 14 days and 21 days immersion, respectively.

The increase in corrosion rate suggests that the protective layer [$Mg(OH)_2$] which forms on the surface during static immersion was not stable and contributed to further corrosion. The above finding was in agreement with electrochemical corrosion study where it was determined that the breakdown potential, $E_b$ (−1.41 V) of as-cast ZK40 alloy was close the corrosion potential, $E_{corr}$ (−1.49 V) which resulted in rapid corrosion and dissolution of the corroded product simultaneously. The average corrosion rate for solution treated ZK40 alloy was slightly reduced from 0.53±0.12 mm/year, to 0.46±0.03 mm/year from 7 days to 14 days but again increased to 0.89 f 0.09 mm/year after 21 days static immersion. The exact reasons for this anomalous corrosion rate are still unknown and subject of further investigation. A possible explanation could be the nature of the hydroxide formed due to the solution treatment causing dissolution of Zinc into the α-phase of Mg and formation of MgZn intermetallic. It is possible that the stability of the Mg-hydroxide due to incorporation of Zn is altered at the 21 day time period probably leading to fine precipitates forming likely increasing the solubility causing an increase in the corrosion rate observed. These are however, largely speculatory at present warranting further study.

Surface morphology of the corroded surfaces as-cast and solution treated ZK40 alloys after 21 days static immersion was shown in FIG. 2.3. It appears that both as-cast and solution treated ZK40 alloys were uniformly corroded. However, the presence of large holes was likely due to severe pitting corrosion along the grain boundary regions which were weak spots due to presence of second phase(s) precipitates that was more prone to attack locally by $Cl^-$, $HCO_3^-$, $SO_4^2$, ions etc. present in the cell culture media.

Cytocompatibility of Mg—Zn—Zr Alloy

Direct MC3T3 Cytocompatibility Using Live/Dead Assay

Cell viability was studied for the pure Mg, AZ31, as-cast and solution treated ZK40 samples with the 3 day cell culture time with extracts. FIG. 2.4 shows the osteoblastic MC3T3-E1 cells cultured in direct αMEM+10% FBS for 3 days and then stained with calcein-AM and EthD-1. Live cells convert calcein AM to the green fluorescent calcein through intracellular esterase activity, while EthD-1 enters cells with compromised membranes where it binds with nucleic acids and produces a bright red fluorescence. As-cast as well as solution treated ZK40 sample show improved cell viability when compared with AZ31 and pure magnesium as the cell density is clearly seen to be more and evenly distributed. There was no significant difference in the shape of the live cells (green) between the control and the studied samples groups. Only a few apoptotic cells (red fluorescence in the nuclei) were seen in each group.

FIG. 2.5 shows the morphology of the fixed MC3T3-E1 cells in 2.5% glutaraldehyde solution for 15 min after 3 days incubation in the α-MEM. The cells can be seen to attach to the surface of the sample and it is also evident that the cells start to proliferte on the surface. The cell spreading can be seen to be uniform with filopodia formations suggesting that the Mg—Zn—Zr sample are stable in the physiological environment and likely forming a protective layer which retards the released ion concentrations ($Mg^{2+}$, $Zn^{2+}$) facilitating cell growth and proliferation.

Indirect MC3T3 Cytocompatibility Using MTT Assay

FIG. 2.6 shows the indirect cytotoxicity results performed using MC3T3-E1 cells and the MTT assay for 3 days extract. For 3 days culture periods, cell viability was almost non-existent with undiluted extract (100%) concentration compared to negative control. However, cell viability was increased as the extract of the corrosion media was diluted to 50%, 25% and 10% and fresh media was added to the cell. The cell viability level was recorded as ~80% for as-cast and pure Magnesium level at the 50% dilution level suggesting the good cell compatibility of ZK40 alloy. The cell compatibility level was further improved with 25% extract dilution. All the three samples of as-cast and solution treated ZK40 and pure Mg showed greater than 75% cell viability level at 50% and 25% extract dilution with respect to the negative control. The above finding are in good agreement with the recent findings reported in the literature which show higher extract concentrations are highly cytotoxic in nature leading to osmotic shock due to the released ion concentration, suggesting that a 10-fold extract dilution will be more suitable and likely sufficient to determine the cytotoxicity level among various magnesium alloys. The ISO protocol of cytotoxicity test also identified 75% or higher cell viability as indicator for non-cytotoxicity and thus the results here suggests the biocompatibility of the studied ZK40 alloy material.

In Vivo Biocompatibility of Mg—Zn—Zr

FIG. 2.7 exhibits the histological image of local sites of implants harvested in murine subcutaneous tissue surrounding as-cast ZK40, pure Mg, and AZ31 after 40 and 70 days. Some visible amount of gas pocket was observed around as-cast ZK40 implantation after 40 days and a significant mass loss of as-cast ZK40, compared to pure Mg and AZ31, was measured after sacrificing the animals and explanting the alloy specimen. Moderate inflammatory response was observed in the H&E histology results (see FIG. 2.7). Abundant population of fibroblasts was observed around the Mg alloy samples. Degradation of as-cast ZK40 was observed to be more progressively pronounced than pure Mg and as-drawn AZ31 (see FIG. 2.8). An acute inflammatory response was however, not apparent in the specimens though analysis of long term responses along with degradation analysis is required to provide a more detailed, accurate and plausible explanation. These studies are planned in the near future.

Conclusions

In the present studies, as-cast and solution treated ZK40 alloys were investigated as a potential biodegradable alloys for possible orthopedic and craniofacial applications. The ZK40 alloy has a comparable corrosion rate with pure Mg and as drawn AZ31. Long term corrosion by static immersion technique however, shows that the corrosion trends for as-cast and solution treated ZK40 alloys are in fact, opposite than pure Mg and AZ31. The average weight loss rate for pure Mg and AZ31 was observed to be stabilized after 7 days immersion and decreased gradually following 14 days and 21 days static immersion, whereas the average weight loss rate for as-cast ZK40 alloy shows an increase in average weight loss rate likely due to formation and dissolution of protective layers simultaneously on the corroded surface. In vitro analysis by direct live-dead assay and indirect MTT assay using murine osteoblast MC3T3 cells show good cell viabiltity compared to pure Mg and AZ31. Direct implantation of as-cast ZK40 samples in mice subcutaneous model also shows no acute inflammatory response and healthy fibroblast formation along the implantation site after 40 and 70 days, suggesting that ZK40 alloy as a potential biodegradable implant. Further, extrusion/rolling, and equal channel angular pressing at elevated temperature have been reported to be capable of removing the voids, solidification shrinkage, etc. present in the as-cast ingots and improve the mechanical strength and corrosion characteristics. Thus, hot extrusion or hot rolling was explored as a potential steps for the use of Mg—Zn—Zr alloy as a potential biodegradable implant material.

Example 3

Effects of Addition of Sr and Ce on the Degradation, Mechanical and Biological Properties of Mg—Zn—Zr Alloys Rationale As discussed above for the each alloy category, a new class of system considered here is alloys containing Sr and Ce. Both Sr and Ce as discussed earlier, naturally exist in bone and have been reported for their biological effect in terms of hMSC differentiation for bone. On the other hand, Sr is known to have grain refining effects while Ce is known to provide a stronger metallurgical corrosion protection layer on Mg alloy, thus significantly improving the quality and expected performance of the resultant alloy. Release of Sr and Ce during degradation of Mg alloys has potential to thus, further enhance the regeneration of bone tissue. Therefore, small but nevertheless noticeable amounts of Sr and Ce as alloying elements have been added to the base Mg—Zn based alloy to study the effect of these elements. The amounts of Sr and Ce addition are thus fixed as 0.25 and 1 wt. %, to systematically investigate the correlation between the amount of the addition and the key three properties, as well as the bone forming ability.

Experimental Design

Mg—Zn—Sr—Zr and Mg—Zn—Ce—Zr (Sr, Ce=1, 0.25) alloys were melted and casted utilizing the same experimental setup as described in the above Example 1. Sr and Ce were accordingly added during melting, using Mg—Sr and Mg—Ce master alloy. Heat treatment conditions were optimized after microstructure and impurity analysis using SEM. After the processing parameters are determined, the in vitro corrosion, mechanical, and biological properties measurements were performed following the experimental design of Example 2 to understand the basic characteristics required for biodegradable Mg alloy.

In addition, bone forming ability of Mg—Zn—Sr—Zr and Mg—Zn—Ce—Zr alloys were assessed using alkaline phosphatase, and mineralization assay. hMSC were cultured with differentiation media supplemented with Mg, Sr, and Ce ions to test the effect of degradation product without engaging direct cell attachment. The alkaline phosphates assay was normalized by DNA quantification. After 1, 2, 3 weeks of culture, the hMSC lysates was mixed with p-nitrophenyl phosphate (pNPP) solution and substrate solution, incubated and observed at the absorbance of 405 nm. Mineralization of osteoblast cells was measured using alizarin red assay after 2 and 3 weeks of culture. Quantitative analysis was performed after alizarin red staining and the stained cells was dissolved for quantitation using plate reader at the absorbance of 605 nm.

Statistical Considerations

The same statistical analyses from Specific Aim 1 and Specific Aim2 were employed for the repeated experiments performed on Mg—Zn—Sr—Zr and Mg—Zn—Ce—Zr alloys. Two-way ANOVA was accordingly used for ALP and mineralization studies with independent variables of the group and time. The significance level was set at $p<0.5$ to prove if Sr or Ce addition has an effect on bone forming ability.

Anticipated Results

As outlined above, Ce and Sr addition to ZK40 alloy is not expected to deteriorate the corrosion resistance although even small amounts of these alloying elements are likely to form small precipitates along the grain boundary or inside of the parent Mg matrix phase. Mechanical properties would correspondingly change, but it is still expected to maintain 80% of the ZK40 alloy in terms of tensile strength. Mg—Zn—Sr—Zr and Mg—Zn—Ce—Zr alloys are projected to exhibit significantly higher level of ALP activity and mineralization while the cell cytotoxicity of the alloys would not be significantly different from ZK40.

Materials and Methods
Design and Synthesis of Alloys

TABLE 3.1

Abbreviated notation and chemical composition of the Mg-Zn alloys.

| Alloys | Mg | Zn | Sr | Ce | Zr |
|---|---|---|---|---|---|
| Mg-Zn-Zr | Bal | 4 | — | — | 0.5 |
| Mg-Zn-0.25Sr-Zr | Bal | 4 | 0.25 | — | 0.5 |
| Mg-Zn-1Sr-Zr | Bal | 4 | 1 | — | 0.5 |
| Mg-Zn-0.25Ce-Zr | Bal | 4 | — | 0.25 | 0.5 |
| Mg-Zn-1Ce-Zr | Bal | 4 | — | 1 | 0.5 |

Table 3.1 tabulates the abbreviated notation and chemical composition of the Mg—Zn alloys that are studied in the current chapter. Mg—Zn—Sr—Zr and Mg—Zn—Ce—Zr (Sr, Ce=1, 0.25) alloys were melted in a mild steel crucible using an electrical resistance furnace and casted in a mild steel mold preheated at 500° C. Pure elemental ingots of Mg (US magnesium Inc. 99.97%), Zn shots (Alfa-Aesar 99.99%), and Mg-30Sr/Mg-30Ce master alloys were weighed accordingly and homogenized at 700° C. to synthesize Mg—Zn—Sr—Zr and Mg—Zn—Ce—Zr alloy in 250 g batch size. At equilibrium, Zirmax® Mg-33.3 wt % Zr (Magnesium Elektron, UK) was added to the molten mixture. Stirring for 10 s after 1 min and 5 min was performed to achieve uniform dispersion and dissolution of zirconium particles in the melt. Finally, the temperature was maintained at 700° C. for 30 minutes and then casted. Following the solution treatment at 300° C. for 1 hour, hot extrusion was performed using an extrusion ratio of 30:1 at North Carolina A&T University (Greensboro, N.C.).

X-Ray Diffraction

X-ray diffraction (XRD) phase analysis was performed using Philips XPERT PRO system employing the $CuK_\alpha$ ($\square$=1.54056 Å) radiation source with a Si-detector. X-ray generator was operated at 45 kV and 40 mA at a 2θ range of 10-80°. X'Pert HighScore Plus version 3.5 software was used to identify the XRD patterns comparing to ICSD database.

ICP Analysis

Elemental analysis on the alloy compositions of was performed using inductively coupled plasma optical emission spectrometry (ICP-OES, iCAP duo 6500, Thermo Scientific). ZK40, ZJ40/41, and ZY40/41 alloy specimens were dissolved in 1% nitric acid. The solutions were then analyzed for the concentration of Mg, Zn, Zr, Ce, Sr, Fe, Mn, Ni, Al, and Cu using known standards.

Microstructure Analysis

The microstructure of heat-treated (T6) and extruded ZK40, ZJ40/41, and ZY40/41 alloys were mounted in epoxy (EpoxiCure, Buehler), and mechanically polished with 9, 3, and 1 µm diamond slurry followed by 0.5 µm colloidal silica to obtain a mirror-like finish using semi-automatic polishing system (Vector, Buehler). Specimens were then subjected to chemical etching in a solution of 5 mL acetic acid, 6 g picric acid, 10 mL water, and 100 mL ethanol followed by washing immediately using isopropanol to clean the surface. The microstructure of the heat-treated (T6) and extruded ZK40, ZJ40/41, and ZY40/41 alloys were observed using optical microscopy (Nikon, Japan). The polished and etched microstructure of ZK40, ZJ40/41, and ZY40/41 alloy specimens were also analyzed using a scanning electron microscope (JSM 6610LV, JEOL, Japan) equipped with an energy dispersion spectrometer (INCA, Oxford Instruments) to identify the secondary precipitates within the grain boundaries. Computer tomographic (Phoenix Nanotom-m 180 kV/15 W X-ray nanoCT® system, GE) images were also captured with a minimum voxel resolution ~80 um to analyze presence of any inclusions, voids, and secondary precipitates in the as cast, annealed ingots.

Immersion Corrosion Measurement

Immersion corrosion properties of heat-treated (T6) and extruded ZK40, ZJ40/41, and ZY40/41 alloys were assessed in conformation with ASTM G31-72. Heat-treated (T6) and extruded ZK40, ZJ40/41, and ZY40/41 alloys were prepared in disks, 5 mm in diameter and 1.5 mm in thickness. These disks were polished up to 1200 grit using SiC paper. Surface area and the weight of each specimen were measured prior to the immersion tests. The specimens were then cleaned in acetone using a sonicator bath and sterilized under UV for 30 min each side. After sterilization, the specimens were immersed for 1, 3, and 5 weeks in Hank's Balanced Salt Solution (HBSS) at 37.4° C. The HBSS media volume to surface area ratio was maintained at 20 ml/cm$^2$. The immersed specimens were subsequently removed from HBSS media at each time point, rinsed with distilled water, and dried at room temperature. Further, the degradation product of each specimen was cleaned with 200 g/L of chromic acid and 10 g/L of $AgNO_3$ solution for 10 min to assess the mass loss similar to the procedure described in Chapter 3 and 4. The difference in mass before and after immersion was recorded, and the degradation rate were calculated using the mass loss, density and surface area according to ASTMG31-72. Averages and standard deviations of 3 sample measurements were reported and one-way ANOVA with Tukey's post-hoc test was used to determine any significant mean differences with a p-value less than 0.05 for each time point.

Tensile Testing

Tensile testing was conducted in accordance with ASTM-E8-04. ZK40, ZJ40/41, and ZY40/41 alloys were machined into a standard dog-bone shape with a gauge length of 13.5 mm, width of 3 mm, and thickness of 3 mm. Uniaxial tensile testing was performed using an Instron machine employing a 5 kN load cell at room temperature at a cross-head speed of 1.3 mm/min. Yield strength (YS), ultimate tensile strength (UTS), Young's modulus (E), and percent elongation (%) were obtained from the stress-strain curve obtained for each specimen. Young's modulus was also determined from the initial linear portion of the curves. Average and standard deviations of these 3 sample measurements are reported in the results sections to follow. Averages and standard deviations of 3 sample measurements were reported and one-way ANOVA with Tukey's post-hoc test was used to determine any significant mean differences with a p-value less than 0.05 for each time point.

MTT Cell Viability Test

In order to study the cytocompatibility of extruded ZK40, ZJ40/41, and ZY40/41 alloys, murine osteoblast-like cell line. MC3T3 (ATCC, Rockville, Md.), was cultured with the extract media prepared by immersing the alloy specimens in culture medium and incubating them for 72 h. Modified Eagle's medium alpha (αMEM) with 10% FBS and 100 U ml$^{-1}$ penicillin-streptomycin was used as cell culture media. The alloy specimens were machined into disks, 10 mm diameter and 5 mm thickness, and polished tip to 1200 grit using SiC paper. The ratio of culture media volume to specimen weight was maintained at 1 mL to 0.2 g in conformation with EN ISO 10993:12. The extract media was filtered using 0.2 µm membrane with this original extract being considered as 100% extract. The chemical concentration of Mg, Zn, Zr, Sr, and Ce in the 100% extract was then measured using an inductively coupled plasma-optical emission spectroscopy (ICP-OES) similar to the procedure described earlier in Chapters 3 and 4. The 100% extract was further diluted to 50%, 25%, and 10% extract solutions. MC3T3 cells were seeded in a 96-well plate with a cell density of 6,000 cells per well and incubated for 24 h. The MC3T3 cells were further incubated with the 100%, 50%, 25%, and 10% extract media. After 72 h of incubation, Vybramt MTT Cell Proliferation Kit (invitrogen Corporation, Karlsruhe. Germany) was used to assess the cell viability. Prior to the MTT assay, the extract media was replaced with fresh culture media to prevent any interaction between Mg ions and 3-(4,5-dimethylthiazol-2-yl)-2,5-diphenyltetrazolium bromide (MITT). 110 μL of 1.2 mM MTT in phosphate buffered saline (PBS) was then added to each well and incubated for 4 h of incubation. Sodium dodecylsulfate-hydrochloric acid solution solution was then added and incubated for 12 h to solubilize the formazan crystal. The absorbance of formazan dye was then measured at a wavelength of 570 nm using Synergy 2 microplate reader (BioTek Instruments. Winooski. Vt.) similar to the procedure described earlier. Averages and standard deviations of 3 sample measurements were reported and one-way ANOVA was used to determine any significant mean differences with a p-value less than 0.05 for each dilution factors of the extract media.

Human Mesenchymal Stem Cell Culture with Salt Solution

Human mesenchymal stem cells (Lonza, Allendale N.J.) were used to assess the effect of Mg, Sr, and Ce ions on the osteogenic differentiation of hMSCs. The third passage cells were cultured with both growth and differentiation media that contain Mg, Ce, and Sr ions. Modified Eagle's medium alpha (αMEM) with 20% FBS and 100U ml$^{-1}$ penicillin-streptomycin was used as the growth media. 100 nM dexamethasone, 50 μM ascorbic acid, and 10 mM β-glycerophosphate were further added to the growth media to generate the osteogenic media. Additionally, 10 mM MgSO$_4$, 0.1/1 mM SrCl$_2$, or 0.1/1 mM CeCl$_3$ were added to the differentiation media as tabulated in Table 3.2. hMSCs were seeded at the cell density of 6000 cells per cm$^2$. and cultured with the growth media for 7 days. Following this, the growth media was replaced with the sample media and cultured for another 7 and 14 days to investigate the alkaline phosphatase activity and osteogenic gene expression. Averages and standard deviations of 3 sample measurements were reported and one-way ANOVA with Tukey's post-hoc test was used to determine any significant mean differences with a p-value less than 0.05 for each time point.

TABLE 3.2

Abbreviated notation and chemical formulation of sample media.

| Abbreviated notation for sample media | Sample media formulation |
|---|---|
| GM | Growth media |
| DM | Differentiation media |
| DM-Mg | 10 mM MgSO$_4$ in the differentiation media |
| DM-Mg-0.1Sr | 10 mM MgSO$_4$ and 0.1 mM SrCl$_2$ in the differentiation media |
| DM-Mg-1Sr | 10 mM MgSO$_4$ and 1 mM SrCl$_2$ in the differentiation media |
| DM-Mg-0.1Ce | 10 mM MgSO$_4$ and 0.1 mM CeCl$_2$ in the differentiation media |
| DM-Mg-1Ce | 10 mM MgSO$_4$ and 1 mM CeCl$_2$ in the differentiation media |

Alkaline Phosphatase Measurement

Alkaline phosphatase (ALP) activity was assessed using an enzymatic assay measuring the conversion of p-nitrophenyl phosphate (pNPP) as a phosphatase substrate. hMSC cells were washed with PBS and lysed using a lysis buffer (CelLytic M, Sigma Aldrich) to prepare the cell lysate containing ALP. pNPP substrate solution was added to the cell lysate to assess the enzymatic reaction. After 30 m incubation, 0.3N NaOH solution was then supplemented to stop the enzymatic reaction, and measure the absorbance at 405 nm. pNPP standard solutions with different concentrations were prepared by diluting the pNPP substrate solution with 0.02N NaOH solution. The ALP activity was determined by comparing the absorbance to the standard curve, and normalized by total double-stranded DNA.

Gene Expression Study Using qRT-PCR hMSCs were cultured with growth media and differentiation media with the different alloying element salts mentioned above in the section 5.2.8. RNA isolation was performed on these hMSCs using a commercially available RNA extraction kit (Nucleospin RNA Extraction Kit, Macherey Nagel). RNA concentration was measured using a microplate reader (Synergy 2. BioTek Instruments) at the wavelength of 260 and 280 nm. Approximately 50 rig of RNA was used for each reverse transcription reaction. Reverse transcription was performed using a commercially available kit (Improm-II Reverse Transcription Kit, Promega). After that, complementary DNAs were subjected to qPCR reactions using SYBR green mastermix (Brilliant II, Agilent) and forward and reverse primers (5'-3') for GAPDH, ALPL and OPN (Integrated DNA Technologies).

Results

Phase and Elemental Analysis

FIG. 3.1 shows x-ray diffraction (XRD) patterns of the base alloy Mg—Zn—Zr (ZK 40), Mg—Zn—Sr—Zr, and Mg—Zn—Ce—Zr alloys after extrusion. The patterns were identified as a single phase α-Mg matrix with hcp crystal structure of pure Mg. Mg—Zn—Zr, Mg—Zn—Sr—Zr, and Mg—Zn—Ce—Zr alloys exhibited presence of no distinct intermetallic phases in combination with Mg, Zn, Ce, Sr, or Zr. The XRD patterns clearly exhibits that α-Mg solid solution single phase was formed in all of the different alloy systems and no detectable amount of any intermetallic content was observed. However, unlike pure Mg, the highest peak intensity for Mg—Zn—Zr, Mg—Zn—Sr—Zr, and Mg—Zn—Ce—Zr alloys was observed for the pyramidal plane. This observation suggests that the orientation of the α-Mg solid solution single phase was altered during alloy synthesis and processing.

Back-scattered electron (BSE) microscopy was employed to observe the microstructure of the extruded Mg alloys to show the influence of the various alloying elements and perform elemental analysis on the alloy matrix and precipitates. In FIG. 3.2, the BSE images of the Mg alloys analyzed in the matrix indicated as M and in the precipitates indicated as P revealed the presence of intermetallic precipitates as high contrast areas along the grain boundaries. Increase in precipitate amounts were observed with an increase in Sr and Ce amount (FIG. 3.2a vs. 5.2b-e). Mg—Zn—Zr showed the formation of solid solution close to its nominal composition and Zn-rich Mg$_7$Zn$_3$ precipitates similar to the case described in Chapter 3 for the ZK40 alloy. 0.25 wt. % Sr addition to Mg—Zn—Zr had no effect on the alloy matrix but caused the presence of Sr and less Zn contents in the precipitate (FIG. 3.2b). Further increasing the Sr content to 1 wt. % Sr addition did not seem to alter the composition of the solid solution or precipitates much showing similar composition range. However, an increased number of precipitate sites were observed (FIG. 3.2d). Cerium addition also exhibited similar effect on the precipitate indicating presence of Ce and decreased amounts of Zn compared to Mg—Zn—Zr (FIG. 3.2c,e). Mg—Zn—Ce—Zr exhibited more precipitates compared to Mg—Zn—Sr—Zr (FIG. 3.2b,d vs. 3.2c,e). Thus, Ce addition was observed to cause more precipitates compared to Sr addition due to the higher solid solution limits of Ce with Mg.

Immersion Corrosion Measurement

An effect of adding Ce and Sr as micro alloying elements on the corrosion resistance of Mg—Zn—Zr alloy was investigated using immersion corrosion measurement in HBSS for 7 and 35 days. In FIG. 3.3, mass loss of the Mg alloys were converted to immersion corrosion rates in millimeter per year (mmpy) as described in earlier chapter 4. Mg—Zn—Sr—Zr alloys does not exhibit any significant difference in the corrosion rate compared to Mg—Zn—Zr. On the other hand, Mg—Zn-1Ce—Zr exhibits a significant increase in corrosion rate after 35 days of immersion whereas Mg—Zn-0.25Ce—Zr still maintained comparable corrosion resistance with other Mg alloys. As observed and discussed in section 5.3.1 in the BSE images, more secondary phase contents in the case of Mg—Zn-1Ce—Zr results in a catastrophic corrosion initiated from the Mg—Zn—Ce mixtures along the grain boundaries. Overall, the addition of 0.25 and 1 wt. % of Sr as well as 0.25 wt. % of Ce did not deteriorate the corrosion resistance significantly compared to commercial AZ31.

Tensile Mechanical Properties

Mechanical properties of the different alloys was determined using tensile tests, the results of which as tabulated in Table 3.4. Mg—Zn—Zr alloy (ZK 40) exhibited an elastic modulus of 45.8 GPa, yield strength of 286.6 MPa (YS), and an ultimate tensile strength of 327.2 MPa (UTS), and 9.3% elongation. Addition of 0.25 wt. % and 1 wt. % Sr to the Mg—Zn—Zr only resulted in a slight decrease in UTS to 317.3 MPa and 320.9 MPa. There were no significant difference in modulus, YS, and elongation. On the other hand, addition of 0.25 wt. % and 1 wt. % Ce to Mg—Zn—Zr exhibited a significant increase in UTS to 335.2 MPa and 341 MPa, respectively. A significant decrease in elongation from 9.3% to 7.6% was also observed in the case of Mg—Zn-1Ce—Zr.

TABLE 3.4

Tensile properties of Mg-Zn-Zr, Mg-Zn-Sr-Zr, and Mg-Zn-Ce-Zr alloys (n = 3, §p < 0.05 denotes a significant difference with all other groups).

| Materials | Modulus (GPa) | Yield Tensile Strength (MPa) | Ultimate Tensile Strength (MPa) | Elongation (%) |
|---|---|---|---|---|
| Mg-Zn-Zr | 45.8 ± 5.2 | 286.6 ± 8.0 | 327.2 ± 6.2 | 9.3 ± 3.5 |
| Mg-Zn-0.25Sr-Zr | 42.4 ± 3.6 | 292.8 ± 6.2 | 317.3 ± 2.4 | 12.6 ± 2.1 |
| Mg-Zn-1Sr-Zr | 41.0 ± 2.5 | 292.7 ± 9.5 | 320.9 ± 1.9 | 9.5 ± 1.0 |
| Mg-Zn-0.25Ce-Zr | 39.7 ± 4.0 | 271.9 ± 7.1 | 335.2 ± 0.4 § | 10.2 ± 1.0 |
| Mg-Zn-1Ce-Zr | 45.9 ± 4.3 | 282.5 ± 3.3 | 341.7 ± 2.9 § | 7.6 ± 1.1 § |

MTT Assay

MC3T3 cell viability was assessed using MTT assay after culturing the cells for 1 and 3 days with extract media containing the degradation products of Mg-based alloys. Compared to the growth media as negative control, the MTT assay result was plotted as shown in FIG. 3.4. 100% extract media of Mg—Zn—Zr, Mg—Zn—Sr—Zr, and Mg—Zn—Ce—Zr alloys, as expected in contrast to commercially available AZ31B or pure Mg, exhibited less than 10% cell viability immediately even after 1 day culture (FIG. 3.4a). The cell viability of these alloys was however restored to ~50% with 50% extract media and increased to ~90% with 25% and 10% extract media FIG. 3.4b showed similar cell viability pattern for the MTT assay after 3 days of culturing the MC3T3 with the extract media. It is suggested 10% extract media is suitable to determine the cytotoxicity of biodegradable Mg alloys due to the nature of the static culture causing cell necrosis induced by osmotic shock of total metal salt concentration as discussed in Chapter 4. ISO 10993:5 protocol determines that achieving 75% or higher cell viability is generally considered non-cytotoxic. Hence, the cell viability of 10% extract media suggests that these alloys are indeed cytocompatible with the MC3T3 cell line.

ALP Activity Measurement

Human mesenchymal stem cells were (hMSC) cultured with growth media for 7 days. ALP expression levels were measured after 7 and 14 days of culturing the hMSCs with osteogenic differentiation media containing alloying elements (FIG. 3.5). Although higher ALP level was observed compared to growth media for all the salt concentrations, there was no significant improvement in ALP expressions in the differentiation media groups with the addition of the alloying element salts. Lower level of ALP activity was observed in differentiation media containing $CeCl_3$ after 7 days but the ALP level was restored compared to differentiation media after 14 days. No other significant difference in ALP expressions was caused by the addition of Mg and Sr ions.

Gene Expression

Alkaline phosphatase (ALPL) and osteopontin (OPN) gene expression are shown in FIG. 3.6. Fold changes of ALPL and OPN was obtained by subtracting GAPDH housekeeping gene expression and subtracting the average of the growth media groups. ALPL expression exhibited a significant increase in DM-Mg-1Sr group. In the case of OPN, Mg, 0.1/1 mM Sr, and 0.1 mM Ce supplemented media exhibited significantly enhanced expression level whereas Ce supplemented media exhibited no significant improvement.

Discussion

Effect of Sr and Ce on Corrosion Resistance and Mechanical Properties

The effect of Sr and Ce additions to Mg based alloys particularly, the Mg—Zn—Zr system, was explored. Additionally, corrosion resistance, mechanical properties, cytocompatibility were studied and the osteogenic response of incorporation of gradually adding Sr and Ce to biodegradable Mg—Zn—Zr alloys was investigated. Mg—Zn—Zr is a commercially available Mg alloy system that was developed and used for structural applications. It has suitable corrosion resistance, mechanical properties and cytocompatibility. Mg—Zn (Mg$_7$Zn$_3$) secondary phase precipitates are observed to form in the grain boundary area. These precipitates are vulnerable to galvanic corrosion and serve as initiators for pitting corrosion. Hence, Sr and Ce have been selected as microalloying elements to alter the composition of these precipitates. Strontium (Sr) refines the grain sizes of Mg alloys and Ce can form stable oxides due to the higher bond energies and bond strengths and affinity of Ce to form cerium oxides thus serving to protect the Mg—Zn—Zr alloy from corrosion. In addition, Sr and Ce have been reported to have a positive effect on the proliferation and osteogenic differentiation of human mesenchymal stem cells.

Strontium (Sr) and Cerium (Ce) were both used as micro alloying elements in the amount of 0.25 wt. % and 1 wt. %. Only small amount of Sr and Ce were used due to the low solubility limit of these alloying elements exceeding which can form more secondary phase precipitates which can deteriorate corrosion resistance leading to galvanic corrosion. Phase analysis was performed on the Mg—Zn—Sr/Ce alloy system using an x-ray diffraction. As shown in FIG. 3.1, no distinct second phase or unalloyed single elements or multiphase alloys or compounds were observed in the Mg—Zn—Zr, Mg—Zn—Sr—Zr, and Mg—Zn—Ce—Zr alloy systems. However, presence of second phase precipitates along the grain boundaries of the Mg alloys were still revealed under back-scattered scanning electron (BSE) microscopy as shown in FIG. 3.2 possibly due to the processing conditions of melting and casting not allowing enough time for complete homogenization of the melt or possibly during extrusion of the alloy, the time, temperature and reduction ratios selected exacerbated causing instabilities to the precipitates leading to further break down and distribution of the precipitate particles within and around the grain boundaries.

The composition of the precipitates in the Mg—Zn—Zr alloy system thus transformed the precipitate compositions to ternary mixtures of Mg, Zn, and Sr/Ce in Mg—Zn—Sr/Ce—Zr alloy systems thus leading to precipitates of Mg—Zn—Sr in the case of Mg—Zn—Sr—Zr system and Mg—Zn—Ce in the Mg—Zn—Zr—Ce system. Although the chemical composition of the precipitates were more similar to the composition of the base alloy (Mg—Zn—Zr (ZK 40) system) in each alloy, more number of precipitates were observed in the BSE images. Ce addition was more prone to form grain boundary precipitates compared to Sr addition (See FIG. 3.2b, d vs. 3.2c, d). As a result of these precipitates from Sr and Ce addition, the immersion corrosion measurements exhibited no significant improvements in corrosion resistance. Except for Mg—Zn-1Ce—Zr alloy composition, the corrosion rates in general for all the other compositions and additions of Sr and Ce were comparable to commercially available AZ31 without displaying any significant difference. Mg—Zn-1Ce—Zr in fact, demonstrated increase in corrosion rates after 35 days of immersion due to the higher volume of precipitates formed as seen in the BSE images.

Precipitates at the grain boundary can also serve to impede dislocation movement as is well-known in the literature leading to improvement in the mechanical strength of Mg alloys.

It is well-known from physical metallurgical principles, precipitation hardening is routinely used to increase precipitation of second phase precipitates from alloying elements or inclusions or impurity phases by performing heat treatment above the melting point of a specific alloying element via the time-temperature-transformation (TTT) diagrams. Although such optimizations were not performed in this study, the initial results presented here clearly show that such optimizations can be conducted to indeed reap the potential of these optimization studies of the addition of Sr and Ce. Nevertheless, it can be seen that the addition of Sr to Mg—Zn—Zr exhibited no significant difference in tensile properties. On the other hand, the ultimate tensile strength was significantly improved to 335 MPa and 342 MPa with Ce-0.25 wt % and 1 wt % additions, respectively. However, as is usually the case with the 1 wt. % of Ce addition, a decrease in elongation was obtained to offset the grain boundary strengthening.

Cytocompatibility and Osteogenic Potential of Sr and Ce Additions to Mg—Zn—Zr Alloys Toxicity of biomaterials are often examined using in vitro experiments prior to initiation of in vivo experiments. In this regard, ISO 10993 protocols have been developed and used for screening polymeric and metallic biomaterials based on the cell viability shown using the MTT assay. Fischer et al. initially reported that MTT assay followed by direct cell culture with Mg alloy materials can result in a false positive due to Formazan salt conversion by actively corroding Mg ions serving to interfere with the assay results. There is known an osmolality issue of Mg ions causing osmotic shock to the cells although Mg alloys implanted in the animal exhibits no significant tissue damage. Hence, in this study the work has focused on the indirect MTT assay results indicating cell viability with 10% extract media serving as a better acceptable indicator to rank the toxicity of Mg alloys. It has been widely accepted that in vitro degradation and cytocompatibility exhibited by Mg during the static immersion tests do not really represent the in vivo implantation response of biodegradable Mg alloys. Mg alloys on the other hand, tend to degrade in a much slower rate during in vivo implantation and hence, exhibit minimal inflammatory response.

Cytocompatibility of the Mg alloys have been examined using MC3T3 cell line in compliance with the ISO standard with modifications. MTT assay after 3 days of culturing MC3T3 cells with the 10% extract media exhibited good cytocompatibility in all the Mg alloys studied compared to pure Mg. Pure Mg and commercial AZ31 were used as experimental control groups and exhibited the cell viability higher than 75% when using 100% extract media.

In addition to cytocompatibility, osteogenic effect of the alloying elements such as Mg, Sr, and Ce was investigated by culturing the human mesenchymal stem cells (hMSC) with osteogenic media supplemented with MgSO$_4$, SrCl$_2$, and CeCl$_3$. However, Zr or Zn ions were not considered for this study since there are no reports on their influence on osteogenic differentiation of hMSCs. Concentration of MgSO$_4$ was maintained at 10 mM as reported to be optimal for hMSC proliferation. SrCl$_2$ and CeCl$_3$ are dissolved in the osteogenic media with 10 mM MgSO$_4$ to reach concentrations of 1 or 0.1 mM since Sr and Ce content in Mg—Zn—Sr/Ce—Zr alloys is limited to 1 wt. % in the present study. Further, hMSC is used instead of MC3T3 since hMSC has the ability to differentiate into multiple lineage whereas MC3T3 is already in the early stage of osteoblast. Confluent hMSCs were cultured with the supplemental media for 7 and 14 days as mature osteoblast can be obtained after 14 days of culturing hMSC in osteogenic media.

Alkaline phosphatase was measured after culturing hMSC for 7 and 14 days since it is an early marker for osteogenic differentation of hMSC. Compared to growth medium, osteogenic media and supplemented media exhibited higher ALP activity. However, no significant improvement in ALP activity was observed with osteogenic media supplemented with Mg, Sr, or Ce (see FIG. 3.5). Hence, the gene expression was quantified using qRT-PCR to investigate any osteogenic effect of these elements. ALPL expressions normalized by GAPDH housekeeping gene seemed to be significantly upregulated with 1 mM Sr containing media as shown in FIG. 3.6. Overall, osteogenic media supplemented with Mg, Sr, and Ce ions however, exhibited no additional improvement in ALP activity and mRNA expression.

Conclusions

The effect of adding Sr and Ce as micro alloying element to biodegradable Mg—Zn—Zr alloy has been studied in terms of corrosion and mechanical properties as well as biological influence of these alloying elements contributing to mineralization and exhibiting any osteogenic potential. Using these micro alloying elements, it was observed that second phase precipitates were formed. The precipitates appeared to be successfully formed owing to the solubility of Sr and Ce in the binary Mg—Zn phase system to correspondingly form Mg—Zn—Sr/Ce ternary phase precipitates in the presence of Zr as well. Unfortunately, it appears that the introduction of additional alloying elements induced formation of more precipitates along the grain boundaries. Thus, a significant improvement in corrosion resistance was not observed though anticipated. On the other hand, the mechanical properties were improved due to the large volume of precipitates formed confirmed by the back scattered SEM analysis showing formation of Mg—Zn—Sr and Mg—Zn—Ce precipitates for Sr and Ce addition. Cytocompatibility of Mg—Zn—Zr was found to be not affected by adding Sr or Ce. Zn however, exhibited low tolerance in the cell viability after culturing MC3T3 cells with different alloying element in the form of chloride salts dissolved in the culture media. Thus, similar cell viability in MTT assay was obtained due to the constant Zn content in Mg—Zn—(Sr/Ce)—Zr alloys. ALP activity and ALPL gene expression exhibited no significant improvement whereas OPN gene exhibited some improvement after culturing hMSCs with osteogenic media supplemented with Mg, Sr, and Ce salts signifying that the alloying elements do not have any potential adverse contribution to the mineralization potency of the alloy system. However, in vivo studies would be required to ascertain the true osteogenic potential of these alloy systems containing Sr and Ce in addition to Zn and Zr.

Example 4

Rat Femoral Fracture Repair Using Intramedullary Pins of Mg—Zn—Sr—Zr Alloy
Rationale Biodegradable Mg—Zn alloys are anticipated to exhibit suitable degradation, mechanical properties, and biocompatibility characteristics desired for various orthopedic applications. It is well-known that depending on the load experienced by the biodegradable Mg—Zn implant device, the degradation rates will vary, and hence, the failure of the implanted device can induce a sudden inflammatory response. To demonstrate the influence of mechanical stress on the biodegradation and mineralization response of the Mg—Zn based alloy, a rat femoral fracture model is selected to investigate the biocompatibility and mineralization potential of the Mg—Zn alloy under load-bearing condition. Although the Mg—Zn alloy can be potentially used as intramedullary rod, the alloy will be implanted in the intramedullary region to support and fix a non-union resulting in healing of the fractured femur causing reunion. Correspondingly, biocompatibility of the Mg—Zn alloy and its degradation products will be assessed using blood test as well as the histology of liver and kidney. Bone healing and local toxicity will be assessed using bone histology and elemental analysis of the muscle.

Experimental Design

To demonstrate the efficacy of the alloy in the above discussed rat femoral fracture model, a single composition of the Mg—Zn alloy was judiciously selected based on the in vitro corrosion resistance and mechanical properties. At the same time, Ti-alloy was used as a control group to mimic the level of toxicity observed in currently used state of the art clinical biomaterial for bone fixation. Intramedullary pins were therefore machined corresponding to the same dimensions. Each pin was inserted in the intramedullary region of the right femur of each Sprague-Dawley rat after osteotomy. The animals with implant device were all sacrificed after 2, 8, and 14 weeks for assessing the biocompatibility of Mg and Ti pins.
Blood Test Whole blood samples were accordingly analyzed for complete blood count panel. Serum samples were analyzed to obtain a comprehensive picture of the metabolic and chemistry profile. The chemistry profile was used to essentially assess the level of phosphorous and magnesium in the blood.
Micro CT Analysis Micro CT imaging was also performed on the original implant and harvested bones. Degradation rates correspondingly have been calculated from the volume loss. Finally, bone healing response has been determined and assessed based on the CT images.

Histology Liver and kidney tissues were also correspondingly fixed using neutral buffered formalin, embedded in paraffin, and sectioned using a microtome. Hematoxylin and eosin staining was performed to examine any tissue damage or abnormal response. Harvested femurs were then subsequently processed as undecalcified bone and embedded in plastic. Embedded tissue were correspondingly sectioned and subjected to various staining methods including Goldner's Masson Trichrome and toluidine blue.
Statistical Considerations Two-way ANOVA statistical analysis was used to determine the mean comparison of degradation rates and blood test results with regards to independent variables, time and group. The significance level was set at $p<0.5$ to prove that Sr or Ce addition indeed have an effect on bone forming ability. Histology results were also accordingly judiciously considered to justify only the subjective positive outcome.
Anticipated Results After 14 weeks, more than 50% volume of the Mg pins is expected to remain following degradation. Callus formation on the fracture site will also be expected to occur while helping to maintain the stability of the fixation. No significant difference between groups and time will be expected from the blood test results and histology outcome. An elevated level of Mg could be likely expected following analysis of the chemistry panel analysis. However, it is anticipated that the level will be maintained within the normal range.
Alloy Processing and Fabrication of Femoral Pins Mg-4Zn-0.1Sr-0.5Zr (Mg—Zn) alloy was synthesized using an electrical resistance furnace (Wenesco Inc.). Pure Mg (US magnesium Inc. 99.97%), Zn shots (Alfa-Aesar 99.99%), Mg-30Sr master alloy were melted in a mild steel crucible. The total melt amount was 250 g. Melting process was performed using 0.5% SF6+balance Ar protective gas atmosphere to protect the molten magnesium alloy from oxygen. The molten mixture of Mg, Zn, and Sr were homogenized at 700° C. and zirconium content was added using Zirmax® (Mg-33.3 wt % Zr) master alloy (Magnesium Elektron Ltd.). After 1 and 5 minutes, the liquid melt was further homogenized by stirring for 10 seconds to dissolve and disperse the zirconium particles uniformly. The melt was maintained at 700° C. for 30 min, following which the molten liquid was poured into a mild steel mold (Ø44.5 mm×82.5 mm) preheated at 500° C.

The middle part of the as-cast Mg—Zn—Sr—Zr (Mg—Zn) alloy following removal of the top, sides and the bottom was machined to a dimension of 37.6 mm diameter and 60 mm height by using a lathe. The as-cast Mg—Zn—Sr—Zr (Mg—Zn) alloy was then heat-treated at 300° C. for 1 hour, quenched in oil, and annealed at 205° C. for 12 hours. Following heat treatment, hot extrusion was performed using an extrusion ratio of 30:1 at North Carolina A&T University (Greensboro, N.C.).

Animal Study Design

The animal study was conducted in accordance with a protocol approved by Animal Care and Use Committee (IACUC) at the University of Pittsburgh. A schematic of the surgical procedure executed is displayed in FIG. 4.1. Groups, time points, and number of animals involved in the current chapter are explained in Table 4.1. 30 Sprague-Dawley rats of approximately 250 g of body weight were used. 15 rats were randomly selected for Ti alloy implantation and the other rats were implanted with Mg alloy pins. For each implant material, 10 rats were implanted with pins for 2 and 14 weeks and 5 rats were implanted with the cuff for 14 weeks. For each pin implanted, the right femur of each rat was approached laterally and an osteotomy was performed in the middle of the femur using a dremel drill with a diamond wheel blade. A pin of Ti or Mg alloy was inserted into the intramedullary region to achieve a stable reunion of the fractured femur. 5 rats from both Ti and Mg groups were sacrificed for fracture healing and toxicity analysis after 2 or 14 weeks of implantation. For each cuff implantations, a cuff of Ti or Mg—Zn alloy was implanted around the unfractured femur for toxicity analysis after 14 weeks.

TABLE 4.1

Groups, time points, and number of animals used for Ti and Mg-Zn device implantation

| Group | Time point | N/time point |
| --- | --- | --- |
| Ti alloy pins | 2 and 14 weeks | 5 |
| Mg-Zn pins | 2 and 14 weeks | 5 |
| Ti alloy cuffs | 14 weeks | 5 |
| Mg-Zn cuffs | 14 weeks | 5 |

Radiographic imaging and computer tomography analysisX-ray images of all animals were obtained after 7 days to observe implant location and alignment of fractured femurs. The Mg—Zn alloy pins before implantation were scanned using micro-computed tomography (microCT) (VivaCT40; Scanco Medical, Switzerland). The harvested femurs were also scanned using microCT after embedding in plastic. Analysis of the microCT images were performed using Mimics (Materialise, Belgium) to calculate the degradation rate of the Mg alloy pins and assess fracture healing. Averages and standard deviations of 5 sample measurements were reported and t-test was used to determine any significant mean differences with a p-value less than 0.05 for Mg—Zn pin groups at different time points.

Blood Test

Blood samples were obtained before operation and after euthanasia at 2 and 14 weeks. The samples collected in K2-EDTA were sent to Marchfield Labs (Cleveland, Ohio) for hematologic analysis. Red blood cell count, hemoglobin, hematocrit, platelet count, and white blood cell count were analyzed using a Sysmex XT2000i Automated Hematology Analyzer (Sysmex Corporation, Japan). For biochemical analysis, the blood samples were maintained at room temperature to clot for 30 minutes and centrifuged at 2,000 rpm for 10 minutes. The supernatant serum samples were analyzed using an Olympus AU chemistry analyzer (Olympus Corporation, Japan). Alanine aminotransferase (ALT), alkaline phosphatase (ALP), total protein, albumin, total and direct bilirubin, cholesterol, glucose, urea, creatinine, phosphorus, chloride, potassium, sodium, and magnesium were accordingly measured. Averages of 3 sample measurements were reported and compared to the reference ranges for each parameter.

ICP Analysis

Harvested liver and kidney tissues were dried in an oven at 70° C. overnight. Dried tissue samples were then ground using a mortar and pestle. 0.5 g of ground tissues were dissolved in 5 mL of concentrated nitric acid that was kept heated at 130° C. for 14 hours, and supplemented with 1 mL of 30% hydrogen peroxide. Sample solutions were then diluted 10 times and measured using an inductively coupled plasma optical emission spectroscopy (ICP-OES, iCAP duo 6500 Thermo Fisher, Waltham, Mass.) with standard solutions of the various elements being analyzed. Averages and standard deviations of 3 sample measurements were reported and one-way ANOVA was used to determine any significant mean differences with a p-value less than 0.05 for all other groups.

Soft Tissue Histology

Harvested liver and kidney tissues were fixed in 10% neutral buffered formalin for 48 hours. The fixed tissues were sectioned in small pieces, dehydrated in ethyl alcohol series from 70% to 100%, cleaned using xylene substitute and embedded in paraffin. Paraffin tissue blocks were then sectioned using a rotary microtome. Tissue slices were accordingly dewrinkled on a warm water bath, and transferred to glass slides. After drying, tissue slides were imaged using an optical microscope after staining with hematoxylin and eosin (dyes) and mounted using a mounting solution.

Bone Tissue Histology

Undecalcified embedding was used to perform histology analysis of the harvested femurs with implants. Harvested femurs were fixed in 70% ethyl alcohol for 72 hours. The fixed femurs were then dehydrated in diluted ethyl alcohol from 70% dilution to 100% consecutively. The femurs were cleaned in xylene and embedded in poly methyl methacrylate (PMMA) (OsteoBed, Life Technology). 7 to 10 um tissue sections were obtained from the embedded femurs using a rotary microtome with a tungsten carbide blade. Sections were adhered to tape to prevent shattering during sectioning. Sections were subjected to Goldner's Masson Trichrome and alkaline phosphatase staining. The stained sections were mounted on a glass slide using a glycerol solution and observed under an optical microscope.

Results

In vivo degradation of the magnesium-zinc-zirconium-strontium (Mg—Zn—Zr—Sr) alloy pins FIG. 4.2 exhibits representative x-ray radiograph images of Ti and Mg—Zn pin implanted rats after 1 week of osteotomy surgery. The images were used to determine the time point for euthanizing each animal based on the quality of fractured femur fixation. In the x-ray image, some visible hydrogen gas evolution was observed around the Mg—Zn implants as shown in FIGS. 4.2b and 4.2c. Rats implanted with both Ti and Mg—Zn pins exhibited normal movement and ambulatory behavior.

Harvested femurs exhibited normal fracture healing response with intramedullary pins. Callus formation was observed around the wound. Callus formed on the femurs with both Ti and Mg—Zn pins exhibited no visible difference. However, the callus formed on the femurs after 8 and 12 weeks of implantation was more hardened compared to the callus after 2 weeks of implantation. The fracture femurs with Mg—Zn pins was not aligned as straight as the femurs with Ti pins.

FIG. 4.3 shows the representative micro-computed tomography (micro-CT) images of rat femurs with Ti or Mg—Zn pins after plastic embedding. Femur with a broken Mg—Zn pin resulted in a misalignment of fractured bones. At 2 weeks, 3 out of 5 Mg—Zn pins were fractured into 2 pieces. Ti pins on the other hand, exhibited no fracture or damage due to the load. Mal-union of the femurs with broken Mg—Zn pins can lead to a significant difference in the fracture healing. However, the micro-Ct images for 14 months for both Ti and Mg—Zn pins implanted shown in FIG. 4.3 indicated that the fracture healing process was not completed. More hydrogen gas bubbles were evolved around Mg—Zn pins following 2 weeks of implantation not distinguishable in micro CT but was noticeable in the histology as discussed later. After 14 weeks, the gas bubbles were however, not distinguishable in the micro-CT images.

The remaining volume of Mg—Zn pins in the intramedullary region was analyzed from the micro-CT images (see FIG. 4.4b). The remaining volume of Mg—Zn pins after 2 weeks of implantation was 87.7%. After 14 weeks, the remaining volume was significantly decreased to 42.0%. Corrosion rates of Mg—Zn pins were calculated from the volume loss and original surface area as shown in FIG. 4.4a. Mg—Zn pins for 2 weeks of implantation exhibited the corrosion rate of 0.91±0.65 mmpy. The corrosion rate at 2 weeks was anticipated to be higher than the other time points since the Mg—Zn pins was exposed to the largest mechanical stress at the 2 week time point. The Mg—Zn pins for 14 weeks of implantation continued to degrade with larger surface area being exposed which resulted in the corrosion rate of 0.77±0.30 mmpy.

Blood Test Results

Table 4.2 summarizes blood test results of rats before and after osteotomy surgeries for 2 and 14 weeks of Ti and Mg—Zn pins/cuffs implantation. Red blood cell, hemoglobin, and platelet count exhibited no significant difference in the groups for the different implants and the different time durations. White blood cell count after 2 weeks of Ti pin implantation was significantly higher compared to the Mg—Zn group. However, it still remained within the reference range.

TABLE 4.2

Hematologic analysis results from blood panel test after Ti pin (2 and 14 weeks), Mg-Zn pin (2 and 14 weeks), and Mg-Zn cuff (2 weeks) implantations.

| Name | Implantation time | Red Blood Cell Count | Hemoglobin | Platelet Count | White Blood Cell Count |
|---|---|---|---|---|---|
| Units | | $10^6$/uL | g/dL | $10^3$/uL | $10^3$/uL |
| Ref. ranges | | (7.00-9.00) | (13.7-16.8) | (680-1280) | (1.1-7.5) |
| Pre-operation | | 7.4 | 14.1 | 618.3 | 6.8 |
| Ti pin | 2 weeks | 7.8 | 14.9 | 656.0 | 9.0 |
| Mg-Zn pin | 2 weeks | 7.4 | 14.1 | 547.0 | 3.7 |
| Ti pin | 14 weeks | 7.5 | 14.0 | 563.0 | 5.9 |
| Mg-Zn pin | 14 weeks | 7.3 | 13.7 | 598.0 | 4.5 |
| Ti cuff | 14 weeks | 7.6 | 13.8 | 637.0 | 5.8 |
| Mg-Zn cuff | 14 weeks | 7.2 | 13.4 | 537.0 | 6.2 |

Biochemical analysis results rats before and after osteotomy surgeries for 2 and 14 weeks of Ti and Mg—Zn pins/cuffs implantation are listed in Table 4.3. ALT after 2 weeks of implantation for both Ti and Mg—Zn pins exhibited significantly higher level compared to the implants for the other time points. However, these ALT values still remain within the reference range. For ALP, TBIL, TP, ALB, UA, CR, and GLB, all groups exhibited no significant difference between implants and implantation duration suggesting no signs of liver or kidney damage due to degradation of Mg—Zn pins.

Calcium, sodium, chloride, phosphorous, and magnesium ion levels in the serum before and after implantation are listed in Table 4.4. No significant difference in these ion levels were found between implants or implantation duration. All values remained within the reference range suggesting that there were no changes to the systemic ion concentration due to implantation and the consequent degradation of the Mg—Zn—Zr—Sr alloy pins.

TABLE 4.3

Biochemical analysis on blood serum after Ti pin (2 and 14 weeks), Mg-Zn pin (2 and 14 weeks), and Mg-Zn cuff (2 weeks) implanations.

| Name | Implantation time | Glucose | ALT (GPT) | ALP | Total Bilirubin | Total Protein | Albumin | Urea N | Creatinine | Globulin | A/G Ratio |
|---|---|---|---|---|---|---|---|---|---|---|---|
| Units | | mg/dL | U/L | U/L | mg/dL | g/dL | g/dL | mg/dL | mg/dL | g/Dl | |
| Ref. ranges | | (70-308) | (59-166) | (232-632) | (0.0-0.1) | (5.8-7.1) | (3.2-3.7) | (13-19) | (0.3-0.5) | (2.6-3.5) | |

TABLE 4.3-continued

Biochemical analysis on blood serum after Ti pin (2 and 14 weeks), Mg-Zn pin (2 and 14 weeks), and Mg-Zn cuff (2 weeks) implanations.

| Name | Implantation time | Glucose | ALT (GPT) | ALP | Total Bilirubin | Total Protein | Albumin | Urea N | Creatinine | Globulin | A/G Ratio |
|---|---|---|---|---|---|---|---|---|---|---|---|
| Unoperated | | 181.2 | 55.8 | 175.2 | 0.17 | 5.7 | 3.3 | 20.7 | 0.37 | 2.4 | 1.4 |
| Ti pin | 2 weeks | 322.0 | 132.6 | 151.2 | 0.14 | 6.2 | 3.3 | 17.6 | 0.42 | 2.9 | 1.1 |
| Mg-Zn pin | 2 weeks | 293.0 | 123.0 | 140.0 | 0.18 | 6.7 | 3.5 | 20.5 | 0.53 | 3.2 | 1.1 |
| Ti pin | 14 weeks | 229.5 | 56.8 | 187.0 | 0.18 | 6.3 | 3.7 | 21.8 | 0.52 | 2.6 | 1.4 |
| Mg-Zn pin | 14 weeks | 124.2 | 57.8 | 181.8 | 0.20 | 6.3 | 3.6 | 22.2 | 0.56 | 2.7 | 1.3 |
| Ti cuff | 14 weeks | 154.4 | 50.2 | 163.6 | 0.18 | 6.2 | 3.6 | 19.6 | 0.52 | 2.6 | 1.4 |
| Mg-Zn cuff | 14 weeks | 203.0 | 59.4 | 190.4 | 0.16 | 6.5 | 3.8 | 23.2 | 0.52 | 2.7 | 1.4 |

TABLE 4.4

Electrolyte levels of blood serum after Ti pin (2 and 14 weeks), Mg-Zn pin (2 and 14 weeks, and Mg-Zn cuff (2 weeks) implantations.

| Name | Implantation time | Calcium | Sodium | Chloride | Phosphorous | Magnesium |
|---|---|---|---|---|---|---|
| Units | | mg/dL | mmol/L | mmol/L | mg/dL | mg/dL |
| Ref. ranges | | (9.5-13.9) | (146-151) | (98-104) | (5.6-16.8) | (3.8-5.5) |
| Unoperated | | 9.8 | 138.2 | 100.5 | 5.5 | 2.0 |
| Ti pin | 2 weeks | 11.5 | 143.8 | 100.2 | 9.7 | 3.4 |
| Mg-Zn pin | 2 weeks | 12.1 | 141.3 | 100.3 | 12.0 | 3.7 |
| Ti pin | 14 weeks | 12.2 | 145.2 | 99.0 | 9.6 | 3.6 |
| Mg-Zn pin | 14 weeks | 11.3 | 146.8 | 100.6 | 9.4 | 3.3 |
| Ti cuff | 14 weeks | 11.6 | 147.6 | 99.6 | 9.2 | 3.3 |
| Mg-Zn cuff | 14 weeks | 12.2 | 148.0 | 99.8 | 8.7 | 3.5 |

ICP Analysis on Liver and Kidney

ICP analysis of the liver or kidney was performed to examine any form of Mg accumulation in the organs after implantation of the Mg—Zn alloy pins and cuffs in comparison to the Ti control. In FIG. 4.5a, Mg concentration determined in the kidney harvested from the experimental groups containing Mg—Zn implants exhibited no accumulation of Mg when compared to the concentration of kidney from the non-operated groups. FIG. 4.5b shows Mg concentration observed in the liver tissue from the non-operated controls to be in the range of 521 µg of Mg per gram of dried tissue. Regardless of implantation time, Mg—Zn alloy groups implanted with pin did not show any significant difference with the control level in Mg concentration of liver samples. The observation was consistent with blood test results indicating that implantation of the Mg—Zn alloy pins and cuffs in the rate femoral model outlined above exhibited no systemic toxicity.

H&E Staining of Liver and Kidney

Hematoxylin and eosin staining of liver and kidney tissue sections were performed to visualize any histological differences in tissue morphology due to Ti and Mg—Zn pins implantation. Liver sections of both Ti and Mg—Zn groups after 2 and 14 weeks of implantation shown in FIG. 4.6 exhibited a normal distribution of hepatocytes with clearly visible nuclei and central vein. In the kidney histology, no visible difference in glomeruli morphology, Bowman's space, capillaries, and convoluted tubules was observed between Ti control and Mg—Zn groups following 14 weeks of implantation. Histological morphology of liver and kidney tissues of all experimental groups displayed similar morphology as the non-operated control, and no difference was observed in between the groups or at different time points although data is not shown. In addition to ICP and blood test results, the H&E staining confirmed no damage to vital kidney and liver organs due to degradation following implantation of the biodegradable Mg—Zn pins. Although the H&E staining cannot be used to determine any accumulation of Mg, the fact that the histology shows normal and functional tissue serves to indicate that it is likely that there is no accumulation related damage of the kidney and liver tissue and it is possible that with time, there will be certainly removal of Mg following the normal excretory process prevalent in the body. More advanced techniques will however be needed to ascertain the definitive accumulation of Mg, Zn, Zr, and Sr present in the alloy pins that were implanted.

Bone Tissue Histology

Goldner's Masson Trichrome staining of rat femoral sections after plastic embedding revealed a typical fracture healing response as shown in FIG. 4.7. After 2 weeks of implantation, the femurs with Ti and Mg—Zn alloy pins exhibited endochondral bone development and fibrous tissue formation around the fracture. Bone tissue section of the femur with Mg—Zn alloy pins after 2 week of implantation exhibited a gas pocket due to the degradation of Mg—Zn pins. After 14 weeks of implantation however, femurs with both Ti and Mg—Zn alloy pins exhibited bone remodeling and intramembraneous bone formation. In addition, the gas pocket of femurs with Mg—Zn pins was filled with fibrous tissues. In any event, fracture repair of either Ti or Mg—Zn groups was not completed after 14 weeks of implantation.

Discussion

Biodegradable Mg alloys have gained considerable attention for their potential to provide comparable or even improved benefits in fracture repair and for bone fixation compared to biodegradable polymer and permanent bioinert metallic devices. Mg is characterized by mechanical properties being matched to natural human bone. Hence, alloys are designed to exhibit mechanical properties with better match to natural bone while exhibiting the desired timely corrosion rates with more biocompatible degradation products as compared to biodegradable polymers that tend to provide acidic by-products while also additionally lacking the desired osteogenic potential to function as an acceptable bone scaffold system. The rapid corrosion of biodegradable Mg alloys can cause hydrogen gas evolution and immature mechanical failure warranting the need for improved alloy design and other surface engineered strategies to control the corrosion rates while preserving the mechanical strengths. Hence, in vivo degradation and toxicity of Mg alloys may demonstrate the much desired biosafety and efficacy as candidate biomaterials for implantable devices. Orthopedic devices are often used in load-bearing conditions and metals often tend to corrode more rapidly when stress is applied via the well-known stress corrosion mechanisms. This is a common fixture and often the mode of much observed problems to date in permanent metal devices which also reveal stress induced corrosion, wear, and debris formation.

The current study tested degradation properties and biocompatibility of Mg—Zn—Sr—Zr alloys under load-bearing condition. Mg alloys are not intended for use as a femoral rod since they are known to degrade in the body. However, a femoral fracture model using intramedullary pins can exert a significant load on the implant material to cause a stress-induced corrosion for examining relevant physiological response such as bone healing, inflammatory response, and systemic toxicity thus serving as an ideal model system to study healing under the presence of stress. Thus, using this fracture model, a group of rats were implanted with femoral cuffs for 14 weeks to compare any difference in systemic toxicity due to implantation site.

In vivo degradation of Mg—Zn pins and cuffs was assessed using x-ray radiographs after 1 week of surgery. It is widely accepted that hydrogen gas bubble evolves in the earlier time points and tend to kinetically slowdown in 2-3 weeks. Mg alloys implanted in bone without a significant load also are reported to show slow degradation exhibiting no gas bubbles while Mg alloys in subcutaneous region exhibit significant gas bubbles due to the surrounding vascularization and presence of blood flow. Both Mg—Zn alloy pins and cuffs were observed to be surrounded with hydrogen gas in the surrounding tissue. Bone histology results were also consistent with the x-ray images showing gas pockets near the fracture site in the image following 2 weeks of Mg—Zn pin implantation (see FIG. 4.2). Both x-ray radiograph and bone histology results indicate that the corrosion of Mg—Zn alloy implants in rat femurs were rapid enough to create gas bubbles. However, the gas bubbles appear to be eliminated after 14 weeks of implantation as shown in the bone tissue histology image.

Computed tomography was used to perform fracture healing and determine quantitatively the degradation rate. Failure of the Mg—Zn alloy pins were observed in fractured femurs after 2 weeks of implantation. After 14 weeks however, callus formation and bone remodeling around the fracture site were exhibited. Femurs with both Ti and Mg—Zn alloy pins revealed similar bone repair response. Rat femoral fracture model typically require up to 5 months to complete the fracture healing process. 3 out 5 rat femurs with implantation of Mg—Zn pins for 14 weeks were observed with a malunion that might have resulted from the breakage of the pins due to the excessive stress experienced by the animals following immediate surgery and allowing the rats to ambulate subjecting the area to significant load serving as a classic stress corrosion fracture model. Despite this, it should be noted that the implants showed acceptable and favorable bone healing response as indicated by the other femurs in union exhibiting better bone healing with more bone remodeling and united callus formation over the cortical bones. This result serves to demonstrate the potential safety and efficacy of the alloy system for potential orthopedic applications. Accelerated corrosion rates of Mg—Zn alloy pins obviously as explained earlier result from stress corrosion. Mg—Zn alloy alloys are in fact, known to degrade with higher corrosion rates compared to Mg alloys under non-load bearing condition according to the literature. Based on the analysis reported here and discussed above, rapid corrosion of Mg—Zn alloy pins under load-bearing condition did not significantly affect the fracture repair in terms of adverse local tissue response. However, mechanical strength of Mg alloys decreases with corrosion and the Mg—Zn alloy pins therefore underwent failure which could have affected the fracture healing outcome negatively although not necessarily serving to negate the potential applicability of the system for orthopedic application with further optimization of the alloy and the processing parameters.

Systemic toxicity of rats with Mg—Zn alloy pins were assessed after 2 and 14 weeks of implantation when 15% and 55% of total volume of the implants were resorbed (see FIG. 4.4). In addition, a group of the Mg—Zn alloy cuffs were assessed to evaluate the toxicity of Mg—Zn alloy in contact with both bone and muscle. After 14 weeks, the cuffs were fully resorbed. Blood and serum examination was focused on hematologic and biochemical analysis to detect any disruption in blood, liver and kidney tissue state. Blood cell count and biochemical parameters were maintained within the reference ranges and there were no significant difference among Ti, Mg—Zn, and control groups. Recent publications also reported no significant abnormality in blood test results following in vivo degradation of Mg alloys. BUN, CR, and UA from serum analysis also indicates no significant changes in the renal function. No accumulation of Mg in liver and kidney were also found following the inductively couple plasma analysis conducted on the digested tissues. Histology of liver and kidney also displayed histomorphology pattern mirroring healthy tissue. Excess Mg in body is known to excrete in urine after renal filtration. Bodily Mg concentration beyond the tolerance limit can however, cause renal failure. Based on the published literature to date, the toxicity test methods described herein are effective since high Mg dose in body does not cause local accumulation in a specific organ other than liver or kidney. In order to track localized Mg accumulation in other organs, biosensors or quantum dot staining methods can be considered to locate the exact location as well as the amount of accumulation. Overall, the observations from blood test, Mg concentration, and histology results consistently indicate that the Mg—Zn alloy implant considered here and their degradation products are indeed biocompatible for potential use as possible orthopedic implants under load-bearing conditions.

Conclusions

Mg—Zn alloy, in comparison to Ti alloy as a control, was examined as femoral pins under load-bearing condition using a rat femoral fracture model. Accelerated degradation of the Mg—Zn alloy pins occurred due to stress corrosion. Hence, hydrogen gas pockets were observed initially and some pins tend to lose their mechanical stability in the early stages of 2 week implantation. However, normal bone healing was displayed following bone histological analysis. No fibrous capsule formation or adverse immune response was observed in local tissues around the Mg—Zn alloy implant devices as well. Furthermore, degradation of Mg—

Zn implants caused no significant changes in hematologic or biochemical markers assessed using blood panel tests. Magnesium concentration of liver and kidney demonstrated no accumulation of Mg in these organs as well following elemental analysis of the tissue for the specific alloying elements. Histology of liver and kidney also displayed no organ damages due to the Mg—Zn alloy implants. Overall, the results suggest that Mg—Zn alloy demonstrates favorable biocompatibility under load-bearing conditions.

General Conclusions

Mg—Zn—Zr alloy was initially studied to explore the potential of its use as a biodegradable metal for orthopedic applications. Both as-cast and solution treated Mg—Zn—Zr was synthesized by melting in an electric resistant furnace, casting in a mild steel mold, and post-processing of heat treatment in a box furnace. X-ray diffraction patterns of as-cast and solution-treated Mg—Zn—Zr exhibited α-Mg phase without any distinct intermetallic peaks. However, back-scattered electron microscopy revealed Mg/Zn intermetallic precipitates along the grain boundaries. Solution treatment of Mg—Zn—Zr was performed to cause phase transformation of these precipitates to reduce the galvanic corrosion between Mg—Zn precipitates and α-Mg matrices. Mg—Zn precipitates were successfully transformed to Mg—Zn—Zr phase mixture which is more close to the nominal composition of the alloy. However, no significant improvement in the corrosion potential or current density was exhibited in the potentiodynamic polarization measurement.

As-cast and solution-treated Mg—Zn—Zr were then subjected to in vitro assessments in terms of corrosion resistance, mechanical properties, and cytocompatibility. Corrosion of Mg—Zn—Zr was improved after solution treatment due to the phase transformation of precipitates. Immersion corrosion rates of solution-treated Mg—Zn—Zr was observed to be lower than that of as-cast Mg—Zn—Zr. Tensile and compressive strengths of both as-cast and solution-treated Mg—Zn—Zr were observed to be higher than pure Mg but not comparable to commercial as-drawn AZ31. Cytocompatibility of Mg—Zn—Zr alloys was assessed using ISO 10993 standards with modifications for biodegradable metals. Good cell viability of MC3T3 murine pre-osteoblast cells was exhibited by both as-cast and solution-treated Mg—Zn—Zr alloys. Promising preliminary in vivo degradation and tissues compatibility results were also exhibited by these alloys when as-cast Mg—Zn—Zr pellets were subcutaneously implanted in nude mice models.

Addition of Sr and Ce as micro alloying element to Mg—Zn—Zr alloys were investigated to further improve corrosion resistance by reducing Zn-rich intermetallic phase in grain boundary precipitates. Microstructure analysis using back-scattered electron microscopy clearly exhibited the phase transformation of precipitates. An introduction of micro alloying element created more precipitates although only 0.25% and 1% addition were introduced into the Mg—Zn—Zr system due to the inherent low solubility of Sr and Ce in Mg. Ce was more prone to form precipitates along the grain boundaries compared to Sr due to the higher melting point of Ce required for homogenization of alloy melts before casting and extrusion. Overall, the corrosion resistance of Mg—Zn-0.25Sr—Zr, Mg—Zn-1Sr—Zr and Mg—Zn-0.25Ce—Zr did not exhibit a significant difference compared to Mg—Zn—Zr. However, Mg—Zn-1Ce—Zr exhibited higher corrosion rate after immersed in Hank's buffered solution for 35 days. In tensile testing, as-extruded Mg—Zn—Zr, Mg—Zn—Sr—Zr, and Mg—Zn—Ce—Zr outperformed commercial AZ31. Ultimate tensile strength increased with Ce addition since more precipitates contributed to dislocation impediment leading to increased strengths. Mg—Zn alloys also exhibited good cytocompatibility with MC3T3. Tolerance of Mg, Zn, Sr, and Ce ion levels were studied using MC3T3 and low Zn tolerance up to 0.1 mM was observed. Osteogenic differentiation ability of Mg, Sr, and Ce were further studied with human mesenchymal stem cells. ALP activity and ALPL gene expression did not exhibit any significant change compared to the differentiation media control. However, OPN gene expression exhibited some improvements with addition of Mg, Sr, and Ce ions in the differentiation media.

In order to demonstrate biocompatibility of Mg—Zn alloys, Mg—Zn-0.25Sr—Zr (Mg—Zn) alloy was selected for rat femoral fracture model intended to create stress corrosion environment. Intramedullary pins of Mg—Zn and Ti alloy control were implanted after osteotomy to assess the degradation and toxicity under load-bearing condition. Accelerated corrosion of Mg—Zn alloy due to stress corrosion was anticipated due to the model selected to test the toxicity of Mg—Zn alloy and its degradation products in an extreme stress corrosion environment. X-ray images after 1 week of Mg—Zn pin implantation exhibited hydrogen gas pockets around the implantation site due to rapid corrosion. Micro computed tomography analysis exhibited higher corrosion rate of Mg—Zn pin compared to in vitro corrosion rate of the Mg—Zn alloy. However, bone histology and CT analysis after 14 weeks of implantation revealed that the gas pockets around Mg—Zn pins were filled with fibrous tissue and normal fracture healing was observed compared to Ti alloy control. Cuffs of Mg—Zn-0.25Sr—Zr and Ti alloy were implanted on rat femurs to investigate any difference in local tissues response or systemic toxicity when these implants are in contact with both bone and soft tissue. In both scenarios, no adverse toxic response was observed in blood panel tests as well as hematoxylin & Eosin staining of liver and kidney after 2 and 14 weeks of Mg—Zn and Ti device implantation. No accumulation of Mg in liver and kidney was confirmed by using inductively coupled plasma analysis on digested organs. Thus by virtue of all the four specific aims, the study essentially shows that the Mg—Zn alloy system is indeed quite promising and when effectively processed could exhibit improved corrosion, tailored mechanical strengths and also likely expected osteogenic potential with the addition of controlled amounts of Sr and Ce.

Based on the Examples conducted, it can be construed that the desired biosafety of Mg—Zn alloys has been clearly demonstrated under both in vitro and in vivo conditions. Various coating techniques such as micro artic oxidation (MAO), layer by layer (LbL) polyelectrolyte coatings, use of synthetic and natural polymers, and a variety of metallic coatings can be applied to the biodegradable Mg—Zn devices. These strategies can help to prevent rapid corrosion and premature mechanical failure while also augmenting delivery of growth factors and signaling molecules to generate a 'smart' scaffold and implant system serving as a scaffold as well as drug and biological molecule delivery system.

Example 5

Synthesize Novel Mg—Y—Ca—Zr Based Alloys and Perform Materials Characterization to Assess the Changes in Microstructure after Addition of Alloying Elements and Post-Processing Treatments Accelerated corrosion of Mg alloys has limited its adoption as a biomaterial due to the accumulation of hydrogen gas pockets around the implant as well as insufficient mechanical performance and implant stability throughout the degradation and tissue healing process. In order to improve corrosion resistance and increase mechanical properties of pure Mg, the addition of suitable alloying elements Y, Ca, Zr, and Zn were introduced as outlined as a rationale for this aim.

In alloying Mg, there are only limited choices biocompatible alloying elements that can be selected among Al, Mn, Zn, Ca, Li, Zr, Y, and rare earth (RE) elements that are used to generate Mg implant materials, generally influencing the mechanical and material properties of Mg alloys. Mg—Y—Ca—Zr alloys have been successfully fabricated as ignition-proof alloys due to their ability to improve oxidation resistance. The introduction of Y can be justified by its ability to contribute to grain boundary strengthening of the magnesium alloys and also improving the corrosion resistance at wt. % higher than 3% when alloyed with Mg. Ca, as well as Y help to form a stable and chemically less reactive hydroxide layer to impart greater corrosion resistance as shown by density functional theory calculations. Ca is also a major component of mineralized natural bone and is the most abundant mineral in the human body that is known to improve the corrosion resistance and mechanical properties of Mg alloys when added up to 1 wt. %. Zr on the other hand, serves as an effective grain refining agent by imparting grain boundary strengthening and corrosion resistance. Zr also is a powerful iron removal agent, typically helping to reduce the content of iron to under 20 ppm in Zr-containing magnesium alloys, thus decreasing the risk for corrosion from iron impurities. Further, adding Ca to Zr-containing alloys promotes solute undercooling, in turn, facilitating more suitable sizes for Zr nuclei to become effective nucleation sites to further reduce grain size. Zn is also one of the most abundant essential elements in the human body, and can improve the corrosion resistance and mechanical properties of Mg alloys as well as the castability in larger amounts (greater than 2 wt. %). The combination of Y and Zn in Mg alloys also has been shown to result in the formation of a specific structure, long period stacking order (LPSO) structure, which consists of periodic stacks of close-packed planes along the atomic c-axis, resulting in high strength and ductility.

The original Mg—Y—Ca—Zr alloy system used in the preliminary studies was modified and enhanced to create the second group of alloys discussed in this thesis. First, the Zr content was increased from 0.4 wt. % to 1 wt. % due to indications from ICP-OES measurements that the amount of Zr going into the solution was much lower than expected in the Mg-alloy cast ingots. This reduction in the amount of Zr is commonly observed due to settling of Zr particles into a Zr rich layer at the bottom of the crucible, with only Zr remaining in the molten Mg solution having an effect in the grain refining process. Hence Zr is added above the final desired weight percentage to compensate for losses during melting, contamination, pickup of iron, precipitation, etc. to maintain adequate levels without further processing. In order to further determine the effects of Y addition on the Mg alloy, an alloy without Y (Mg-1Zr-0.6Ca) was also synthesized to compare to the alloys containing Y.

Alloys containing Y and Zr have achieved clinical success having been used in drug eluting stents in patients with de-novo coronary lesions and screws in hallux valgus surgery (which received CE marking of Medical Devices for medical applications within Europe). Both devices demonstrated good safety profiles and performance as alternative to resorbable polymeric and metallic materials.

In addition to selection of alloying elements, processing methods also highly influence the microstructure and hence properties of the alloys. In this study, T4 solution treatment at 525° C. for 8 hours was attempted to reduce the volume fraction of secondary phases by providing the driving force for favoring diffusion into the α-Mg matrix. Hot extrusion was also conducted as a means to impart grain refinement, which is in actuality a more effective approach for producing homogenous and fine grains than other methods for producing wrought Mg such as rolling and forging.

The nominal compositions of the various alloys and processing methods used for generating the alloys considered in this specific aim are listed in Table 5.1. The alloy abbreviations used to designate the alloys discussed in this thesis shown in Table 5.1 were determined using ASTM B 275 standard on codification, where no more than two letters representing alloying elements of the two greatest amounts are to be listed. W represents yttrium, X represents calcium, K represents Zr, and Z represents Zn. The codification WX11 and WX41 alloys in the as-cast and T4 heat treated form was changed to WK11 and WK41 after addition of 1.0 wt. % Zr made it the second greatest alloying element present, thus replacing the X for calcium with a K for zirconium.

TABLE 5.1

Nominal composition of Mg alloys (wt. %) investigated in this work.

| Alloy | Y | Ca | Zr | Zn | Mg | Condition tested |
|---|---|---|---|---|---|---|
| WX11 | 1.0 | 0.6 | 0.4 | 0.0 | Balance | As-cast and T4 |
| WX41 | 4.0 | 0.6 | 0.4 | 0.0 | Balance | As-cast and T4 |
| KX11 | 0.0 | 0.6 | 1.0 | 0.0 | Balance | Extruded |
| WK11 | 1.0 | 0.6 | 1.0 | 0.0 | Balance | Extruded |
| WK41 | 4.0 | 0.6 | 1.0 | 0.0 | Balance | Extruded |
| WZ42 | 4.0 | 0.6 | 1.0 | 2.0 | Balance | Extruded |

Materials and Methods

Metallurgical Processing of Ma-Y—Ca—Zr Based Alloys

Elemental ingots of Mg (US Magnesium Inc., Salt Lake City, Utah, 99.97%), Ca (Alfa-Aesar, Ward Hill, Mass., 99.5%), and Zn (Alfa-Aesar, 99.99%) were weighed according to the nominal composition and melted in a mild steel crucible using an electrical resistance furnace (Wenesco Inc., Chicago, Ill.) with the addition of a Mg-30Y wt. % master alloy melted from pure Mg and Y (Alfa-Aesar, 99.9%) prepared inside a graphite crucible melted using an induction furnace (MTI Corporation, Richmond, Calif.) purged with ultrahigh-purity (UHP) Ar and vacuumed to avoid oxidation of the pure elements. The master alloys and pure elements were cleaned thoroughly to remove residue and oxide scale and melted in a mild steel crucible using the Wenesco electrical resistance furnace under the protection of Ar+0.5% $SF_6$ cover gas. The melting and pouring temperature was 750° C., and once the temperature was reached, equivalent amount of zirconium was added using Zirmax (Mg-33.3% Zr) master alloy (Magnesium Elektron Ltd., Manchester, UK). After the Mg—Zr master alloy was added, the melt was stirred for 10 s at an interval of 1 min and 5 min to dissolve and disperse the zirconium particles uniformly into the melt. The melt was held for an additional 30 min and poured into a cylindrical mild steel mold preheated to 500° C. with dimensions of 44.5 mm diameter×82.5 mm length. The holding and stirring times to release Zr particles from the Zirmax master alloy was essential to achieve higher solubility of Zr in the melt and optimal grain refinement. To compare as-cast samples to solution treated samples, a heat treatment of (T4) at 525° C. for 6 h was performed on the alloy ingots inside a tubular furnace covered under continuous UHP Ar flow and quenched in room temperature water.

Extruded alloys were prepared from as-cast alloys by first applying solution treatment at 400° C. for 20 hours and quenching in room temperature water to increase the alloys' ductility and homogenize the secondary phases while not causing grain growth, as shown in Appendix B. After reducing the ingot diameter to 37.8 mm using a lathe, the alloys were hot extruded with an extrusion ratio of 10 and 30 at the following temperatures:

TABLE 5.2

Temperatures used to preheat ingots for 30 minutes and during extrusion of solution treated alloys.

| Alloy | Extrusion temperature | |
|---|---|---|
| | ER 10 | ER 30 |
| KX11 | 350° C. | |
| WK11 | 350° C. | |
| WK41 | 400° C. | |
| WZ42 | 425° C. | 450° C. |

ER = extrusion ratio.

The alloys were compared to as-cast Mg (US Magnesium Inc.), as-drawn 99.9% pure Mg (Goodfellow Corp., Coraopolis, Pa.), and as-drawn AZ31 (Goodfellow Corp.) in reported tests. Inductively coupled plasma optical emission spectroscopy (ICP-OES, iCAP duo 6500 Thermo Fisher, Waltham, Mass.), was used to experimentally confirm the alloy compositions and presence of impurities by dissolving alloy samples in 15% nitric acid, diluting in water 5×, and measuring concentration of the alloying elements and impurity elements of the solution containing the dissolved alloys.

Phase Characterization of Mg—Y—Ca—Zr Based Alloys

In order to determine the phase formation, X-ray diffraction (XRD) was conducted using Philips X'Pert PRO diffractometer employing CuK$_\alpha$ ($\lambda$=1.54056 Å) radiation with a Si-detector (X'celerator). The X-ray generator operated at 45 kV and 40 mA at a 2θ range of 10-80°. Peak identification was determined using the X'Pert High Score Plus software.

Microstructure Analysis of Mg—Y—Ca—Zr Based Alloys

Samples of the Mg alloys were mounted in epoxy, mechanically polished (Tegramin-20, Struers, Ballerup, Denmark) with 1200 grit SiC paper down to 0.05 µm with an alumina slurry, and chemically etched in a solution of 5 mL acetic acid, 6 g picric acid, 10 mL water, and 100 mL ethanol. The microstructure was observed using optical microscopy (Axiovert 40 MAT, Carl Zeiss, Jena, Germany) and scanning electron microscopy (SEM, JEOL JSM-6610, JEOL Ltd., Tokyo, Japan) with energy dispersive X-ray (EDX, EDAX Genesis, Mahwah, N.J.) to conduct elemental analysis. Average grain size was measured according to ASTM E112 following the Abrams three-circle procedure with ~70 grains considered for each calculation.

Results

Materials Properties of as-Cast and Solution Treated Mg—Y-0.6Ca-0.4Zr Based Alloys Inductively coupled plasma optical emission spectroscopy (ICP-OES) measurements (Table 5.3) showed some reduction in alloying elements from their as-weighed nominal compositions likely due to the re-melting process. A reduction in Zr was primarily due to settling of large zirconium particles and clusters in the liquid melt and was counteracted by adding more Zr when melting, increasing from the content in the preliminary study of 0.4 wt. % (for WX11 and WX41 alloys) to 1.0 wt. % (for KX11, WK11, WK41, and WZ42 alloys). Low impurity levels were observed, as necessary to avoid substantial galvanic corrosion.

TABLE 5.3

Chemical composition and impurities of Mg-based alloys (wt. %) as measured by ICP-OES.

| | Chemical compositions (wt. %) | | | | | | | | | | |
|---|---|---|---|---|---|---|---|---|---|---|---|
| Alloy | Y | Ca | Zr | Zn | Al | Cu | Fe | Mn | Ni | Si | Mg |
| WX11 | 0.66 ± 0.03 | 0.52 ± .01 | 0.13 ± 0.004 | — | — | 0.016 | 0.003 | 0.008 | 0.008 | 0.006 | Balance |
| WX41 | 3.18 ± 0.10 | 0.63 ± 0.41 | 0.074 ± 0.013 | — | — | 0.15 | 0.009 | 0.005 | 0.003 | 0.007 | Balance |
| KX11 | 0.0033 | 0.52 ± 0.002 | 0.62 ± 0.005 | <0.0001 | 0.0003 | 0.0005 | 0.0008 | 0.003 | <0.0001 | <0.0001 | Balance |
| WK11 | 0.98 ± 0.003 | 0.51 ± 0.002 | 0.63 ± 0.003 | <0.0001 | 0.0003 | 0.008 | 0.001 | 0.003 | <0.0001 | <0.0001 | Balance |
| WK41 | 3.37 ± 0.18 | 0.40 ± 0.065 | 0.51 ± 0.009 | <0.0001 | <0.0001 | 0.004 | 0.003 | 0.003 | <0.0001 | <0.0001 | Balance |
| WZ42 | 3.98 ± 0.033 | 0.54 ± 0.005 | 0.61 ± 0.008 | 2.00 ± 0.015 | <0.0001 | 0.002 | 0.001 | 0.003 | <0.0001 | <0.0001 | Balance |

The presence of different phases in the Mg alloys was characterized by X-ray diffraction (XRD) as shown in FIG. 5.1. The XRD patterns show that all the alloys were composed of hcp α-Mg, without detecting the presence of any unalloyed Y, Ca, Zr, or intermetallic phases. However, there was a distinct preferential orientation of the Mg plane in all of the synthesized as-cast and solution treated alloys compared to as-cast pure Mg which shows the typical Mg (002) plane to be the most intense peak likely due to the presence of Zr acting as nucleating sites for grain refinement leading to possible preferential orientation.

FIG. 5.1 shows XRD patterns of as-cast pure Mg, WX11, and WX41.

FIG. 5.2 shows optical microscopy images of the microstructure of as-cast and solution treated WX11 and WX41 alloys containing grains of α-Mg with secondary phases (dark regions) located at the grain boundaries and precipitates within the matrix.

The average grain size of the alloys was: WX11 as-cast—79 μm, WX11 T4 treated—98 μm, WX41 as-cast—98 μm, and WX41 T4—200 μm, dominated by the presence of uniform equiaxed α-Mg grains throughout the microstructure. As expected, the solution treatment led to an increase in the grain size. However, addition of alloying elements greatly reduced the grain size compared to high-purity Mg as shown in FIG. 5.2e, which noticeably lacked the presence of dark secondary phases. As-drawn AZ31, having undergone grain refinement due to the commercial drawing process, exhibited much finer grain size (as shown in FIG. 5.2f) compared to the Mg—Y—Ca—Zr alloys WX11 and WX41 and pure Mg which received no bulk forming processes.

SEM and EDX (as shown in FIG. 5.3) confirmed the optical microscopy images in that the WX11 and WX41 as-cast alloys contained grain boundaries and precipitates of higher amounts of Y and Ca (as shown in FIGS. 5.2a and c), indicating the presence of secondary phases of composition, with lower amounts of Y, Ca, and Zr at the grain boundaries but consisting mostly of Y in precipitates, due to precipitate segregation during solidification, a common phenomenon with casting. T4 solution treatment successfully dissolved these secondary phases into the bulk α-Mg, leading to partial homogenization of the as-cast alloy. The Y-rich intermetallic particles were observed to contain about 75% wt. % Y to form αY, which were still present after T4 solution treatment (as shown in FIGS. 5.3b and d). A higher volume fraction of second phase particles was observed in the WX41 alloys due to its higher Y content compared to WX11. The increase in grain size after T4 solution treatment was likely due to energy driving coalescence of smaller grains along the triple point grain boundary regions and formation of supersaturated α-Mg solid solution after the precipitates dissolved into the matrix as to be expected following heat treatment.

Changes in Phase and Microstructure with Extrusion and Addition of Y and Zn to Mg—Y-1Zr-0.6Ca Based Alloys The modified Mg—Y—Ca—Zr alloy system contained 1.0 wt. % Zr. An alloy without Y (Mg-1Zr-0.6Ca) and an alloy containing Zn (Mg-4Y-2Zn-1Zr-0.6Ca) were also synthesized to compare the materials and in vitro characteristics to the Mg—Y—Zr—Ca alloys. These alloys were extruded at an extrusion ratio of 10 (initial cross sectional area divided by final cross sectional area) at temperatures shown in Table 5.2 and subject to further analysis.

FIG. 5.1. shows XRD patterns of extruded KX11, WK11, WK41, and WZ42.XRD (FIG. 5.1) of the Mg alloys shows that after extrusion for KX11, WK11, and WK41, the alloys consisted still mainly of single phase Mg. The addition of Y led to a shift in all the peak positions, particularly of the oriented peak at ~37° 2☐ value due to the lattice expansion caused by the introduction of Y into the Mg hcp lattice. Similar preferred orientation is seen here unaffected by the increase in Zr content. As expected, the WZ42 alloy, which contained Y and Zn, contained the presence of the LPSO phase $Mg_{12}YZn$.

FIG. 5.5 shows optical micrographs showing the microstructure of Mg alloys extruded with extrusion ratio 10:a,f) KX11, b,g) WK11, c,h) WK41, d,i) WZ42 and extrusion ratio 30-e,j) WZ42, with sections take in the transverse direction (top, a-e) and longitudinal direction (bottom, f-j).

After extrusion, the Mg alloys underwent significant grain refinement as shown in the optical microscopy images of microstructure (as shown in FIG. 5.5). Compared to the as-cast and T4 treated alloy microstructure as shown in FIG. 5.2, after hot extrusion, the grain size was reduced to well under 50 μm. The WZ42 alloy contained grains both small and large, and when extruded at an extrusion ratio of 30 compared to 10, resulted in more of the large grains of ~20-40 m being disrupted into more refined grains of <15 μm in the transverse direction.

Further inspection of the microstructure was conducted using SEM and EDX (as shown in FIG. 5.6). Bright regions in the back-scattered SEM images revealed intermetallic phases consisting of Mg, Ca, Y. and Zr, as well as impurity elements of Al, however since an extremely low concentration of Al was measured in the alloys using ICP-OES in Table 5.3, the Al detected by EDX may have come from the alumina slurry used during polishing. Non-equilibrium phases containing alloying elements were present in KX11 and WK11 (as shown in FIG. 5.6a and b). WK41 (as shown in FIG. 5.6c) contained the phase $Mg_2Y$ as it contained more Y, ~4 wt. %, compared to WK11 which only contains ~1 wt. % Y. In the WZ42 alloy, a unique LPSO phase consisting of Mg, Zn, and Y roughly corresponding to $Mg_{12}YZn$ with Mg atomic percent 12 times that of Y was confirmed by SEM and EDX analysis shown in FIG. 5.2d. The amount of bright regions of precipitates in the alloys increased with the higher amount of alloying elements added to the Mg solution, in the order of KX11<WK11<WK41<WZ42. The size of the secondary phases, with the exception of the LPSO phase in the WZ42 alloy, appeared to be generally smaller, <2 μm, and more dispersed in the extruded alloys seen in FIG. 5.6 compared to the as-cast and T4 heat treated alloys as shown in FIG. 5.3.

FIG. 5.2. shows SEM images and EDX analysis at indicated locations of Mg alloys after polishing and etching: a) KX11; b) WK11; c) WK41; d) WZ42 after extrusion with extrusion ratio of 10. Sections were taken in the transverse plane to the direction of extrusion. Scale bar=10 μm.

Discussion

Alloying elements strongly affect the microstructure and mechanical properties of magnesium alloys. Higher Y content has been reported to result in grain coarsening, which was observed to a small degree in in FIG. 5.2 when comparing the WX11 to the WX41 alloys. The measured Zr content as seen in Table 5.3 was also reduced in the WX41 alloy, which may also have contributed to the higher grain size compared to WX11. Y-rich intermetallic particles with Y wt. % of ~75% were observed in the Mg—Y—Zr—Ca alloys as has been observed in Mg—Y binary alloys, though implementation of T4 solution treatment resulted in dissolution of second phase precipitates from the grain boundaries as well as grain coarsening.

The alloy compositions studied were modified and expanded after the initial studies using as-cast Mg—Y based alloys. First, to further explore the effect of Y and Zn addition, a composition without Y was added to compare with the Y-containing alloys, and added Zn to explore the effects of the LPSO phase of $Mg_{12}YZn$ intermetallic. Due to a loss of Zr during melting which was observed in the as-cast alloys, which saw a diminished Zr content from the nominal concentration of 0.40% reduced to 0.13% and 0.074% wt. % as measured by ICP-OES for the WX11 and WX41 alloys, respectively, the amount of Zr added to the initial melts was increased. The loss of Zr occurred because once saturation with Zr has been achieved, Zr is continually lost from the Mg solution as it reacts with iron from the crucible and other contaminants, also forming hydrides with hydrogen. Thus, it is crucial to add an excess of active Zr to the melt to compensate for the losses occurring. Another change that was implemented was reducing the temperature for heat treatment. As seen in FIGS. 5.2b and 5.2d, significant grain growth was observed after conducting heat treatment on the WX11 and WX11 alloys at 525° C., reducing the positive effects of grain refinement imparted by the Zr addition. The temperature of solution treatment was reduced to 400° C. while extending the time from 8 hours to 20 hours, still resulting in diffusion of precipitates while lowering corrosion rate and avoiding significant grain growth.

This modified alloy system was then hot extruded which drastically changed the alloy microstructure. While the X-ray diffraction patterns still showed single-phase Mg for all alloys except WZ42 which contained LPSO $Mg_{12}YZn$, the grain size dramatically decreased after extrusion. Extrusion process for Mg alloys is a thermo-mechanical process influenced by the working temperature and extrusion ratio. Increasing extrusion temperature increases grain size due to dynamic recrystallization where nucleation and growth of new grains occur during deformation. However, the effect of extrusion ratio on grain size has been met with contradictory results, with some studies reporting a grain size decrease with increasing extrusion ratio whereas other reported the contrary. Here, a breakdown was observed of the large LPSO phase grains, while overall the grains seen in the longitudinal section did not appear to drastically change. The occurrence of this fiber-shaped LPSO phase elongated along the direction of extrusion has been observed in other Mg—Zn—Y containing alloys, where a higher extrusion ratio generated more heat during extrusion bringing about dynamic recrystallization, seen to a greater effect in the extrusion ratio 30 WZ42 alloy. This effect may be due to conflicting influences of a higher temperature used for extrusion performed at extrusion ratio 30 (450° C.) as opposed to 425° C. when the alloy was extruded at an extrusion ratio of 10, acting to recrystallize and grow grains while the higher deformation served to reduce grain size. All the alloys appeared to undergo partial dynamic recrystallization with a combination of fine equiaxed grains and long elongated grains retained from the original solution treated microstructure.

Example 6

Characterize the Effects of Yttrium and Zinc Addition and Post-Processing on Corrosion Behavior and Mechanical Properties of Magnesium-Yttrium-Calcium-Zirconium Critical in gaining a deep understanding of the Mg—Y—Ca—Zr based alloys of this work was to draw relationships between the microstructure and composition with the functional properties of corrosion behavior and mechanical properties. For orthopedic biomaterials, both characteristics are essential in determining the efficacy of a device.

The first major challenge in developing a biodegradable osteosyntheses response was to achieve mechanical properties that are in the likely same range as those characteristic of permanent metallic implants. Biodegradable materials must maintain stability in complex in vivo environments, bearing a combination of various mechanical loads including tension, compression, and fluid shear stress. Whereas degradable polymers have improved since the 1980s due to progress in knowledge and production methods, their mechanical properties still do not approach those of permanent metals. Thus, devices made from biodegradable polymers are designed to compensate the lack of strength and rigidity though the use of larger, bulkier designs. Naturally, the location of the skeletal injury often dictates the mechanical requirements of the implant and material. As the material degrades, the decrease in strength should be steady, predictable, and repeatable, resulting in gradual transfer of load to the surrounding and newly formed bone whose growth may be encouraged by the increased loading.

The property of degradation of implanted materials for orthopedic devices is also of interest to eliminate the need for device removal in a second surgery while providing room for growth of native tissue. No implant residues should remain, while the degradation products can be metabolized by the human body at an appropriate rate to maintain load for the given application.

As discussed earlier, alloying elements were added to contribute to improvement of the mechanical properties and corrosion resistance. A common effect of their incorporation was to impart solid solution strengthening, precipitation strengthening, and grain boundary strengthening. The post-processing technique of heat treatment to diffuse the secondary phases limits the extent of microgalvanic corrosion wherein the anodic α-Mg matrix has a lower corrosion potential than any secondary phases, corroding preferentially as a galvanic couple. Grain refinement achieved through hot extrusion also was expected to improve the mechanical strength by grain boundary strengthening. This aim sought to assess the effects of these alloy additions, namely progressively increasing Y content and Zn incorporation, as well as the effect of heat treatment and extrusion on the mechanical properties and degradation of the resultant Mg alloy systems in order to determine optimal processing conditions for achieving high strength and corrosion resistant alloys.

Materials and Methods

Corrosion Testing of Mg—Y—Ca—Zr Based Alloys

The potentiodynamic polarization technique was used to test corrosion of the WX11 and WX41 as-cast and T4 treated alloys. Samples were connected to a copper wire using silver epoxy and mounted in epoxy resin. The mounted samples of dimensions 10 mm×10 mm×1 mm were mechanically polished, sonicated in isopropyl alcohol, and dried in air. The potentiodynamic corrosion study was carried out with an electrochemical workstation (CH-604A, CH Instruments, Inc., Austin, Tex.) at a scanning rate of 1 mV/s and potential window of 500 mV above and below the open circuit potential. A three electrode cell was employed with platinum as the counter electrode, Ag/AgCl as the reference electrode, and the sample as the working electrode. The test was performed in Dulbecco's Modified Eagle Medium (DMEM, with 4.5 g/l glucose, L-glutamine, and sodium pyruvate, Cellgro, Manassas, Va.) supplemented with 10% fetal bovine serum (FBS), 100 U/ml penicillin, and 100 μg/ml streptomycin at pH 7.2±0.2 and held at 37.4° C. Before each measurement, the sample was immersed in the corrosion media to provide stability. The cathodic and anodic portions of the generated Tafel plots were fit linearly to allow calculation of corrosion potential, $E_{corr}$, and corrosion current density, $i_{corr}$.

Corrosion of the Mg alloys was also measured using mass loss in a corrosion solution. Polished samples of the as-cast and T4 treated WX11 and WX41 were immersed in DMEM with 10% fetal bovine serum (FBS), 100 U/ml penicillin, and 100 μg/ml streptomycin at 37° C., while the extruded KX11, WK11, WK41, and WZ42 alloys were immersed in HBSS at 37° C. Samples removed after up to 5 weeks of immersion were dried at room temperature and their surfaces and surface cross sections analyzed using SEM and EDX to analyze the surface layer composition and morphology. The sample masses were measured after immersion in a solution containing 200 g/L of chromic acid and 10 g/L of $AgNO_3$ for 1 minute to remove the corrosion products. The corrosion rate was calculated according to ASTM G31-72 using the following equation:

$$C=(K \times W)/(A \times T \times D)$$

Where C is the corrosion rate (mm year$^{-1}$, mmpy), the constant K is $8.76 \times 10^4$, W is the mass loss (g), A is the sample area exposed to solution (cm$^{-2}$), T is the time of exposure (h), and D is the density of the material (g cm$^{-3}$).

Microhardness Testing of Ma-Y—Ca—Zr Based Alloys

Vickers microhardness was measured by applying a load of 100 g for 10 s to samples polished and etched for microstructure, and measuring the indentation created by the square pyramidal diamond indenter using optical microscopy. The Vickers Pyramid number (HV) was determined by F/A, where F is the force applied to the diamond indenter in kilograms-force and A is the surface area of the resulting indentation in square millimeters. A was determined by the formula:

$$A = \frac{d^2}{2\sin\left(\frac{136°}{2}\right)}$$

where d is the average length of the diagonal left by the indenter in millimeters. The HV number was then calculated by:

$$HV = \frac{F}{A} = \frac{2\sin\left(\frac{136°}{2}\right)F}{d^2}$$

where F is in kgf.

Mechanical Testing of Mg—Y—Ca—Zr Based Alloys

For mechanical testing, samples were machined along the long axis of the Mg alloy ingots and extruded rods in dimensions in accordance with ASTM-E8-04 for tensile testing and ASTM-E9-09 for compressive testing. Tensile bar samples with a gauge area of 3×3 mm and length of 12 mm were machined for tensile samples. Compressive cylindrical samples were machined of 10 mm diameter×20 mm length. Compressive and tensile testing for as-cast and T4 solution treated alloys WX11 and WX41 were conducted by OrthoKinetic Testing Technologies, LLC (Southport, N.C.) at room temperature using an MTSI 1—50 kN electromechanical load frame (MTS, Eden Prairie, Minn.) with laser extensometer. For extruded alloys KX11, WK11, WK41, and WZ42, tensile tests were performed using an Instron 5566 mechanical testing system (Instron, Norwood, Mass.) with static axial clip-on extensometer. Tensile tests were conducted at room temperature at a crosshead speed of 1.3 mm/min, while compression tests were carried out at a speed of 2 mm/min. Engineering yield strength, ultimate strength, Young's modulus (E), percent elongation were determined from the stress-strain curves. Ultimate strengths of the alloys were determined as the maximum tensile stress from the stress-strain curves. Yield strengths were determined as the stress at the yield point during the tensile tests.

Statistical Analysis

Statistical analysis was conducted using SPSS Statistics 17.0 (SPSS Inc., Chicago, Ill.). Differences between groups were analyzed using one-way ANOVA with post-hoc testing using Tukey's test when group sizes were equal or Gabriel's pairwise test when group sizes were unequal. $P<0.05$ was accepted as a statistically significant difference between means and is denoted in figures. Error bars within figures represent standard deviation.

Results

Corrosion Behavior of Mg—Y—Ca—Zr Based Alloys as a Result of Y and Zn Additions

The corrosion rates of the as-cast and T4 Mg—Y—Ca—Zr alloys (WX11 and WX41) compared to pure as-cast Mg and as-drawn AZ31 were calculated based on mass loss after immersion as well as by potentiodynamic polarization measurements, and are shown along with corrosion potential and concentration of Mg ions released into the immersion solution in FIG. 6.1. The corrosion potential (FIG. 6.1b) of the WX41 alloys was higher than the WX11 alloys and the control materials, pure Mg and AZ31, respectively. T4 solution treated alloys conducted on the as-cast WX11 and WX41 alloys at 525° C. also demonstrated a higher corrosion potential and breakdown potential compared to their as-cast counterparts. Potentiodynamic corrosion rates of the WX41 alloys were lower than the WX11 alloys and were similar to that of commercial AZ31. Solution treatment increased potentiodynamic corrosion rate of the WX11 alloy, though did not affect WX41.

FIG. 6.1a shows that alloy corrosion rate calculated from the mass loss immersion test appeared to start stabilizing after 2 weeks of immersion. After 2 weeks of immersion, the corrosion rate of WX41 as-cast was significantly lower than those of the WX11 alloys. The 2 week corrosion rates of the WX41 alloys were also not significantly different than high-purity Mg. After 3 weeks of immersion, once again the WX41 as-cast alloys demonstrated a lower corrosion rate compared to WX11, and similar to high purity Mg. T4 solution treatment did not appear to have a major effect on immersion corrosion rate. The corrosion media used for the mass loss corrosion experiments was used to determine concentration of Mg released into solution after 1, 2, and 3 weeks (FIG. 6.1c). The WX41 alloys again showed higher corrosion resistance compared to WX11, releasing lower concentration of Mg at each time point, comparable to as-cast pure Mg and commercially obtained AZ31. Heat treatment did not seem to affect Mg ion released.

FIG. 6.1. shows corrosion properties of Mg—Y—Ca—Zr alloys, as-cast 99.99% pure Mg, and AZ31 in DMEM with 10% FBS: a) corrosion rate as measured using mass loss after 1, 2, and 3 weeks immersion (n=3 per group per time point) and potentiodynamic corrosion (n=1 per group). Significant difference (p<0.05) between * and **; between † and ‡, between §. b) corrosion potential and breakdown potential (n=1 per group); c) concentration of Mg released in corrosion media after 1, 2, and 3 weeks immersion (n=3 per group per time point). Significant difference (p<0.05) between * and **; † and ‡.

FIG. 6.2 shows SEM micrographs of the Mg—Y—Ca—Zr alloys after potentiodynamic polarization test cleaned with $CrO_3/AgNO_3$ solution to remove the corrosion products. All the samples demonstrated localized pitting corrosion, a commonly seen phenomena in Mg alloys including Y-containing alloys, while the as-cast alloys (FIGS. 6.2a and c) also show corrosion occurring at corrosion-prone grain boundary regions (arrows) due to higher secondary phase localization.

FIG. 6.2. shows SEM images showing surface morphologies of a) WX11 as-cast; b) WX11 T4 heat treated; c) WX41 as-cast; d) WX41 T4 heat treated; e) pure Mg; f) AZ31 after potentiodynamic polarization in DMEM with 10% FBS at 37° C. and cleaning with $CrO_3/AgNO_3$ solution. Arrows denote corrosion at grain boundaries.

Micrographs of dried samples after 3 weeks immersion were captured using SEM to further assess corrosion (FIG. 6.3). Localized corrosion was observed with deposits of corrosion product rich in C and O on the corroded surface (EDX shown in FIGS. 6.3a and b). The region immediately surrounding these corrosion deposits was generally rich in Mg (FIGS. 6.3a and e). Finally, most of the surface of the samples was covered in a layer rich in O, Ca, P, and Mg. Ca and P that are essential components in bone, and have been reported as forming a layer of amorphous calcium phosphate layer on rare earth containing alloys after degradation in vivo. After removal of corrosion products, SEM shown in FIG. 6.4 revealed that the 3 week immersion corrosion samples exhibited linked up corrosion cavities on all materials.

FIG. 6.3. shows SEM images showing surface morphologies of a) WX11 as-cast; b) WX11 T4 heat treated; c) WX41 as-cast; d) WX41 T4 heat treated; e) pure Mg; f) AZ31 after 3 weeks static immersion in DMEM with 10% FBS at 37° C. EDX was performed at various spots as denoted by arrows.

FIG. 6.4. shows SEM images showing surface morphologies of a) WX11 as-cast; b) WX11 T4 heat treated; c) WX41 as-cast; d) WX41 T4 heat treated; e) pure Mg; f) AZ31 after 3 weeks static immersion in DMEM with 10% FBS at 37° C. and cleaning with $CrO_3/AgNO_3$ solution.

Extruded alloys also underwent corrosion testing after being immersed in solution for 1, 3, and 5 weeks at 37° C., with average values plotted in FIG. 6.5. Compared to the commercial material controls, the alloys demonstrated a significantly lower corrosion rate than pure Mg but generally higher than AZ31 but comparable or lower than in-house generated AZ31, despite most alloy corrosion rates not being significantly different from AZ31 after 1 week degradation. AZ31 alloy produced using the same conditions as the other novel alloys (AZ31 in-house) and also extruded at a ratio of 10 corroded more rapidly than the commercially obtained AZ31, with corrosion rates similar to or higher than the Mg—Y—Ca—Zr based alloys. Finally, a comparison between WZ42 extruded at an extrusion ratio of 30 resulted in higher corrosion rates than when the same composition alloy was extruded at a lower ratio of 10, with this result potentially compounded by the additional 25° C. required for an extrusion ratio of 30 allowing further precipitation of intermetallics. Generally a trend was observed where the corrosion rate was reduced by increasing the Y content. Alloying WK41 with Zn (WZ42) did not significantly affect the corrosion rate. No discernable correlations were observed between corrosion rates and time of immersion.

Comparing the immersion corrosion rates of the extruded alloys to the as-cast and solution treated (FIG. 6.1), both groups of alloys degraded faster relative to extruded commercial AZ31. Furthermore, for both as-cast/solution treated and extruded alloys, an increasing content of Y reduced the corrosion rate, an important aspect of introducing and increasing the amounts of Y.

FIG. 6.5. shows average corrosion rates of extruded Mg—Y—Ca—Zr-based alloys compared to extruded pure Mg and AZ31 (in commercial and produced in-house forms). Groups labeled * were significantly different (p<0.05) from one another at that time point and those labeled † were significantly different (p<0.05) from all other groups at that time point. n=3 for all groups at all time points.

Following removal of degradation products to measure mass loss, samples immersed for 1 week were imaged for their surface morphology (FIG. 6.6), and cross section imaged after 5 weeks immersion (FIG. 6.7) using SEM. The surfaces of all the Mg alloys revealed filiform corrosion with the presence of pits. Still, the surface after 1 week remained largely uniform having undergone little corrosion. Pure Mg however did suffer from more severe pitting corrosion, with pits in the discontinuous surface seen in FIG. 6.7a. Fairly uniform surfaces of the alloys developed were seen in the cross sectional images after 5 weeks, with regions that appeared flat with scattered pits, most prevalent in WK11, pure Mg, and AZ31 cast in-house. While the depth of corrosion in WZ42 with ER 10 appeared greater than ER 30, the latter form of the alloy's surface appeared to be more discontinuous with cracks visible on the surface layer. The more rapid corrosion of AZ31 cast in-house compared to commercial AZ31 was visible in the deep pits seen in FIG. 6.7c.

FIG. 6.6 shows SEM images at 50× and 250× magnification showing surface morphologies of extruded a) pure Mg, b) commercially obtained AZ31, alloys produced in-house extruded with extrusion ratio of 10:c) AZ31, d) KX11, e) WK11, f) WK41, and g) WZ42 after 1 week static immersion in HBSS at 37° C. and cleaning with $CrO_3/AgNO_3$ solution.

FIG. 6.7 shows SEM images at 100× and 250× magnification showing cross sectional morphologies of extruded a) pure Mg, AZ31 obtained b) commercially and c) processed in-house, and d) KX11, e) WK11, f) WK41, and g) WZ42 alloys extruded with extrusion ratio 10 and h) WZ42 extruded with extrusion ratio of 30 after 5 weeks static immersion in HBSS at 37° C. and cleaning with $CrO_3/AgNO_3$ solution. Location of sample metal and mounting epoxy is indicated in a).

Microhardness of Mg—Y—Ca—Zr Based Alloys as a Result of Y and Zn Additions

Microhardness results shown in FIG. 6.8 demonstrated significantly increased values over pure Mg upon the addition of alloying elements. Furthermore, a significant increase in microhardness was observed with the addition of Zn to the Y containing alloys. No change was observed in the microhardness of the WZ42 alloy extruded at a ratio of 10 compared to 30.

FIG. 6.8 shows Vickers microhardness of extruded Mg alloys. Group labeled * was significantly different (p<0.05) than all other groups, and groups labeled † were significantly different (p<0.05) from all other groups but not from one another. ER=extrusion ratio. n=5 for all groups at all time points.

Mechanical Properties of Mg—Y—Ca—Zr Based Alloys as a Result of Y and Zn Additions and Extrusion Compression and tensile mechanical properties of the as-cast and heat treated alloys are presented in FIG. 6.9. Ultimate compressive strain (FIG. 6.9a) of as-cast WX11 and WX41 alloys were significantly larger than that of as-cast pure Mg and as-drawn AZ31. Ultimate compressive strength (FIG. 6.9a) for the as-cast experimental alloys was also greater than for as-cast pure Mg, while AZ31 exhibited significantly greater ultimate compressive strength over all of the other materials tested due to the significant work hardening and grain refinement imparted on it by the drawing process. T4 solution treatment applied to the as-cast alloys at 525° C. resulted in a significant reduction in compressive strength and strain, while an increase in compressive yield strength (FIG. 6.9b) was observed with an increased Y content. As-cast WX41 demonstrated significantly higher ultimate tensile strength (FIG. 6.9c) than as-cast WX11. Similar to compression test results, applying the T4 solution applied at 525° C. to the as-cast Mg—Y—Ca—Zr alloys resulted in a reduction in the ultimate tensile strength and tensile yield strength compared to the as-cast alloys, while no significant effect on tensile strain could be observed after heat treatment. AZ31 displayed much higher tensile strength and strain over the other tested materials. Tensile properties of the Mg—Y—Ca—Zr alloys were either greatly improved or observed to be comparable to those of pure Mg. Values of Young's modulus (FIG. 6.9d) for the tested alloys varied between 34-60 GPa, similar to the measured value for AZ31 (42 GPa), with high variance within the groups observed.

FIG. 6.9. shows mechanical properties of Mg—Y—Ca—Zr alloys, pure Mg, and AZ31: a) ultimate compressive strength and ultimate compressive strain; Significant difference ($p<0.05$) between * and all other groups; †, ‡ and other groups. b) compressive yield strength; Significant difference ($p<0.05$) between * and all other groups; †, ‡ and other groups. c) ultimate tensile strength and ultimate tensile strain; Significant difference ($p<0.05$) between *, § with all other groups; †, ‡ with other groups. d) tensile yield strength and Young's modulus; Significant difference ($p<0.05$) between § with all other groups; †, ‡ with other groups. $n \leq 3$ for all groups at all time points.

Tensile mechanical properties of the extruded alloys are reported in FIG. 6.10 and FIG. 6.11. Ultimate tensile strength (FIG. 6.10) for all the extruded Mg alloys developed in this work were significantly higher than the commercial controls—extruded pure Mg and AZ31. While the ultimate tensile strength remained similar for KX11, WK11, and WK41, it was drastically improved upon adding Zn to the composition in the form of WZ42, for which strength was significantly higher when extruded at ER 10 versus 30. The ultimate tensile strain of all measured extruded materials were all similar except for KX11, which had a significantly higher elongation than all other groups save AZ31.

Yield strength (FIG. 6.11) of the extruded alloy KX11, WK11, WK41, and WZ42 were higher than commercial pure Mg and commercially obtained extruded AZ31, with WK41 having the lowest yield strength among those alloys in its system, whereas again the WZ42 alloys possessed significantly higher strength. The Young's modulus of all the tested alloys were not significantly different from each other, ranging from 40-60 GPa.

FIG. 6.10 shows average ultimate tensile strength and strain of extruded Mg alloys. Measurements of ultimate tensile strains labeled * were significantly different ($p<0.05$) from each other. Measurements of ultimate tensile stress labeled † were significantly different ($p<0.05$) from all other groups but not from one another. Measurements of ultimate tensile stress labeled were significantly different from all other groups. ER=extrusion ratio. n=5 for all groups at all time points.

FIG. 6.11 shows average tensile yield strength and Young's modulus of extruded Mg alloys. Measurements of yield strength labeled * were significantly different ($p<0.05$) from all other groups; groups labeled † and ‡ were significantly different ($p<0.05$) from all other groups but not from one another. ER=extrusion ratio. n=5 for all groups at all time points.

Discussion

In this specific aim, the three main variables of: 1) alloy composition (increasing amount of Y and addition of Zn), 2) extruded versus non-extruded, and 3) as-cast versus T4 solution treated were explored for their effects on corrosion behavior and mechanical properties.

Corrosion resistance has been a major point of interest in magnesium alloy research due to severe pitting corrosion observed in Mg alloys when exposed to physiological chloride environment beyond 150 mmol/L as well as at sites of low hydrogen overpotential. Microstructure and grain size play crucial roles in controlling corrosion, with reports of an increase in grain size resulting in a change in corrosion resistance. Comparing the immersion corrosion rates of the extruded alloys (FIG. 6.5) to the as-cast and solution treated alloys (FIG. 6.1a), both groups of alloys degraded faster relative to extruded commercial AZ31. Corrosion rates of the extruded alloys did not improve significantly over the as-cast and T4 treated alloys studied here, and may be due to a number of causes. On one hand, it has been demonstrated that increasing grain size through heat treatments at various temperatures of AZ31B-H24 resulted in an increase in corrosion rate as explained by the grain boundaries acting as a physical corrosion barrier. Fine grained alloy microstructures processed by friction stir processing of Mg—Y-RE and equal channel angular pressing (ECAP) of AZ31 also displayed better corrosion behavior as a result of the finer grained alloys. Small grain size was suggested to lead to greater corrosion resistance by the presence of a more compact layer of phosphorous containing compounds and magnesium hydroxide when the alloy is exposed to physiological medium serving to protect against the action of chloride ions resulting in higher charge transfer resistance as well as more uniform corrosion with smaller pits because of the fine grain size. On the other hand however, conflicting studies have shown that reduction in grain size leads to a decrease in corrosion resistance, through addition of a grain-refining agent or ECAP as a result of corrosion initiation and propagation at grain boundaries, with corrosion filaments following grain boundary paths, acting as sites of micro-galvanic corrosion. It is expected that the lack of noticeable change in corrosion from change in grain size as stemming from a combination of these conflicting effects on corrosion by microstructural variations.

Another method of controlling corrosion rate was by applying a T4 solution treatment to reduce the volume fraction of secondary phases by diffusion into the α-Mg matrix, thus limiting the extent of microgalvanic corrosion where the anodic α-Mg matrix has a lower corrosion potential than any secondary phase, corroding preferentially as a galvanic couple. This was observed in comparing the corrosion surface of as-cast to solution heat treated alloys in FIG. 6.1, where the as-cast alloys with higher secondary phase concentration at the grain boundaries encountered visible corrosion at these grain boundaries, which was not seen in the solution treated alloys.

Differing the Y content in Mg-alloys may affect the corrosion behavior as reported by Liu and colleagues. By increasing Y content, the volume fraction of Y-containing intermetallics increases, thereby enhancing the microgalvanic corrosion. On the other hand, Liu et al. determined that increasing Y above 3% may also result in a more protective passivation layer of $Y_2O_3$ and decreased cathodic current, which was also determined theoretically.

This stronger passivation of alloys containing greater Y content was shown in the higher corrosion potentials (FIG. 6.1b) of as-cast and T4 treated WX41 compared to the as-cast and T4 treated versions of WX11. T4 solution treatment was also observed to shift the corrosion potential of the Mg—Y—Ca—Zr alloys to more noble potentials due to the reduction of intermetallic particles along the grain boundaries into the solid solution, possibly allowing for the protective oxide layer to cover a larger region of the alloy surface, after heat treating Mg—Zn-RE-Zr alloys. After solution treatment, more positive breakdown potentials of the Mg—Y—Ca—Zr alloys were also observed, indicating a higher resistance to the breakdown of the passive film and onset of pitting corrosion. The potentiodynamic corrosion rates (FIG. 6.1a) as calculated using corrosion current density of the Mg—Y—Ca—Zr alloys decreased with an increase in Y content, which occurs through suppression of the cathodic reaction in the corrosion process. Immersion corrosion (FIG. 6.1a) and Mg concentration measurements (FIG. 6.1c) confirmed this reduction in corrosion rate from WX11 to WX41 alloys. In the extruded alloys, an increase in Y content similarly led to a reduction in corrosion rate as seen in the results of FIG. 6.5. KX11, the alloy processed without Y exhibited the highest corrosion rate while also displaying a surface most affected by corrosion compared to the alloys containing Y which displayed a more uniform surface (FIG. 6.6). Filiform corrosion has been observed in Mg—Y containing alloys which occurs due to the non-uniform hydroxide film on the surface allowing for locations of active corrosion to remain which can propagate. This active corrosion site produces high concentrations of local $Mg^{2+}$ which attracts chloride ion, allowing the filiform corrosion to be maintained in random directions. This corrosion mechanism was confined to the surface due to the formation of $Mg(OH)_2$ and other passivating products such as $Y_2O_3$ which prevents the corrosion from propagating into the interior of the Mg sample as seen in the cross sectional images of the experimental alloys in FIG. 6.7d-h.

Solution treatment of the as-cast alloys WX11 and WX41 caused a large increase in the potentiodynamic corrosion rate of WX11, while only a slight increase in corrosion rate was observed for WX41. However, these trends were not reflected in the immersion corrosion and Mg concentration measurements, where T4 treatment did not result in a marked change or decrease in the corrosion rate. This may have been due to a combination of T4 treatment dissolving the intermetallic phases, reducing microgalvanic galvanic corrosion, while also increasing grain size, which may retard passivation kinetics. The linked up corrosion cavities seen on the surface of the alloys are commonly observed on corroded Mg alloys.

Corrosion rate calculated from potentiodynamic polarization curves were lower than those calculated from mass loss during immersion possibly because the corrosion mechanism of Mg involves a fraction of the uni-positive Mg ion reacting as an intermediate step, reacting chemically as well as partially electrochemically, causing electrochemical measurements to underestimate the corrosion rate compared to weight loss or hydrogen evolution methods. Corrosion products developed over a 3 week immersion period in DMEM with 10% FBS (FIG. 6.3) revealed large amounts of Ca and P in deposits (EDX in FIG. 6.3a & b), consistent with observations of aggregations of calcium-containing corrosion products. The presence of Ca and P containing cations may result in passivation and pit formation (as seen in FIG. 6.2) because of the precipitation of phosphate and carbonate salts.

Interestingly, a stark contrast was observed between the commercially obtained AZ31 and AZ31 as-cast, heat treated, and extruded in-house at an extrusion ratio of 10. Likely the differences in production process where industrial scale methods of generating bulk quantities in more controlled environments resulted in a more homogenous AZ31 with fewer impurities compared to the lab-scale operation which was used to produce AZ31 in-house. These impurities, defects, and inclusions likely led to the more rapid corrosion of our AZ31.

Experimental error propagation resulting in variation in immersion corrosion rates within groups may have arisen due to variabilities in weight measurement from the scale, variations in the surface area from machining error, and slight differences in immersion time, in addition to variation between sample homogeneity and surface finish through machining and polishing.

Mechanical properties of Mg alloys are known to be sensitive to changes in microstructure according to the Hall-Petch relation where finer grains results in higher grain boundary strengthening. In this work, grain size increased after performing T4 solution treatment on as-cast alloys, but decreased after performing hot extrusion. Appropriately, the as-cast Mg—Y—Ca—Zr alloys maintained higher strength in compression and tension and higher compressive strain compared to the alloys after grain coarsening occurred from solution treatment. The higher presence of secondary phases in the as-cast Mg—Y—Ca—Zr alloys may have contributed to precipitation strengthening by acting as impediments for dislocation movement during plastic deformation. This phenomenon as well as solid solution strengthening has been utilized in RE containing alloys, and may explain the marginally higher tensile strengths for as-cast alloys containing higher Y content. As-drawn AZ31 solidifies with a fine grain size to meet mechanical property requirements for industrial applications, while the as-cast high purity Mg devoid of any alloying elements exhibited comparatively low mechanical properties, suffering from a lack of solid solution strengthening or precipitation strengthening. The extruded pure Mg also demonstrated significantly lower strength compared to all alloys tested. After extrusion, significant grain refinement occurred causing a significant increase in strength, with ultimate tensile strength of the as-cast and T4 treated alloys before extrusion not exceeding 175 MPa increasing to over 286 MPa for alloys following hot extrusion. Unlike the increase in strength seen after increasing the Y content in as-cast WX41 versus WX11 (FIG. 6.9), an increase in Y did not result in an increase in strength in the extruded alloys. Despite the higher percentage of alloying elements and precipitates, extruded WK41 which contained 4 wt. % Y did not show higher strength than KX11 and WK11 which contained 0 and 1 wt. %, respectively. This is likely due to the higher temperature to preheat the alloy slug held during extrusion required to soften the ingot to allow to pass through the die for WK41 which causes the alloy to undergo a higher extent of dynamic recrystallization and grain growth, hence reducing strength. With the introduction of Zn and thereby the LPSO phase in the WZ42 alloy, high microhardness and strength with moderate elongation were observed, with the Hall-Petch relationship and alignment of the LPSO phase along the direction of extrusion acting as hardening phases via a short-fiber strengthening mechanism like a composite material. WZ42 extruded at a ratio of 30 may have seen its slight reduction in ultimate tensile strength due to higher deformation and temperature increase during hot extrusion leading to further dynamic recrystallization. Finally, a significantly higher elongation in the KX11 alloy lacking Y has been confirmed experimentally where higher Y content led to weakened ductility as greater Y content in the solid solution and precipitates deteriorate the alloy ductility.

The Young's modulus of the tested alloys all were in a similar range being more appropriate for orthopedic applications than stainless steel or titanium as they were closer to the modulus of natural bone (6-24 GPa). This may reduce the risk of stress shielding compared to the traditionally used permanent metals.

Experimental error resulting in variation in mechanical testing results within groups may have occurred due to slight variability in sample dimensions from machining error, variances in data collection of the force and strain measured by the mechanical testing unit, and deviations in sample alignment when positioning samples, in addition to differences in sample to sample homogeneity.

Compared to other alloys reported in literature, the high strength of the WZ42 alloy compared especially favorably. In a comprehensive representation of degradable metals (FIG. 6.12), WZ42 exhibits a yield tensile strength approaching that of wrought Fe, above any other Mg alloy reported thus far, with a moderate elongation of ~15%. Due to the high strength and reasonable ductility, this alloy was selected as the most optimum candidate for in vivo rat animal testing described in detail in Specific Aim 4. The other extruded alloys, KX11, WK11, WK41, also demonstrated high strength comparatively with moderate elongation. The as-cast WX11 and WX41 alloys demonstrated similar mechanical properties to the other cast Mg alloys included in the figure.

FIG. 6.12 shows the yield tensile strength and elongation of cast and wrought Mg alloys with alloys from this thesis included—WX11 and WX41 in as-cast form and KX11, WK11, WK41, and WZ42 extruded at a ratio of 10.

Example 7

Evaluate the effect of yttrium and zinc addition, post processing, and alloying element salts, on cell viability and proliferation of pre-osteoblast and human mesenchymal stem cells. further evaluate expression of osteoblast differentiation markers and biocompatibility in murine subcutaneous tissue Introduction The degradation of Mg alloys gives rise to metal cations, oxides, hydroxides, phosphates, and carbonates, while also changing local pH and generating hydrogen gas which leads to gas pocket formation when implanted into animals. Below a threshold concentration, these degradation products are considered tolerable by the human body and do not result in any catastrophic outcomes leading to loss of patient life. The effects of the degradation products on local cells and tissue and their ability to be cleared by the body depends largely on their solubility in aqueous solutions. The most common and by far, the most stable byproduct of Mg alloy degradation is $Mg(OH)_2$ which has a moderate solubility $(K_{sp})$ of $8.9 \times 10^{-12}$ with the next product that is formed by conversion of the hydroxide to a salt being $MgCl_2$ which in contrast, is extremely soluble. The toxicity of the other alloying elements and their salts also must be considered to gain a full understanding of the potential toxicity of Mg alloys. Not only is it important to understand the toxicity and cellular responses to degradation products of the Mg alloys, but it is also extremely important to consider the direct interaction between the implant surface and local cells to ensure that the cells may attach and proliferate on the Mg implant surface.

For bone applications, implant materials should allow for growth of surrounding bone tissue and thereby reduce the incidence of implant loosening. From this standpoint, Mg has shown advantages of stimulating bone formation around and in contact with Mg implants to allow for better implant stability, integration with surrounding bone, and replacement of the biomaterial by native tissue. To compare between different materials and their characteristics before proceeding with costly and time-consuming animal tests and to reduce the ethical burden of these trials, in vitro tests are used to preselect the appropriate implant material candidates.

In addition to testing the alloys themselves, it was also sought to assess the individual contributions of each alloying element to the effects on cell response. Table 6.1 lists the toxicity and tolerance information on Mg and the alloying elements used in this study. In this aim it was decided to expand on these tests of the alloying element salts while also adding alloy extracts to pre-osteoblast and human mesenchymal stem cells to evaluate their viability, proliferation, and differentiation into the osteoblast lineage. In addition, a preliminary murine subcutaneous implant model was used to compare WX11 and WX41 as-cast samples for local toxicity and corrosion as an in vivo biocompatibility pilot study.

TABLE 6.1

Summary of the pathophysiology and toxicology of Mg and alloying elements used in the alloys of this work. The toxicity levels for bone cells are according to the cytotoxicity test of the metal salts; (+) represents mild toxicity, (+ −) symbolizes moderate toxicity, and (−) indicates severe toxicity.

| Element | Human amount | Blood serum level | Pathophysiology | Toxicology | Daily allowance | Toxicity bone cells |
|---|---|---|---|---|---|---|
| Mg | 25 g | 0.73-1.06 mM | Activator of many enzymes; co-regulator of prostein synthesis and muscle contraction; stabilizer of DNA and RNA | Excessive Mg leads to nausea | 0.7 g | + |
| Ca | 1100 g | 0.919-0.993 mM | More than 99% has a structure function in the | Inhibit the intestinal | 0.8 g | + |

TABLE 6.1-continued

Summary of the pathophysiology and toxicology of Mg and alloying elements used in the alloys of this work. The toxicity levels for bone cells are according to the cytotoxicity test of the metal salts; (+) represents mild toxicity, (+ −) symbolizes moderate toxicity, and (−) indicates severe toxicity.

| Element | Human amount | Blood serum level | Pathophysiology | Toxicology | Daily allowance | Toxicity bone cells |
|---|---|---|---|---|---|---|
| | | | skeleton; the solution Ca has a signal function, including muscle contraction, blood clotting, cell function, etc. | absorption of other essential minerals | | |
| Zn | 2 g | 12.4-17.4 µM | Trace element; appears in all enzyme classes; most Zn appears in muscle | Neurotoxic and hinder bone development at higher concentration | 15 mg | − |
| Zr | <250 mg | 0.011 mg/dm$^{-3}$ | Probably excreted in feces; low systemic toxicity to animals | High concentration in liver and gall bladder | 3.5 mg 53 µg | + |
| Y | 0.5 mg | 0.1 mg/l | Substituted for Ca$^{2+}$ and matters when the metal ion at the active site; compound of drugs for treatment of cancer | Concentrated in liver, kidney, spleen, lungs, high affinity for bone in areas of high osteoblastic activity | 4.4 µg | + − |

Materials and Methods

Cell Culture and Maintenance

MC3T3 pre-osteoblast cell line and human mesenchymal stem cells (hMSCs) were used to test the cytocompatibility of the alloys studied. These two cell lines were used to test the effects of the alloys on both osteoblast pre-cursor cells, hMSCs, and further differentiated mesenchymal cells, pre-osteoblasts, before full osteoblastic maturity. Their culture conditions are described below.

Mouse Pre-Osteoblast Cell Line (MC3T3-E1)

The murine pre-osteoblastic cell line (MC3T3-E1, American Type Culture Collection, Rockville, Md.) were cultured in growth media consisting of modified Eagle's medium alpha (αMEM, Life Technologies, Carlsbad, Calif.), 10% fetal bovine serum (FBS), 100 U/ml penicillin, and 100 µg/ml streptomycin at 37° C. in an environment of 95% relative humidity with 5% $CO_2$. Cells after passage four were used in all experiments at a seeding density of 50,000 cells mL$^{-1}$. For osteogenic differentiation studies, MC3T3-E1 growth media was used supplemented with 100 nM dexamethasone, 50 µM ascorbic acid, and 10 mM β-glycerophosphate, also known as differentiation inducing media.

Human Mesenchymal Stem Cells (hMSCs)

hMSCs obtained from normal human bone marrow (Lonza, Allendale, N.J.) were cultured in growth media of αMEM with 20% FBS, 100 U/ml penicillin, and 100 µg/ml streptomycin at 37° C. in an environment of 95% relative humidity with 5% $CO_2$. Cells after passage three were used. In osteogenic differentiation studies, growth media was supplemented with 100 nM dexamethasone, 50 µM ascorbic acid, and 10 mM β-glycerophosphate as differentiation inducing media.

Direct LIVE/DEAD Cell Viability and Adhesion Test

MC3T3-E1 cells were cultured directly on the Mg alloys, as-cast and extruded pure magnesium, and extruded AZ31. 1 mm thick samples were polished up to 1200 grit, ultrasonically cleaned in isopropyl alcohol, air dried, and UV sterilized for 1 h. The alloy samples were incubated in cell culture media for 10 min after which cells were seeded on the samples at a density of 4×10$^4$ cells/mL. Cell viability was evaluated at 1 and 3 days using the LIVE/DEAD Viability/Cytotoxicity Kit (Invitrogen Corporation, Karlsruhe, Germany) following the manufacturer protocol. This kit determines cell viability by differentiating between live and dead cells with fluorescence microscopy of two different wavelengths. Briefly, the Mg—Y—Ca—Zr samples with attached MC3T3-E1 cells were washed with PBS and stained for 30 min at room temperature with 2 µmol/L ethidium homodimer$^{-1}$ and 4 µmol/L calcein AM in PBS. After incubation in the LIVE/DEAD solution for 30 min in room temperature, live cells and dead cells images were captured using fluorescence microscopy.

F-Actin and Nuclei Staining, SEM/EDX Imaging of Fixed Cells

MC3T3 cells seeded on alloys cultured for 72 hours were fixed with 4% paraformaldehyde, permeabilized with 0.1% Tween 20 solution. F-actin staining was performed using tetramethyl rhodamine isothiocyanate-conjugated phalloidin and nuclei staining was performed using DAPI. Fluorescence images were visualized with a fluorescence microscope. Following fluorescence imaging, samples were dehydrated in a gradient ethanol/PBS mixture (30%, 50%, 70%, 90%, 95%, 100%) for about 10 minutes each and dried. Sample surfaces with attached cells were then observed by SEM and surface elemental composition was measured using EDX.

Alloy Degradation Product Extract Collection for Indirect In Vitro Tests

Mg alloy samples, as-cast and extruded pure magnesium, and extruded AZ31 were polished up to 1200 grit, ultrasonically cleaned in isopropyl alcohol, air dried, and sterilized by ultraviolet radiation for 1 h. The specimens were incubated in MC3T3 growth media, hMSC growth or differentiation media at 37° C. in a humidified atmosphere with 5% $CO_2$ for 72 h. The sample weight to extraction medium ratio for as-cast and T4 treated WX11 and WX41 was 0.2 g/mL in accordance with the EN ISO standard 10933:12, while for studies involving extruded KX11, WK11, WK41, and WZ42 the ratio used was ~0.8 cm$^2$/ml media to provide further dilution. This starting extraction ratio was designated as 100% extract, with less concentrated extracts prepared by diluting the 100% extract to concentrations of 50%, 25%, and 10% or 25%, 10%, 1%, and 0.1% to explore a broader range of concentration. Extracts were sterile filtered through 0.2 μm syringe filters before being added to cells in the MTT, CyQUANT, alkaline phosphatase assays below.

MTT Cytotoxicity Test

MC3T3 cells were seeded in 96-well cell culture plates at 6×10$^3$ cells/200 μl medium in each well and incubated for 24 h. Culture medium without extract served as the negative control and 10% DMSO culture medium as the positive control. After the 24 hour incubation, medium was replaced with 200 μl of extraction medium with varying concentrations and incubated for 1 and 3 days. The cytotoxicity of the corrosion extracts were tested using the MTT assay. Media and extracts were replaced with fresh cell culture medium to prevent interference of the magnesium in the extract with the tetrazolium salt. The MTf assay was performed according to the Vybrant MTT Cell Proliferation Kit (Invitrogen Corp.) by first adding 10 W of 12 mM 3-(4,5-Dimethylthiazol-2-yl)-2,5-diphenyltetrazolium bromide (MTT) dissolved in phosphate buffer solution (PBS) to each well. The samples were incubated with MTT for 4 h, after which 100 μl formazan solubilization SDS-HCl solution was added to each well and incubated for up to 12 h. The absorbance of the samples was measured using the Synergy 2 Multi-Mode Microplate Reader (BioTek Instruments, Winooski, Vt.) at a wavelength of 570 nm. The absorbance of the samples with mean positive control subtracted was divided by the absorbance of the mean positive control subtracted from the mean negative control to determine percent viability of cells compared to the controls, where cells cultured with fresh media constituted 100% cell viability.

CyQUANT Proliferation Test

MC3T3 and hMSC cells were seeded in 96-well cell culture plates at 6×10$^3$ cells/200 μl medium in each well and incubated for 24 h. Culture medium without extract served as the negative control and 10% DMSO culture medium as the positive control. After the 24 hour incubation, medium was replaced with 200 μl of extraction medium with varying concentrations and incubated for 1, 3, and 5 days. The effects on cell proliferation from the corrosion extracts were tested using the CyQUANT assay, where the CyQUANT dye binding solution binds to cellular DNA, which is highly regulated and closely proportional to cell number. The media was removed and cells rinsed with Dulbecco's Phosphate-Buffered Saline (DPBS). After removing the DPBS, 50 μL of the CyQUANT dye binding solution was added to each well which was then covered and incubated at 37° C. for 30 minutes, the fluorescence intensity of each sample well was measured using the microplate reader with excitation at 485 nm and emission detection at 530 nm. The fluorescence intensity of the samples was divided by the intensity of the mean negative controls (cells cultured in fresh media) to determine percent viability of cells compared to the control, with cells cultured with fresh media constituting 100% normal proliferation. After measurement the cells were also imaged using fluorescence microscopy with excitation wavelength ~494 nm and emission ~517 nm.

Alkaline Phosphatase Activity

Alkaline phosphatase plays an important role in the mineralization process by hydrolyzing organic phosphate substrates to release free inorganic phosphate, a mineralization promoter, and decreasing the concentration of extracellular pyrophosphate, an inhibitor of mineral formation. ALP activity was quantified using the p-nitrophenol phosphate (pNPP) technique. After 3, 7, and 14 days of culture of hMSCs with the different extract media collected in growth media, the cells were rinsed with DPBS and lysed for 20 min using cell lysate (Sigma-Aldrich). ALP activity was measured using pNpp as the substrate according to the manufacturer's protocol. The substrate solution was incubated with cell lysis supernatant for 1 h at 37° C. without exposure to light, followed by termination of the reaction by adding 0.5 M NaOH. pNpp produced was measured at 410 nm using the microplate reader and normalized to the total DNA content as measured using the Quant-iT DNA assay (Thermo Fisher). ALP activity was compared to hMSCs cultured in growth media and differentiation media.

Quantitative Real-Time Polymerase Chain Reaction (qRT-PCR)

After culturing in osteogenic media, RNA extraction was performed using the NucleoSpin RNA II kit (Macherey Nagel, Bethlehem, Pa.) according to the manufacturer's protocol. The RNA concentration and purity were determined by measuring the absorbance at 260 and 280 nm using a microplate reader. Reverse transcription was then performed using the ImProm II Promega reverse transcription kit (Promega, Madison, Wis.) according to the manufacturer's protocol. Forward and reverse primers (5'-3') (Integrated DNA Technologies) for human glyceraldehyde 3-phosphate dehydrogenase (GAPDH), runt-related transcription factor 2 (RUNX2), alkaline phosphatase (ALP), and osteocalcin (OCN) were used in the qRT-PCR experiments. RUNX2 is the first transcription factor required for inducing mesenchymal cells into immature osteoblasts, where its expression is upregulated. ALP is an important enzyme maximally expressed during the matrix maturation phase of osteoblast differentiation as it provides high concentrations of phosphate at the site of mineral deposition. OCN is a bone-specific protein synthesized by osteoblasts that indicates osteogenic maturation, implicating bone mineralization and calcium ion homeostasis.

In Vivo Murine Subcutaneous Study

All experimental procedures for the murine subcutaneous study were approved by the Animal Care and Use Committee (IACUC) at the University of Cincinnati. Healthy nude mice were housed under controlled conditions and maintained with a standard pellet diet and water. Mice were anesthetized using isoflurane through a nosecone. A skin incision was made to create a subcutaneous pocket on the back of the mouse. Pure Mg, AZ31, and WX11 and WX41 as-cast alloys of dimensions 5 mm diameter×1.4 mm thickness were inserted into the pocket and the incisions were closed by surgical staples. After 7, 40 and 70 days, the mice were sacrificed in a $CO_2$ chamber followed by the cervical dislocation. The Mg/Mg alloy implants with surrounding tissue were recovered, carefully separated from the tissue, cleaned, air-dried, and the final mass was measured to determine change in mass due to corrosion to calculate corrosion rate according to the mass loss equation in section 0. Tissue surrounding the implant was fixed in 10% formalin in PBS, paraffin-embedded, and sectioned (4 μm/section) for hematoxylin-eosin (H&E) staining. 70 day explanted samples were also imaged using SEM and analyzed using EDX before and after removal of corrosion products.

Results

Cell Viability and Adhesion on Surface of Mg—Y—Ca—Zr Based Alloys

FIG. 7.1 shows pre-osteoblast MC3T3-E1 cells cultured directly on the WX11 and WX41 alloys for 1 and 3 days, and then stained with calcein-AM (green fluorescence in live cells) and ethidium homodimer-1 (red fluorescence in dead cells). After 1 and 3 days of culture, both WX11 and WX41 as-cast and T4 heat treated alloys (FIG. 7.1*a-d, h-k*) demonstrated comparable live cell density compared to pure Mg (FIG. 7.1*e* & 1) and AZ31 (FIG. 7.1*f* & *m*). Relatively few apoptotic cells compared to live cells were observed on each material, indicating generally good cell viability. Tissue culture plastic displayed higher cell viability compared to the Mg-based materials. No significant differences in cell morphology were observed among the different groups. Cell density was still high among the Mg—Y—Ca—Zr alloys after 3 days culture compared to 1 day, indicating the cells were not significantly affected by prolonged direct exposure times to the corroded environment.

FIG. 7.1 shows fluorescent images of live (green) and dead (red) MC3T3-E1 cells attached after 1 and 3 days culture on a & h) WX11 as-cast; b & i) WX11 T4 heat treated; c & j) WX41 as-cast; d & k) WX41 T4 heat treated; e & 1) pure Mg; f & m) AZ31 as-drawn; g & n) tissue culture plastic.

The direct live/dead assay for extruded alloys (FIG. 7.2) displayed high cell density of attached live MC3T3 cells on the extruded alloys after 1 and 3 days of culture. Relatively few apoptotic cells compared to live cells and normal cell morphology was observed on each alloy, indicating high cell viability. After 1 day, cell density on the WZ42 alloy appeared similar to that of tissue culture plastic, and higher than the other alloys. After 3 days culture, live cell attachment on the WK41 and WZ42 alloys was very high and similar to that on tissue culture plastic. Comparing the cell density on the alloys from 1 to 3 days, the increasing number indicated healthy cell proliferation. Cell morphology shown in the f-actin and nuclei staining of FIG. 7.3 shows healthy, spread cell morphology with filaments plainly observed demonstrating good cell adhesion.

FIG. 7.2 shows live (green) and dead (red) MC3T3 cells on the surface of polished and extruded Mg alloy surfaces after 1 (above) and 3 (below) days of culture. Scale bar=200 μm.

FIG. 7.3 shows phalloidin staining for F-actin (red) and DAPI staining for cell nuclei (blue) of MC3T3 cells on the surface of polished extruded Mg alloy surfaces after 3 days of culture. Scale bar=20 μm.

The alloy samples with MC3T3 cells attached to the surface were then imaged using SEM (FIG. 7.4). High cell attachment, especially seen in samples WK41 and WZ42 alloys was confirmed, as well as the relatively lower cell number attached to the KX11 alloy. Deposits of corrosion product were also observed on the surface of the corroded Mg alloys, as seen in the brighter areas in the SEM images.

FIG. 7.4 shows SEM images of MC3T3 cells attached to surface of extruded a) commercially obtained AZ31, b) pure Mg, c) KX11, d) WK11, e) WK41, and f) WZ42 after 3 days culture.

Full frame EDX analysis was also performed on various regions throughout the samples during imaging with SEM. Calcium and phosphorous weight percentages were graphed in FIG. 7.5 which shows maximal Ca and P content present in the WZ42 alloy, while the surface of the KX11 alloy having the lowest concentration present. Percentage P present in the substrate surface rose with the addition of Y in the alloys.

FIG. 7.5 shows average weight % of Ca and P on the surface of extruded Mg alloy samples after 3 days culture with MC3T3 cells, as determined by EDX. Groups marked with * were significantly different from one another. n=4 for each group.

Viability and Proliferation of Cells Indirectly Exposed to Degradation Products of Mg—Y—Ca—Zr Based Alloys FIG. 7. shows the indirect cytotoxicity results of WX11 samples performed using MC3T3-E1 cells and the MTT assay. For both culture periods, cell viability was expectedly most reduced with 100% extract concentration, and increased as the extract percentage decreased. After 1 day of culture with extracts (FIG. 7.*a*), no cytotoxicity was observed for 25% and 10% extract concentrations as no reduction in cell viability was observed. After 3 days of culture (FIG. 7.*b*), the cell viability was reduced to above 70% at 25% and 10% extract concentrations. This is consistent with findings that show high extract concentrations are cytotoxic and lead to osmotic shock, suggesting that a 10-fold extract dilution be used as an indicator for acceptable cytocompatibility response for as-cast magnesium materials. WX11 as-cast also displayed significantly higher cell viability at 50% extract concentration compared to WX11 T4, WX41 as-cast, WX41 T4, and pure Mg after 1 day and 3 days in extract media. After 1 day of culture with extract, however, WX11 and WX41 as-cast and T4 treated alloys showed significantly higher cell viability compared to pure Mg at 25% extract concentration, though no difference between them could be observed after 3 days of culture.

FIG. 7.6 shows viability of MC3T3 cells cultured for a) 1 day and b) 3 days in extract media from as-cast and T4 heat treated WX11 and WX41 alloys and as-cast pure Mg. Significant difference (p<0.05) between * and other groups or as connected. n=5 per extract concentration per group per time point.

The MTT assay conducted with MC3T3 cells with extract from extruded alloys (FIG. 7.6) displayed low toxicity of the alloy extract, with at least 70% cell viability observed for all extract dilutions. Reduction of cell viability by more than 30% is considered a cytotoxic effect according to EN ISO 10993:5, thus the alloys may be considered non-cytotoxic. Comparing the alloys, WK11 and WK41 were observed to cause slightly reduced viability after 3 days culture at 100% extract concentration, though viability was restored after 3 days of culture.

FIG. 7.6 shows viability of MC3T3 cells cultured for a) 1 day and b) 3 days in extract media containing degradation products from extruded alloys and commercial AZ31 and pure Mg. Groups labeled * significantly different (p<0.05) from one another. Groups labeled with † significantly different (p<0.05) with groups labeled with. n=4 per extract concentration per group per time point.

Proliferation of Pre-Osteoblasts and Human Mesenchymal Stem Cells Indirectly Exposed to Degradation Products of Mg—Y—Ca—Zr Based Alloys Proliferation of MC3T3 cells was assessed using the CyQUANT assay which utilizes the PicoGreen fluorochrome to bind to dsDNA to indicate relative levels of proliferation. After 3 days culture of MC3T3 cells with extruded alloy extracts (FIG. 7.7), proliferation was again most reduced with 100% extract concentration, and increased as the extract percentage decreased. With 100% extract concentration, WZ42 yielded significantly higher proliferation compared to the other groups. All the alloys displayed similar proliferation at all other concentrations. However, the extract collected from extruded AZ31 obtained commercially resulted in reduced proliferation compared to other groups when diluted to 1% and 0.1% while the AZ31 made in-house and extruded to the 10:1 ratio indicated much higher proliferation than commercial AZ31 and similar to the other Mg alloys. Fluorescent images showing cells incorporating the DNA-binding dye are shown in FIG. 7.8 confirms the stable proliferation of cells exposed to alloy extract, with generally higher cell density with decreasing extract concentration.

FIG. 7.7 shows proliferation of MC3T3 cells cultured for 3 days with extruded alloy extracts of AZ31, KX11, WK11, WK41, and WZ42 diluted to 25%, 10%, 1%, and 0.1%, compared to commercial pure Mg and AZ31 as a percentage of control cells cultured with regular extract media. Groups labeled * significantly different (p<0.05) from other groups at same extract concentration. n=4 per extract concentration per group per time point.

FIG. 7.8 shows florescence images of MC3T3 cells exposed to extruded alloy extracts diluted to 25%, 10%, 1%, and 0.1%, after 3 days culture with DNA bound to the CyQUANT dye. Scale bar (lower right, same for all images) =200 μm.

Cell proliferation was also tested using hMSCs for 1, 3, and 5 days culture (FIG. 7.9). For the alloys tested, near or above 100% proliferation compared to the growth media control without extract was observed for all the three time points. Cell number was also significantly higher compared to that of AZ31 after 1 day culture and at 100% extract concentration after 3 and 5 days culture. Fluorescent images showing cells incorporating the DNA-binding dye after 5 days culture, confirming the attachment of proliferating of cells exposed to alloy extract.

FIG. 7.9 shows proliferation of hMSCs cultured for a) 1 days, b) 3 days, and c) 5 days with extruded alloy extracts diluted to 50%, 25%, and 10% of AZ31, KX11, WK11, WK41, AND WZ42, compared to commercial pure Mg and AZ31 as a percentage of control cells cultured with regular extract media. Groups labeled * significantly different (p<0.05) from one another. Groups labeled with † significantly different (p<0.05) from all other groups at that time point. Groups labeled with ‡ significantly different from all other groups at that time point except WK41. n=4 per extract concentration per group per time point.

FIG. 7.10 shows florescence images of hMSCs exposed to extruded alloy extracts diluted to 50%, 25%, and 10% after 5 days culture with DNA bound to the CyQUANT dye. Scale bar (lower right, same for all images)=200 μm.

Differentiation of Human Mesenchymal Stem Cells Indirectly Exposed to Degradation Products of Mg—Y—Ca—Zr Based Alloys Human mesenchymal stem cells (hMSCs) were exposed to degradation products of the Mg alloys as collected in growth media and their ALP activity was accordingly compared to cells cultured in fresh growth media and differentiation media (FIG. 7.11) after 3 days, 7 days and 14 days of culture with extracts. Higher ALP activity with lower concentration of extract was observed overall, with the highest ALP activity of the hMSCs occurring when exposed to 10% extract media. The ALP activity in cells exposed to Mg alloy extracts at lower concentrations of 10% and 25% remained similar to that of cells cultured with regular growth media after 3 days, while all groups demonstrated lower ALP activity than cells cultured in differentiation media, as expected. After 3 days, no difference in the ALP activity between the alloy extracts was observed. Higher ALP activity with the Mg alloy WZ42 was observed at 50%, 25%, and 10% extract concentration compared to commercial AZ31 and pure Mg at 7 days. After 14 days culture, no significant difference in ALP activity between the alloy extract groups and the growth media control were observed.

FIG. 7.11 shows ALP quantification (normalized with DNA) using hMSCs in indirect method for extruded Mg alloys after a) 3 days, b) 7 days, and c) 14 days of culture with extracts diluted to 50%, 25%, and 10%. GM=growth media control; DM=differentiation media control. Groups labeled * significantly different (p<0.05) from one another. Groups labeled with † significantly different (p<0.05) from all other groups at that time point. n=4 per extract concentration per group per time point.

Osteogenic differentiation markers based roughly on their stages of upregulation in differentiating mesenchymal stem cells—early (RUNX2), middle (ALP), and late stage (OCN), were measured to determine the effect of the degradation product of the Mg alloys on differentiation of hMSCs following 7 days, 14 days and 21 days exposure to 10% dilution extracts collected in hMSC differentiation media (FIG. 7.12). WZ42 was the only alloy observed that appeared to result in upregulation of osteogenic markers, with higher fold increase compared to cells cultured in differentiation media without extracts of ALP after 7 days and 21 days culture, with higher osteocalcin expression observed after 14 days. Severe downregulation of osteocalcin, the late stage osteogenic differentiation marker at 14 and 21 days was observed in cells exposed to extract products of AZ31 and pure Mg. Relative to these controls materials—AZ31 and pure Mg, the novel alloys tested displayed upregulation of RUNX2 after 7 days, ALP after 14 days (except for WK11), and OCN after 21 days. However, this study was only completed with n=1 and additional experiments with large sample sizes is necessary.

FIG. 7.12 shows qRT-PCR gene expression data showing the expression of RUNX2, ALP, and OCN hMSCs cultured for a) 7 days, b) 14 days), and c) 21 days with 10% extracts diluted in differentiation media normalized with respect to cells cultured in growth media and compared to differentiation media group where media did not contain extracts. n=1 for all groups.

Proliferation of Human Mesenchymal Stem Cells Exposed to Salts of Mg Y, Ca, Zr, Zn, and Al hMSCs cultured with chloride salts in growth media of Mg (in concentrations of 50 mM, 20 mM, 10 mM, and 1 mM) and Y, Ca, Zr, Zn, and Al (in concentrations of 1 mM, 0.1 mM, 0.01 mM, and 0.001 mM) were assessed for proliferation using the CyQUANT assay after culture for 1, 3, and 5 days and normalized with respect to regular growth media. After 1 day culture (FIG. 7.13a), proliferation in the presence of Ca, Y, Zr, and Al was generally unaffected by the presence of the metal salts at all concentrations. For Mg and Zn, the upper concentrations tested (50 mM for Mg and 1 mM for Zn) both exhibited reduced proliferation of the hMSCs though this was restored with further dilution. At 3 days of culture (FIG. 7.13b), again high concentration of Mg and Zn reduced cell number, but an increase in cell number was observed at higher concentrations of Y, Zr, and Al. These trends were also retained after 5 days of culture. The dyed cells were imaged and shown in FIG. 7.14, confirming the differences in cell numbers quantified in FIG. 7.13.

FIG. 7.13 shows proliferation of hMSCs cultured for a) 1 days, b) 3 days, and c) 5 days with chloride salts of Mg (in concentrations of 50 mM, 20 mM, 10 mM, and 1 mM) and Y. Ca, Zr, Zn, and Al (in concentrations of 1 mM, 0.1 mM, 0.01 mM, and 0.001 mM) dissolved in growth media, as a percentage of control cells cultured with growth media and differentiation media. Groups labeled * were significantly different (p<0.05) from control cells cultured in fresh growth media. n=3 per extract concentration per group per time point.

FIG. 7.14 shows florescence images of hMSCs exposed to alloying element chloride salts of Mg (in concentrations of 50 mM, 20 mM, 10 mM, and 1 mM) and Y, Ca, Zr, Zn, and Al (in concentrations of 1 mM, 0.1 mM, 0.01 mM, and 0.001 mM) dissolved in growth media after 5 days culture with DNA bound to the CyQUANT dye. Scale bar (lower right, same for all images)=200 μm.

Differentiation of Human Mesenchymal Stem Cells Exposed to Salts of Mg Y, Ca, Zr, Zn, and Al ALP activity of hMSCs exposed to metal salts of elements present in the Mg alloys was compared to cells: cultured in fresh growth media and differentiation media (FIG. 7.15) after 14 days culture. Compared to growth media, the diluent in which the salts were dissolved into, Mg at 20 mM and 10 mM, Ca at 0.01 mM, and Zn at 1 mM resulted in cells with higher ALP activity than growth media and similar to that of hMSCs cultured in differentiation media. High concentration of Al (1 mM and 0.1 mM) reduced cellular expression of ALP.

FIG. 7.15 shows ALP quantification (normalized with DNA) using hMSCs in culture with chloride salts of Mg (in concentrations of 50 mM, 20 mM, 10 mM, and 1 mM) and Y, Ca, Zr, Zn, and Al (in concentrations of 1 mM, 0.1 mM, 0.01 mM, and 0.001 mM) dissolved in growth media for 14 days. Significant difference between groups labeled * and growth media control ALP activity. GM=growth media control; DM=differentiation media control. n=3 per extract concentration per group per time point.

In Vivo Murine Subcutaneous Study

H&E staining of the local site of implantation of Mg—Y—Ca—Zr as-cast alloys, pure Mg, and AZ31 in the subcutis of nude mice is shown in FIG. 7.16a-l. Minimal toxicity of the implanted alloys to the surrounding tissue was observed, while the region surrounding the implants appeared to be undergoing normal tissue repair. No significant accumulation of inflammatory cells was observed, whereas a layer of tissue composed of pink-stained collagen fibers and reactive fibroblasts was seen after 7 days. At this time point, a relatively high density of fibroblasts in tissues adjacent to as-cast WX11 and WX41 alloy pellets suggests their presence did not inhibit the normal healing response in the implantation site. After 40 and 70 days implantation, dense collagenous connective tissue was seen surrounding the location of the Mg implants, without the presence of a high density of chronic inflammatory cells. Normal adipocytes could be faintly distinguished past the dermis.

FIG. 7.16 shows a-l) Histology images (H&E staining) of the skin above the implants of a, e, i) WX11 and b, f, j) WX41 as-cast alloys, c, g, k) pure Mg, and d, h, 1) AZ31 after 7 days (a-d), 40 days (e-h), and 70 days (i-l) in the subcutis of nude mice.

In vivo corrosion as determined through mass loss (FIG. 7.17) of as-cast WX41 was much lower than as-cast WX11 and similar to pure Mg and slightly higher compared to AZ31 after 70 days. This result is consistent with the in vitro corrosion behavior of the Mg—Y—Ca—Zr alloys, in which the higher Y-containing alloy, WX41, corroded more slowly than WX11.

FIG. 7.17 shows corrosion rate as calculated by mass loss of pellet samples before and after murine subcutaneous implantation at time points of 40 and 70 days. n=1 for each group.

The samples explanted after 70 day implantation were dried and imaged using SEM to assess the corrosion products formed (FIG. 7.18) in comparison to those formed after static immersion (FIG. 6.3). After in vivo corrosion, it can be seen from the elemental maps of the corrosion products, layers rich in C and O were observed to have formed on the alloy surface, similar to results from the immersion study. The cracked corrosion layer was seen to contain higher Ca and P content compared to agglomerates of corrosion deposits. Removal of corrosion products revealed widespread corrosion resulting in irregular surface topography on all the explanted alloy materials as seen in FIG. 7.19.

FIG. 7.18 shows SEM images showing surface morphologies of a) WX11 as-cast; b) WX41 as-cast; c) pure Mg; d) AZ31 after 70 days implantation in murine subcutaneous tissue. EDX was performed at various spots as denoted by arrows.

FIG. 7.19 shows SEM images showing surface morphologies of a) WX11 as-cast; b) WX41 as-cast; c) pure Mg; d) AZ31 after 70 days implantation in murine subcutaneous tissue and cleaning with $CrO_3/AgNO_3$ solution.

Discussion

The alloying elements used in this study have all shown to be biocompatible based on the literature as well as indicated in Table 6.1 showing the daily allowance and toxicity. Y has been shown to be non-toxic in longevity studies, non-hepatotoxic, and incorporated in alloys which were clinically well-tolerated as an absorbable metal stent and fixation screw for chevron osteotomies in hallux valgus surgeries. Y also has a high affinity for areas of osteoblastic activity in bone through events leading to organic matrix formation and may promote osteoblast proliferation and differentiation at concentrations of $1 \times 10^{-9}$-$1 \times 10^{-4}$ M and $1 \times 10^{-7}$ M, respectively, which may be related to altered vitronectin and collagen conformation and bioactivity. Ca is well-known and an essential component in bone, while requiring Mg for incorporation into bone. Zr ions have low cytotoxicity and zirconium coatings have demonstrated improved osseointegration of metal implants in vivo. Effects on in vitro cytocompatibility, proliferation, and differentiation from the Mg—Y—Ca—Zr alloys discussed above were determined by 1) exposing murine pre-osteoblast and human mesenchymal stem cells to media containing degradation products of the materials, 2) seeding cells directly onto the alloys and observing live and dead cell densities through the LIVE/DEAD assay, and 3) adding media containing various concentrations of the alloying element salts to the cells.

FIG. 7. and FIG. 7.6 present the results from the MTT assay, in which at high extract concentrations, (100% and 50%), cell viability was reduced in the as-cast and T4 treated alloys of FIG. 7, as well as with the extruded WK11 alloy in day 1 and WK11 and WK41 alloys at day 3 at 100% extract concentration. This was likely due to reports of high extract concentrations causing cellular osmotic shock, suggesting a 10-fold extract dilution be used as an acceptable dilution for as-cast magnesium materials. Indeed, at lower concentrations of extract (25% and 10% for as-cast and T4 treated WX11 and WX41 alloys and 50%, 25%, and 10% for all extruded alloys), high cell viability was observed for the alloys, indicating higher alloy degradation products resulted in lower cytotoxicity. Higher than 100% cell viability was observed from 25% and 10% extracts of WX11 and WX41 as-cast and T4 treated alloys after 1 day of culture, which may be facilitated by enhanced osteoblast activity in the presence of corrosion product magnesium hydroxide. Similarly, high density of live cells was observed attached to the surface of the Mg—Y—Ca—Zr alloys in FIG. 7.1 and FIG. 7.2, by directly culturing cells onto Mg-alloy substrates, the assay qualitatively shows the effect of hydrogen gas production, increased pH levels, and local concentration of corrosion products on cell attachment and viability. The differences observed in the corrosion rate however, did not appear to have bearing on the in vitro cytocompatibility results, with all as-cast and T4 treated Mg alloys harboring similar number of attached active cells, while appearing to have lower cell density compared to tissue culture plastic. This is consistent with these alloys' 3 day MTT results at 100% and 50% extract concentrations in which cell viability was lower than the control. The elongated, spread morphology of the adherent cells on the Mg—Y—Ca—Zr alloys after both 1 and 3 days of culture confirmed the cytocompatibility of the alloys, which did not corrode too rapidly to inhibit cell attachment. It appeared that higher densities were present on relatively slower corroding alloys (WK41 and WZ42 compared to KX11), which also were revealed to have higher percentages of Ca and P deposited on their surface where cells were attaching (FIG. 7.5). This may indicate a correlation between corrosion stability with higher amounts of CaP deposits forming on the Mg alloy surface allowing for improved osteoblast adhesion and proliferation, as has been observed with CaP coatings on the surface of titanium.

In this study, cytocompatibility was conducted using MC3T3-E1 cells with samples immersed in αMEM+10% FBS, and the presented results may vary with the use of different cell lines and respective cell culture media. Cells cultured in other media such as DMEM may exhibit different cytocompatibility results compared to αMEM, due to the presence of higher L-glutamine content in DMEM, which functions as a chelating agent for magnesium ions, potentially causing increased Mg ion release from alloys immersed in DMEM. Thus, the obtained cytocompatibility results presented here should be solely considered under cell culture conditions using αMEM as opposed to other media such as DMEM or HBSS, which would likely result in a higher corrosion rate of tested alloys, applying a different local environment to cultured cells.

Proliferation of the extruded alloys was also measured using the CyQUANT assay of DNA quantification. Proliferation was reduced with higher concentration of Mg alloy extract in FIG. 7.7 similar to reduced viability seen in the MTT assay. hMSC proliferation on the other hand, was higher than MC3T3 cells in the presence of extract media, suggesting greater tolerance of hMSCs compared to MC3T3 cells. With hMSCs after 5 days of culture, proliferation was higher than cells cultured in regular growth media. There was an observed increase in hMSC proliferation with Mg-1Y (wt. %) alloy having a superior effect on proliferation compared to Mg-2Ca alloy. The increased proliferation was influenced via SMAD-dependent signaling pathway, with the largest increase in SMAD4 observed in the Y containing alloy. $Y^{3+}$ ions also promoted the proliferation of mouse osteoblasts. However, AZ31 resulted in reduced proliferation of both MC3T3 cells and hMSCs, with this negative effect on cell viability also being observed by other groups studying both AZ31 and AZ91. Little induction of differentiation due to the presence of Mg alloy extract media was observed as measured by ALP activity (FIG. 7.11) and RUNX2, ALP, and OCN expression (FIG. 7.12), with WZ42 alloy demonstrating a higher propensity compared to the other Mg alloy and pure Mg groups studied for promoting osteogenic differentiation. This may be due to this alloy containing a combination of Y—which promotes differentiation into osteoblast at low concentrations, while also including Zn excluded in the other alloys—which stimulates ALP activity and collagen concentration when tested with concentrations between 1 and 25 μM. Mg—Y also was found to increase levels of ALP in hMSCs compared to other Mg alloys and pure Mg.

In order to elucidate the effects of alloy addition to cells, it was also considered that each alloying element in the form of chloride salt be dissolved individually in media to use for cell culture and evaluation. It was found that in the range of concentrations tested (0.001 mM-1 mM) of Ca, Y, Zr, and Al, cell proliferation was not affected, while at high concentrations of Mg (50 mM) and Zn (1 mM), proliferation was reduced, though upon further dilution the reduction in proliferation was restored. The 50 mM Mg concentration was above that of 10 mM Mg ions that literature observed to result in in approximately 50% reduction in viability of MG-63 osteoblasts. The 1 mM Zn concentration also was above the IC50 of 0.09 mM for MC3T3 and L929 cells reported in literature. Literature also reported that the MC3T3 cell IC50 for Zr as 2.83 mM and for Al as 2.92 mM, above the maximum 1 mM used, resulting in no loss in proliferation. The IC50 for MC3T3 cells exposed to Y however, was 0.142 mM. In the present study, as seen in FIG. 7.10, the 1 mM concentration Y salt did not cause a decrease in hMSC proliferation.

Promotion of osteoblastic differentiation of hMSCs due to alloying element salts was also investigated, which concluded that Mg at concentrations of 10-20 mM resulted in increased ALP activity from cells in the differentiation media. It has been observed that 5 and 10 mM $MgSO_4$ concentration enhanced mineralization of ECM from human bone marrow stromal cells (hBMSCs) with maximum promotion of osteogenic factors at 10 mM Mg via HIF-2α and PGC-1α. The increase in activity for Zn at 1 mM concentration may not be indicative of a positive effect on differentiation due to the reduction in cell number that resulted from Zn addition as seen in FIG. 7.13, since ALP activity is normalized to DNA quantity.

Variations in the various in vitro cell tests conducted in this specific aim may be due to a number of factors. First, cell number may have varied from well to well, while variations in alloy sample dimensions and surface finishing may have deviated resulting in differences in the local environment of degradation products that cells were exposed to. Variations in pipetting volume of reagents and media may also have caused slight experimental error, as well as the method of measurements such as the microplate reader.

Past studies have shown acceptable host response and biocompatibility of RE-containing Mg alloys upon in vivo implantation. Subcutaneous implantation of Mg-1.5% Nd-0.5% Y-0.5% Zr alloys with and without 0.4% Ca demonstrated adequate Mg metabolism, renal function, and host-tissue response as the Ti-6Al-4V control implant. The murine subcutaneous study was conducted here in order to compare the in vivo corrosion and local tissue response of the selected materials: WX11 as-cast, WX41 as-cast, pure Mg, and AZ31. Histological slides stained using H&E (FIG. 7.16) showed the Mg—Y—Ca—Zr alloys did not introduce toxicity or excessive inflammatory response to the surrounding tissue, presenting an acceptable host response with natural wound healing occurring as seen in the presence of a high density of fibroblasts which deposit collagen fibers in order to form new extracellular matrix during the tissue repair process. This dense connective tissue was observed adjacent to the Mg alloy implants at all time points, indicating biocompatibility at varying magnitudes of alloy degradation. The in vivo mass loss corrosion rates (FIG. 7.17) of the tested Mg alloys were lower than those measured from in vitro immersion. It has been concluded that in vitro corrosion tests could not accurately predict in vivo corrosion rates after observing a four order of magnitude reduction of corrosion rate in vivo compared to in vitro. Different environmental conditions, dynamic blood flow around the implant, and variations in pH as well as the local chemical environment of buffering ions could also be among reasons that could be provided to explain the discrepancy. The lower corrosion rates measured in vivo versus in vitro was in agreement with studies of Mg alloys implanted intramedullary in guinea pig femurs and in a subcutaneous environment in Lewis rats. Explanted samples displayed the formation of similar corrosion products and morphology to samples from immersion testing. After 70 days implantation, the extent of in vivo corrosion is clearly greater than after 3 weeks in vitro, as can be construed from the SEM images of the surfaces seen in FIG. 7.18 and FIG. 7.19. At the same time, corrosion products rich in C and O with the presence of Ca and P were still identified. The corrosion product morphology of a cracked corrosion layer with corrosion products deposited on top as seen both in vitro and in vivo is in agreement with results found in other studies.

Nonetheless, in vivo corrosion rate following 40 and 70 days of implantation for as-cast WX41 was lower than as-cast WX11 and comparable to pure Mg and AZ31 after 70 days, which was consistent with the measured in vitro corrosion rates (FIG. 6.1). This result is in agreement with established knowledge that while in vitro corrosion tests currently cannot accurately predict those seen in vivo, they may serve as a relatively inexpensive screening method to assess the relative corrosion resistance of Mg alloys. It can therefore serve to select alloys that could potentially yield a favorable response in vivo since a faster corroding alloy composition compared to a more stable system could likely also display faster corrosion under in vivo conditions. On an absolute scale, it may not be easy to derive the same conclusions due to the various factors of materials as well as the local chemical and biological environments that can affect the corrosion response of a given magnesium alloy.

Example 8

Assess the in vivo corrosion, bone formation, and host response of magnesium-yttrium-zinc-calcium-zirconium alloy in a rat femur osteotomy model Introduction Magnesium based alloys have received the most attention in the medical products space for use in orthopedic applications ever since its reintroduction into biomedical research this millennium. Numerous studies in small animals (e.g. mice, rats, guinea pigs, and rabbits), large animals (e.g. sheep and goats), as well as humans have overall shown the good biocompatibility of magnesium alloys when implanted within in or surrounding bone. This combined with the high strength to weight ratio of Mg and its ability to degrade, thus reducing the need for secondary removal surgeries as conducted for permanent metallic hardware, have made Mg and Mg alloys an attractive option that is poised to be at the forefront to challenge the dominance of the current state of the art inert metallic and degradable polymeric orthopedic device landscape. Other important properties of magnesium that have been demonstrated include enhanced bone formation adjacent to or near the Mg alloy, high deposition of Ca—P minerals, and direct contact between the degradation product layer of Mg and new bone.

Of the various studies involving implantation of Mg alloys into bone, the vast majority comprised implanting rods, pins, or screws of Mg alloys into the femoral diaphysis (~8), with a few in the femoral condyle and marrow cavity. None of the 23 papers reviewed by Zheng et al wherein Mg alloy was implanted into the bone, none represented a load bearing model, in every case a hole was predrilled into the bone with the implant then either press fit or screwed into place. The only cases in which a Mg implant was used to bear load to provide fixation for fractured bone was the plate and screw studies conducted by Chaya et al. In these studies, a full fracture was created in the ulna of New Zealand white rabbits with holes predrilled into the two sides of the fractured ulna to allow for placement of the plate and screw to stabilize the fracture. Despite these studies being the only assessments of a loaded fracture environment evaluating Mg orthopedic implants, all the rabbit radii were left intact during healing, which provided additional support to the fracture, supplementing that of the plate and screw.

In this study, it was decided to pursue a fully load bearing model where a full fracture of the rat femur was only fixed using implant pins of the Mg alloy Mg—Y—Zn—Zr—Ca (WZ42), whose materials and biological characteristics have been described in the preceding sections, and compared to the performance of the common medical titanium alloy, Ti6Al4V. No additional support was used to immobilize the pins intentionally to assess the influence of stress corrosion environment on the bone healing while also evaluating the safety and toxicity of the alloys. This model selected has conceptual similarities mimicking orthopedic fixation devices such as Kirschner wires (K-wires) and Steinmann pins, thin rods that are drilled through bone fracture fragments to maintain the anatomical congruity and biomechanical stability required for optimal bone healing. Unfortunately, currently used K-wires need to be removed after the bone has healed, necessitating a secondary procedure. To allow for easy removal, the ends of the wires are usually left outside the skin, forming a "pin-tract" that acts as a conduit for causing infection and other complications. These shortcomings of these common orthopedic devices could be avoided though through the use of degradable Mg alloy K-wires.

In addition to the intramedullary fracture fixation pins, in separate animals, WZ42 wires were wrapped around the mid-diaphyseal region of unfractured femurs forming a cuff to compare degradation and tissue response to the Mg alloy implanted in different regions—intramedullary versus over the cortical bone. Furthermore, another goal of the study was to assess systemic toxicity through a complete blood profile as well as organ and tissue analysis comprising kidney and liver.

Materials and Methods

Preparation of Mg—Y—Zn—Ca—Zr Implants

The WZ42 alloy was melt and cast, with the nominal composition of Mg-4.0% Y-2.0% Zn-1.0% Zr-0.6% Ca (wt. %). After casting, a solution treatment of 400° C. was applied for 20 hours and the ingot was quenched in room temperature water to increase the alloys' ductility and homogenize the secondary phases. The ingot diameter was machined using a lathe down to 37.8 mm to allow it to be extruded with an extrusion ratio of 30 while being heated at 450° C. The extruded WZ42 rod of diameter ~6.9 mm and control material of Ti6Al4V rod of diameter 5 mm (Goodfellow Corporation, Coraopolis, Pa.) were machined using a lathe into pins with dimensions of 15 mm length×1.66 mm diameter and wires of 20 mm length and 0.68 mm diameter. Schematics and photographs of machined pins and wire cuffs are shown in FIG. 8.1. The implants were sonicated in washes of pure acetone and isopropanol and dried before undergoing sterilization by gamma radiation (2×106 cGy, 23.5 Gy/min, cesium 137 source, Mark I 68, J L Shepherd and Associates, San Fernando, Calif.).

FIG. 8.1. Schematic (a) and photograph (b) of pins (lower) inserted into the femoral intramedullary cavity and wire cuffs (upper) wrapped around the mid-diaphyseal region. In a) the wire was machined straight then bent around the femur during surgery.

Animal Model

All animal experiments were approved by the University of Pittsburgh's Institutional Animal Case and Use Committee (IACUC). Before surgery, female Sprague-Dawley rats weighing 250-300 g were anesthetized by inhalation of isoflurane at a concentration of 2-5% for initiation of sedation, and 0.25-4% for maintenance. Each rat only received surgery in their right hind limb. Photographs of the surgical procedure are shown in FIG. 8.2a-8.2g. First, the right hind limbs were shaved and disinfected, and an approximately 2 cm incision was made over the right femur, with location indicated in FIG. 8.2a. The skin and mid-diaphysis region of the right femurs were exposed through a lateral approach. A complete femoral osteotomy was created using a hand held drill (FIG. 8.2b). The WZ42 or Ti6Al4V fixation pins were inserted first into the intramedullary space of the distal portion of the fractured femur (FIG. 8.2c), then inserted into the intramedullary space of the proximal femur (FIG. 8.2d), with the fracture approximated as seen in FIG. 8.2e. In the case of the wire cuffs, the right femur was not cut, and the wires were wrapped around the midsection of the diaphysis and pressed against the bone to avoid translation along the shaft of the femur or migration (FIG. 8.2g). After the samples were implanted, the fascia and muscles were closed with VICRYL (J315) and the skin closed using non-absorbable monofilament polyamide sutures.

Post-operative pain and distress was observed daily for expressions of stress and behavioral abnormalities, changes in movement, food, and water intake. Furthermore, the right hind limbs were observed visually for signs of infection or presence of gas pockets.

FIGS. 8.2(a)-(g). Surgical procedure used to implant metallic samples: a) Photograph of pins inserted into the femoral intramedullary cavity (bottom) and wire cuffs wrapped around the mid-diaphyseal region (top). Pin modela) Lines indicating where incision was made to expose the femur; b) Fracture being created in rat femur using circular saw; c) Pin inserted into marrow space of one side of fractured femur; d) Pin inserted into other side of femur to bridge the fractured femur; e) Fracture closed with pin maintaining alignment and fixation; f) Surgical site fully closed and sutured. Cuff model-g) After incision to expose femur, the bone was left intact without osteotomy and a wire was wrapped around the midsection of the femur.

Groups of 5 animals for both WZ42 and Ti6Al4V pins were used for each time point of 2, 8, and 14 weeks for blood, liver, kidney, histology, and micro-CT analysis, and groups of 6 animals were implanted with wire cuffs with a single time point of 14 weeks, as displayed in Table 8.2. Rats were sacrificed using a gradual overdose of carbon dioxide followed by cervical dislocation. Immediately following sacrifice, the liver, kidney, and experimental group femurs were collected and stored for further analysis as described in the following sections. Three rats receiving no surgery were also sacrificed to serve as an operated control group.

TABLE 8.2

Summary of number of rats in each groups at time points used in study.

|  | 2 weeks | 8 weeks | 14 weeks | 14 weeks |
|---|---|---|---|---|
|  | Intramedullary Pin | | | Cuff |
| Ti6Al4V | 5 | 5 | 5 | 6 |
| WZ42 | 5 | 5 | 5 | 6 |

X-Ray Imaging

X-ray imaging was performed on rats one week post-operatively to examine the position of the implants and stability of the fracture.

Blood-Cell Count and Serum Biochemical Measurements

Blood samples were collected from animals before operation under anesthesia by tail snip and terminally (2, 8, and 14 weeks after implantation) by cardiac puncture and aspiration. For determination of blood cell count, blood was collected in K2-EDTA tubes and analysis was performed by Marshfield Labs (Cleveland, Ohio) using a Sysmex XT2000i Automated Hematology Analyzer (Sysmex Corporation, Kobe, Japan). Serum samples were obtained by centrifuging collected blood at 2,000 rpm for 10 minutes at 4° C. Serum biochemical tests were conducted by Marshfield Labs using an Olympus AU chemistry analyzer (Olympus Corporation, Tokyo, Japan).

Micro-Computed Tomography Imaging

Plastic embedded rat femurs as were used for high resolution micro-computed tomography (μCT) scanning. Samples were scanned with continuous rotation μCT at 10.5 μm voxel size before implantation and immediately after retrieval post-operatively at 2, 8, and 14 weeks. The reconstructed data sets were used to generate a 3D volume from which we distinguished the remaining metal rod from surrounding degradation products and bone by using a histogram of grey values based on densities. A density threshold for the metal pins was used to isolate the volume of remaining magnesium alloy from surrounding material and compared to volume of the pins before implantation to estimate in vivo corrosion rate using the following equation:

$$C = (K \times V)/(A \times T)$$

Where C is the corrosion rate (mm year$^{-1}$, mmpy), the constant K is $8.76 \times 10^4$, V is the volume loss (cm$^3$), A is the initial sample area exposed (cm$^2$), and T is the time of exposure (h).

Histological Preparation and Analysis

Specimens of liver and kidney were fixed in 10% neutral buffered formalin, dehydrated, and infiltrated and embedded in paraffin. They were then inspected with hematoxylin and eosin (H&E) staining to assess whether the degradation of the WZ42 alloy resulted in any pathological changes in these critical visceral organs.

Femurs were fixed in 70% ethanol, dehydrated, and infiltrated and embedded in Osteo-Bed Plus methyl methacrylate-based embedding kit (Polysciences, Inc., Warrington, Pa.). The plastic blocks were sectioned with a rotary microtome (Leica RM 2255, Leica Biosystems, Buffalo Grove, Ill.) and stained using Goldner's Trichrome and alkaline phosphatase stains.

Tissue Digestion and Elemental Analysis

Liver and kidney tissues were digested to allow for measurement of elemental concentration using ICP-OES. First, tissues were dried at 70° C. for 24 hours, then homogenized and weighed. Samples were then digested by immersion in 20 ml nitric acid/g tissue for 6 hours at 70° C., followed by adding 4 ml hydrogen peroxide/g tissue for 1 hour, and 4 ml sulfuric acid/g tissue for 1 hour. Samples were then diluted 50× in water purified by a Milli-Q system (18 MΩ cm deionized water, Milli-Q Academic, Millipore, Billerica, Mass.), filtered in 0.45 μm syringe filters, and analyzed for Mg concentration by ICP-OES (Thermo Fisher).

Results

Fixation of Femoral Defect Using Mg—Y—Zn—Ca—Zr Alloy Pin

In order to provide fixation of a full osteotomy to the midsection of a femur, pins with sharpened ends were fabricated from the WZ42 alloy and Ti6Al4V alloy and inserted into the intramedullary cavity of the two halves of the fragmented femur. In addition, WZ42 and Ti6Al4V wires were wrapped around the midsection of native femurs to compare tissue response of the biomaterials inserted in the bone versus at the outer surface of the bone. The pins were successfully inserted into all femurs during surgery with the fractures being approximated as seen in the 7 day X-ray images of FIGS. 8.3a and b despite slight mismatches between the pin diameter and the diameter of the intramedullary cavity observed in some cases (FIG. 8.3c, red arrow) resulting in a small gap. Some wire cuffs snapped during implantation but all maintained fixation around the femur as shown in FIG. 8.3d and e.

FIG. 8.3 shows one week X-ray images of implanted WZ42 magnesium alloy (a) and Ti6Al4V (b) K-wires (designated by white arrow) in the right femur of rats; c) fracture misalignment (red arrow) and empty spaces near the WZ42 implants (yellow arrow, circled) were observed in some X-ray images. One week X-ray images of implanted WZ42 magnesium alloy (d) and Ti6Al4V (e) wire cuffs (designated by white arrow) in the right femur of rats.

Small pockets of empty space, as seen in FIG. 8.3c, noted by the yellow arrow, were observed in the X-rays of 75% of rats with implanted WZ42 alloy pins or cuffs, likely caused by hydrogen gas evolved from the degrading Mg implants. Despite their presence in the X-ray images, no bulges in the skin in the hind limb of rats were observed during frequent visual inspection of the rats. The rats regained mobility by 7 days post-operation.

Systemic Toxicity to Mg—Y—Zn—Ca—Zr Implants

Total blood cell count is listed in Table 8.3 below, which generally did not indicate any disturbances in the blood count, with parameters remaining within references ranges or near pre-operation levels. Small differences from the reference ranges or unoperated levels were observed from low platelet counts for WZ42 cuffs, and WZ42 and Ti6Al4V pins at 14 weeks, while elevated postoperative white blood cell count were seen at 2 weeks for both WZ42 and Ti6Al4V pins.

TABLE 8.3

Average blood cell count of unoperated animals and animals implanted with WZ42 and Ti6Al4V alloy pins at 2, 8, and 14 weeks after implantation.

| Name | Implantation time | Red Blood Cell Count | Hemoglobin | Platelet Count | White Blood Cell Count |
|---|---|---|---|---|---|
| Units |  | $10^6$/uL | g/dL | $10^3$/uL | $10^3$/uL |
| Ref ranges |  | (7.00-9.00) | (13.7-16.8) | (680-1280) | (1.1-7.5) |
| Unoperated |  | 7.4 ± 0.3 | 14.1 ± 0.9 | 618.3 ± 200.6 | 6.8 ± 2.3 |
| WZ42 pin | 2 weeks | 8.0 | 14.3 | 839.0 | 8.6 |
| Ti6Al4V pin | 2 weeks | 7.8 | 14.9 | 656.0 | 9.0 |
| WZ42 pin | 8 weeks | 7.4 ± 0.5 | 13.8 ± 1.2 | N/A | 6.8 |
| Ti6Al4V pin | 8 weeks | 7.4 ± 0.3 | 14.2 ± 0.4 | 637.8 ± 168.6 | 5.9 ± 1.6 |
| WZ42 pin | 14 weeks | 7.7 ± 0.4 | 14.2 ± 0.5 | 595.8 ± 179.8 | 5.9 ± 2.1 |
| Ti6Al4V pin | 14 weeks | 7.5 ± 0.4 | 14.0 ± 0.7 | 563.0 ± 164.5 | 5.9 ± 2.7 |
| WZ42 cuff | 14 weeks | 7.1 ± 0.2 | 13.9 ± 0.4 | 461.0 ± 56.6 | 2.2 ± 1.0 |
| Ti6Al4V cuff | 14 weeks | 7.6 ± 0.4 | 13.8 ± 0.7 | 637.0 ± 96.5 | 5.8 ± 1.4 |

Similarly, serum biochemical parameters are shown in Table 8.4, with kidney function measured by creatinine and urea levels, and liver function measured by albumin, alkaline phosphatase, bilirubin, and glucose. All parameters remained within the reference ranges or near pre-operation levels, demonstrating little effect of the implanted alloy materials on the kidney and liver function and metabolism.

TABLE 8.4

Average values of serum metabolic parameters unoperated animals and animals implanted with WX42 and Ti6Al4V alloy pins at 2, 8 and 14 weeks after implantation.

| Name | Implantation time | Glucose | ATL(GPT) | ALP | Total Bilirubin | Total Protein |
|---|---|---|---|---|---|---|
| Units |  | mg/dL | U/L | U/L | mg/dL | g/dL |
| Ref. ranges |  | (70-308) | (59-166) | (232-632) | (0.1-0.1) | (5.8-7.1) |
| Unoperated |  | 181.2 ± 19.8 | 55.8 ± 9.2 | 175.2 ± 20.3 | 0.17 ± 0.10 | 5.7 ± 0.1 |

TABLE 8.4-continued

| | | | | | | |
|---|---|---|---|---|---|---|
| WZ42 pin | 2 weeks | 155.8 ± 26.7 | 57.3 ± 7.9 | 148.3 ± 13.6 | 0.18 ± 0.05 | 6.3 ± 0.3 |
| Ti6Al4V pin | 2 weeks | 322.0 ± 94.4 | 66.3 ± 20.3 | 151.2 ± 21.8 | 0.14 ± 0.05 | 6.2 ± 0.1 |
| WZ42 pin | 8 weeks | 294.5 ± 205.0 | 80.4 ± 13.9 | 163.2 ± 30.4 | 0.24 ± 0.05 | 6.4 ± 0.3 |
| Ti6Al4V pin | 8 weeks | 204.8 ± 75.9 | 54.5 ± 17.9 | 201.5 ± 40.2 | 0.18 ± 0.05 | 6.4 ± 0.3 |
| WZ42 pin | 14 weeks | 177.8 ± 47.1 | 65.6 ± 8.7 | 183.8 ± 33.3 | 0.20 ± 0.00 | 6.4 ± 0.1 |
| Ti6Al4V pin | 14 weeks | 229.5 ± 198.5 | 56.8 ± 15.8 | 187.0 ± 33.5 | 0.18 ± 0.04 | 6.3 ± 0.3 |
| WZ42 cuff | 14 weeks | 123.6 ± 36.3 | 64.0 ± 7.7 | 155.2 ± 21.7 | 0.20 ± 0.00 | 6.3 ± 0.3 |
| Ti6Al4V cuff | 14 weeks | 154.4 ± 53.6 | 50.2 ± 3.4 | 163.6 ± 30.3 | 0.18 ± 0.04 | 6.2 ± 0.3 |

| Name | Albumin | Urea N | Creatinine | Globulin | A/G Ratio |
|---|---|---|---|---|---|
| Units | g/dL | mg/dL | mg/dL | g/Dl | |
| Ref. ranges | (3.2-3.7) | (13-19) | (0.3-0.5) | (2.6-3.5) | |
| Unoperated | 3.3 ± 0.1 | 20.7 ± 1.9 | 0.37 ± 0.08 | 2.4 ± 0.1 | 1.4 ± 0.1 |
| WZ42 pin | 3.3 ± 0.2 | 20.3 ± 5.6 | 0.50 ± 0.00 | 3.0 ± 0.1 | 1.1 ± 0.1 |
| Ti6Al4V pin | 3.3 ± 0.1 | 17.6 ± 2.1 | 0.42 ± 0.04 | 2.9 ± 0.2 | 1.1 ± 0.1 |
| WZ42 pin | 3.5 ± 0.1 | 23.6 ± 2.1 | 0.52 ± 0.08 | 2.9 ± 0.3 | 1.2 ± 0.1 |
| Ti6Al4V pin | 3.7 ± 0.2 | 21.8 ± 2.9 | 0.53 ± 0.05 | 2.7 ± 0.1 | 1.3 ± 0.1 |
| WZ42 pin | 3.6 ± 0.1 | 22.2 ± 1.6 | 0.56 ± 0.05 | 2.7 ± 0.1 | 1.3 ± 0.1 |
| Ti6Al4V pin | 3.7 ± 0.2 | 21.8 ± 2.5 | 0.52 ± 0.04 | 2.6 ± 0.2 | 1.4 ± 0.1 |
| WZ42 cuff | 3.7 ± 0.2 | 24.8 ± 2.2 | 0.58 ± 0.04 | 2.6 ± 0.2 | 1.4 ± 0.1 |
| Ti6Al4V cuff | 3.6 ± 0.1 | 19.6 ± 1.9 | 0.52 ± 0.04 | 2.6 ± 0.2 | 1.4 ± 0.1 |

Electrolyte parameters calcium, sodium, chloride, phosphorous, and magnesium were measured from serum samples which are shown in Table 8.5. Importantly, magnesium levels remained in the low end of the reference ranges indicating no accumulation of degrading Mg from the implants in the collected blood. All other electrolytes similarly remained consistent with unoperated rats and the prescribed allowable reference ranges.

TABLE 8.5

Average values of electrolyte parameters of unoperated animals and animals implanted with WX42 and Ti6A14V alloy pins at 2, 8, and 14 weeks after implantation.

| Name | Implantation time | Calcium | Sodium | Chloride | Phosphorous | Magnesium |
|---|---|---|---|---|---|---|
| Units | | mg/dL | mmol/L | mmol/L | mg/dL | mg/dL |
| Ref. ranges | | (9.5-13.9) | (146-151) | (98-104) | (5.6-16.8) | (3.8-5.5) |
| Unoperated | | 9.8 ± 0.2 | 138.2 ± 1.9 | 100.5 ± 1.0 | 5.5 ± 0.2 | 2.0 ± 0.2 |
| WZ42 pin | 2 weeks | 11.2 ± 0.1 | 144.8 ± 1.7 | 101.0 ± 1.4 | 8.5 ± 0.9 | 2.9 ± 0.3 |
| Ti6Al4V pin | 2 weeks | 11.5 ± 0.5 | 143.8 ± 1.6 | 100.2 ± 2.2 | 9.7 ± 1.9 | 3.4 ± 0.4 |
| WZ42 pin | 8 weeks | 11.6 ± 0.5 | 144.4 ± 1.9 | 100.6 ± 2.8 | 9.7 ± 1.4 | 3.5 ± 0.5 |
| Ti6Al4V pin | 8 weeks | 11.8 ± 0.6 | 146.5 ± 1.0 | 100.0 ± 1.4 | 11.3 ± 0.8 | 3.9 ± 0.4 |
| WZ42 pin | 14 weeks | 11.4 ± 0.3 | 147.8 ± 1.9 | 100.2 ± 2.0 | 9.8 ± 0.7 | 3.6 ± 0.2 |
| Ti6Al4V pin | 14 weeks | 12.2 ± 1.1 | 145.2 ± 2.6 | 99.0 ± 2.0 | 9.6 ± 1.2 | 3.6 ± 0.6 |
| WZ42 cuff | 14 weeks | 11.3 ± 0.2 | 147.0 ± 0.7 | 101.4 ± 0.9 | 9.1 ± 1.4 | 3.2 ± 0.2 |
| Ti6Al4V cuff | 14 weeks | 11.6 ± 0.3 | 147.6 ± 1.1 | 99.6 ± 1.7 | 9.2 ± 0.7 | 3.3 ± 0.2 |

ICP-OES results of the acid-digested liver and kidney (FIG. 8.4) demonstrated no accumulation of Mg exceeding the normal levels seen in unoperated control rats was observed in the collected liver and kidney tissue in the WZ42 or Ti6Al4V groups. Ca and Zn concentration in the liver and kidney also did not deviate from the normal levels. The concentration of other alloying elements (Y and Zr) measured from the digested liver and kidney were also perceived to be too low to be differentiated from normal levels, with Y being present in <0.7 μg/g dry mass in both liver and kidney, and Zr present in <2.2 μg dry mass in both liver and kidney.

FIG. 8.4 shows average Mg (a), Ca (b), and Zn (c) concentration in digested liver and kidney samples of rats implanted with femoral pins and cuffs of WZ42 and Ti6Al4V for 8 and 14 weeks compared to unoperated control rats. Significant difference *(p<0.05) between Mg concentration in kidneys of rats implanted with WZ42 pins for 8 weeks and unoperated control rats and between † (p<0.05) between Zn concentrations in kidneys of rats implanted with WZ42 pins for 8 weeks and cuffs. n≤3 per extract concentration per group per time point.

Histological Examination of Liver and Kidneys

Liver and kidneys explanted from the Sprague-Dawley rats sacrificed at 8 and 14 weeks were processed into pathological sections and stained with hematoxylin and eosin (H&E). Optical microscopy images (FIG. 8.5 for kidney and FIG. 8.6 for liver) revealed that the cellular structure of the liver and kidney did not undergo morphological changes or infiltration by inflammatory cells. No signs of obvious abnormalities were observed in any of the organs sections.

FIG. 8.5 shows photomicrographs of H&E stained kidneys of rats with femurs fixed by pins of WZ42 (a, c) and Ti6Al4V (b, d) after 8 weeks (a, b) and 16 weeks (c, d). Stained images of kidneys from rats with implanted wire cuffs of WZ42 (e) and Ti6Al4V (f) wrapped around bone for 14 weeks. Photomicrograph g) from rat that was left unoperated. Scale bar=50 μm.

FIG. 8.6 shows photomicrographs of H&E stained livers of rats with femurs fixed by pins of WZ42 (a, c) and Ti6Al4V (b, d) after 8 weeks (a, b) and 16 weeks (c, d). Stained images of livers from rats implanted with wire cuffs of WZ42 (e) and Ti6Al4V (f) wrapped around bone for 14 weeks. Photomicrograph g) from rat that was left unoperated. Scale bar=50 μm.

In Vivo Corrosion of Mg—Y—Zn—Ca—Zr Alloy Pins and Morphology of Surrounding Bone Example micro-CT slices obtained from the femur-implant complex are shown in FIG. 8.7.

FIG. 8.7 determines volume of the degrading WZ42 alloy, pins were distinguished from surrounding bone in micro-CT scans based on density thresholding with representative examples highlighted in green after implantation times of a) 2 weeks, b) 8 weeks, c) 14 weeks. Cuffs were fully degraded after 14 weeks (d) but new bone formation was seen in the region the wires occupied (arrows).

After two weeks, the pins had broken as seen in FIG. 8.7a. These pin failures occurred at the site of the femoral fracture, resulting in malunion. In addition, sites of corrosion appeared at junctions where the pins were clamped in collets during machining. Both these two regions where the corrosion/failure occurred corresponded with regions of higher stress. Progressive degradation throughout the pins was observed at 8 and 14 weeks (FIGS. 8.7b and c). Regions of the pin surrounded by the cortical bone appeared to degrade more slowly. Micro-CT scans of intact femurs with WZ42 wire cuffs wrapped around the midsection of the diaphysis (FIG. 8.7d) revealed what appeared to be new bone formation in the region surrounding the degrading cuffs, despite the cuffs having completely degraded after 14 weeks indicating the favorable response of the implanted Mg alloys.

Following segmentation of the remaining WZ42 pins from the surrounding degraded product and bone, a 3D reconstruction of the pins was created from which the volume was calculated. This remaining volume was used to calculate the corrosion rate at the end of 2, 8, and 14 weeks as shown in FIG. 8.8.

FIG. 8.8 shows corrosion rate and % volume remaining of WZ42 pins implanted in rat femurs for 2, 8, and 14 weeks. n≥2 for each group at each time point. * and † represent significant difference (p<0.05) compared to measurements made at other time points.

Degradation was found to occur more rapid initially at 2 weeks, after which the corrosion appeared to have reduced and stabilized as seen by the lower corrosion rates perceived at 8 and 14 weeks. This may be related to passivation of the WZ42 alloy and callus formation limiting fluid exposure to the degrading alloy after early stages of bone healing.

Local Tissue Response to Mg—Y—Zn—Ca—Zr Alloy Pin

Femur explants were collected after 2, 8, and 14 weeks to assess the local tissue response to the WZ42 pins and cuffs and observe any fracture healing. Sections of the bone from femurs containing the pins were stained using Goldner's Trichrome and are shown in FIG. 8.9.

After 2 weeks in rats implanted with the WZ42 alloy, empty pockets were observed over the fracture site in the fibrous tissue over the bone. This was likely due to accumulation of hydrogen gas forming gas pockets (GP) from the degrading magnesium alloy, as this is not observed in the Ti6Al4V pins. The presence of osteoids (Od) was observed surrounding the bone with fibrous tissue (Ft) surrounding the fracture site indicated by the dashed line demarcating the implant-bone interface. After 8 weeks, the gas pocket over the fracture site was not perceived to be as prominent, potentially due to a slowing of the corrosion rate, dissipation of gas, and ingrowth of fibrous tissue. A greater presence of osteoids as well as new bone formation (Nb) in the periosteal region was observed progressively after 8 and 14 weeks. After 14 weeks, the fracture was not yet completely healed when fixed with either WZ42 or Ti6Al4V pins.

FIG. 8.9 shows photomicrographs of Goldner's Trichrome stained sections (40×) of soft and hard tissue at the defect site fixed by pins of WZ42 magnesium alloy (a, c, e) and Ti6Al4V (b, d, f) after 2 weeks (a, b), 8 weeks (c, d), and 14 weeks (e, f) of implantation; g) representation of region of interest imaged along longitudinal plane at defect site. Cytoplasm, fibrin, muscle, and osteoids are represented in red; collagen and bone are represented in green. The dashed line approximates the implant pin-bone interface. Scale bar=200 μm. Abbreviations: GP, gas pocket; Od, osteoids; FT, fibrous tissue; Nb, new bone.

Alkaline phosphatase staining was conducted to indicate osteoblast activity and the process of new bone formation in the region surrounding the defect. Osteoblast activity was more prolific surrounding the fracture in the femurs containing WZ42 (FIG. 8.10a, c, e) compared to the femurs containing Ti6Al4V (FIG. 8.10b, d, f). Presence of osteoblasts appeared to peak at 8 weeks for the WZ42 group.

FIG. 8.10 shows photomicrographs of the localization of ALP at 40× and 100× (inset) of tissue at the defect site fixed by pins of WZ42 magnesium alloy (a, c, e) and Ti6Al4V (b, d, f) after 2 weeks (a, b), 8 weeks (c, d), and 14 weeks (e, f) of implantation. Scale bar=200 μm in 40× images, 100 μm in 100×. Pin located on left side of image in all.

In Goldner's Trichrome stained sections of tissue near the site of wire cuff implantation (FIG. 8.11), new bone as seen in light blue-green as well as fibrous tissue was found in the region surrounding the Mg alloy cuff implant (FIG. 8.11a). On the other hand, new bone formation was not seen around the inert Ti6Al4V cuff (FIG. 8.11b).

FIG. 8.11 shows photomicrographs of Goldner's Trichrome stained sections (40×) of soft and hard tissue at the implant-bone interface where wire cuffs of WZ42 magnesium alloy (a) and Ti6Al4V (b) were wrapped around bone for 14 weeks of implantation. c) Representation of region of interest imaged along longitudinal plane at defect site. Cytoplasm, fibrin, muscle, and osteoids are represented in red; collagen and bone are represented in green. The dashed line approximates the location of the WZ42 wire. Scale bar=200 μm. Abbreviations: FT, fibrous tissue; Nb, new bone; M, muscle; Ti, Ti6Al4V wire.

Discussion

In this specific aim, the effects of the WZ42 magnesium alloy in terms of biocompatibility and systemic toxicity, degradation behavior, and local tissue response and healing was investigated. This animal model, a closed femoral fracture stabilized by an intramedullary pin, has been characterized by various groups studying the expression of genes for bone and cartilage matrix constituents and growth factors, the production of cytokines, cell proliferation and apoptosis, and to compare metals for bone healing and mineralization by permanent metals. Despite these instances of stainless steel and Ni—Ti alloys being used to fix full osteotomies in rats, such an aggressive model representing a manifestation of large dynamic stress that favors corrosion had not been tested with magnesium alloys. In fact, no models of full load-bearing had been applied to a fracture fixation device manufactured from magnesium to date. It was also the intent to confirm the safety of Mg in this aggressive model and analyze the degradation behavior as a result of the high stress being placed on the Mg pins.

To assess the safety of the WZ42 implants, biochemical analysis of the blood and serum was also conducted. The lower than expected platelet levels for the WZ42 and Ti6Al4V pin groups at 14 weeks and WZ42 wire cuff group also at 14 weeks was likely due to platelet clumping in samples, which was reported in many samples analyzed. The elevated levels of white blood cells 2 weeks after surgeries for both WZ42 as well as Ti alloys represents a common indication of normal inflammation seen after surgical procedures are performed. Blood cell counts measured at later time points saw the white blood cell count return to normal levels, suggesting that signs of any immediate infection or a long-term inflammatory response was not present. The consistent electrolyte levels as measured in blood and the stable Mg concentration measured in the digested kidney and liver signifies that the degradation of WZ42 did not cause disturbances in the balance of electrolytes necessary for the body's normal function. Other studies have similarly found that blood biochemistry and liver and kidney function were not affected by magnesium alloy degradation when implanted in bone, indicating the general safety of degradation Mg alloys. Variability observed in the blood testing was expected from animal to animal, with additional error stemming from differences in blood sample quality such as hemolysis, clotting, and lipemia.

Along with the unaltered serum biochemical parameters suggesting that liver and kidney functions were not affected by the WZ42 alloy degradation, concentrations of Mg, Ca, and Zn (elements contained in the WZ42 alloy) in the liver and kidney did not rise above levels measured in unoperated rats (FIG. 8.24) with Y and Zr too low to be differentiated from baseline levels. Concentrations were also consistent with rats implanted with Ti6Al4V samples compared at the same time points. Expected differences between animals, potentially incomplete dissolution of tissue in acid, and deviations in ICP-OES measurements may have resulted in variations in ion concentrations within groups.

To further demonstrate systemic biocompatibility, H&E staining of the liver and kidney did not reveal any signs of organ damage. No dark deposits of focal mineralizations, acute inflammatory cells, or necrosis were observed in the kidney tissue. In the liver, no aggregates of inflammatory cells or features of hepatocellular necrosis such as irregular patchy areas of coagulation necrosis were observed. These results clearly suggest that the degradation products of the WZ42 alloy have good systemic biocompatibility. Hartwig stated that intake of high concentration of Mg ions would not cause adverse reactions due to the high aptitude for the excretory system of the kidney and storage buffering capacity from bones to allow the body to maintain a balance of serum magnesium.

Progressive degradation was observed in the intramedullary WZ42 pins as seen in the reducing cross sectional area of the implants seen in FIG. 8.26 (a-c), and calculated corrosion rate and volume loss shown in FIG. 8.27. Degradation appeared to occur preferentially at the fracture site, perpendicular to the fracture, where the stresses acting on the implanted pin would be perceived to be the highest. This synergy of mechanical loading combined with the corrosive environment of surrounding fluids in the body has been shown to cause sudden fracture of implants via the well-known stress corrosion cracking (SCC) mechanism. This embrittlement phenomenon can occur even when applied stress does not exceed the yield strength of the material, reducing the time to fracture and causing premature brittle failure. Magnesium, suffering from pitting corrosion, a source from which SCC can develop, has shown susceptibility to SCC in chloride solutions and simulated body fluids. Other localized regions of corrosion, such as near the end of the pin in FIG. 8.7a, occurred due to pre-existing flaws imparted during machining, which increased the susceptibility to SCC. Degradation at the site of fracture was also promoted by the higher exposure to the surrounding fluid electrolyte, acting to produce fluid shear stress and remove local OH⁻ ions to reduce the protection from the passivation layer. The reduction in corrosion rate after the initial 2 week time point occurred as the surface of the Mg implant as expected became passivated and enclosed in fibrous tissue and newly formed bone, as observed in other studies of Mg implanted into bone. The percentage volume remaining did not significantly change between 2 and 8 weeks because measurements were taken from different samples at each time point. For the implants used to calculate the 8 week measurements, the corrosion rate was lower so that over time, the volume remaining ended up the being not significantly different from the samples measured after 2 weeks which degraded at a much faster rate. In another sense, the corrosion rate for 8 week samples was approximately one quarter of the 2 week corrosion rate, however, since the volume remaining was compounded over four times the length of time, the volume remaining ended up being similar. The variation between samples that caused the difference in degradation for 2 versus 8 week samples may be due to variability in when the pins failed, or pins not being fully surrounded by cortical bone thus being exposed to more surrounding fluid leading to more rapid corrosion.

The effect of the degrading Mg alloy on the surrounding tissue was investigated via Goldner's Trichrome and ALP staining after 2, 8, and 14 weeks implantation of the WZ42 and Ti6Al4V intramedullary pins and extra-cortical cuffs. After 2 weeks in rats implanted with the WZ42 alloy (FIG. 8.3a, FIG. 8.9a), gas pockets (GP) were observed over the fracture site forming empty cavities in the surrounding in fibrous tissue. This was likely due to accumulation of hydrogen gas from the degrading magnesium alloy, as this is not observed in the Ti6Al4V pins. The presence of osteoids (Od) was observed near bone with fibrous tissue (Ft), or callus surrounding the fracture site, part of the normal bone healing process. After 8 weeks (FIG. 8.7c), the gas pocket over the fracture site was not as prominent, potentially due to slowing of corrosion rate, dissipation of gas, and ingrowth of fibrous tissue. A greater presence of osteoids as well as new bone formation (Nb) in the periosteal region was observed progressively after 8 and 14 weeks. After 14 weeks (FIG. 8.9e), the fracture was not yet completely healed when fixed with either WZ42 or Ti6Al4V pins. The elevated new bone formation seen in the WZ42 group at 8 and 14 weeks that was further confirmed by ALP staining. Osteoblast activity as indicated by ALP staining demonstrated promotion of new bone formation in the region surrounding the defect, at the leading edge to heal the fracture. Presence of osteoblasts peaked at 8 weeks for the WZ42 group with higher activity compared to the Ti6Al4V group. In the case of the wire cuff placed over the cortical bone (FIG. 8.11a), new bone formation as seen in blue was found in the region surrounding the Mg alloy cuff implant compared to the inert Ti6Al4V. Despite the fracture not having healed fully due to the instability of the intramedullary fixation, the healing process did not appear to be encumbered. In fact, the prevalence of new bone formation as seen in the mineralized new bone and osteoblast activity in regions adjacent to both types of Mg alloy implants confirms results of numerous studies reporting enhanced new bone formation around Mg-based implants related to the cellular activity of Mg and due to osteoconductivity of the phosphate layer forming on the surface of magnesium-based implants. Additionally, the consistent observations of a normal healing response of a fibrous capsule enclosing the operation site with no abnormal presence of inflammatory cells at the implant site as seen in other reports of Mg scaffolds showing good biocompatibility indicated the local biosafety of the Mg alloy.

Overall, the positive biocompatibility and signs of healing with new bone formation indicate that the WZ42 alloy is a suitable candidate for orthopedic applications. Care must be taken however with limiting the mechanical stresses placed on the implant and that a consistent surface finish of the alloy is achieved by machining so as to reduce the onset of rapid corrosion and potential failure brought on by stress corrosion cracking. The model tested here represented an unusually high dynamic stress initiator on the implant site thus loading the femur and thereby completely transferring the load onto the Mg intramedullary pin intentionally leading to a highly aggressive load and corrosion condition causing the pins to ultimately fail. This aggressive load model nevertheless showed that despite having such an aggressive condition that could be perceived as an extreme event, the local and systemic safety of the alloy was still maintained under such high stresses leading to the alloy undergoing accelerated corrosion. Despite this release of degradation products, hydrogen gas formation was not externally noticeable and the surrounding tissue response, kidney and liver, and blood parameters all remained normal. Thus, with temporary unloading as is required in the treatment of orthopedic injuries, the risk of failure of the WZ42 alloy would likely be diminished, still rendering the alloy as a promising orthopedic implant material, with possibilities in other medical device applications to be explored. In summary, considering the aggressive nature of the model providing high stress and accelerated corrosion conditions initially as is demonstrated by the results discussed, the fact that bone healing was observed as well as more importantly, all the serum and blood pathology profiles being normal combined with the histological analyses of the vital organs (liver and kidney) indicates the promise of the particular alloy, WZ42 for orthopedic fixation applications. The high strength and the favorable in vitro results further complements the in vivo results discussed herein showing the promise of the system for possible exploration of its efficacy in other medical device applications. It is of the opinion of the inventors that semi or non-load bearing environments be placed on orthopedic Mg implants to fully demonstrate their safety and efficacy in these settings before targeting more demanding applications, wherein the implants are exposed to dynamic mechanical stresses. Normally, orthopedic injuries are immobilized during early treatment, which should help reduce risk of Mg device failure as seen in the model here. Already, this pathway of lesser resistance has been observed in the Syntellix and K-Met screws used for minimally demanding bone fixation. To take the alloys further, a similar, low mechanical stress demanding application may be targeted followed by studying their response using an external fixation or immobilization device to minimize the influence of stress corrosion.

OVERALL CONCLUSIONS

A variety of alloy design parameters were modified to achieve the enhanced properties, including the addition of varying amounts of yttrium from 0 to 4.0 wt. %, adding Zn, applying the solution heat treatment, and hot working of the alloys using hot extrusion at various extrusion ratios. The work presented here represents novel alloy materials development for medical devices encompassing the selection of the alloy material components and analyzing the desired properties for various testing based on FDA, ISO, and ASTM standards adopted for degradable metals, for the ultimate goal of vetting the materials for orthopedic implant application, which was tested in the animal study. This thorough process described and discussed here can be applied to other degradable materials, serving as a basis for materials testing for resorbable orthopedic devices.

A variety of Mg-based alloys were processed, with the intention to control the corrosion rate, improve the mechanical properties, and maintain low toxicity in in vitro and in vivo studies. The initial study investigated as-cast and solution heat treated Mg—Y—Ca—Zr alloys containing 1 wt. % and 4 wt. % Y found that higher Y content present in WX41 contributed to an increase in grain size, while T4 solution treatment also resulted in grain coarsening. Upon applying extrusion to the cast alloys and heat treated alloys, grain size was dramatically reduced through the hot working and dynamic recrystallization processes. Despite X-ray diffraction showing the presence of single phase magnesium in all the alloys except the LPSO phases observed in the as-cast WZ42, secondary phase precipitates containing the alloying elements of Y, Ca, Zr, and Zn were present in all alloys at both the grain boundaries and within the grains. These precipitates became more dispersed after heat treatment and broken down during extrusion. The WZ42 alloy containing Y and Zn also contained the secondary phase $Mg_{12}YZn$ intermetallic which yielded enhanced properties.

The corrosion and mechanical properties of the Mg-based alloys was investigated following synthesis and processing the alloys. Changes in the grain size through extrusion or heat treatment appeared to result in more uniform corrosion with the secondary phases being dissolved or disrupted to disperse the sites for microgalvanic corrosion. By increasing the Y content in the Mg-based alloys, a more passive layer was formed as reported in first-principle studies on the stability of Y in Mg alloys conducted in the group earlier. Strength of the alloys likewise improved with greater Y content in as-cast form, however in extruded alloys, addition of Y did not result in significant increase in strength due to the higher temperature required for extrusion leading to dynamic recrystallization and grain growth, partially negating the grain refining effect of extrusion and precipitation strengthening of the secondary phase. With extrusion and the significant grain refinement imparted, drastic improvements in strength and elongation however occurred as explained through the Hall-Petch relationship. Above all other alloys and the commercial pure Mg and AZ31 materials tested, the WZ42 (Mg—Y—Zn—Zr—Ca) alloy demonstrated significantly higher strength, placing it at the upper end of Mg alloys reported in literature, while maintaining a relatively low corrosion rate among those tested.

The results in earlier sections elucidated the effects on pre-osteoblasts and human mesenchymal stem cells cultured in vitro when directly in contact with the alloys and indirectly when in the presence of media containing the degradation products and alloying element chloride salts of the alloys discussed previously. High viability of the alloys, especially in extruded state was confirmed by MTT and Live/dead assays. The inspiration for the indirect studies drew from FDA recommendation of the use of ISO 10993: 12 where extract is collected from implant materials to expose to cells, as well as reports that diluting the collected extract at least 10× is required to obtain reliable in vitro cytotoxicity results of degradable materials. When testing both alloy extracts and the alloying element salts themselves, Mg—Y alloy degradation products and Y salts resulted in improved proliferation and higher ALP activity suggesting promotion of osteogenic differentiation. The WZ42 alloy in particular allowed for maximum proliferation and osteogenic differentiation.

To culminate the transition from materials development to in vivo safety evaluation, the WZ42 pins were implanted into the intramedullary cavity of fractured rat femurs and as wires wrapped around the midsection of un-altered femurs, comparing the alloy to Ti6Al4V. Rats were sacrificed at 2, 8, and 14 weeks with material performance assessed based on 1) systemic toxicity analyzed by bloodwork, liver, and kidney histology, degradation product accumulation), 2) degradation measured by micro-CT reconstructions of the remaining WZ42 implants, and 3) local tissue response evaluated by histopathology of the local bone and surrounding soft tissue. After successful implantation and maintained fracture stability after 1 week as confirmed by X-ray, it was found that degradation occurred leading to intramedullary pin failure due to perceived high stress related corrosion. Micro-CT analysis from 2 weeks onward revealed alloy pin degradation and fracture validating the stress corrosion cracking hypothesis initiated at the osteotomy site of high mechanical loading. However, the WZ42 alloy was still found to be with no recognizable accumulation of Mg or alloying elements in the blood, liver, or kidney, with no adverse effects in the blood count, metabolism, or kidney and liver function. Finally, histology of the local area at the implant site showed normal fracture healing and new bone formation. No abnormal inflammatory response was observed surrounding the implants.

Overall, the encouraging mechanical, bio-corrosion, and biological properties of the Mg—Y—Ca—Zn—Zr alloys, especially the WZ42 alloy, are indicative of their potential as viable orthopedic and craniofacial implant biomaterials. Various alloys in the Mg—Y—Ca—Zn—Zr system are suitable for use in various germane and critical orthopedic medical devices under low, semi-load as well as load bearing conditions optimally targeted to balance the corrosion and mechanical response with the desired biological outcome.

The invention claimed is:

1. A biodegradable medical implant device, comprising:
   a biodegradable, extruded metal alloy, consisting of:
   about 4.0 weight percent of yttrium;
   from about 0.5-0.6 weight percent of calcium;
   from about 0.6-1.0 weight percent of zirconium;
   about 2.0 weight percent of zinc; and
   a balance of magnesium including impurities, based on the total weight of the composition,
   wherein the biodegradable, extruded metal alloy is a solid solution, and intermetallic phases are precluded other than a long period stacking order phase $Mg_{12}YZn$, and
   wherein the metal alloy has ultimate tensile strength from about 375 to about 410 MPa and yield tensile strength from about 335 to about 345 MPa, and exhibits proliferation of cells and corresponding osteogenic differentiation.

2. The medical implant device of claim 1, wherein the calcium constitutes about 0.6 weight percent and the zirconium constitutes about 1.0 weight percent.

3. The medical implant device of claim 1, wherein the zirconium constitutes about 0.6 weight percent.

4. The medical implant device of claim 1, wherein the impurities comprise one or more of iron, nickel, and copper.

5. The medical implant device of claim 1, wherein the impurities constitute 20 ppm or less.

6. The medical implant device of claim 1, wherein the metal alloy has elongation about 15%.

* * * * *